_(12)_ United States Patent
Bartsevich et al.

(10) Patent No.: US 10,603,363 B2
(45) Date of Patent: Mar. 31, 2020

(54) TREATMENT OF RETINITIS PIGMENTOSA USING ENGINEERED MEGANUCLEASES

(71) Applicant: Precision BioSciences, Inc., Durham, NC (US)

(72) Inventors: Victor Bartsevich, Durham, NC (US); Derek Jantz, Durham, NC (US); James Jefferson Smith, Morrisville, NC (US); Michael G. Nicholson, Chapel Hill, NC (US)

(73) Assignee: Precision BioSciences, Inc., Durham, NC (US)

( * ) Notice: Subject to any disclaimer, the term of this patent is extended or adjusted under 35 U.S.C. 154(b) by 26 days.

(21) Appl. No.: 15/758,366

(22) PCT Filed: Sep. 8, 2016

(86) PCT No.: PCT/US2016/050809
§ 371 (c)(1),
(2) Date: Mar. 8, 2018

(87) PCT Pub. No.: WO2017/044649
PCT Pub. Date: Mar. 16, 2017

(65) Prior Publication Data
US 2018/0250370 A1    Sep. 6, 2018

Related U.S. Application Data

(60) Provisional application No. 62/215,460, filed on Sep. 8, 2015.

(51) Int. Cl.
| | |
|---|---|
| *C12N 9/22* | (2006.01) |
| *C12N 15/55* | (2006.01) |
| *C12N 15/861* | (2006.01) |
| *A61K 38/46* | (2006.01) |
| *C12N 15/90* | (2006.01) |
| *C12N 15/52* | (2006.01) |
| *A61P 27/00* | (2006.01) |

(52) U.S. Cl.
CPC .............. *A61K 38/465* (2013.01); *C12N 9/22* (2013.01); *C12N 15/52* (2013.01); *C12N 15/907* (2013.01); *A61P 27/00* (2018.01); *C12N 2750/14143* (2013.01)

(58) Field of Classification Search
None
See application file for complete search history.

(56) References Cited

U.S. PATENT DOCUMENTS

| | | | |
|---|---|---|---|
| 8,021,867 B2* | 9/2011 | Smith | C12N 15/8213 |
| | | | 435/196 |
| 2012/0204282 A1 | 8/2012 | Zhang | |
| 2013/0183282 A1* | 7/2013 | Lemaire | C12N 9/22 |
| | | | 424/94.6 |

FOREIGN PATENT DOCUMENTS

| | | |
|---|---|---|
| WO | WO 2007/047859 A2 | 4/2007 |
| WO | WO 2011/095475 A1 | 8/2011 |
| WO | WO 2011/141825 A1 | 11/2011 |
| WO | WO 2012/167192 A2 | 12/2012 |

OTHER PUBLICATIONS

Arnould et al., Engineered I-CreI derivatives cleaving sequences from the human XPC gene can induce highly efficient gene correction in mammalian cells. J. Mol. Biol., 2007, 371, 49-65.*
Uniprot, Accession No. P05725, 2015, www.uniport.org.*
International Search Report and Written Opinion for International Application No. PCT/US2016/050809 dated Nov. 30, 2016.
International Preliminary Report on Patentability for International Application No. PCT/US2016/050809 dated Mar. 22, 2018.

* cited by examiner

*Primary Examiner* — Robert B Mondesi
*Assistant Examiner* — Todd M Epstein
(74) *Attorney, Agent, or Firm* — Wolf, Greenfield & Sacks, P.C.

(57) ABSTRACT

Disclosed are recombinant meganucleases engineered to recognize and cleave recognition sequences present in a mutant RHO P23H allele. The invention further relates to the use of such recombinant meganucleases in methods for treating retinitis pigmentosa, wherein the mutant RHO P23H allele is preferentially targeted, cleaved, and inactivated.

10 Claims, 32 Drawing Sheets

Specification includes a Sequence Listing.

A.

| Allele | 49 | | | | | | | | | | | | | | | | | | | | 70 |
|---|---|---|---|---|---|---|---|---|---|---|---|---|---|---|---|---|---|---|---|---|---|---|
| Rhodopsin Wild-Type | A | C | G | G | T | G | T | G | G | T | A | C | G | C | A | G | C | C | C | C | T |
| Rhodopsin P23H Allele | A | C | G | G | T | G | T | G | G | T | A | C | G | C | A | G | C | C | A | C | T |

Meganuclease Recognition Sequence

B.

RHO1 Half-Site   RHO2 Half-Site

| Mutant RHO P23H Allele | 49 | | | | | | | | | | | | | | | | | | | | 70 |
|---|---|---|---|---|---|---|---|---|---|---|---|---|---|---|---|---|---|---|---|---|---|
| | A | C | G | G | T | G | T | G | G | T | A | C | G | C | A | G | C | C | A | C | T |
| | T | G | C | C | C | A | C | A | C | C | A | T | G | C | G | T | C | G | G | T | G | A |

C.

First Subunit – RHO1    Second Subunit – RHO2

HVR1    Linker    HVR2

Second Subunit – RHO2    First Subunit – RHO1

HVR2    Linker    HVR1

Figure 1

RHO1 Half-Site Binding Sequences

| SEQ ID NO: | | 198 | | | Hypervariable Region 1 (HVR1) | | 271 |
|---|---|---|---|---|---|---|---|
| 102 | RHO2-L3-59 | KEFLLLYLAGFVDGDGS | IWASIIPEQGYKFKHRLRLSFTVAQKTQRRWFLDKLVDEIGVGYVYDQGSVSEYRLSE |
| 103 | RHO2-L5-14 | KEFLLLYLAGFVDGDGS | IWASIIPEQGYKFKHRLRLSFTVAQKTQRRWFLDKLVDEIGVGYVYDQGSVSEYRLSE |
| 104 | RHO 1/2-L2-49 | KEFLLLYLAGFVDGDGS | IWASIIPEQGYKFKHRLRLSFTVAQKTQRRWFLDKLVDEIGVGYVYDQGSVSEYRLSE |
| 105 | RHO 1-2x.179 | KEFLLLYLAGFVDGDGS | IWASIIPEQGYKFKHRLRLSFTVAQKTQRRWFLDKLVDEIGVGYVYDQGSVSTYRLSQ |
| 106 | RHO 1-2x.4 | KEFLLLYLAGFVDGDGS | IWATIMPEQRQKFFKHRLYFEVCQKTQRRWFLDKLVDEIGVGYVYDSGSVSEYRLSQ |
| 107 | RHO 1-2x.207 | KEFLLLYLAGFVDGDGS | IWASIOPEQTDKFKHRLRLYFEASQKTQRRWFLDKLVDEIGVGYVYDQGSVSEYRLSQ |
| 108 | RHO 1-2x.277 | KEFLLLYLAGFVDGDGS | IWASIOPEDQVYKFKHRLRLRFEAVFQKTQRRWFLDKLVDEIGVGYVYDQGSVSEYRLSQ |
| 109 | RHO 1-2x.292 | KEFLLLYLAGFVDGDGS | IWASIEPVQYKFKHRLRLSFAVSQKTQRRWFLDKLVDEIGVGYVYDQGSVSCYRLSQ |
| 110 | RHO 1-2x.324 | KEFLLLYLAGFVDGDGS | IWASITPSQAGKFKHRLRLYFEVSQKTQRRWFLDKLVDEIGVGYVYDQGSVSEYRLSQ |
| 111 | RHO 1-2x.371 | KEFLLLYLAGFVDGDGS | IWASIIPEAQRYKFKHRLRLIFAVYQKTQRRWFLDKLVDEIGVGYVYDQGSVSEYRLSQ |
| 112 | RHO 1-2x.164 | KEFLLLYLAGFVDGDGS | IWASIYATIEPAQFKFKHRLSLRFAVYQKTQRRWFLDKLVDEIGVGYVYDQGSVSEYRLSQ |
| 113 | RHO 1-2x.181 | KEFLLLYLAGFVDGDGS | IWASIYATIEPCQFKFKHRLRLIFAVYQKTQRRWFLDKLVDEIGVGYVYDQGSVSRYQLSQ |
| 114 | RHO 1-2x.184 | KEFLLLYLAGFVDGDGS | IWASIYATIOPDQVQKFKHRLRLIFAVYQKTQRRWFLDKLVDEIGVGYVYDTGSVSEYRLSE |
| 115 | RHO-1/2-L1-21 | KEFLLLYLAGFVDGDGS | IWASIIPEQGYKFKHRLRLSFTVAQKTQRRWFLDKLVDEIGVGYVYDQGSVSEYRLSE |
| 116 | RHO-1/2-L1-43 | KEFLLLYLAGFVDGDGS | IWASIIPEQGYKFKHRLRLSFTVAQKTQRRWFLDKLVDEIGVGYVYDQGSVSEYRLSE |
| 117 | RHO-1/2-L1-45 | KEFLLLYLAGFVDGDGS | IWASIIPEQGYKFKHRLRLSFTVAQKTQRRWFLDKLVDEIGVGYVYDQGSVSEYRLSE |
| 118 | RHO-1/2-L1-60 | KEFLLLYLAGFVDGDGS | IWASIIPEQGYKFKHRLRLSFTVAQKTQRRWFLDKLVDEIGVGYVYDQGSVSEYRLSE |
| 119 | RHO-1/2-L1-61 | KEFLLLYLAGFVDGDGS | IWASIIPEQGYKFKHRLRLSFTVAQKTQRRWFLDKLVDEIGVGYVYDQGSVSEYRLSE |
| 120 | RHO-1/2-L1-58 | KEFLLLYLAGFVDGDGS | IWASIIPEQGYKFKHRLRLSFTVAQKTQRRWFLDKLVDEIGVGYVYDQGSVSEYRLSE |
| 121 | RHO-1/2-L1-7 | KEFLLLYLAGFVDGDGS | IWASIIPEQGYKFKHRLRLSFTVAQKTQRRWFLDKLVDEIGVGYVYDQGSVSEYRLSE |
| 122 | RHO-1/2-L1-13 | KEFLLLYLAGFVDGDGS | IWASIIPEQGYKFKHRLRLSFTVAQKTQRRWFLDKLVDEIGVGYVYDQGSVSEYRLSE |
| 123 | RHO-1/2-L1-18 | KEFLLLYLAGFVDGDGS | IWASIIPEQGYKFKHRLRLSFTVAQKTQRRWFLDKLVDEIGVGYVYDQGSVSEYRLSE |
| 124 | RHO-1/2-L1-70 | KEFLLLYLAGFVDGDGS | IWASIIPEQGYKFKHRLRLSFTVAQKTQRRWFLDKLVDEIGVGYVYDQGSVSEYRLSE |
| 125 | RHO-1/2-L1-86 | KEFLLLYLAGFVDGDGS | IWASIIPEQGYKFKHRLRLSFTVAQKTQRRWFLDKLVDEIGVGYVYDQGSVSEYRLSE |
| 126 | RHO-1/2-L2-13 | KEFLLLYLAGFVDGDGS | IWASIIPEQGYKFKHRLRLSFTVAQKTQRRWFLDKLVDEIGVGYVYDQGSVSEYRLSE |
| 127 | RHO-1/2-L2-24 | KEFLLLYLAGFVDGDGS | IWASIIPEQGYKFKHRLRLSFTVAQKTQRRWFLDKLVDEIGVGYVYDQGSVSEYRLSE |
| 128 | RHO-1/2-L2-37 | KEFLLLYLAGFVDGDGS | IWASIIPEQGYKFKHRLRLSFTVAQKTQRRWFLDKLVDEIGVGYVYDQGSVSEYRLSE |
| 129 | RHO-1/2-L2-58 | KEFLLLYLAGFVDGDGS | IWASIIPEQGYKFKHRLRLSFTVAQKTQRRWFLDKLVDEIGVGYVYDQGSVSEYRLSE |
| 130 | RHO-1/2-L2-31 | KEFLLLYLAGFVDGDGS | IWASIIPEQGYKFKHRLRLSFTVAQKTQRRWFLDKLVDEIGVGYVYDQGSVSEYRLSE |
| 131 | RHO-1/2-L2-29 | KEFLLLYLAGFVDGDGS | IWASIIPEQGYKFKHRLRLSFTVAQKTQRRWFLDKLVDEIGVGYVYDQGSVSEYRLSE |
| 132 | RHO-1/2-L2-61 | KEFLLLYLAGFVDGDGS | IWASIIPEQGYKFKHRLRLSFTVAQKTQRRWFLDKLVDEIGVGYVYDQGSVSEYRLSE |

RHO1 Half-Site Binding Sequences (cont.)

RHO1 Half-Site Binding Sequences (cont.)

Figure 2C

RHO1 Half-Site Binding Sequences (cont.)

```
              272                                                                              344
RHO2-L3-59    IKPLHNFLTQLQPFLKLKQKQANLVLKIHEQLPSAKESPDKFLEVCTWVDQIAALNDSKTRKTTSETVRAVLD
RHO2-L5-14    IKPLHNFLTQLQPFLKLKQKQANLVLKIHEQLPSAKESPDKFLEVCTWVDQIAALNDSKTRKTTSETVRAVLD
RHO-1/2-L2-49 IKPLHNFLTQLQPFLKLKQKQANLVLKIHEQLPSAKESPDKFLEVCTWVDQIAALNDSKTRKTTSETVRAVLD
RHO 1-2x.179  IKPLHNFLTQLQPFLKLKQKQANLVLKIHEQLPSAKESPDKFLEVCTWVDQIAALNDSKTRKTTSETVRAVLD
RHO 1-2x.4    IKPLHNFLTQLQPFLKLKQKQANLVLKIHEQLPSAKESPDKFLEVCTWVDQIAALNDSKTRKTTSETVRAVLD
RHO 1-2x.207  IKPLHNFLTQLQPFLKLKQKQANLVLKIHEQLPSAKESPDKFLEVCTWVDQIAALNDSKTRKTTSETVRAVLD
RHO 1-2x.277  IKPLHNFLTQLQPFLKLKQKQANLVLKIHEQLPSAKESPDKFLEVCTWVDQIAALNDSKTRKTTSETVRAVLD
RHO 1-2x.292  IKPLHNFLTQLQPFLKLKQKQANLVLKIHEQLPSAKESPDKFLEVCTWVDQIAALNDSKTRKTTSETVRAVLD
RHO 1-2x.324  IKPLHNFLTQLQPFLKLKQKQANLVLKIHEQLPSAKESPDKFLEVCTWVDQIAALNDSKTRKTTSETVRAVLD
RHO 1-2x.371  IKPLHNFLTQLQPFLKLKQKQANLVLKIHEQLPSAKESPDKFLEVCTWVDQIAALNDSKTRKTTSETVRAVLD
RHO 1-2x.164  IKPLHNFLTQLQPFLKLKQKQANLVLKIHEQLPSAKESPDKFLEVCTWVDQIAALNDSKTRKTTSETVRAVLD
RHO 1-2x.181  IKPLHNFLTQLQPFLKLKQKQANLVLKIHEQLPSAKESPDKFLEVCTWVDQIAALNDSKTRKTTSETVRAVLD
RHO 1-2x.184  IKPLHNFLTQLQPFLKLKQKQANLVLKIHEQLPSAKESPDKFLEVCTWVDQIAALNDSKTRKTTSETVRAVLD
RHO-1/2-L1-21 IKPLHNFLTQLQPFLKLKQKQANLVLKIHEQLPSAKESPDKFLEVCTWVDQIAALNDSKTRKTTSETVRAVLD
RHO-1/2-L1-43 IKPLHNFLTQLQPFLKLKQKQANLVLKIHEQLPSAKESPDKFLEVCTWVDQIAALNDSKTRKTTSETVRAVLD
RHO-1/2-L1-45 IKPLHNFLTQLQPFLKLKQKQANLVLKIHEQLPSAKESPDKFLEVCTWVDQIAALNDSKTRKTTSETVRAVLD
RHO-1/2-L1-60 IKPLHNFLTQLQPFLKLKQKQANLVLKIHEQLPSAKESPDKFLEVCTWVDQIAALNDSKTRKTTSETVRAVLD
RHO-1/2-L1-61 IKPLHNFLTQLQPFLKLKQKQANLVLKIHEQLPSAKESPDKFLEVCTWVDQIAALNDSKTRKTTSETVRAVLD
RHO-1/2-L1-58 IKPLHNFLTQLQPFLKLKQKQANLVLKIHEQLPSAKESPDKFLEVCTWVDQIAALNDSKTRKTTSETVRAVLD
RHO-1/2-L1-7  IKPLHNFLTQLQPFLKLKQKQANLVLKIHEQLPSAKESPDKFLEVCTWVDQIAALNDSKTRKTTSETVRAVLD
RHO-1/2-L1-13 IKPLHNFLTQLQPFLKLKQKQANLVLKIHEQLPSAKESPDKFLEVCTWVDQIAALNDSKTRKTTSETVRAVLD
RHO-1/2-L1-18 IKPLHNFLTQLQPFLKLKQKQANLVLKIHEQLPSAKESPDKFLEVCTWVDQIAALNDSKTRKTTSETVRAVLD
RHO-1/2-L1-70 IKPLHNFLTQLQPFLKLKQKQANLVLKIHEQLPSAKESPDKFLEVCTWVDQIAALNDSKTRKTTSETVRAVLD
RHO-1/2-L1-86 IKPLHNFLTQLQPFLKLKQKQANLVLKIHEQLPSAKESPDKFLEVCTWVDQIAALNDSKTRKTTSETVRAVLD
RHO-1/2-L2-13 IKPLHNFLTQLQPFLKLKQKQANLVLKIHEQLPSAKESPDKFLEVCTWVDQIAALNDSKTRKTTSETVRAVLD
RHO-1/2-L2-24 IKPLHNFLTQLQPFLKLKQKQANLVLKIHEQLPSAKESPDKFLEVCTWVDQIAALNDSKTRKTTSETVRAVLD
RHO-1/2-L2-37 IKPLHNFLTQLQPFLKLKQKQANLVLKIHEQLPSAKESPDKFLEVCTWVDQIAALNDSKTRKTTSETVRAVLD
RHO-1/2-L2-58 IKPLHNFLTQLQPFLKLKQKQANLVLKIHEQLPSAKESPDKFLEVCTWVDQIAALNDSKTRKTTSETVRAVLD
RHO-1/2-L2-31 IKPLHNFLTQLQPFLKLKQKQANLVLKIHEQLPSAKESPDKFLEVCTWVDQIAALNDSKTRKTTSETVRAVLD
RHO-1/2-L2-29 IKPLHNFLTQLQPFLKLKQKQANLVLKIHEQLPSAKESPDKFLEVCTWVDQIAALNDSKTRKTTSETVRAVLD
RHO-1/2-L2-61 IKPLHNFLTQLQPFLKLKQKQANLVLKIHEQLPSAKESPDKFLEVCTWVDQIAALNDSKTRKTTSETVRAVLD
```

Figure 2D

RHO1 Half-Site Binding Sequences (cont.)

| | 272 | | 344 |
|---|---|---|---|
| RHO2-L3-2 | IKPLHNFLLT | QLQPFLKLKQKQANLVLKIIEQLPSAKESPDKFLEVCTWVDQIAALNDSKTRKTTSETVRAVLD |
| RHO2-L3-3 | IKPLHNFLLT | QLQPFLKLKQKQANLVLKIIEQLPSAKESPDKFLEVCTWVDQIAALNDSKTRKTTSETVRAVLD |
| RHO2-L3-5 | IKPLHNFLLT | QLQPFLKLKQKQANLVLKIIEQLPSAKESPDKFLEVCTWVDQIAALNDSKTRKTTSETVRAVLD |
| RHO2-L3-10 | IKPLHNFLLT | QLQPFLKLKQKQANLVLKIIEQLPSAKESPDKFLEVCTWVDQIAALNDSKTRKTTSETVRAVLD |
| RHO2-L3-11 | IKPLHNFLLT | QLQPFLKLKQKQANLVLKIIEQLPSAKESPDKFLEVCTWVDQIAALNDSKTRKTTSETVRAVLD |
| RHO2-L3-12 | IKPLHNFLLT | QLQPFLKLKQKQANLVLKIIEQLPSAKESPDKFLEVCTWVDQIAALNDSKTRKTTSETVRAVLD |
| RHO2-L3-13 | IKPLHNFLLT | QLQPFLKLKQKQANLVLKIIEQLPSAKESPDKFLEVCTWVDQIAALNDSKTRKTTSETVRAVLD |
| RHO2-L3-28 | IKPLHNFLLT | QLQPFLKLKQKQANLVLKIIEQLPSAKESPDKFLEVCTWVDQIAALNDSKTRKTTSETVRAVLD |
| RHO2-L3-29 | IKPLHNFLLT | QLQPFLKLKQKQANLVLKIIEQLPSAKESPDKFLEVCTWVDQIAALNDSKTRKTTSETVRAVLD |
| RHO2-L3-57 | IKPLHNFLLT | QLQPFLKLKQKQANLVLKIIEQLPSAKESPDKFLEVCTWVDQIAALNDSKTRKTTSETVRAVLD |
| RHO2-L3-80 | IKPLHNFLLT | QLQPFLKLKQKQANLVLKIIEQLPSAKESPDKFLEVCTWVDQIAALNDSKTRKTTSETVRAVLD |
| RHO2-L3-85 | IKPLHNFLLT | QLQPFLKLKQKQANLVLKIIEQLPSAKESPDKFLEVCTWVDQIAALNDSKTRKTTSETVRAVLD |
| RHO2-L3-86 | IKPLHNFLLT | QLQPFLKLKQKQANLVLKIIEQLPSAKESPDKFLEVCTWVDQIAALNDSKTRKTTSETVRAVLD |
| RHO2-L3-92 | IKPLHNFLLT | QLQPFLKLKQKQANLVLKIIEQLPSAKESPDKFLEVCTWVDQIAALNDSKTRKTTSETVRAVLD |
| RHO2-L3-4 | IKPLHNFLLT | QLQPFLKLKQKQANLVLKIIEQLPSAKESPDKFLEVCTWVDQIAALNDSKTRKTTSETVRAVLD |
| RHO2-L3-20 | IKPLHNFLLT | QLQPFLKLKQKQANLVLKIIEQLPSAKESPDKFLEVCTWVDQIAALNDSKTRKTTSETVRAVLD |
| RHO2-L3-72 | IKPLHNFLLT | QLQPFLKLKQKQANLVLKIIEQLPSAKESPDKFLEVCTWVDQIAALNDSKTRKTTSETVRAVLD |
| RHO1-L1-4 | IKPLHNFLLT | QLQPFLKLKQKQANLVLKIIEQLPSAKESPDKFLEVCTWVDQIAALNDSKTRKTTSETVRAVLD |
| RHO1-L1-8 | IKPLHNFLLT | QLQPFLKLKQKQANLVLKIIEQLPSAKESPDKFLEVCTWVDQIAALNDSKTRKTTSETVRAVLD |
| RHO1-L1-13 | IKPLHNFLLT | QLQPFLKLKQKQANLVLKIIEQLPSAKESPDKFLEVCTWVDQIAALNDSKTRKTTSETVRAVLD |
| RHO1-L1-19 | IKPLHNFLLT | QLQPFLKLKQKQANLVLKIIEQLPSAKESPDKFLEVCTWVDQIAALNDSKTRKTTSETVRAVLD |
| RHO1-L1-58 | IKPLHNFLLT | QLQPFLKLKQKQANLVLKIIEQLPSAKESPDKFLEVCTWVDQIAALNDSKTRKTTSETVRAVLD |
| RHO1-L1-69 | IKPLHNFLLT | QLQPFLKLKQKQANLVLKIIEQLPSAKESPDKFLEVCTWVDQIAALNDSKTRKTTSETVRAVLD |
| RHO1-L1-80 | IKPLHNFLLT | QLQPFLKLKQKQANLVLKIIEQLPSAKESPDKFLEVCTWVDQIAALNDSKTRKTTSETVRAVLD |
| RHO1-L1-82 | IKPLHNFLLT | QLQPFLKLKQKQANLVLKIIEQLPSAKESPDKFLEVCTWVDQIAALNDSKTRKTTSETVRAVLD |
| RHO1-L1-73 | IKPLHNFLLT | QLQPFLKLKQKQANLVLKIIEQLPSAKESPDKFLEVCTWVDQIAALNDSKTRKTTSETVRAVLD |
| RHO1-L1-85 | IKPLHNFLLT | QLQPFLKLKQKQANLVLKIIEQLPSAKESPDKFLEVCTWVDQIAALNDSKTRKTTSETVRAVLD |
| RHO1-L1-86 | IKPLHNFLLT | QLQPFLKLKQKQANLVLKIIEQLPSAKESPDKFLEVCTWVDQIAALNDSKTRKTTSETVRAVLD |
| RHO-1/2-L4-10 | IKPLHNFLLT | QLQPFLKLKQKQANLVLKIIEQLPSAKESPDKFLEVCTWVDQIAALNDSKTRKTTSETVRAVLD |

Figure 2E

RHO1 Half-Site Binding Sequences (cont.)

| | 272 | | 344 |
|---|---|---|---|
| RHO-1/2-L4-29 | IKPLHNFLTQLQPFLKLKQKQANLVLKIIEQLPSAKESPDKFLEVCTWVDQIAALNDSKTRKTTSETVRAVLD | | |
| RHO-1/2-L4-65 | IKPLHNFLTQLQPFLKLKQKQANLVLKIIEQLPSAKESPDKFLEVCTWVDQIAALNDSKTRKTTSETVRAVLD | | |
| RHO-1/2-L4-66 | IKPLHNFLTQLQPFLKLKQKQANLVLKIIEQLPSAKESPDKFLEVCTWVDQIAALNDSKTRKTTSETVRAVLD | | |
| RHO-1/2-L4-85 | IKPLHNFLTQLQPFLKLKQKQANLVLKIIEQLPSAKESPDKFLEVCTWVDQIAALNDSKTRKTTSETVRAVLD | | |
| | 81 | | 153 |
| RHO 1-2x.216 | IKPLHNFLTQLQPFLKLKQKQANLVLKIIEQLPSAKESPDKFLEVCTWVDQIAALNDSKTRKTTSETVRAVLD | | |
| RHO 1-2x.241 | IKPLHNFLTQLQPFLKLKQKQANLVLKIIEQLPSAKESPDKFLEVCTWVDQIAALNDSKTRKTTSETVRAVLD | | |
| RHO 1-2x.94 | IKPLHNFLTQLQPFLKLKQKQANLVLKIIEQLPSAKESPDKFLEVCTWVDQIAALNDSKTRKTTSETVRAVLD | | |
| RHO 1-2x.95 | IKPLHNFLTQLQPFLKLKQKQANLVLKIIEQLPSAKESPDKFLEVCTWVDQIAALNDSKTRKTTSETVRAVLD | | |
| RHO 1-2x.1 | IKPLHNFLTQLQPFLKLKQKQANLVLKIIEQLPSAKESPDKFLEVCTWVDQIAALNDSKTRKTTSETVRAVLD | | |
| RHO 1-2x.60 | IKPLHNFLTQLQPFLKLKQKQANLVLKIIEQLPSAKESPDKFLEVCTWVDQIAALNDSKTRKTTSETVRAVLD | | |
| RHO 1-2x.74 | IKPLHNFLTQLQPFLKLKQKQANLVLKIIEQLPSAKESPDKFLEVCTWVDQIAALNDSKTRKTTSETVRAVLD | | |
| RHO 1-2x.88 | IKPLHNFLTQLQPFLKLKQKQANLVLKIIEQLPSAKESPDKFLEVCTWVDQIAALNDSKTRKTTSETVRAVLD | | |
| RHO 1-2x.294 | IKPLHNFLTQLQPFLKLKQKQANLVLKIIEQLPSAKESPDKFLEVCTWVDQIAALNDSKTRKTTSETVRAVLD | | |
| RHO 1-2x.302 | IKPLHNFLTQLQPFLKLKQKQANLVLKIIEQLPSAKESPDKFLEVCTWVDQIAALNDSKTRKTTSETVRAVLD | | |
| RHO 1-2x.306 | IKPLHNFLTQLQPFLKLKQKQANLVLKIIEQLPSAKESPDKFLEVCTWVDQIAALNDSKTRKTTSETVRAVLD | | |
| RHO 1-2x.338 | IKPLHNFLTQLQPFLKLKQKQANLVLKIIEQLPSAKESPDKFLEVCTWVDQIAALNDSKTRKTTSETVRAVLD | | |
| RHO 1-2x.348 | IKPLHNFLTQLQPFLKLKQKQANLVLKIIEQLPSAKESPDKFLEVCTWVDQIAALNDSKTRKTTSETVRAVLD | | |
| RHO 1-2x.356 | IKPLHNFLTQLQPFLKLKQKQANLVLKIIEQLPSAKESPDKFLEVCTWVDQIAALNDSKTRKTTSETVRAVLD | | |
| RHO 1-2x.364 | IKPLHNFLTQLQPFLKLKQKQANLVLKIIEQLPSAKESPDKFLEVCTWVDQIAALNDSKTRKTTSETVRAVLD | | |
| RHO 1-2x.142 | IKPLHNFLTQLQPFLKLKQKQANLVLKIIEQLPSAKESPDKFLEVCTWVDQIAALNDSKTRKTTSETVRAVLD | | |
| RHO 1-2x.177 | IKPLHNFLTQLQPFLKLKQKQANLVLKIIEQLPSAKESPDKFLEVCTWVDQIAALNDSKTRKTTSETVRAVLD | | |
| RHO 1-2x.148 | IKPLHNFLTQLQPFLKLKQKQANLVLKIIEQLPSAKESPDKFLEVCTWVDQIAALNDSKTRKTTSETVRAVLD | | |
| RHO 1-2x.20 | IKPLHNFLTQLQPFLKLKQKQANLVLKIIEQLPSAKESPDKFLEVCTWVDQIAALNDSKTRKTTSETVRAVLD | | |
| RHO 1-2x.55 | IKPLHNFLTQLQPFLKLKQKQANLVLKIIEQLPSAKESPDKFLEVCTWVDQIAALNDSKTRKTTSETVRAVLD | | |
| RHO 1-2x.197 | IKPLHNFLTQLQPFLKLKQKQANLVLKIIEQLPSAKESPDKFLEVCTWVDQIAALNDSKTRKTTSETVRAVLD | | |
| RHO 1-2x.252 | IKPLHNFLTQLQPFLKLKQKQANLVLKIIEQLPSAKESPDKFLEVCTWVDQIAALNDSKTRKTTSETVRAVLD | | |
| RHO 1-2x.372 | IKPLHNFLTQLQPFLKLKQKQANLVLKIIEQLPSAKESPDKFLEVCTWVDQIAALNDSKTRKTTSETVRAVLD | | |
| RHO 1-2x.151 | IKPLHNFLTQLQPFLKLKQKQANLVLKIIEQLPSAKESPDKFLEVCTWVDQIAALNDSKTRKTTSETVRAVLD | | |

Figure 2F

Figure 3A. RHO2 Half-Site Binding Sequences

RHO2 Half-Site Binding Sequences (cont.)

| SEQ ID NO: | | 7 | Hypervariable Region 2 (HVR2) | 80 |
|---|---|---|---|---|
| 221 | RHO2-L3-2 | KEFLLYLAGFVDGDGS | IYARIFKGQHWKFKHHIRLTFNVSQKTQRRWFLDKLVDEIGVGYVSDYGSQSNYYLSE |
| 222 | RHO2-L3-3 | KEFLLYLAGFVDGDGS | IFARIFKGQHWKFKHHIRLTFNVSQKTQRRWFLDKLVDEIGVGYVSDYGSTSNYYLSE |
| 223 | RHO2-L3-5 | KEFLLYLAGFVDGDGS | IFARIFKGQHWKFKHHIRLTFNVAQKTQRRWFLDKLVDEIGVGYVNDYGSNSNYYLSE |
| 224 | RHO2-L3-10 | KEFLLYLAGFVDGDGS | IYARIFKGQHWKFKHHIRLTFNVTQKTQRRWFLDKLVDEIGVGYVTDHGSMSNYYLSE |
| 225 | RHO2-L3-11 | KEFLLYLAGFVDGDGS | IYARIFKGQHWKFKHHIRLTFAVTQKTQRRWFLDKLVDEIGVGYVSDYGSMSHYYLSE |
| 226 | RHO2-L3-12 | KEFLLYLAGFVDGDGS | IYARIFKGQHWKFKHHIRLTFNVSQKTQRRWFLDKLVDEIGVGYVTDHGSCSNYYLSE |
| 227 | RHO2-L3-13 | KEFLLYLAGFVDGDGS | IYARIFKGQHWKFKHHIRLTFNVTQKTQRRWFLDKLVDEIGVGYVSDYGSMSHYYLSE |
| 228 | RHO2-L3-28 | KEFLLYLAGFVDGDGS | IYARIFKGQHWKFKHHIRLTFNVTQKTQRRWFLDKLVDEIGVGYVTDEGSQSNYYLSE |
| 229 | RHO2-L3-29 | KEFLLYLAGFVDGDGS | IYARIFKGQHWKFKHHIRLTFNVSQKTQRRWFLDKLVDEIGVGYVSDYGSISNYYLSE |
| 230 | RHO2-L3-57 | KEFLLYLAGFVDGDGS | IYARIFKGQHWKFKHHIRLTFNVSQKTQRRWFLDKLVDEIGVGYVSDYGSSSNYYLSE |
| 231 | RHO2-L3-80 | KEFLLYLAGFVDGDGS | IFARIFKGQHWKFKHHIRLTFNVTQKTQRRWFLDKLVDEIGVGYVTDYGSNSNYYLSE |
| 232 | RHO2-L3-85 | KEFLLYLAGFVDGDGS | IYARIFKGQHWKFKHHIRLTFNVSQKTQRRWFLDKLVDEIGVGYVDDGSMSAYYLSE |
| 233 | RHO2-L3-86 | KEFLLYLAGFVDGDGS | IYARIFKGQHWKFKHHIRLTFNVSQKTQRRWFLDKLVDEIGVGYVCDGSNSNYYLSE |
| 234 | RHO2-L3-92 | KEFLLYLAGFVDGDGS | IYARIFKGQHWKFKHHIRLTFNVSQKTQRRWFLDKLVDEIGVGYVADYGSMSNYYLSE |
| 235 | RHO2-L3-4 | KEFLLYLAGFVDGDGS | IYARIFKGQHWKFKHHIRLTFNVCVSQKTQRRWFLDKLVDEIGVGYVCDSGSMSAYYLSE |
| 236 | RHO2-L3-20 | KEFLLYLAGFVDGDGS | IFARIFKGQHWKFKHHIRLTFNVSQKTQRRWFLDKLVDEIGVGYVTDWGSNSAYYLSE |
| 237 | RHO2-L3-72 | KEFLLYLAGFVDGDGS | IYARIFKGQHWKFKHHIRLTFHVSQKTQRRWFLDKLVDEIGVGYVTDWGSVSGYYLSE |
| 238 | RHO1-L1-4 | KEFLLYLAGFVDGDGS | IYARIFKGQHWKFKHHIRLTFHVSQKTQRRWFLDKLVDEIGVGYVTDWGSVSGYYLSE |
| 239 | RHO1-L1-8 | KEFLLYLAGFVDGDGS | IYARIFKGQHWKFKHHIRLTFHVSQKTQRRWFLDKLVDEIGVGYVTDWGSVSGYYLSE |
| 240 | RHO1-L1-13 | KEFLLYLAGFVDGDGS | IYARIFKGQHWKFKHHIRLTFHVSQKTQRRWFLDKLVDEIGVGYVTDWGSVSGYYLSE |
| 241 | RHO1-L1-19 | KEFLLYLAGFVDGDGS | IYARIFKGQHWKFKHHIRLTFHVSQKTQRRWFLDKLVDEIGVGYVTDWGSVSGYYLSE |
| 242 | RHO1-L1-58 | KEFLLYLAGFVDGDGS | IYARIFKGQHWKFKHHIRLTFHVSQKTQRRWFLDKLVDEIGVGYVTDWGSVSGYYLSE |
| 243 | RHO1-L1-69 | KEFLLYLAGFVDGDGS | IYARIFKGQHWKFKHHIRLTFHVSQKTQRRWFLDKLVDEIGVGYVTDWGSVSGYYLSE |
| 244 | RHO1-L1-80 | KEFLLYLAGFVDGDGS | IYARIFKGQHWKFKHHIRLTFHVSQKTQRRWFLDKLVDEIGVGYVTDWGSVSGYYLSE |
| 245 | RHO1-L1-82 | KEFLLYLAGFVDGDGS | IYARIFKGQHWKFKHHIRLTFHVSQKTQRRWFLDKLVDEIGVGYVTDWGSVSGYYLSE |
| 246 | RHO1-L1-73 | KEFLLYLAGFVDGDGS | IYARIFKGQHWKFKHHIRLTFHVSQKTQRRWFLDKLVDEIGVGYVTDWGSVSGYYLSE |
| 247 | RHO1-L1-85 | KEFLLYLAGFVDGDGS | IYARIFKGQHWKFKHHIRLTFHVSQKTQRRWFLDKLVDEIGVGYVTDWGSVSGYYLSE |
| 248 | RHO1-L1-86 | KEFLLYLAGFVDGDGS | IYARIFKGQHWKFKHHIRLTFHVSQKTQRRWFLDKLVDEIGVGYVTDWGSVSGYYLSE |
| 249 | RHO-1/2-L4-10 | KEFLLYLAGFVDGDGS | IYARIFKGQHWKFKHHIRLTFCVSQKTQRRWFLDKLVDEIGVGYVDSGSCSNYYLSE |

Figure 3B

RHO2 Half-Site Binding Sequences (cont.)

| SEQ ID NO: | Name | Sequence (7-80) | Hypervariable Region 2 (HVR2) |
|---|---|---|---|
| 250 | RHO-1/2-L4-29 | KEFLLYLAGFVDGDGSIYARIFKGQHWKFKHIRLTFCVSQKTQRRWFLDKLVDEIGVGYVNDSGSCSNYYLSE | |
| 251 | RHO-1/2-L4-65 | KEFLLYLAGFVDGDGSIYARIFKGQHWKFKHIRLTFMNVSQKTQRRWFLDKLVDEIGVGYVVDSGSQSNYYLSE | |
| 252 | RHO-1/2-L4-66 | KEFLLYLAGFVDGDGSIYARIFKGQHWKFKHIRLTFCVSQKTQRRWFLDKLVDEIGVGYVVDNGSMSNYYLSE | |
| 253 | RHO-1/2-L4-85 | KEFLLYLAGFVDGDGSIYARIFKGQHWKFKHIRLTFCVTQKTQRRWFLDKLVDEIGVGYVHDMGSCSMYYLSE | |

Sequences 198-271:

| SEQ ID NO: | Name |
|---|---|
| 254 | RHO 1-2x.216 |
| 255 | RHO 1-2x.241 |
| 256 | RHO 1-2x.94 |
| 257 | RHO 1-2x.95 |
| 258 | RHO 1-2x.1 |
| 259 | RHO 1-2x.60 |
| 260 | RHO 1-2x.74 |
| 261 | RHO 1-2x.88 |
| 262 | RHO 1-2x.294 |
| 263 | RHO 1-2x.302 |
| 264 | RHO 1-2x.306 |
| 265 | RHO 1-2x.338 |
| 266 | RHO 1-2x.348 |
| 267 | RHO 1-2x.356 |
| 268 | RHO 1-2x.364 |
| 269 | RHO 1-2x.142 |
| 270 | RHO 1-2x.177 |
| 271 | RHO 1-2x.148 |
| 272 | RHO 1-2x.20 |
| 273 | RHO 1-2x.55 |
| 274 | RHO 1-2x.197 |
| 275 | RHO 1-2x.252 |
| 276 | RHO 1-2x.372 |
| 277 | RHO 1-2x.151 |

Each sequence follows the pattern: KEFLLYLAGFVDGDGSIYARIEPRQTAKFKHYLRLTFHVSQKTQRRWFLDKLVDEIGVGYVVDQGSVSQYFLSE (or variants thereof at hypervariable positions).

Figure 3C

RHO2 Half-Site Binding Sequences (cont.)

| | 81 | 153 |
|---|---|---|
| RHO2-L3-59 | IKPLHNFLTQLQPFLKLKQKQANLVLKIHEQLPSAKESPDKFLEVCTWVDQIAALNDSKTRKTTSETVRAVLD |
| RHO2-L5-14 | IKPLHNFLTQLQPFLKLKQKQANLVLKIHEQLPSAKESPDKFLEVCTWVDQIAALNDSKTRKTTSETVRAVLD |
| RHO-1/2-L2-49 | IKPLHNFLTQLQPFLKLKQKQANLVLKIHEQLPSAKESPDKFLEVCTWVDQIAALNDSKTRKTTSETVRAVLD |
| RHO 1-2x.179 | IKPLHNFLTQLQPFLKLKQKQANLVLKIHEQLPSAKESPDKFLEVCTWVDQIAALNDSKTRKTTSETVRAVLD |
| RHO 1-2x.4 | IKPLHNFLTQLQPFLKLKQKQANLVLKIHEQLPSAKESPDKFLEVCTWVDQIAALNDSKTRKTTSETVRAVLD |
| RHO 1-2x.207 | IKPLHNFLTQLQPFLKLKQKQANLVLKIHEQLPSAKESPDKFLEVCTWVDQIAALNDSKTRKTTSETVRAVLD |
| RHO 1-2x.277 | IKPLHNFLTQLQPFLKLKQKQANLVLKIHEQLPSAKESPDKFLEVCTWVDQIAALNDSKTRKTTSETVRAVLD |
| RHO 1-2x.292 | IKPLHNFLTQLQPFLKLKQKQANLVLKIHEQLPSAKESPDKFLEVCTWVDQIAALNDSKTRKTTSETVRAVLD |
| RHO 1-2x.324 | IKPLHNFLTQLQPFLKLKQKQANLVLKIHEQLPSAKESPDKFLEVCTWVDQIAALNDSKTRKTTSETVRAVLD |
| RHO 1-2x.371 | IKPLHNFLTQLQPFLKLKQKQANLVLKIHEQLPSAKESPDKFLEVCTWVDQIAALNDSKTRKTTSETVRAVLD |
| RHO 1-2x.164 | IKPLHNFLTQLQPFLKLKQKQANLVLKIHEQLPSAKESPDKFLEVCTWVDQIAALNDSKTRKTTSETVRAVLD |
| RHO 1-2x.181 | IKPLHNFLTQLQPFLKLKQKQANLVLKIHEQLPSAKESPDKFLEVCTWVDQIAALNDSKTRKTTSETVRAVLD |
| RHO 1-2x.184 | IKPLHNFLTQLQPFLKLKQKQANLVLKIHEQLPSAKESPDKFLEVCTWVDQIAALNDSKTRKTTSETVRAVLD |
| RHO-1/2-L1-21 | IKPLHNFLTQLQPFLKLKQKQANLVLKIHEQLPSAKESPDKFLEVCTWVDQIAALNDSKTRKTTSETVRAVLD |
| RHO-1/2-L1-43 | IKPLHNFLTQLQPFLKLKQKQANLVLKIHEQLPSAKESPDKFLEVCTWVDQIAALNDSKTRKTTSETVRAVLD |
| RHO-1/2-L1-45 | IKPLHNFLTQLQPFLKLKQKQANLVLKIHEQLPSAKESPDKFLEVCTWVDQIAALNDSKTRKTTSETVRAVLD |
| RHO-1/2-L1-60 | IKPLHNFLTQLQPFLKLKQKQANLVLKIHEQLPSAKESPDKFLEVCTWVDQIAALNDSKTRKTTSETVRAVLD |
| RHO-1/2-L1-61 | IKPLHNFLTQLQPFLKLKQKQANLVLKIHEQLPSAKESPDKFLEVCTWVDQIAALNDSKTRKTTSETVRAVLD |
| RHO-1/2-L1-58 | IKPLHNFLTQLQPFLKLKQKQANLVLKIHEQLPSAKESPDKFLEVCTWVDQIAALNDSKTRKTTSETVRAVLD |
| RHO-1/2-L1-7 | IKPLHNFLTQLQPFLKLKQKQANLVLKIHEQLPSAKESPDKFLEVCTWVDQIAALNDSKTRKTTSETVRAVLD |
| RHO-1/2-L1-13 | IKPLHNFLTQLQPFLKLKQKQANLVLKIHEQLPSAKESPDKFLEVCTWVDQIAALNDSKTRKTTSETVRAVLD |
| RHO-1/2-L1-18 | IKPLHNFLTQLQPFLKLKQKQANLVLKIHEQLPSAKESPDKFLEVCTWVDQIAALNDSKTRKTTSETVRAVLD |
| RHO-1/2-L1-70 | IKPLHNFLTQLQPFLKLKQKQANLVLKIHEQLPSAKESPDKFLEVCTWVDQIAALNDSKTRKTTSETVRAVLD |
| RHO-1/2-L1-86 | IKPLHNFLTQLQPFLKLKQKQANLVLKIHEQLPSAKESPDKFLEVCTWVDQIAALNDSKTRKTTSETVRAVLD |
| RHO-1/2-L2-13 | IKPLHNFLTQLQPFLKLKQKQANLVLKIHEQLPSAKESPDKFLEVCTWVDQIAALNDSKTRKTTSETVRAVLD |
| RHO-1/2-L2-24 | IKPLHNFLTQLQPFLKLKQKQANLVLKIHEQLPSAKESPDKFLEVCTWVDQIAALNDSKTRKTTSETVRAVLD |
| RHO-1/2-L2-37 | IKPLHNFLTQLQPFLKLKQKQANLVLKIHEQLPSAKESPDKFLEVCTWVDQIAALNDSKTRKTTSETVRAVLD |
| RHO-1/2-L2-58 | IKPLHNFLTQLQPFLKLKQKQANLVLKIHEQLPSAKESPDKFLEVCTWVDQIAALNDSKTRKTTSETVRAVLD |
| RHO-1/2-L2-31 | IKPLHNFLTQLQPFLKLKQKQANLVLKIHEQLPSAKESPDKFLEVCTWVDQIAALNDSKTRKTTSETVRAVLD |
| RHO-1/2-L2-29 | IKPLHNFLTQLQPFLKLKQKQANLVLKIHEQLPSAKESPDKFLEVCTWVDQIAALNDSKTRKTTSETVRAVLD |
| RHO-1/2-L2-61 | IKPLHNFLTQLQPFLKLKQKQANLVLKIHEQLPSAKESPDKFLEVCTWVDQIAALNDSKTRKTTSETVRAVLD |

Figure 3D

RHO2 Half-Site Binding Sequences (cont.)

| | 81 | 153 |
|---|---|---|
| RHO2-L3-2 | IKPLHNFLTQLQPFLKLKQKQANLVLKIIEQLPSAKESPDKFLEVCTWVDQIAALNDSKTRKTTSETVRAVLD | |
| RHO2-L3-3 | IKPLHNFLTQLQPFLKLKQKQANLVLKIIEQLPSAKESPDKFLEVCTWVDQIAALNDSKTRKTTSETVRAVLD | |
| RHO2-L3-5 | IKPLHNFLTQLQPFLKLKQKQANLVLKIIEQLPSAKESPDKFLEVCTWVDQIAALNDSKTRKTTSETVRAVLD | |
| RHO2-L3-10 | IKPLHNFLTQLQPFLKLKQKQANLVLKIIEQLPSAKESPDKFLEVCTWVDQIAALNDSKTRKTTSETVRAVLD | |
| RHO2-L3-11 | IKPLHNFLTQLQPFLKLKQKQANLVLKIIEQLPSAKESPDKFLEVCTWVDQIAALNDSKTRKTTSETVRAVLD | |
| RHO2-L3-12 | IKPLHNFLTQLQPFLKLKQKQANLVLKIIEQLPSAKESPDKFLEVCTWVDQIAALNDSKTRKTTSETVRAVLD | |
| RHO2-L3-13 | IKPLHNFLTQLQPFLKLKQKQANLVLKIIEQLPSAKESPDKFLEVCTWVDQIAALNDSKTRKTTSETVRAVLD | |
| RHO2-L3-28 | IKPLHNFLTQLQPFLKLKQKQANLVLKIIEQLPSAKESPDKFLEVCTWVDQIAALNDSKTRKTTSETVRAVLD | |
| RHO2-L3-29 | IKPLHNFLTQLQPFLKLKQKQANLVLKIIEQLPSAKESPDKFLEVCTWVDQIAALNDSKTRKTTSETVRAVLD | |
| RHO2-L3-57 | IKPLHNFLTQLQPFLKLKQKQANLVLKIIEQLPSAKESPDKFLEVCTWVDQIAALNDSKTRKTTSETVRAVLD | |
| RHO2-L3-80 | IKPLHNFLTQLQPFLKLKQKQANLVLKIIEQLPSAKESPDKFLEVCTWVDQIAALNDSKTRKTTSETVRAVLD | |
| RHO2-L3-85 | IKPLHNFLTQLQPFLKLKQKQANLVLKIIEQLPSAKESPDKFLEVCTWVDQIAALNDSKTRKTTSETVRAVLD | |
| RHO2-L3-86 | IKPLHNFLTQLQPFLKLKQKQANLVLKIIEQLPSAKESPDKFLEVCTWVDQIAALNDSKTRKTTSETVRAVLD | |
| RHO2-L3-92 | IKPLHNFLTQLQPFLKLKQKQANLVLKIIEQLPSAKESPDKFLEVCTWVDQIAALNDSKTRKTTSETVRAVLD | |
| RHO2-L3-4 | IKPLHNFLTQLQPFLKLKQKQANLVLKIIEQLPSAKESPDKFLEVCTWVDQIAALNDSKTRKTTSETVRAVLD | |
| RHO2-L3-20 | IKPLHNFLTQLQPFLKLKQKQANLVLKIIEQLPSAKESPDKFLEVCTWVDQIAALNDSKTRKTTSETVRAVLD | |
| RHO2-L3-72 | IKPLHNFLTQLQPFLKLKQKQANLVLKIIEQLPSAKESPDKFLEVCTWVDQIAALNDSKTRKTTSETVRAVLD | |
| RHO1-L1-4 | IKPLHNFLTQLQPFLKLKQKQANLVLKIIEQLPSAKESPDKFLEVCTWVDQIAALNDSKTRKTTSETVRAVLD | |
| RHO1-L1-8 | IKPLHNFLTQLQPFLKLKQKQANLVLKIIEQLPSAKESPDKFLEVCTWVDQIAALNDSKTRKTTSETVRAVLD | |
| RHO1-L1-13 | IKPLHNFLTQLQPFLKLKQKQANLVLKIIEQLPSAKESPDKFLEVCTWVDQIAALNDSKTRKTTSETVRAVLD | |
| RHO1-L1-19 | IKPLHNFLTQLQPFLKLKQKQANLVLKIIEQLPSAKESPDKFLEVCTWVDQIAALNDSKTRKTTSETVRAVLD | |
| RHO1-L1-58 | IKPLHNFLTQLQPFLKLKQKQANLVLKIIEQLPSAKESPDKFLEVCTWVDQIAALNDSKTRKTTSETVRAVLD | |
| RHO1-L1-69 | IKPLHNFLTQLQPFLKLKQKQANLVLKIIEQLPSAKESPDKFLEVCTWVDQIAALNDSKTRKTTSETVRAVLD | |
| RHO1-L1-80 | IKPLHNFLTQLQPFLKLKQKQANLVLKIIEQLPSAKESPDKFLEVCTWVDQIAALNDSKTRKTTSETVRAVLD | |
| RHO1-L1-82 | IKPLHNFLTQLQPFLKLKQKQANLVLKIIEQLPSAKESPDKFLEVCTWVDQIAALNDSKTRKTTSETVRAVLD | |
| RHO1-L1-73 | IKPLHNFLTQLQPFLKLKQKQANLVLKIIEQLPSAKESPDKFLEVCTWVDQIAALNDSKTRKTTSETVRAVLD | |
| RHO1-L1-85 | IKPLHNFLTQLQPFLKLKQKQANLVLKIIEQLPSAKESPDKFLEVCTWVDQIAALNDSKTRKTTSETVRAVLD | |
| RHO1-L1-86 | IKPLHNFLTQLQPFLKLKQKQANLVLKIIEQLPSAKESPDKFLEVCTWVDQIAALNDSKTRKTTSETVRAVLD | |
| RHO-1/2-L4-10 | IKPLHNFLTQLQPFLKLKQKQANLVLKIIEQLPSAKESPDKFLEVCTWVDQIAALNDSKTRKTTSETVRAVLD | |

Figure 3E

RHO2 Half-Site Binding Sequences (cont.)

```
                  81                                                                                          153
RHO-1/2-L4-29     IKPLHNFLTQLQPFLKLKQKQANLVLKIIEQLPSAKESPDKFLEVCTWVDQIAALNDSKTRKTTSETVRAVLD
RHO-1/2-L4-65     IKPLHNFLTQLQPFLKLKQKQANLVLKIIEQLPSAKESPDKFLEVCTWVDQIAALNDSKTRKTTSETVRAVLD
RHO-1/2-L4-66     IKPLHNFLTQLQPFLKLKQKQANLVLKIIEQLPSAKESPDKFLEVCTWVDQIAALNDSKTRKTTSETVRAVLD
RHO-1/2-L4-85     IKPLHNFLTQLQPFLKLKQKQANLVLKIIEQLPSAKESPDKFLEVCTWVDQIAALNDSKTRKTTSETVRAVLD 272                                                                                         344
RHO 1-2x.216      IKPLHNFLTQLQPFLKLKQKQANLVLKIIEQLPSAKESPDKFLEVCTWVDQIAALNDSKTRKTTSETVRAVLD
RHO 1-2x.241      IKPLHNFLTQLQPFLKLKQKQANLVLKIIEQLPSAKESPDKFLEVCTWVDQIAALNDSKTRKTTSETVRAVLD
RHO 1-2x.94       IKPLHNFLTQLQPFLKLKQKQANLVLKIIEQLPSAKESPDKFLEVCTWVDQIAALNDSKTRKTTSETVRAVLD
RHO 1-2x.95       IKPLHNFLTQLQPFLKLKQKQANLVLKIIEQLPSAKESPDKFLEVCTWVDQIAALNDSKTRKTTSETVRAVLD
RHO 1-2x.1        IKPLHNFLTQLQPFLKLKQKQANLVLKIIEQLPSAKESPDKFLEVCTWVDQIAALNDSKTRKTTSETVRAVLD
RHO 1-2x.60       IKPLHNFLTQLQPFLKLKQKQANLVLKIIEQLPSAKESPDKFLEVCTWVDQIAALNDSKTRKTTSETVRAVLD
RHO 1-2x.74       IKPLHNFLTQLQPFLKLKQKQANLVLKIIEQLPSAKESPDKFLEVCTWVDQIAALNDSKTRKTTSETVRAVLD
RHO 1-2x.88       IKPLHNFLTQLQPFLKLKQKQANLVLKIIEQLPSAKESPDKFLEVCTWVDQIAALNDSKTRKTTSETVRAVLD
RHO 1-2x.294      IKPLHNFLTQLQPFLKLKQKQANLVLKIIEQLPSAKESPDKFLEVCTWVDQIAALNDSKTRKTTSETVRAVLD
RHO 1-2x.302      IKPLHNFLTQLQPFLKLKQKQANLVLKIIEQLPSAKESPDKFLEVCTWVDQIAALNDSKTRKTTSETVRAVLD
RHO 1-2x.306      IKPLHNFLTQLQPFLKLKQKQANLVLKIIEQLPSAKESPDKFLEVCTWVDQIAALNDSKTRKTTSETVRAVLD
RHO 1-2x.338      IKPLHNFLTQLQPFLKLKQKQANLVLKIIEQLPSAKESPDKFLEVCTWVDQIAALNDSKTRKTTSETVRAVLD
RHO 1-2x.348      IKPLHNFLTQLQPFLKLKQKQANLVLKIIEQLPSAKESPDKFLEVCTWVDQIAALNDSKTRKTTSETVRAVLD
RHO 1-2x.356      IKPLHNFLTQLQPFLKLKQKQANLVLKIIEQLPSAKESPDKFLEVCTWVDQIAALNDSKTRKTTSETVRAVLD
RHO 1-2x.364      IKPLHNFLTQLQPFLKLKQKQANLVLKIIEQLPSAKESPDKFLEVCTWVDQIAALNDSKTRKTTSETVRAVLD
RHO 1-2x.142      IKPLHNFLTQLQPFLKLKQKQANLVLKIIEQLPSAKESPDKFLEVCTWVDQIAALNDSKTRKTTSETVRAVLD
RHO 1-2x.177      IKPLHNFLTQLQPFLKLKQKQANLVLKIIEQLPSAKESPDKFLEVCTWVDQIAALNDSKTRKTTSETVRAVLD
RHO 1-2x.148      IKPLHNFLTQLQPFLKLKQKQANLVLKIIEQLPSAKESPDKFLEVCTWVDQIAALNDSKTRKTTSETVRAVLD
RHO 1-2x.20       IKPLHNFLTQLQPFLKLKQKQANLVLKIIEQLPSAKESPDKFLEVCTWVDQIAALNDSKTRKTTSETVRAVLD
RHO 1-2x.55       IKPLHNFLTQLQPFLKLKQKQANLVLKIIEQLPSAKESPDKFLEVCTWVDQIAALNDSKTRKTTSETVRAVLD
RHO 1-2x.197      IKPLHNFLTQLQPFLKLKQKQANLVLKIIEQLPSAKESPDKFLEVCTWVDQIAALNDSKTRKTTSETVRAVLD
RHO 1-2x.252      IKPLHNFLTQLQPFLKLKQKQANLVLKIIEQLPSAKESPDKFLEVCTWVDQIAALNDSKTRKTTSETVRAVLD
RHO 1-2x.372      IKPLHNFLTQLQPFLKLKQKQANLVLKIIEQLPSAKESPDKFLEVCTWVDQIAALNDSKTRKTTSETVRAVLD
RHO 1-2x.151      IKPLHNFLTQLQPFLKLKQKQANLVLKIIEQLPSAKESPDKFLEVCTWVDQIAALNDSKTRKTTSETVRAVLD
```

Figure 3F

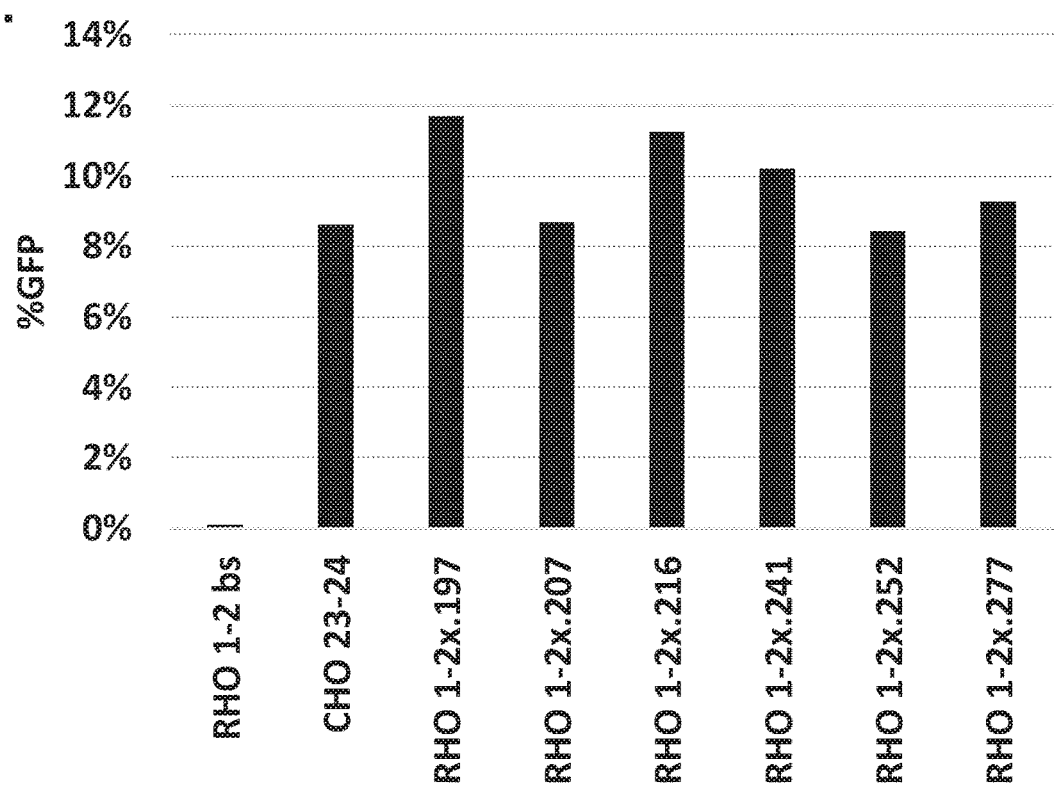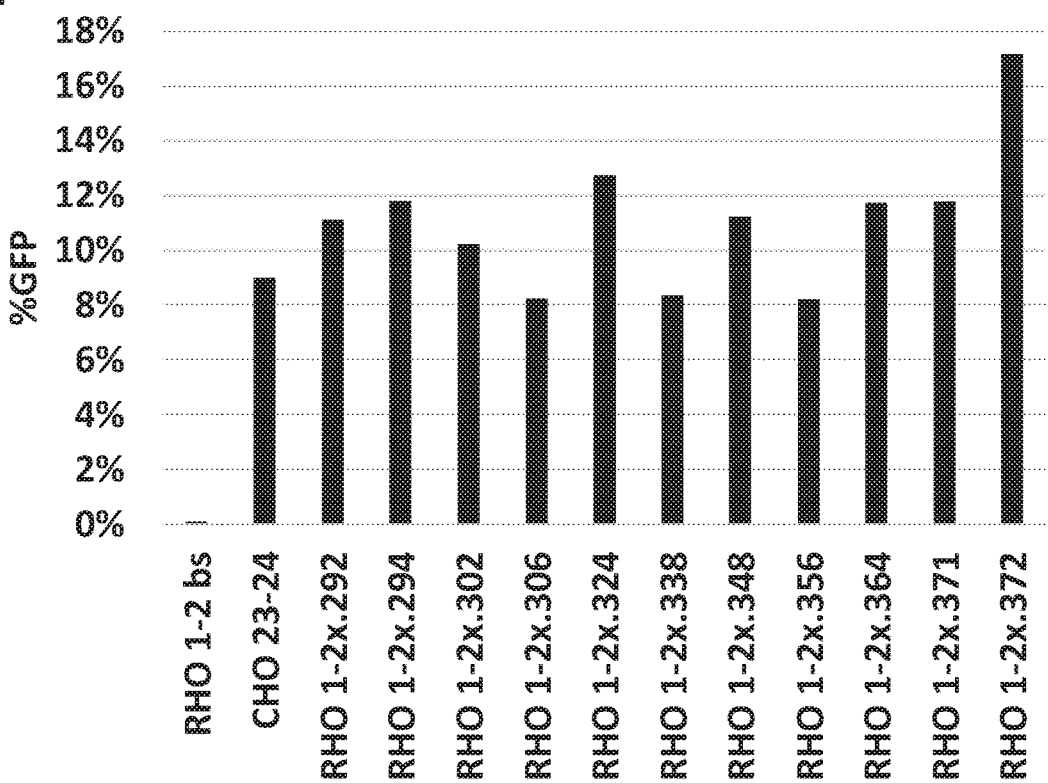
Figure 5 (cont.)

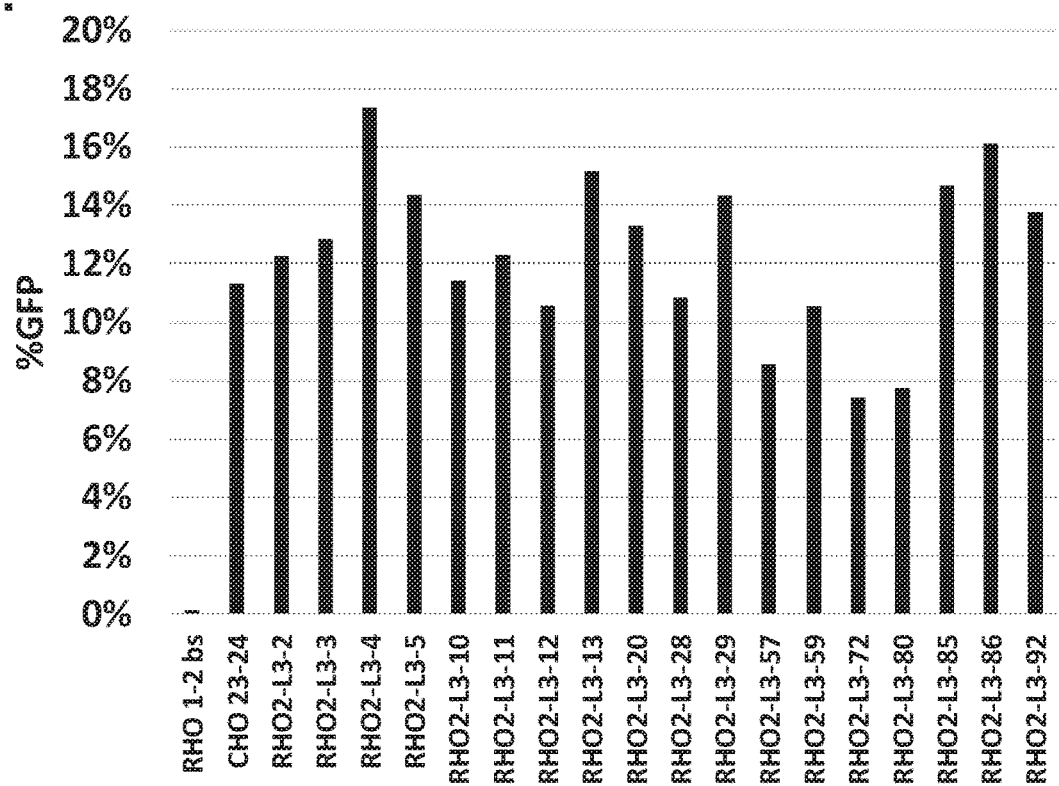
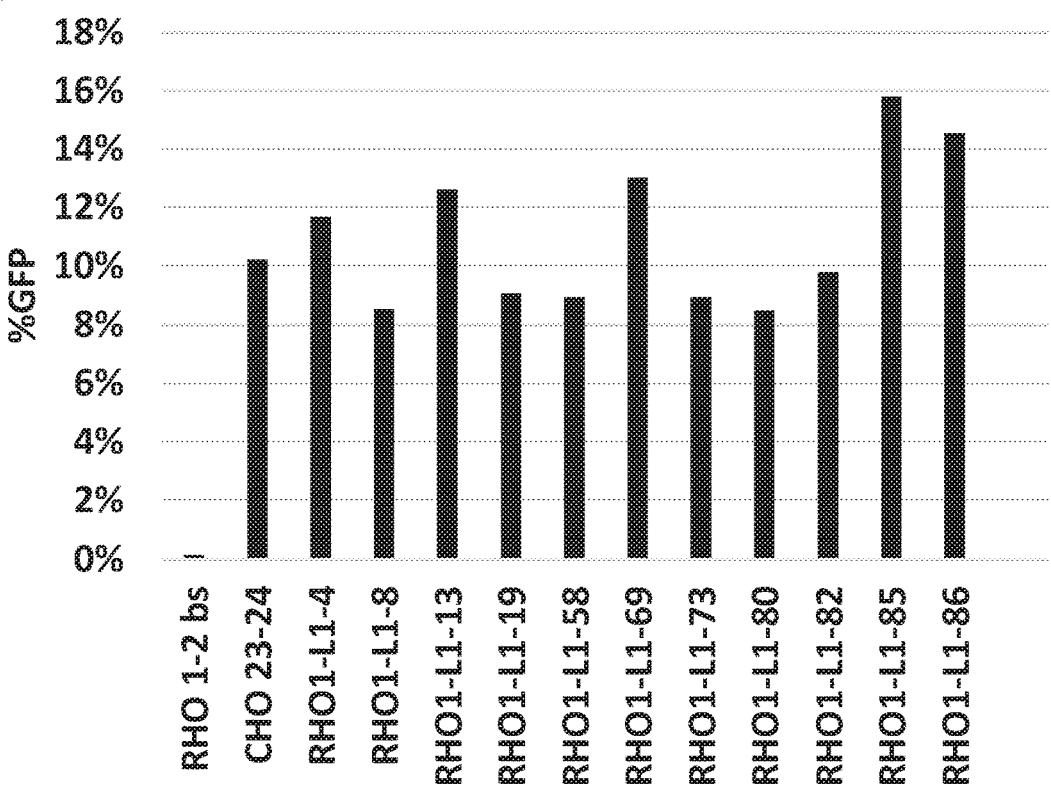
Figure 5 (cont.)

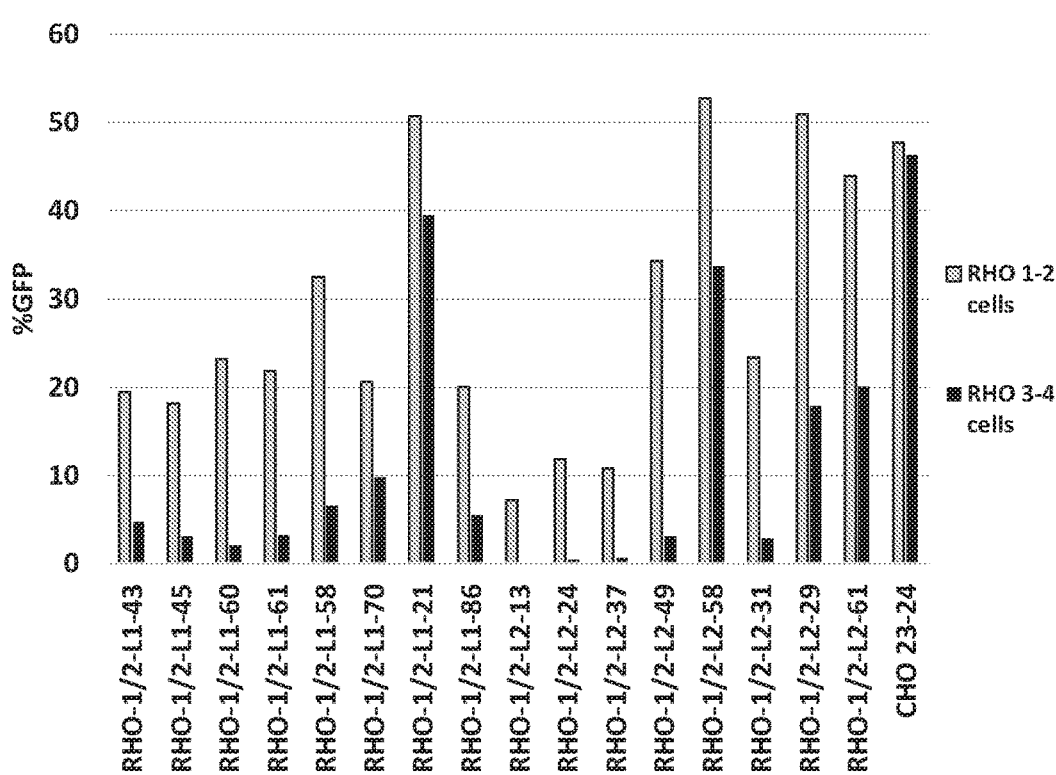
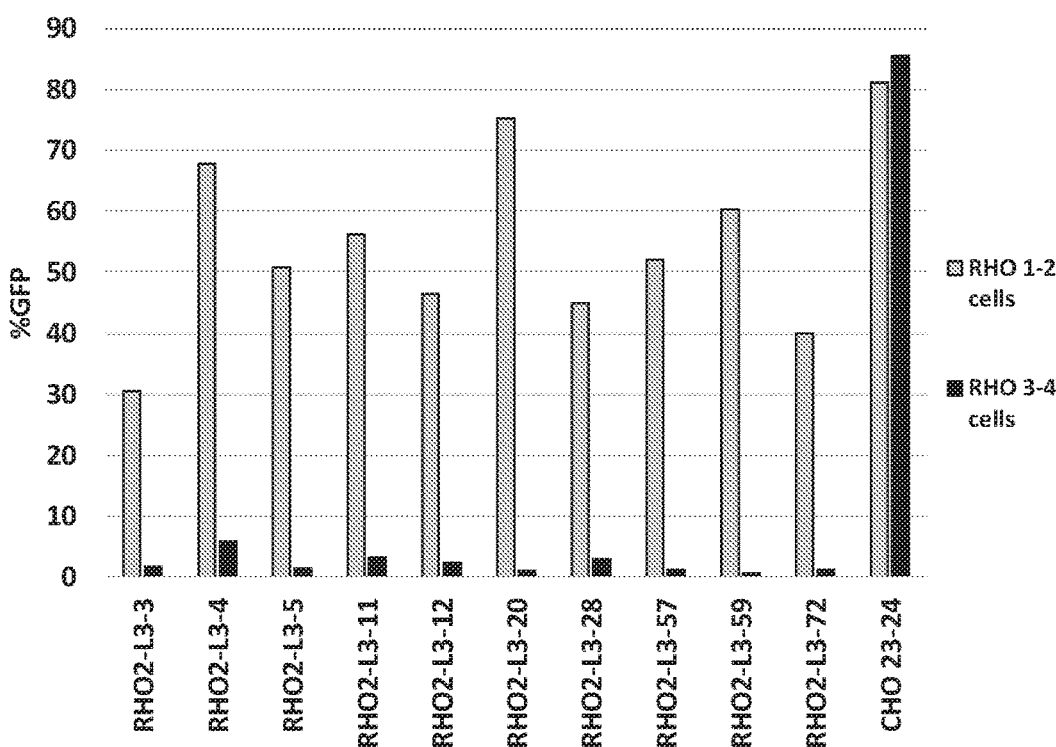
Figure 7 (cont.)

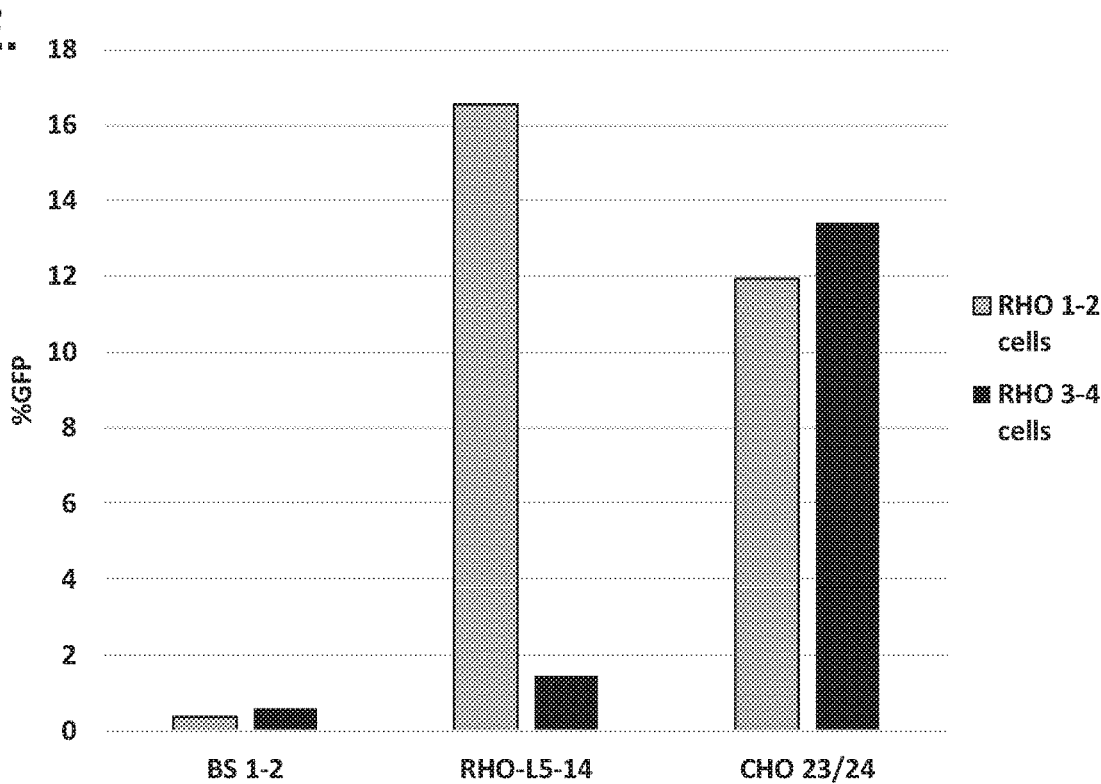
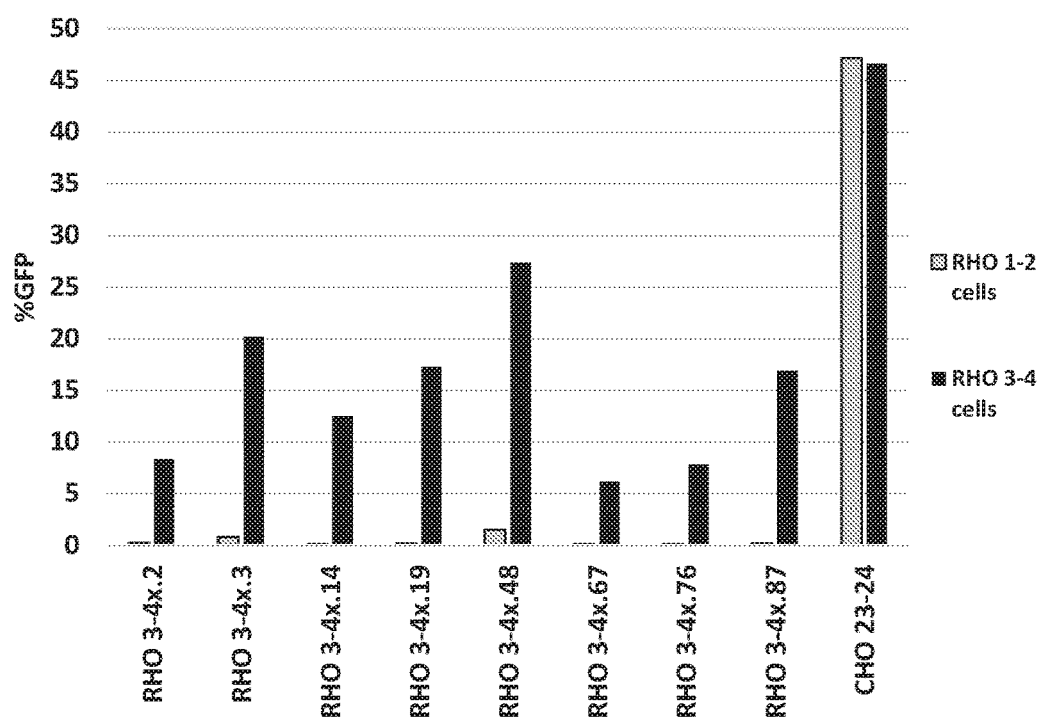
Figure 7 (cont.)

A.
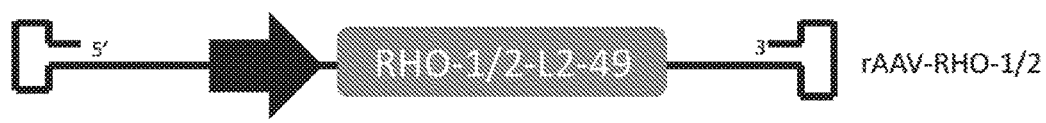
B.
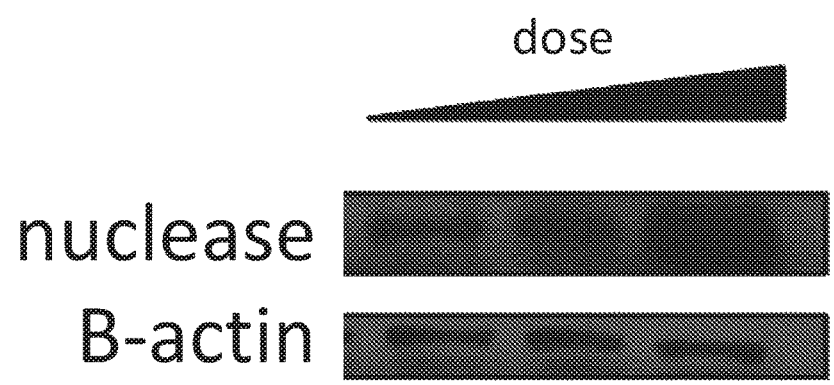
Figure 8

1. RHO P23H CHO reporter AAV2CMV L3 1e8
2. RHO P23H CHO reporter AAV2CMV L3 1e8
3. RHO P23H CHO reporter AAV2CMV L3 1e9
4. RHO P23H CHO reporter AAV2CMV L3 1e9
5. RHO P23H CHO reporter AAV2CMV L3 2e9
6. RHO P23H CHO reporter AAV2CMV L3 2e9
7. RHO P23H CHO reporter AAV2CMV L5 1e8
8. RHO P23H CHO reporter AAV2CMV L5 1e8
9. RHO P23H CHO reporter AAV2CMV L5 1e9
10. RHO P23H CHO reporter AAV2CMV L5 1e9
11. RHO P23H CHO reporter AAV2CMV L5 2e9
12. RHO P23H CHO reporter AAV2CMV L5 2e9

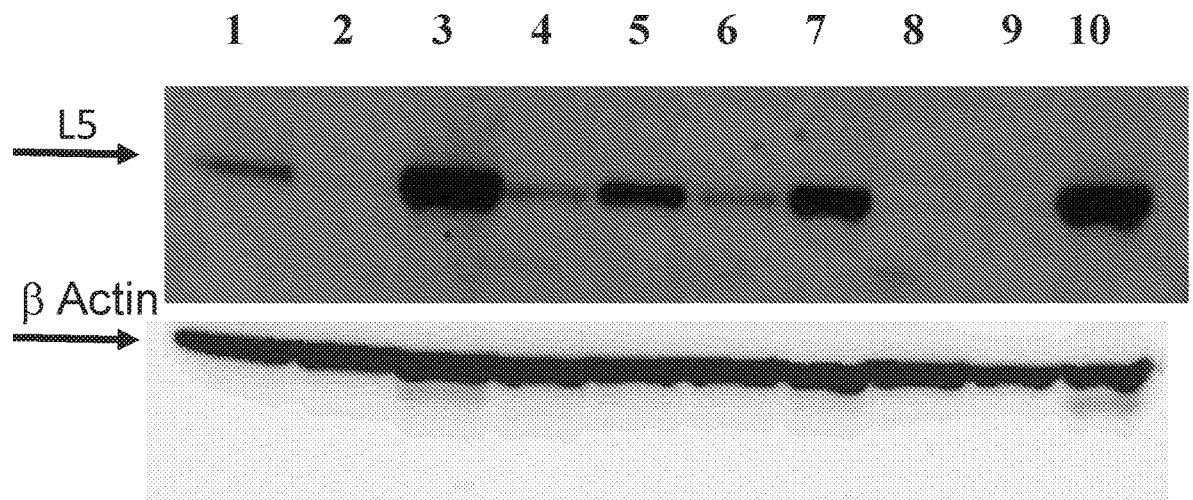

1-Mouse 1 OD retina injected with AAV5GRKL5
2-Mouse 1 OS retina injected with AAV5GRKL5
3-Mouse 2 OD retina injected with AAV5GRKL5
4-Mouse 2 OS retina injected with AAV5GRKL5
5-Mouse 3 OD retina injected with AAV5GRKL5
6-Mouse 3 OS retina injected with AAV5GRKL5
7-Mouse 4 OD retina injected with AAV5GRKL5
8-Mouse 4 OS retina injected with AAV5GRKL5
9-Mouse 5 OD retina injected with AAV5GRKL5
10-Mouse 5 OS retina injected with AAV5GRKL5

Figure 15

SEQUENCE LISTING

```
<160> NUMBER OF SEQ ID NOS: 281

<210> SEQ ID NO 1
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 1
acgggtgtgg tacgcagcca ct                                                22

<210> SEQ ID NO 2
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 2
ccacttcgag tacccacagt ac                                                22

<210> SEQ ID NO 3
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 3
gggtgtggta cgcagccact tc                                                22

<210> SEQ ID NO 4
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 4
gcagccactt cgagtaccca ca                                                22

<210> SEQ ID NO 5
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 5
acgggtgtgg tacgcagccc ct                                                22

<210> SEQ ID NO 6
<211> LENGTH: 354
<212> TYPE: PRT
<213> ORGANISM: Artificial Sequence
<220> FEATURE:
```

<223> OTHER INFORMATION: Synthetic Polypeptide

<400> SEQUENCE: 6

Met Asn Thr Lys Tyr Asn Lys Glu Phe Leu Leu Tyr Leu Ala Gly Phe
1               5                   10                  15

Val Asp Gly Asp Gly Ser Ile Phe Ala Arg Ile Phe Lys Gly Gln His
            20                  25                  30

Trp Lys Phe Lys His Tyr Ile Arg Leu Thr Phe Thr Val Ala Gln Lys
        35                  40                  45

Thr Gln Arg Arg Trp Phe Leu Asp Lys Leu Val Asp Glu Ile Gly Val
    50                  55                  60

Gly Tyr Val Thr Asp Trp Gly Ser Val Ser His Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Trp Ala Ser Ile Ile Pro Glu Gln Gly Tyr
    210                 215                 220

Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 7
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 7

```
Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Phe Lys Gly Gln His
            20                  25                  30

Trp Lys Phe Lys His Tyr Ile Arg Leu Thr Phe Cys Val Arg Gln Lys
        35                  40                  45

Thr Gln Arg Arg Trp Phe Leu Asp Lys Leu Val Asp Glu Ile Gly Val
    50                  55                  60

Gly Tyr Val Thr Asp Ser Gly Ser Val Ser Ala Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
        180                 185                 190

Gly Thr Gly Tyr Asn Lys Glu Phe Leu Leu Tyr Leu Ala Gly Phe Val
    195                 200                 205

Asp Gly Asp Gly Ser Ile Trp Ala Ser Ile Ile Pro Glu Gln Gly Tyr
210                 215                 220

Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro
```

<210> SEQ ID NO 8
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 8

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Phe Lys Gly Gln His
            20                  25                  30

Trp Lys Phe Lys His His Ile Arg Leu Thr Phe His Val Ser Gln Lys
        35                  40                  45

Thr Gln Arg Arg Trp Phe Leu Asp Lys Leu Val Asp Glu Ile Gly Val
    50                  55                  60

Gly Tyr Val Thr Asp Trp Gly Ser Val Ser Gly Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Trp Ala Ser Ile Ile Pro Glu Gln Gly Tyr
    210                 215                 220

Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 9
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 9

```
Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Glu Pro Arg Gln Thr
            20                  25                  30

Ala Lys Phe Lys His Tyr Leu Arg Leu Thr Phe His Val Ser Gln Lys
            35                  40                  45

Thr Gln Arg Arg Trp Phe Leu Asp Lys Leu Val Asp Glu Ile Gly Val
        50                  55                  60

Gly Tyr Val Thr Asp Trp Gly Ser Val Ser Gly Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
            165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
            195                 200                 205

Asp Gly Asp Gly Ser Ile Trp Ala Ser Ile Pro Glu Gln Gly Tyr
210                 215                 220

Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
            245                 250                 255

Tyr Val Val Asp Gln Gly Ser Val Ser Glu Tyr Arg Leu Ser Glu Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro
```

<210> SEQ ID NO 10
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 10

```
Met Asn Thr Lys Tyr Asn Lys Glu Phe Leu Leu Tyr Leu Ala Gly Phe
  1               5                  10                  15

Val Asp Gly Asp Gly Ser Ile Tyr Ala Arg Ile Glu Pro Arg Gln Thr
             20                  25                  30

Ala Lys Phe Lys His Tyr Leu Arg Leu Thr Phe His Val Ser Gln Lys
         35                  40                  45

Thr Gln Arg Arg Trp Phe Leu Asp Lys Leu Val Asp Glu Ile Gly Val
     50                  55                  60

Gly Tyr Val Val Asp Gln Gly Ser Val Ser Gln Tyr Phe Leu Ser Glu
 65                  70                  75                  80

Ile Lys Pro Leu His Asn Phe Leu Thr Gln Leu Gln Pro Phe Leu Lys
                 85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
                180                 185                 190

Gly Thr Gly Tyr Asn Lys Glu Phe Leu Leu Tyr Leu Ala Gly Phe Val
            195                 200                 205

Asp Gly Asp Gly Ser Ile Tyr Ala Thr Ile Met Pro Glu Gln Arg Gln
210                 215                 220

Lys Phe Lys His Arg Leu Arg Leu Tyr Phe Glu Val Cys Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Gln Gly Ser Val Ser Thr Tyr Arg Leu Ser Gln Ile
                260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
        290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro

<210> SEQ ID NO 11
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 11

Met Asn Thr Lys Tyr Asn Lys Glu Phe Leu Leu Tyr Leu Ala Gly Phe
```

```
             1               5              10              15
           Val Asp Gly Asp Gly Ser Ile Tyr Ala Arg Ile Glu Pro Arg Gln Asn
                          20              25              30

Phe Lys Phe Lys His Thr Leu Arg Leu Thr Phe Val Ser Gln Lys
                     35              40              45

Thr Gln Arg Arg Trp Phe Leu Asp Lys Leu Val Asp Glu Ile Gly Val
                50              55              60

Gly Tyr Val Thr Asp Trp Gly Ser Val Ser Gly Tyr Tyr Leu Ser Gln
           65                  70              75                  80

Ile Lys Pro Leu His Asn Phe Leu Thr Gln Leu Gln Pro Phe Leu Lys
                          85              90              95

Leu Lys Gln Lys Gln Ala Asn Leu Val Leu Lys Ile Ile Glu Gln Leu
                         100             105             110

Pro Ser Ala Lys Glu Ser Pro Asp Lys Phe Leu Glu Val Cys Thr Trp
                         115             120             125

Val Asp Gln Ile Ala Ala Leu Asn Asp Ser Lys Thr Arg Lys Thr Thr
                130             135             140

Ser Glu Thr Val Arg Ala Val Leu Asp Ser Leu Pro Gly Ser Val Gly
           145                 150             155                 160

Gly Leu Ser Pro Ser Gln Ala Ser Ser Ala Ala Ser Ala Ser Ser
                         165             170             175

Ser Pro Gly Ser Gly Ile Ser Glu Ala Leu Arg Ala Gly Ala Gly Ser
                         180             185             190

Gly Thr Gly Tyr Asn Lys Glu Phe Leu Leu Tyr Leu Ala Gly Phe Val
                         195             200             205

Asp Gly Asp Gly Ser Ile Tyr Ala Thr Ile Ile Pro Ser Gln Thr Asp
                         210             215             220

Lys Phe Lys His Arg Leu Arg Leu Tyr Phe Ala Val Ser Gln Lys Thr
           225                 230             235             240

Gln Arg Arg Trp Phe Leu Asp Lys Leu Val Asp Glu Ile Gly Val Gly
                         245             250             255

Tyr Val Ile Asp Ser Gly Ser Val Ser Glu Tyr Arg Leu Ser Glu Ile
                         260             265             270

Lys Pro Leu His Asn Phe Leu Thr Gln Leu Gln Pro Phe Leu Lys Leu
                         275             280             285

Lys Gln Lys Gln Ala Asn Leu Val Leu Lys Ile Ile Glu Gln Leu Pro
                         290             295             300

Ser Ala Lys Glu Ser Pro Asp Lys Phe Leu Glu Val Cys Thr Trp Val
           305                 310             315             320

Asp Gln Ile Ala Ala Leu Asn Asp Ser Lys Thr Arg Lys Thr Thr Ser
                         325             330             335

Glu Thr Val Arg Ala Val Leu Asp Ser Leu Ser Glu Lys Lys Lys Ser
                         340             345             350

Ser Pro

<210> SEQ ID NO 12
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 12

Met Asn Thr Lys Tyr Asn Lys Glu Phe Leu Leu Tyr Leu Ala Gly Phe
           1               5              10              15
```

Val Asp Gly Asp Gly Ser Ile Tyr Ala Arg Ile Glu Pro Arg Gln Gly
            20                  25                  30

Asn Lys Phe Lys His Tyr Leu Arg Leu Thr Phe Asn Val Cys Gln Lys
            35                  40                  45

Thr Gln Arg Arg Trp Phe Leu Asp Lys Leu Val Asp Glu Ile Gly Val
 50                  55                  60

Gly Tyr Val Ile Asp Arg Gly Ser Val Ser Asp Tyr Tyr Leu Ser Glu
 65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
            195                 200                 205

Asp Gly Asp Gly Ser Ile Tyr Ala Ser Ile Gln Pro Asp Gln Val Tyr
            210                 215                 220

Lys Phe Lys His Arg Leu Arg Leu Arg Phe Ala Val Phe Gln Lys Thr
225                 230                 235                 240

Gln Arg Arg Trp Phe Leu Asp Lys Leu Val Asp Glu Ile Gly Val Gly
            245                 250                 255

Tyr Val Tyr Asp His Gly Ser Val Ser Glu Tyr Arg Leu Ser Gln Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 13
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 13

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Glu Pro Arg Gln Thr
            20                  25                  30

Ala Lys Phe Lys His Tyr Leu Arg Leu Thr Phe His Val Ser Gln Lys
        35                  40                  45

Thr Gln Arg Arg Trp Phe Leu Asp Lys Leu Val Asp Glu Ile Gly Val
    50                  55                  60

Gly Tyr Val Val Asp Gln Gly Ser Val Ser Gln Tyr Phe Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
        180                 185                 190

Gly Thr Gly Tyr Asn Lys Glu Phe Leu Leu Tyr Leu Ala Gly Phe Val
    195                 200                 205

Asp Gly Asp Gly Ser Ile Tyr Ala Ser Ile Glu Pro Val Gln Thr Tyr
210                 215                 220

Lys Phe Lys His Arg Leu Arg Leu Ser Phe Ala Val Ser Gln Lys Thr
225                 230                 235                 240

Gln Arg Arg Trp Phe Leu Asp Lys Leu Val Asp Glu Ile Gly Val Gly
                245                 250                 255

Tyr Val Cys Asp Val Gly Ser Val Ser Glu Tyr Arg Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 14
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 14

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Glu Pro Arg Gln Thr

```
                    20                  25                  30

Ala Lys Phe Lys His Tyr Leu Arg Leu Thr Phe His Val Ser Gln Lys
            35                  40                  45

Thr Gln Arg Arg Trp Phe Leu Asp Lys Leu Val Asp Glu Ile Gly Val
        50                  55                  60

Gly Tyr Val Val Asp Gln Gly Ser Val Ser Gln Tyr Tyr Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Ser Ile Thr Pro Ser Gln Ala Gly
    210                 215                 220

Lys Phe Lys His Arg Leu Arg Leu Tyr Phe Glu Val Ser Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Gln Gly Ser Val Ser Cys Tyr Arg Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 15
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 15

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Tyr Pro Lys Gln Ser
            20                  25                  30
```

Ser Lys Phe Lys His His Leu Arg Leu Thr Phe His Val Ser Gln Lys
            35                  40                  45

Thr Gln Arg Arg Trp Phe Leu Asp Lys Leu Val Asp Glu Ile Gly Val
    50                  55                  60

Gly Tyr Val Tyr Asp Ser Gly Ser Val Ser Gln Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ala Ser Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Thr Ile Glu Pro Ala Gln Arg Tyr
    210                 215                 220

Lys Phe Lys His Arg Leu Arg Leu Lys Phe Ala Val Ser Gln Lys Thr
225                 230                 235                 240

Gln Arg Arg Trp Phe Leu Asp Lys Leu Val Asp Glu Ile Gly Val Gly
                245                 250                 255

Tyr Val Ala Asp Gln Gly Ser Val Ser Glu Tyr Arg Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 16
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 16

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Glu Pro Glu Gln Thr
            20                  25                  30

```
Ala Lys Phe Lys His Met Leu Arg Leu Thr Phe Arg Val Ser Gln Lys
            35                  40                  45

Thr Gln Arg Arg Trp Phe Leu Asp Lys Leu Val Asp Glu Ile Gly Val
        50                  55                  60

Gly Tyr Val Asn Asp Ser Gly Ser Val Ser Gly Tyr Tyr Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Thr Ile Glu Pro Gln Gln Pro Gly
210                 215                 220

Lys Phe Lys His Arg Leu Ser Leu Arg Phe Ala Val Tyr Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Pro Gly Ser Val Ser Glu Tyr Arg Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro
```

<210> SEQ ID NO 17
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 17

```
Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Glu Pro Arg Gln Thr
            20                  25                  30

Ala Lys Phe Lys His Tyr Leu Arg Leu Thr Phe His Val Ser Gln Lys
```

```
            35                  40                  45
Thr Gln Arg Arg Trp Phe Leu Asp Lys Leu Val Asp Glu Ile Gly Val
 50                  55                  60
Gly Tyr Val Val Asp Gln Gly Ser Val Ser Gln Tyr Phe Leu Ser Gln
 65                  70                  75                  80
Ile Lys Pro Leu His Asn Phe Leu Thr Gln Leu Gln Pro Phe Leu Lys
                 85                  90                  95
Leu Lys Gln Lys Gln Ala Asn Leu Val Leu Lys Ile Ile Glu Gln Leu
            100                 105                 110
Pro Ser Ala Lys Glu Ser Pro Asp Lys Phe Leu Glu Val Cys Thr Trp
            115                 120                 125
Val Asp Gln Ile Ala Ala Leu Asn Asp Ser Lys Thr Arg Lys Thr Thr
 130                 135                 140
Ser Glu Thr Val Arg Ala Val Leu Asp Ser Leu Pro Gly Ser Val Gly
 145                 150                 155                 160
Gly Leu Ser Pro Ser Gln Ala Ser Ser Ala Ala Ser Ser Ala Ser Ser
                165                 170                 175
Ser Pro Gly Ser Gly Ile Ser Glu Ala Leu Arg Ala Gly Ala Gly Ser
            180                 185                 190
Gly Thr Gly Tyr Asn Lys Glu Phe Leu Leu Tyr Leu Ala Gly Phe Val
            195                 200                 205
Asp Gly Asp Gly Ser Ile Tyr Ala Ser Ile Gly Pro Glu Gln Ser Ser
 210                 215                 220
Lys Phe Lys His Arg Leu Arg Leu Leu Phe Ala Val Ala Gln Lys Thr
 225                 230                 235                 240
Gln Arg Arg Trp Phe Leu Asp Lys Leu Val Asp Glu Ile Gly Val Gly
                245                 250                 255
Tyr Val Val Asp Gln Gly Ser Val Ser Glu Tyr Arg Leu Ser Gln Ile
            260                 265                 270
Lys Pro Leu His Asn Phe Leu Thr Gln Leu Gln Pro Phe Leu Lys Leu
            275                 280                 285
Lys Gln Lys Gln Ala Asn Leu Val Leu Lys Ile Ile Glu Gln Leu Pro
            290                 295                 300
Ser Ala Lys Glu Ser Pro Asp Lys Phe Leu Glu Val Cys Thr Trp Val
 305                 310                 315                 320
Asp Gln Ile Ala Ala Leu Asn Asp Ser Lys Thr Arg Lys Thr Thr Ser
                325                 330                 335
Glu Thr Val Arg Ala Val Leu Asp Ser Leu Ser Glu Lys Lys Lys Ser
            340                 345                 350
Ser Pro

<210> SEQ ID NO 18
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 18

Met Asn Thr Lys Tyr Asn Lys Glu Phe Leu Leu Tyr Leu Ala Gly Phe
  1               5                  10                  15
Val Asp Gly Asp Gly Ser Ile Tyr Ala Arg Ile Glu Pro Lys Gln Thr
                 20                  25                  30
Ala Lys Phe Lys His His Leu Cys Leu Arg Phe His Val Ser Gln Lys
             35                  40                  45
```

Thr Gln Arg Arg Trp Phe Leu Asp Lys Leu Val Asp Glu Ile Gly Val
             50                  55                  60

Gly Tyr Val Val Asp His Gly Ser Val Ser Gln Tyr Phe Leu Ser Gln
 65                  70                  75                  80

Ile Lys Pro Leu His Asn Phe Leu Thr Gln Leu Gln Pro Phe Leu Lys
                 85                  90                  95

Leu Lys Gln Lys Gln Ala Asn Leu Val Leu Lys Ile Ile Glu Gln Leu
                100                 105                 110

Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
            195                 200                 205

Asp Gly Asp Gly Ser Ile Tyr Ala Thr Ile Gln Pro Asp Gln Asn Gln
210                 215                 220

Lys Phe Lys His Arg Leu Arg Leu Tyr Phe Ala Val Tyr Gln Lys Thr
225                 230                 235                 240

Gln Arg Arg Trp Phe Leu Asp Lys Leu Val Asp Glu Ile Gly Val Gly
            245                 250                 255

Tyr Val Tyr Asp Thr Gly Ser Val Ser Arg Tyr Gln Leu Ser Gln Ile
            260                 265                 270

Lys Pro Leu His Asn Phe Leu Thr Gln Leu Gln Pro Phe Leu Lys Leu
275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
            325                 330                 335

Glu Thr Val Arg Ala Val Leu Asp Ser Leu Ser Glu Lys Lys Lys Ser
            340                 345                 350

Ser Pro

<210> SEQ ID NO 19
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 19

Met Asn Thr Lys Tyr Asn Lys Glu Phe Leu Leu Tyr Leu Ala Gly Phe
 1               5                  10                  15

Val Asp Gly Asp Gly Ser Ile Tyr Ala Arg Ile Glu Pro Arg Gln Thr
                 20                  25                  30

Ala Lys Phe Lys His Tyr Leu Arg Leu Thr Phe His Val Ser Gln Lys
             35                  40                  45

Thr Gln Arg Arg Trp Phe Leu Asp Lys Leu Val Asp Glu Ile Gly Val
        50                  55                  60

Gly Tyr Val Thr Asp Trp Gly Ser Val Ser Gly Tyr Tyr Leu Ser Glu
 65                  70                  75                  80

Ile Lys Pro Leu His Asn Phe Leu Thr Gln Leu Gln Pro Phe Leu Lys
                 85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
            195                 200                 205

Asp Gly Asp Gly Ser Ile Trp Ala Ser Ile Ile Pro Glu Gln Gly Tyr
        210                 215                 220

Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 20
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 20

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Glu Pro Arg Gln Arg
            20                  25                  30

Val Lys Phe Lys His Phe Leu Arg Leu Thr Phe His Val Ser Gln Lys
        35                  40                  45

Thr Gln Arg Arg Trp Phe Leu Asp Lys Leu Val Asp Glu Ile Gly Val

```
            50                  55                  60
Gly Tyr Val Thr Asp Trp Gly Ser Val Ser Gly Tyr Tyr Leu Ser Glu
 65                  70                  75                  80

Ile Lys Pro Leu His Asn Phe Leu Thr Gln Leu Gln Pro Phe Leu Lys
                 85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Trp Ala Ser Ile Ile Pro Glu Gln Gly Tyr
    210                 215                 220

Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 21
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 21

Met Asn Thr Lys Tyr Asn Lys Glu Phe Leu Leu Tyr Leu Ala Gly Phe
  1               5                  10                  15

Val Asp Gly Asp Gly Ser Ile Tyr Ala Arg Ile Glu Pro Arg Gln Gly
             20                  25                  30

Cys Lys Phe Lys His Val Leu Arg Leu Thr Phe His Val Ser Gln Lys
         35                  40                  45

Thr Gln Arg Arg Trp Phe Leu Asp Lys Leu Val Asp Glu Ile Gly Val
     50                  55                  60
```

```
Gly Tyr Val Thr Asp Trp Gly Ser Val Ser Gly Tyr Leu Ser Glu
 65                  70                  75                  80

Ile Lys Pro Leu His Asn Phe Leu Thr Gln Leu Gln Pro Phe Leu Lys
                 85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
            195                 200                 205

Asp Gly Asp Gly Ser Ile Trp Ala Ser Ile Ile Pro Glu Gln Gly Tyr
210                 215                 220

Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 22
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 22

Met Asn Thr Lys Tyr Asn Lys Glu Phe Leu Leu Tyr Leu Ala Gly Phe
  1               5                  10                  15

Val Asp Gly Asp Gly Ser Ile Tyr Ala Arg Ile Glu Pro Arg Gln Val
             20                  25                  30

Cys Lys Phe Lys His Ile Leu Arg Leu Thr Phe His Val Ser Gln Lys
         35                  40                  45

Thr Gln Arg Arg Trp Phe Leu Asp Lys Leu Val Asp Glu Ile Gly Val
 50                  55                  60
```

```
Gly Tyr Val Thr Asp Trp Gly Ser Val Ser Gly Tyr Tyr Leu Ser Glu
 65                  70                  75                  80

Ile Lys Pro Leu His Asn Phe Leu Thr Gln Leu Gln Pro Phe Leu Lys
                 85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Trp Ala Ser Ile Ile Pro Glu Gln Gly Tyr
    210                 215                 220

Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 23
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 23

Met Asn Thr Lys Tyr Asn Lys Glu Phe Leu Leu Tyr Leu Ala Gly Phe
  1               5                  10                  15

Val Asp Gly Asp Gly Ser Ile Tyr Ala Arg Ile Glu Pro Arg Gln Cys
                 20                  25                  30

Phe Lys Phe Lys His Cys Leu Arg Leu Thr Phe His Val Ser Gln Lys
             35                  40                  45

Thr Gln Arg Arg Trp Phe Leu Asp Lys Leu Val Asp Glu Ile Gly Val
         50                  55                  60

Gly Tyr Val Thr Asp Trp Gly Ser Val Ser Gly Tyr Tyr Leu Ser Glu
```

```
                65                  70                  75                  80
        Ile Lys Pro Leu His Asn Phe Leu Thr Gln Leu Gln Pro Phe Leu Lys
                        85                  90                  95

Leu Lys Gln Lys Gln Ala Asn Leu Val Leu Lys Ile Ile Glu Gln Leu
                    100                 105                 110

Pro Ser Ala Lys Glu Ser Pro Asp Lys Phe Leu Glu Val Cys Thr Trp
                    115                 120                 125

Val Asp Gln Ile Ala Ala Leu Asn Asp Ser Lys Thr Arg Lys Thr Thr
                130                 135                 140

Ser Glu Thr Val Arg Ala Val Leu Asp Ser Leu Pro Gly Ser Val Gly
        145                 150                 155                 160

Gly Leu Ser Pro Ser Gln Ala Ser Ser Ala Ala Ser Ser Ala Ser Ser
                        165                 170                 175

Ser Pro Gly Ser Gly Ile Ser Glu Ala Leu Arg Ala Gly Ala Gly Ser
                    180                 185                 190

Gly Thr Gly Tyr Asn Lys Glu Phe Leu Leu Tyr Leu Ala Gly Phe Val
                    195                 200                 205

Asp Gly Asp Gly Ser Ile Trp Ala Ser Ile Ile Pro Glu Gln Gly Tyr
                210                 215                 220

Lys Phe Lys His Arg Leu Arg Leu Ser Phe Thr Val Ala Gln Lys Thr
        225                 230                 235                 240

Gln Arg Arg Trp Phe Leu Asp Lys Leu Val Asp Glu Ile Gly Val Gly
                        245                 250                 255

Tyr Val Val Asp Gln Gly Ser Val Ser Glu Tyr Arg Leu Ser Glu Ile
                    260                 265                 270

Lys Pro Leu His Asn Phe Leu Thr Gln Leu Gln Pro Phe Leu Lys Leu
                    275                 280                 285

Lys Gln Lys Gln Ala Asn Leu Val Leu Lys Ile Ile Glu Gln Leu Pro
                290                 295                 300

Ser Ala Lys Glu Ser Pro Asp Lys Phe Leu Glu Val Cys Thr Trp Val
        305                 310                 315                 320

Asp Gln Ile Ala Ala Leu Asn Asp Ser Lys Thr Arg Lys Thr Thr Ser
                        325                 330                 335

Glu Thr Val Arg Ala Val Leu Asp Ser Leu Ser Glu Lys Lys Lys Ser
                    340                 345                 350

Ser Pro

<210> SEQ ID NO 24
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 24

Met Asn Thr Lys Tyr Asn Lys Glu Phe Leu Leu Tyr Leu Ala Gly Phe
        1               5                   10                  15

Val Asp Gly Asp Gly Ser Ile Tyr Ala Arg Ile Glu Pro Arg Gln Arg
                        20                  25                  30

Phe Lys Phe Lys His Cys Leu Arg Leu Thr Phe His Val Ser Gln Lys
                    35                  40                  45

Thr Gln Arg Arg Trp Phe Leu Asp Lys Leu Val Asp Glu Ile Gly Val
                50                  55                  60

Gly Tyr Val Thr Asp Trp Gly Ser Val Ser Gly Tyr Tyr Leu Ser Glu
        65                  70                  75                  80
```

```
Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
        180                 185                 190

Gly Thr Gly Tyr Asn Lys Glu Phe Leu Leu Tyr Leu Ala Gly Phe Val
            195                 200                 205

Asp Gly Asp Gly Ser Ile Trp Ala Ser Ile Ile Pro Glu Gln Gly Tyr
        210                 215                 220

Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 25
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 25

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Glu Pro Arg Gln Phe
            20                  25                  30

Cys Lys Phe Lys His Ile Leu Arg Leu Thr Phe His Val Ser Gln Lys
        35                  40                  45

Thr Gln Arg Arg Trp Phe Leu Asp Lys Leu Val Asp Glu Ile Gly Val
    50                  55                  60

Gly Tyr Val Thr Asp Trp Gly Ser Val Ser Gly Tyr Tyr Leu Ser Glu
65                  70                  75                  80
```

```
Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
            195                 200                 205

Asp Gly Asp Gly Ser Ile Trp Ala Ser Ile Pro Glu Gln Gly Tyr
210                 215                 220

Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 26
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 26

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Glu Pro Arg Gln Ala
            20                  25                  30

Phe Lys Phe Lys His Ala Leu Arg Leu Thr Phe His Val Ser Gln Lys
        35                  40                  45

Thr Gln Arg Arg Trp Phe Leu Asp Lys Leu Val Asp Glu Ile Gly Val
    50                  55                  60

Gly Tyr Val Thr Asp Trp Gly Ser Val Ser Gly Tyr Tyr Leu Ser Glu
65                  70                  75                  80

Ile Lys Pro Leu His Asn Phe Leu Thr Gln Leu Gln Pro Phe Leu Lys
```

```
                        85                  90                  95

Leu Lys Gln Lys Gln Ala Asn Leu Val Leu Lys Ile Ile Glu Gln Leu
                100                 105                 110

Pro Ser Ala Lys Glu Ser Pro Asp Lys Phe Leu Glu Val Cys Thr Trp
                115                 120                 125

Val Asp Gln Ile Ala Ala Leu Asn Asp Ser Lys Thr Arg Lys Thr Thr
            130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
                180                 185                 190

Gly Thr Gly Tyr Asn Lys Glu Phe Leu Tyr Leu Ala Gly Phe Val
                195                 200                 205

Asp Gly Asp Gly Ser Ile Trp Ala Ser Ile Pro Glu Gln Gly Tyr
            210                 215                 220

Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
                260                 265                 270

Lys Pro Leu His Asn Phe Leu Thr Gln Leu Gln Pro Phe Leu Lys Leu
                275                 280                 285

Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro

<210> SEQ ID NO 27
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 27

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Glu Pro Arg Gln Thr
                20                  25                  30

Cys Lys Phe Lys His Ile Leu Arg Leu Thr Phe His Val Ser Gln Lys
            35                  40                  45

Thr Gln Arg Arg Trp Phe Leu Asp Lys Leu Val Asp Glu Ile Gly Val
        50                  55                  60

Gly Tyr Val Thr Asp Trp Gly Ser Val Ser Gly Tyr Tyr Leu Ser Glu
65                  70                  75                  80

Ile Lys Pro Leu His Asn Phe Leu Thr Gln Leu Gln Pro Phe Leu Lys
                85                  90                  95
```

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
            195                 200                 205

Asp Gly Asp Gly Ser Ile Trp Ala Ser Ile Ile Pro Glu Gln Gly Tyr
210                 215                 220

Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
            245                 250                 255

Tyr Val Asp Gln Gly Ser Val Ser Glu Tyr Arg Leu Ser Glu Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 28
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 28

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Glu Pro Arg Gln Cys
            20                  25                  30

Phe Lys Phe Lys His Gly Leu Arg Leu Thr Phe His Val Ser Gln Lys
            35                  40                  45

Thr Gln Arg Arg Trp Phe Leu Asp Lys Leu Val Asp Glu Ile Gly Val
        50                  55                  60

Gly Tyr Val Thr Asp Trp Gly Ser Val Ser Gly Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
                100                 105                 110

Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Trp Ala Ser Ile Ile Pro Glu Gln Gly Tyr
    210                 215                 220

Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 29
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 29

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Glu Pro Arg Gln Ser
                20                  25                  30

Ser Lys Phe Lys His Leu Leu Arg Leu Thr Phe His Val Ser Gln Lys
            35                  40                  45

Thr Gln Arg Arg Trp Phe Leu Asp Lys Leu Val Asp Glu Ile Gly Val
        50                  55                  60

Gly Tyr Val Thr Asp Trp Gly Ser Val Ser Gly Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu

```
              100                 105                 110
Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
        130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
                180                 185                 190

Gly Thr Gly Tyr Asn Lys Glu Phe Leu Leu Tyr Leu Ala Gly Phe Val
            195                 200                 205

Asp Gly Asp Gly Ser Ile Trp Ala Ser Ile Ile Pro Glu Gln Gly Tyr
        210                 215                 220

Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 30
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 30

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Tyr Leu Gly Gln His
            20                  25                  30

Trp Lys Phe Lys His Tyr Val Arg Leu Thr Phe His Val Ser Gln Lys
        35                  40                  45

Thr Gln Arg Arg Trp Phe Leu Asp Lys Leu Val Asp Glu Ile Gly Val
    50                  55                  60

Gly Tyr Val Thr Asp Trp Gly Ser Val Ser Gly Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110
```

Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
            165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
            195                 200                 205

Asp Gly Asp Gly Ser Ile Trp Ala Ser Ile Ile Pro Glu Gln Gly Tyr
            210                 215                 220

Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
            245                 250                 255

Tyr Val Val Asp Gln Gly Ser Val Ser Glu Tyr Arg Leu Ser Glu Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
            325                 330                 335

Glu Thr Val Arg Ala Val Leu Asp Ser Leu Ser Glu Lys Lys Lys Ser
            340                 345                 350

Ser Pro

<210> SEQ ID NO 31
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 31

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Tyr Leu Gly Gln His
            20                  25                  30

Tyr Lys Phe Lys His Tyr Ile Arg Leu Thr Phe His Val Ser Gln Lys
            35                  40                  45

Thr Gln Arg Arg Trp Phe Leu Asp Lys Leu Val Asp Glu Ile Gly Val
50                  55                  60

Gly Tyr Val Thr Asp Trp Gly Ser Val Ser Gly Tyr Tyr Leu Ser Glu
65                  70                  75                  80

Ile Lys Pro Leu His Asn Phe Leu Thr Gln Leu Gln Pro Phe Leu Lys
            85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
            165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
            195                 200                 205

Asp Gly Asp Gly Ser Ile Trp Ala Ser Ile Ile Pro Glu Gln Gly Tyr
210                 215                 220

Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
            245                 250                 255

Tyr Val Val Asp Gln Gly Ser Val Ser Glu Tyr Arg Leu Ser Glu Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
            325                 330                 335

Glu Thr Val Arg Ala Val Leu Asp Ser Leu Ser Glu Lys Lys Lys Ser
            340                 345                 350

Ser Pro

<210> SEQ ID NO 32
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 32

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Tyr Asn Ala Gln Tyr
            20                  25                  30

Tyr Lys Phe Lys His Tyr Ile Arg Leu Thr Phe His Val Ser Gln Lys
        35                  40                  45

Thr Gln Arg Arg Trp Phe Leu Asp Lys Leu Val Asp Glu Ile Gly Val
    50                  55                  60

Gly Tyr Val Thr Asp Trp Gly Ser Val Ser Gly Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

```
            115                 120                 125
Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
                180                 185                 190

Gly Thr Gly Tyr Asn Lys Glu Phe Leu Leu Tyr Leu Ala Gly Phe Val
            195                 200                 205

Asp Gly Asp Gly Ser Ile Trp Ala Ser Ile Ile Pro Glu Gln Gly Tyr
    210                 215                 220

Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
            260                 265                 270

Lys Pro Leu His Asn Phe Leu Thr Gln Leu Gln Pro Phe Leu Lys Leu
    275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 33
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 33

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Glu Arg Arg Gln Asn
            20                  25                  30

Phe Lys Phe Lys His His Ile Arg Leu Thr Phe His Val Ser Gln Lys
        35                  40                  45

Thr Gln Arg Arg Trp Phe Leu Asp Lys Leu Val Asp Glu Ile Gly Val
    50                  55                  60

Gly Tyr Val Thr Asp Trp Gly Ser Val Ser Gly Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125
```

```
Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
                180                 185                 190

Gly Thr Gly Tyr Asn Lys Glu Phe Leu Leu Tyr Leu Ala Gly Phe Val
                195                 200                 205

Asp Gly Asp Gly Ser Ile Trp Ala Ser Ile Ile Pro Glu Gln Gly Tyr
    210                 215                 220

Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
                260                 265                 270

Lys Pro Leu His Asn Phe Leu Thr Gln Leu Gln Pro Phe Leu Lys Leu
                275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro

<210> SEQ ID NO 34
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 34

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Glu Arg Gln Cys
                20                  25                  30

Val Lys Phe Lys His Tyr Leu Arg Leu Thr Phe His Val Ser Gln Lys
                35                  40                  45

Thr Gln Arg Arg Trp Phe Leu Asp Lys Leu Val Asp Glu Ile Gly Val
    50                  55                  60

Gly Tyr Val Thr Asp Trp Gly Ser Val Ser Gly Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
                100                 105                 110

Pro Ser Ala Lys Glu Ser Pro Asp Lys Phe Leu Glu Val Cys Thr Trp
                115                 120                 125
```

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
            165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Tyr Leu Ala Gly Phe Val
            195                 200                 205

Asp Gly Asp Gly Ser Ile Trp Ala Ser Ile Ile Pro Glu Gln Gly Tyr
210                 215                 220

Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 35
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 35

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Glu Tyr Arg Gln Gly
            20                  25                  30

Ala Lys Phe Lys His Tyr Leu Arg Leu Thr Phe His Val Ser Gln Lys
            35                  40                  45

Thr Gln Arg Arg Trp Phe Leu Asp Lys Leu Val Asp Glu Ile Gly Val
    50                  55                  60

Gly Tyr Val Thr Asp Trp Gly Ser Val Ser Gly Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr

```
Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
            165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
            195                 200                 205

Asp Gly Asp Gly Ser Ile Trp Ala Ser Ile Ile Pro Glu Gln Gly Tyr
            210                 215                 220

Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
                260                 265                 270

Lys Pro Leu His Asn Phe Leu Thr Gln Leu Gln Pro Phe Leu Lys Leu
                275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro

<210> SEQ ID NO 36
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 36

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Glu Pro Arg Gln Ser
                20                  25                  30

Gly Lys Phe Lys His Tyr Ile Arg Leu Thr Phe His Val Ser Gln Lys
            35                  40                  45

Thr Gln Arg Arg Trp Phe Leu Asp Lys Leu Val Asp Glu Ile Gly Val
50                  55                  60

Gly Tyr Val Thr Asp Trp Gly Ser Val Ser Gly Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
                100                 105                 110

Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
130                 135                 140
```

```
Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
            165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Trp Ala Ser Ile Ile Pro Glu Gln Gly Tyr
        210                 215                 220

Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
                260                 265                 270

Lys Pro Leu His Asn Phe Leu Thr Gln Leu Gln Pro Phe Leu Lys Leu
                275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro

<210> SEQ ID NO 37
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 37

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Phe Lys Gly Gln His
            20                  25                  30

Trp Lys Phe Lys His His Ile Arg Leu Thr Phe Asn Val Ser Gln Lys
        35                  40                  45

Thr Gln Arg Arg Trp Phe Leu Asp Lys Leu Val Asp Glu Ile Gly Val
    50                  55                  60

Gly Tyr Val Ser Asp Thr Gly Ser Gln Ser Asn Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140
```

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
            165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
            195                 200                 205

Asp Gly Asp Gly Ser Ile Trp Ala Ser Ile Ile Pro Glu Gln Gly Tyr
210                 215                 220

Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
            245                 250                 255

Tyr Val Val Asp Gln Gly Ser Val Ser Glu Tyr Arg Leu Ser Glu Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
            325                 330                 335

Glu Thr Val Arg Ala Val Leu Asp Ser Leu Ser Glu Lys Lys Lys Ser
            340                 345                 350

Ser Pro

<210> SEQ ID NO 38
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 38

Met Asn Thr Lys Tyr Asn Lys Glu Phe Leu Leu Tyr Leu Ala Gly Phe
1               5                   10                  15

Val Asp Gly Asp Gly Ser Ile Phe Ala Arg Ile Phe Lys Gly Gln His
            20                  25                  30

Trp Lys Phe Lys His His Ile Arg Leu Thr Phe Asn Val Ser Gln Lys
            35                  40                  45

Thr Gln Arg Arg Trp Phe Leu Asp Lys Leu Val Asp Glu Ile Gly Val
50                  55                  60

Gly Tyr Val Asn Asp Tyr Gly Ser Thr Ser Asn Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly

```
145                 150                 155                 160
Gly Leu Ser Pro Ser Gln Ala Ser Ser Ala Ser Ser Ala Ser Ser
                165                 170                 175
Ser Pro Gly Ser Gly Ile Ser Glu Ala Leu Arg Ala Gly Ala Gly Ser
                180                 185                 190
Gly Thr Gly Tyr Asn Lys Glu Phe Leu Tyr Leu Ala Gly Phe Val
                195                 200                 205
Asp Gly Asp Gly Ser Ile Trp Ala Ser Ile Ile Pro Glu Gln Gly Tyr
                210                 215                 220
Lys Phe Lys His Arg Leu Arg Leu Ser Phe Thr Val Ala Gln Lys Thr
225                 230                 235                 240
Gln Arg Arg Trp Phe Leu Asp Lys Leu Val Asp Glu Ile Gly Val Gly
                245                 250                 255
Tyr Val Val Asp Gln Gly Ser Val Ser Glu Tyr Arg Leu Ser Glu Ile
                260                 265                 270
Lys Pro Leu His Asn Phe Leu Thr Gln Leu Gln Pro Phe Leu Lys Leu
                275                 280                 285
Lys Gln Lys Gln Ala Asn Leu Val Leu Lys Ile Ile Glu Gln Leu Pro
                290                 295                 300
Ser Ala Lys Glu Ser Pro Asp Lys Phe Leu Glu Val Cys Thr Trp Val
305                 310                 315                 320
Asp Gln Ile Ala Ala Leu Asn Asp Ser Lys Thr Arg Lys Thr Thr Ser
                325                 330                 335
Glu Thr Val Arg Ala Val Leu Asp Ser Leu Ser Glu Lys Lys Lys Ser
                340                 345                 350
Ser Pro

<210> SEQ ID NO 39
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 39

Met Asn Thr Lys Tyr Asn Lys Glu Phe Leu Leu Tyr Leu Ala Gly Phe
1               5                   10                  15
Val Asp Gly Asp Gly Ser Ile Phe Ala Arg Ile Phe Lys Gly Gln His
                20                  25                  30
Trp Lys Phe Lys His His Ile Arg Leu Thr Phe Asn Val Ala Gln Lys
            35                  40                  45
Thr Gln Arg Arg Trp Phe Leu Asp Lys Leu Val Asp Glu Ile Gly Val
    50                  55                  60
Gly Tyr Val Thr Asp His Gly Ser Asn Ser Asn Tyr Tyr Leu Ser Glu
65                  70                  75                  80
Ile Lys Pro Leu His Asn Phe Leu Thr Gln Leu Gln Pro Phe Leu Lys
                85                  90                  95
Leu Lys Gln Lys Gln Ala Asn Leu Val Leu Lys Ile Ile Glu Gln Leu
                100                 105                 110
Pro Ser Ala Lys Glu Ser Pro Asp Lys Phe Leu Glu Val Cys Thr Trp
                115                 120                 125
Val Asp Gln Ile Ala Ala Leu Asn Asp Ser Lys Thr Arg Lys Thr Thr
        130                 135                 140
Ser Glu Thr Val Arg Ala Val Leu Asp Ser Leu Pro Gly Ser Val Gly
145                 150                 155                 160
```

```
Gly Leu Ser Pro Ser Gln Ala Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
            195                 200                 205

Asp Gly Asp Gly Ser Ile Trp Ala Ser Ile Ile Pro Glu Gln Gly Tyr
210                 215                 220

Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
                260                 265                 270

Lys Pro Leu His Asn Phe Leu Thr Gln Leu Gln Pro Phe Leu Lys Leu
                275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro

<210> SEQ ID NO 40
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 40

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Phe Lys Gly Gln His
                20                  25                  30

Trp Lys Phe Lys His His Ile Arg Leu Thr Phe Asn Val Thr Gln Lys
            35                  40                  45

Thr Gln Arg Arg Trp Phe Leu Asp Lys Leu Val Asp Glu Ile Gly Val
50                  55                  60

Gly Tyr Val Ser Asp Tyr Gly Ser Met Ser Asn Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
                100                 105                 110

Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160
```

```
Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
        180                 185                 190

Gly Thr Gly Tyr Asn Lys Glu Phe Leu Leu Tyr Leu Ala Gly Phe Val
        195                 200                 205

Asp Gly Asp Gly Ser Ile Trp Ala Ser Ile Ile Pro Glu Gln Gly Tyr
        210                 215                 220

Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
                260                 265                 270

Lys Pro Leu His Asn Phe Leu Thr Gln Leu Gln Pro Phe Leu Lys Leu
                275                 280                 285

Lys Gln Lys Gln Ala Asn Leu Val Leu Lys Ile Ile Glu Gln Leu Pro
                290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro

<210> SEQ ID NO 41
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 41

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Phe Lys Gly Gln His
                20                  25                  30

Trp Lys Phe Lys His His Ile Arg Leu Thr Phe Ala Val Thr Gln Lys
            35                  40                  45

Thr Gln Arg Arg Trp Phe Leu Asp Lys Leu Val Asp Glu Ile Gly Val
    50                  55                  60

Gly Tyr Val Thr Asp His Gly Ser Cys Ser Asn Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
```

```
                    165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Trp Ala Ser Ile Ile Pro Glu Gln Gly Tyr
    210                 215                 220

Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Ser
            340                 345                 350

Ser Pro

<210> SEQ ID NO 42
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 42

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Phe Lys Gly Gln His
                20                  25                  30

Trp Lys Phe Lys His His Ile Arg Leu Thr Phe Asn Val Ser Gln Lys
            35                  40                  45

Thr Gln Arg Arg Trp Phe Leu Asp Lys Leu Val Asp Glu Ile Gly Val
        50                  55                  60

Gly Tyr Val Gly Asp Tyr Gly Ser Met Ser His Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175
```

```
Ser Pro Gly Ser Gly Ile Ser Glu Ala Leu Arg Ala Gly Ala Gly Ser
            180                 185                 190

Gly Thr Gly Tyr Asn Lys Glu Phe Leu Tyr Leu Ala Gly Phe Val
        195                 200                 205

Asp Gly Asp Gly Ser Ile Trp Ala Ser Ile Pro Glu Gln Gly Tyr
    210                 215                 220

Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
                260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro

<210> SEQ ID NO 43
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 43

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Phe Lys Gly Gln His
                20                  25                  30

Trp Lys Phe Lys His His Ile Arg Leu Thr Phe Asn Val Ser Gln Lys
            35                  40                  45

Thr Gln Arg Arg Trp Phe Leu Asp Lys Leu Val Asp Glu Ile Gly Val
    50                  55                  60

Gly Tyr Val Thr Asp Phe Gly Ser Gln Ser Gln Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175
```

```
Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Trp Ala Ser Ile Ile Pro Glu Gln Gly Tyr
    210                 215                 220

Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 44
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 44

Met Asn Thr Lys Tyr Asn Lys Glu Phe Leu Leu Tyr Leu Ala Gly Phe
1               5                   10                  15

Val Asp Gly Asp Gly Ser Ile Phe Ala Arg Ile Phe Lys Gly Gln His
            20                  25                  30

Trp Lys Phe Lys His His Ile Arg Leu Thr Phe Asn Val Thr Gln Lys
        35                  40                  45

Thr Gln Arg Arg Trp Phe Leu Asp Lys Leu Val Asp Glu Ile Gly Val
    50                  55                  60

Gly Tyr Val Ser Asp Tyr Gly Ser Ile Ser Asn Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
```

```
                180                 185                 190
Gly Thr Gly Tyr Asn Lys Glu Phe Leu Leu Tyr Leu Ala Gly Phe Val
            195                 200                 205

Asp Gly Asp Gly Ser Ile Trp Ala Ser Ile Ile Pro Glu Gln Gly Tyr
        210                 215                 220

Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
            245                 250                 255

Tyr Val Val Asp Gln Gly Ser Val Ser Glu Tyr Arg Leu Ser Glu Ile
        260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
        290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
            325                 330                 335

Glu Thr Val Arg Ala Val Leu Asp Ser Leu Ser Glu Lys Lys Lys Ser
            340                 345                 350

Ser Pro

<210> SEQ ID NO 45
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 45

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Phe Lys Gly Gln His
            20                  25                  30

Trp Lys Phe Lys His His Ile Arg Leu Thr Phe Asn Val Thr Gln Lys
        35                  40                  45

Thr Gln Arg Arg Trp Phe Leu Asp Lys Leu Val Asp Glu Ile Gly Val
    50                  55                  60

Gly Tyr Val Ile Asp Tyr Gly Ser Ile Ser Asn Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190
```

```
Gly Thr Gly Tyr Asn Lys Glu Phe Leu Leu Tyr Leu Ala Gly Phe Val
            195                 200                 205

Asp Gly Asp Gly Ser Ile Trp Ala Ser Ile Ile Pro Glu Gln Gly Tyr
    210                 215                 220

Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
            245                 250                 255

Tyr Val Val Asp Gln Gly Ser Val Ser Glu Tyr Arg Leu Ser Glu Ile
                260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
        290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 46
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 46

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Phe Lys Gly Gln His
            20                  25                  30

Trp Lys Phe Lys His His Ile Arg Leu Thr Phe Asn Val Thr Gln Lys
        35                  40                  45

Thr Gln Arg Arg Trp Phe Leu Asp Lys Leu Val Asp Glu Ile Gly Val
    50                  55                  60

Gly Tyr Val Thr Asp Tyr Gly Ser Ser Asn Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190
```

```
Gly Thr Gly Tyr Asn Lys Glu Phe Leu Leu Tyr Leu Ala Gly Phe Val
            195                 200                 205

Asp Gly Asp Gly Ser Ile Trp Ala Ser Ile Ile Pro Glu Gln Gly Tyr
        210                 215                 220

Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
                260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
        290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro

<210> SEQ ID NO 47
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 47

Met Asn Thr Lys Tyr Asn Lys Glu Phe Leu Leu Tyr Leu Ala Gly Phe
1               5                   10                  15

Val Asp Gly Asp Gly Ser Ile Phe Ala Arg Ile Phe Lys Gly Gln His
            20                  25                  30

Trp Lys Phe Lys His His Ile Arg Leu Thr Phe Asn Val Ser Gln Lys
        35                  40                  45

Thr Gln Arg Arg Trp Phe Leu Asp Lys Leu Val Asp Glu Ile Gly Val
    50                  55                  60

Gly Tyr Val Thr Asp Gly Gly Ser Ser Ser Asn Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ala Ser Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
```

```
            195                 200                 205
Asp Gly Asp Gly Ser Ile Trp Ala Ser Ile Pro Glu Gln Gly Tyr
210                 215                 220

Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
                260                 265                 270

Lys Pro Leu His Asn Phe Leu Thr Gln Leu Gln Pro Phe Leu Lys Leu
                275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro

<210> SEQ ID NO 48
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 48

Met Asn Thr Lys Tyr Asn Lys Glu Phe Leu Leu Tyr Leu Ala Gly Phe
1               5                   10                  15

Val Asp Gly Asp Gly Ser Ile Phe Ala Arg Ile Phe Lys Gly Gln His
                20                  25                  30

Trp Lys Phe Lys His His Ile Arg Leu Thr Phe Asn Val Ser Gln Lys
            35                  40                  45

Thr Gln Arg Arg Trp Phe Leu Asp Lys Leu Val Asp Glu Ile Gly Val
    50                  55                  60

Gly Tyr Val Tyr Asp His Gly Ser Gln Ser Asn Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
                100                 105                 110

Pro Ser Ala Lys Glu Ser Pro Asp Lys Phe Leu Glu Val Cys Thr Trp
                115                 120                 125

Val Asp Gln Ile Ala Ala Leu Asn Asp Ser Lys Thr Arg Lys Thr Thr
            130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ala Ser Ser Ala Ser Ser
                165                 170                 175

Ser Pro Gly Ser Gly Ile Ser Glu Ala Leu Arg Ala Gly Ala Gly Ser
                180                 185                 190

Gly Thr Gly Tyr Asn Lys Glu Phe Leu Leu Tyr Leu Ala Gly Phe Val
            195                 200                 205
```

```
Asp Gly Asp Gly Ser Ile Trp Ala Ser Ile Ile Pro Glu Gln Gly Tyr
            210                 215                 220

Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
            260                 265                 270

Lys Pro Leu His Asn Phe Leu Thr Gln Leu Gln Pro Phe Leu Lys Leu
                275                 280                 285

Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 49
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 49

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Phe Lys Gly Gln His
            20                  25                  30

Trp Lys Phe Lys His His Ile Arg Leu Thr Phe Asn Val Ser Gln Lys
        35                  40                  45

Thr Gln Arg Arg Trp Phe Leu Asp Lys Leu Val Asp Glu Ile Gly Val
    50                  55                  60

Gly Tyr Val Cys Asp Asn Gly Ser Asn Ser Asn Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205
```

Asp Gly Asp Gly Ser Ile Trp Ala Ser Ile Ile Pro Glu Gln Gly Tyr
    210                 215                 220

Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
                260                 265                 270

Lys Pro Leu His Asn Phe Leu Thr Gln Leu Gln Pro Phe Leu Lys Leu
                275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro

<210> SEQ ID NO 50
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 50

Met Asn Thr Lys Tyr Asn Lys Glu Phe Leu Leu Tyr Leu Ala Gly Phe
1               5                   10                  15

Val Asp Gly Asp Gly Ser Ile Phe Ala Arg Ile Phe Lys Gly Gln His
                20                  25                  30

Trp Lys Phe Lys His His Ile Arg Leu Thr Phe Asn Val Ser Gln Lys
                35                  40                  45

Thr Gln Arg Arg Trp Phe Leu Asp Lys Leu Val Asp Glu Ile Gly Val
50                  55                  60

Gly Tyr Val Ala Asp Tyr Gly Ser Thr Ser Asn Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
                100                 105                 110

Pro Ser Ala Lys Glu Ser Pro Asp Lys Phe Leu Glu Val Cys Thr Trp
                115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
                180                 185                 190

Gly Thr Gly Tyr Asn Lys Glu Phe Leu Leu Tyr Leu Ala Gly Phe Val
                195                 200                 205

Asp Gly Asp Gly Ser Ile Trp Ala Ser Ile Ile Pro Glu Gln Gly Tyr

```
                210                 215                 220
Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
                260                 265                 270

Lys Pro Leu His Asn Phe Leu Thr Gln Leu Gln Pro Phe Leu Lys Leu
                275                 280                 285

Lys Gln Lys Gln Ala Asn Leu Val Leu Lys Ile Ile Glu Gln Leu Pro
                290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro

<210> SEQ ID NO 51
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 51

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Phe Lys Gly Gln His
                20                  25                  30

Trp Lys Phe Lys His His Ile Arg Leu Thr Phe Cys Val Ser Gln Lys
                35                  40                  45

Thr Gln Arg Arg Trp Phe Leu Asp Lys Leu Val Asp Glu Ile Gly Val
    50                  55                  60

Gly Tyr Val Ala Asp Tyr Gly Ser Met Ser Asn Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
                100                 105                 110

Pro Ser Ala Lys Glu Ser Pro Asp Lys Phe Leu Glu Val Cys Thr Trp
                115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
                180                 185                 190

Gly Thr Gly Tyr Asn Lys Glu Phe Leu Leu Tyr Leu Ala Gly Phe Val
                195                 200                 205

Asp Gly Asp Gly Ser Ile Trp Ala Ser Ile Ile Pro Glu Gln Gly Tyr
                210                 215                 220
```

```
Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
            245                 250                 255

Tyr Val Val Asp Gln Gly Ser Val Ser Glu Tyr Arg Leu Ser Glu Ile
        260                 265                 270

Lys Pro Leu His Asn Phe Leu Thr Gln Leu Gln Pro Phe Leu Lys Leu
    275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
            325                 330                 335

Glu Thr Val Arg Ala Val Leu Asp Ser Leu Ser Glu Lys Lys Lys Ser
        340                 345                 350

Ser Pro

<210> SEQ ID NO 52
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 52

Met Asn Thr Lys Tyr Asn Lys Glu Phe Leu Leu Tyr Leu Ala Gly Phe
1               5                   10                  15

Val Asp Gly Asp Gly Ser Ile Met Ala Arg Ile Phe Lys Gly Gln His
            20                  25                  30

Trp Lys Phe Lys His Tyr Ile Arg Leu Thr Leu Cys Val Arg Gln Lys
        35                  40                  45

Thr Gln Arg Arg Trp Phe Leu Asp Lys Leu Val Asp Glu Ile Gly Val
    50                  55                  60

Gly Tyr Val Cys Asp Ser Gly Ser Met Ser Ala Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ala Ser Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Trp Ala Ser Ile Ile Pro Glu Gln Gly Tyr
    210                 215                 220
```

-continued

```
Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
            245                 250                 255

Tyr Val Asp Gln Gly Ser Val Ser Glu Tyr Arg Leu Ser Glu Ile
        260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro
```

<210> SEQ ID NO 53
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 53

```
Met Asn Thr Lys Tyr Asn Lys Glu Phe Leu Leu Tyr Leu Ala Gly Phe
1               5                   10                  15

Val Asp Gly Asp Gly Ser Ile Phe Ala Arg Ile Phe Lys Gly Gln His
            20                  25                  30

Trp Lys Phe Lys His His Ile Arg Leu Thr Phe Asn Val Ser Gln Lys
        35                  40                  45

Thr Gln Arg Arg Trp Phe Leu Asp Lys Leu Val Asp Glu Ile Gly Val
    50                  55                  60

Gly Tyr Val Thr Asp Gly Gly Ser Ser Ser Asn Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Trp Ala Ser Ile Ile Pro Glu Gln Gly Tyr
    210                 215                 220

Lys Phe Lys His Arg Leu Arg Leu Ser Phe Thr Val Ala Gln Lys Thr
```

```
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
                260                 265                 270

Lys Pro Leu His Asn Phe Leu Thr Gln Leu Gln Pro Phe Leu Lys Leu
                275                 280                 285

Lys Gln Lys Gln Ala Asn Leu Val Leu Lys Ile Ile Glu Gln Leu Pro
                290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro

<210> SEQ ID NO 54
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 54

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Phe Lys Gly Gln His
                20                  25                  30

Trp Lys Phe Lys His His Ile Arg Leu Thr Phe His Val Ser Gln Lys
                35                  40                  45

Thr Gln Arg Arg Trp Phe Leu Asp Lys Leu Val Asp Glu Ile Gly Val
            50                  55                  60

Gly Tyr Val Thr Asp Trp Gly Ser Val Ser Gly Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
                100                 105                 110

Pro Ser Ala Lys Glu Ser Pro Asp Lys Phe Leu Glu Val Cys Thr Trp
                115                 120                 125

Val Asp Gln Ile Ala Ala Leu Asn Asp Ser Lys Thr Arg Lys Thr Thr
            130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
                180                 185                 190

Gly Thr Gly Tyr Asn Lys Glu Phe Leu Leu Tyr Leu Ala Gly Phe Val
                195                 200                 205

Asp Gly Asp Gly Ser Ile Trp Ala Ser Ile Leu Pro Glu Ser Arg Met
            210                 215                 220

Lys Phe Lys His Arg Leu Arg Leu Gly Phe Thr Val Ala Gln Lys Thr
225                 230                 235                 240
```

Gln Arg Arg Trp Phe Leu Asp Lys Leu Val Asp Glu Ile Gly Val Gly
            245                 250                 255

Tyr Val Val Asp Gln Gly Ser Val Ser Glu Tyr Arg Leu Ser Glu Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
        290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 55
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 55

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Phe Lys Gly Gln His
            20                  25                  30

Trp Lys Phe Lys His His Ile Arg Leu Thr Phe His Val Ser Gln Lys
        35                  40                  45

Thr Gln Arg Arg Trp Phe Leu Asp Lys Leu Val Asp Glu Ile Gly Val
    50                  55                  60

Gly Tyr Val Thr Asp Trp Gly Ser Val Ser Gly Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Trp Ala Gln Ile Leu Pro Glu Lys Lys Cys
    210                 215                 220

Ala Phe Lys His Arg Leu Arg Leu Trp Phe Thr Val Ala Gln Lys Thr
225                 230                 235                 240

```
Gln Arg Arg Trp Phe Leu Asp Lys Leu Val Asp Glu Ile Gly Val Gly
            245                 250                 255

Tyr Val Val Asp Gln Gly Ser Val Ser Glu Tyr Arg Leu Ser Glu Ile
        260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
        290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
            325                 330                 335

Glu Thr Val Arg Ala Val Leu Asp Ser Leu Ser Glu Lys Lys Lys Ser
        340                 345                 350

Ser Pro

<210> SEQ ID NO 56
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 56

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Phe Lys Gly Gln His
            20                  25                  30

Trp Lys Phe Lys His His Ile Arg Leu Thr Phe His Val Ser Gln Lys
        35                  40                  45

Thr Gln Arg Arg Trp Phe Leu Asp Lys Leu Val Asp Glu Ile Gly Val
    50                  55                  60

Gly Tyr Val Thr Asp Trp Gly Ser Val Ser Gly Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Trp Ala Cys Ile Val Pro Glu Lys Ala Ser
    210                 215                 220

Arg Phe Lys His Arg Leu Arg Leu Ala Phe Thr Val Ala Gln Lys Thr
225                 230                 235                 240

Gln Arg Arg Trp Phe Leu Asp Lys Leu Val Asp Glu Ile Gly Val Gly
```

```
            245                 250                 255
Tyr Val Val Asp Gln Gly Ser Val Ser Glu Tyr Arg Leu Ser Glu Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
            325                 330                 335

Glu Thr Val Arg Ala Val Leu Asp Ser Leu Ser Glu Lys Lys Lys Ser
            340                 345                 350

Ser Pro
```

<210> SEQ ID NO 57
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 57

```
Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Phe Lys Gly Gln His
            20                  25                  30

Trp Lys Phe Lys His His Ile Arg Leu Thr Phe His Val Ser Gln Lys
        35                  40                  45

Thr Gln Arg Arg Trp Phe Leu Asp Lys Leu Val Asp Glu Ile Gly Val
    50                  55                  60

Gly Tyr Val Thr Asp Trp Gly Ser Val Ser Gly Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Trp Ala Thr Ile Val Pro Glu Lys Ser Ser
    210                 215                 220

Ile Phe Lys His Arg Leu Arg Leu Tyr Phe Thr Val Ala Gln Lys Thr
225                 230                 235                 240

Gln Arg Arg Trp Phe Leu Asp Lys Leu Val Asp Glu Ile Gly Val Gly
                245                 250                 255
```

```
Tyr Val Val Asp Gln Gly Ser Val Ser Glu Tyr Arg Leu Ser Glu Ile
                260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
        290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 58
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 58

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Phe Lys Gly Gln His
            20                  25                  30

Trp Lys Phe Lys His His Ile Arg Leu Thr Phe His Val Ser Gln Lys
        35                  40                  45

Thr Gln Arg Arg Trp Phe Leu Asp Lys Leu Val Asp Glu Ile Gly Val
    50                  55                  60

Gly Tyr Val Thr Asp Trp Gly Ser Val Ser Gly Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Trp Ala Ser Ile Val Pro Glu Glu Arg Thr
    210                 215                 220

Arg Phe Lys His Arg Leu Arg Leu Tyr Phe Thr Val Ala Gln Lys Thr
225                 230                 235                 240

Gln Arg Arg Trp Phe Leu Asp Lys Leu Val Asp Glu Ile Gly Val Gly
                245                 250                 255
```

```
Tyr Val Val Asp Gln Gly Ser Val Ser Glu Tyr Arg Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 59
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 59

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Phe Lys Gly Gln His
            20                  25                  30

Trp Lys Phe Lys His His Ile Arg Leu Thr Phe His Val Ser Gln Lys
        35                  40                  45

Thr Gln Arg Arg Trp Phe Leu Asp Lys Leu Val Asp Glu Ile Gly Val
    50                  55                  60

Gly Tyr Val Thr Asp Trp Gly Ser Val Ser Gly Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Trp Ala Arg Ile Glu Pro Glu Lys Gly Gly
    210                 215                 220

Arg Phe Lys His Arg Leu Arg Leu Tyr Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
```

```
                        260                 265                 270

Lys Pro Leu His Asn Phe Leu Thr Gln Leu Gln Pro Phe Leu Lys Leu
                275                 280                 285

Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 60
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 60

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Phe Lys Gly Gln His
            20                  25                  30

Trp Lys Phe Lys His His Ile Arg Leu Thr Phe His Val Ser Gln Lys
        35                  40                  45

Thr Gln Arg Arg Trp Phe Leu Asp Lys Leu Val Asp Glu Ile Gly Val
    50                  55                  60

Gly Tyr Val Thr Asp Trp Gly Ser Val Ser Gly Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Trp Ala Ser Ile Ser Pro Glu Val Arg Ala
    210                 215                 220

Pro Phe Lys His Arg Leu Arg Leu Tyr Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
            260                 265                 270
```

```
Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
        290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 61
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 61

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Phe Lys Gly Gln His
            20                  25                  30

Trp Lys Phe Lys His His Ile Arg Leu Thr Phe His Val Ser Gln Lys
        35                  40                  45

Thr Gln Arg Arg Trp Phe Leu Asp Lys Leu Val Asp Glu Ile Gly Val
    50                  55                  60

Gly Tyr Val Thr Asp Trp Gly Ser Val Ser Gly Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Trp Ala Ser Ile Leu Pro Glu Thr Ser Ala
    210                 215                 220

Arg Phe Lys His Arg Leu Arg Leu Phe Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
            260                 265                 270
```

```
Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 62
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 62

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Phe Lys Gly Gln His
            20                  25                  30

Trp Lys Phe Lys His His Ile Arg Leu Thr Phe His Val Ser Gln Lys
        35                  40                  45

Thr Gln Arg Arg Trp Phe Leu Asp Lys Leu Val Asp Glu Ile Gly Val
    50                  55                  60

Gly Tyr Val Thr Asp Trp Gly Ser Val Ser Gly Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Trp Ala Ala Ile Leu Pro Glu Gln Ser Tyr
    210                 215                 220

Arg Phe Lys His Arg Leu Arg Leu Ala Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
            260                 265                 270

Lys Pro Leu His Asn Phe Leu Thr Gln Leu Gln Pro Phe Leu Lys Leu
```

```
            275                 280                 285
Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 63
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 63

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Phe Lys Gly Gln His
            20                  25                  30

Trp Lys Phe Lys His His Ile Arg Leu Thr Phe His Val Ser Gln Lys
        35                  40                  45

Thr Gln Arg Arg Trp Phe Leu Asp Lys Leu Val Asp Glu Ile Gly Val
    50                  55                  60

Gly Tyr Val Thr Asp Trp Gly Ser Val Ser Gly Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Trp Ala Ser Ile Leu Pro Glu Arg Lys Thr
    210                 215                 220

Lys Phe Lys His Arg Leu Arg Leu Ala Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
            260                 265                 270

Lys Pro Leu His Asn Phe Leu Thr Gln Leu Gln Pro Phe Leu Lys Leu
        275                 280                 285
```

```
Lys Gln Lys Gln Ala Asn Leu Val Leu Lys Ile Ile Glu Gln Leu Pro
        290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
            325                 330                 335

Glu Thr Val Arg Ala Val Leu Asp Ser Leu Ser Glu Lys Lys Lys Ser
            340                 345                 350

Ser Pro

<210> SEQ ID NO 64
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 64

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Phe Lys Gly Gln His
            20                  25                  30

Trp Lys Phe Lys His His Ile Arg Leu Thr Phe His Val Ser Gln Lys
        35                  40                  45

Thr Gln Arg Arg Trp Phe Leu Asp Lys Leu Val Asp Glu Ile Gly Val
    50                  55                  60

Gly Tyr Val Thr Asp Trp Gly Ser Val Ser Gly Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Trp Ala Cys Ile Glu Pro Glu Arg Gly Tyr
    210                 215                 220

Arg Phe Lys His Arg Leu Arg Leu Ala Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
            260                 265                 270

Lys Pro Leu His Asn Phe Leu Thr Gln Leu Gln Pro Phe Leu Lys Leu
        275                 280                 285
```

```
Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro

<210> SEQ ID NO 65
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 65

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Phe Lys Gly Gln His
                20                  25                  30

Trp Lys Phe Lys His Tyr Ile Arg Leu Thr Phe Cys Val Ser Gln Lys
            35                  40                  45

Thr Gln Arg Arg Trp Phe Leu Asp Lys Leu Val Asp Glu Ile Gly Val
    50                  55                  60

Gly Tyr Val Asn Asp Ser Gly Ser Cys Ser Asn Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
                100                 105                 110

Pro Ser Ala Lys Glu Ser Pro Asp Lys Phe Leu Glu Val Cys Thr Trp
                115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
                180                 185                 190

Gly Thr Gly Tyr Asn Lys Glu Phe Leu Leu Tyr Leu Ala Gly Phe Val
            195                 200                 205

Asp Gly Asp Gly Ser Ile Trp Ala Arg Ile Glu Pro Glu Leu Arg Leu
    210                 215                 220

Arg Phe Lys His Arg Leu Arg Leu Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
                260                 265                 270

Lys Pro Leu His Asn Phe Leu Thr Gln Leu Gln Pro Phe Leu Lys Leu
                275                 280                 285

Lys Gln Lys Gln Ala Asn Leu Val Leu Lys Ile Ile Glu Gln Leu Pro
```

```
                290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro

<210> SEQ ID NO 66
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 66

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Phe Lys Gly Gln His
                20                  25                  30

Trp Lys Phe Lys His Tyr Ile Arg Leu Thr Phe Cys Val Ser Gln Lys
            35                  40                  45

Thr Gln Arg Arg Trp Phe Leu Asp Lys Leu Val Asp Glu Ile Gly Val
    50                  55                  60

Gly Tyr Val Asn Asp Ser Gly Ser Cys Ser Asn Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
                100                 105                 110

Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
                180                 185                 190

Gly Thr Gly Tyr Asn Lys Glu Phe Leu Leu Tyr Leu Ala Gly Phe Val
            195                 200                 205

Asp Gly Asp Gly Ser Ile Trp Ala Gln Ile Val Pro Glu Arg Ala Gly
    210                 215                 220

Arg Phe Lys His Arg Leu Arg Leu Tyr Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
                260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
    290                 295                 300
```

```
Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro

<210> SEQ ID NO 67
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 67

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Phe Lys Gly Gln His
                20                  25                  30

Trp Lys Phe Lys His His Ile Arg Leu Thr Phe Asn Val Ser Gln Lys
            35                  40                  45

Thr Gln Arg Arg Trp Phe Leu Asp Lys Leu Val Asp Glu Ile Gly Val
        50                  55                  60

Gly Tyr Val Cys Asp Ser Gly Ser Gln Ser Asn Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Trp Ala Ser Ile Thr Pro Glu Pro Thr Ala
    210                 215                 220

Ser Phe Lys His Arg Leu Arg Leu Tyr Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300
```

```
Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
            325                 330                 335

Glu Thr Val Arg Ala Val Leu Asp Ser Leu Ser Glu Lys Lys Lys Ser
            340                 345                 350

Ser Pro

<210> SEQ ID NO 68
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 68

Met Asn Thr Lys Tyr Asn Lys Glu Phe Leu Leu Tyr Leu Ala Gly Phe
1               5                   10                  15

Val Asp Gly Asp Gly Ser Ile Phe Ala Arg Ile Phe Lys Gly Gln His
            20                  25                  30

Trp Lys Phe Lys His His Ile Arg Leu Thr Phe Cys Val Ser Gln Lys
        35                  40                  45

Thr Gln Arg Arg Trp Phe Leu Asp Lys Leu Val Asp Glu Ile Gly Val
    50                  55                  60

Gly Tyr Val Val Asp Asn Gly Ser Met Ser Asn Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Trp Ala Ser Ile Asn Pro Glu Pro Ser Tyr
    210                 215                 220

Arg Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320
```

```
              305                 310                 315                 320
Asp Gln Ile Ala Ala Leu Asn Asp Ser Lys Thr Arg Lys Thr Thr Ser
                        325                 330                 335

Glu Thr Val Arg Ala Val Leu Asp Ser Leu Ser Glu Lys Lys Lys Ser
                340                 345                 350

Ser Pro

<210> SEQ ID NO 69
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 69

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Phe Lys Gly Gln His
                20                  25                  30

Trp Lys Phe Lys His His Ile Arg Leu Thr Phe Cys Val Thr Gln Lys
            35                  40                  45

Thr Gln Arg Arg Trp Phe Leu Asp Lys Leu Val Asp Glu Ile Gly Val
    50                  55                  60

Gly Tyr Val His Asp Tyr Gly Ser Cys Ser Asn Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Trp Ala Ser Ile Leu Pro Glu His Gln Tyr
    210                 215                 220

Arg Phe Lys His Arg Leu Arg Leu Gly Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320
```

-continued

```
Asp Gln Ile Ala Ala Leu Asn Asp Ser Lys Thr Arg Lys Thr Thr Ser
                325                 330                 335
Glu Thr Val Arg Ala Val Leu Asp Ser Leu Ser Glu Lys Lys Lys Ser
            340                 345                 350
Ser Pro

<210> SEQ ID NO 70
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 70

Met Asn Thr Lys Tyr Asn Lys Glu Phe Leu Leu Tyr Leu Ala Gly Phe
1               5                   10                  15
Val Asp Gly Asp Gly Ser Ile Tyr Ala Ala Ile Asp Pro Asp Gln Lys
            20                  25                  30
Tyr Lys Phe Lys His Arg Leu Arg Leu Ile Phe Ala Val Cys Gln Lys
        35                  40                  45
Thr Gln Arg Arg Trp Phe Leu Asp Lys Leu Val Asp Glu Ile Gly Val
    50                  55                  60
Gly Tyr Val Val Asp His Gly Ser Val Ser Glu Tyr Arg Leu Ser Gln
65                  70                  75                  80
Ile Lys Pro Leu His Asn Phe Leu Thr Gln Leu Gln Pro Phe Leu Lys
                85                  90                  95
Leu Lys Gln Lys Gln Ala Asn Leu Val Leu Lys Ile Ile Glu Gln Leu
            100                 105                 110
Pro Ser Ala Lys Glu Ser Pro Asp Lys Phe Leu Glu Val Cys Thr Trp
        115                 120                 125
Val Asp Gln Ile Ala Ala Leu Asn Asp Ser Lys Thr Arg Lys Thr Thr
    130                 135                 140
Ser Glu Thr Val Arg Ala Val Leu Asp Ser Leu Pro Gly Ser Val Gly
145                 150                 155                 160
Gly Leu Ser Pro Ser Gln Ala Ser Ser Ala Ser Ser Ala Ser Ser
                165                 170                 175
Ser Pro Gly Ser Gly Ile Ser Glu Ala Leu Arg Ala Gly Ala Gly Ser
            180                 185                 190
Gly Thr Gly Tyr Asn Lys Glu Phe Leu Leu Tyr Leu Ala Gly Phe Val
        195                 200                 205
Asp Gly Asp Gly Ser Ile Tyr Ala Arg Ile Glu Pro Arg Gln Thr Ala
    210                 215                 220
Lys Phe Lys His Tyr Leu Arg Leu Thr Phe His Val Ser Gln Lys Thr
225                 230                 235                 240
Gln Arg Arg Trp Phe Leu Asp Lys Leu Val Asp Glu Ile Gly Val Gly
                245                 250                 255
Tyr Val Val Asp Gln Gly Ser Val Ser Gln Tyr Phe Leu Ser Glu Ile
            260                 265                 270
Lys Pro Leu His Asn Phe Leu Thr Gln Leu Gln Pro Phe Leu Lys Leu
        275                 280                 285
Lys Gln Lys Gln Ala Asn Leu Val Leu Lys Ile Ile Glu Gln Leu Pro
    290                 295                 300
Ser Ala Lys Glu Ser Pro Asp Lys Phe Leu Glu Val Cys Thr Trp Val
305                 310                 315                 320
```

```
Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 71
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 71

Met Asn Thr Lys Tyr Asn Lys Glu Phe Leu Leu Tyr Leu Ala Gly Phe
1               5                   10                  15

Val Asp Gly Asp Gly Ser Ile Tyr Ala Thr Ile Glu Pro Ala Gln Arg
            20                  25                  30

Tyr Lys Phe Lys His Arg Leu Arg Leu Lys Phe Ala Val Ser Gln Lys
        35                  40                  45

Thr Gln Arg Arg Trp Phe Leu Asp Lys Leu Val Asp Glu Ile Gly Val
    50                  55                  60

Gly Tyr Val Ala Asp Gln Gly Ser Val Ser Glu Tyr Arg Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Arg Ile Glu Pro Arg Gln Thr Ala
    210                 215                 220

Lys Phe Lys His Tyr Leu Arg Leu Thr Phe His Val Ser Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Gln Tyr Phe Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
```

```
                    325                 330                 335

Glu Thr Val Arg Ala Val Leu Asp Ser Leu Ser Glu Lys Lys Lys Ser
                340                 345                 350

Ser Pro

<210> SEQ ID NO 72
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 72

Met Asn Thr Lys Tyr Asn Lys Glu Phe Leu Leu Tyr Leu Ala Gly Phe
1               5                   10                  15

Val Asp Gly Asp Gly Ser Ile Tyr Ala Thr Ile Asn Pro Asp Gln Thr
            20                  25                  30

Asn Lys Phe Lys His Arg Leu Arg Leu Trp Phe Ala Val Cys Gln Lys
        35                  40                  45

Thr Gln Arg Arg Trp Phe Leu Asp Lys Leu Val Asp Glu Ile Gly Val
    50                  55                  60

Gly Tyr Val Ala Asp Thr Gly Ser Val Ser Glu Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Arg Ile Glu Pro Arg Gln Thr Ala
    210                 215                 220

Lys Phe Lys His Tyr Leu Arg Leu Thr Phe His Val Ser Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Gln Tyr Phe Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335
```

-continued

```
Glu Thr Val Arg Ala Val Leu Asp Ser Leu Ser Glu Lys Lys Lys Ser
                340                 345                 350
Ser Pro

<210> SEQ ID NO 73
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 73

Met Asn Thr Lys Tyr Asn Lys Glu Phe Leu Leu Tyr Leu Ala Gly Phe
1               5                   10                  15

Val Asp Gly Asp Gly Ser Ile Tyr Ala Cys Ile Glu Pro Ala Gln Asn
                20                  25                  30

Ser Lys Phe Lys His Tyr Leu Arg Leu Arg Phe Glu Val Ser Gln Lys
            35                  40                  45

Thr Gln Arg Arg Trp Phe Leu Asp Lys Leu Val Asp Glu Ile Gly Val
        50                  55                  60

Gly Tyr Val Tyr Asp Gln Gly Ser Val Ser Ser Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
                100                 105                 110

Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
        130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Arg Ile Glu Pro Arg Gln Thr Ala
    210                 215                 220

Lys Phe Lys His Tyr Leu Arg Leu Thr Phe His Val Ser Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Gln Tyr Phe Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335
```

```
Glu Thr Val Arg Ala Val Leu Asp Ser Leu Ser Glu Lys Lys Lys Ser
            340                 345                 350

Ser Pro

<210> SEQ ID NO 74
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 74

Met Asn Thr Lys Tyr Asn Lys Glu Phe Leu Leu Tyr Leu Ala Gly Phe
1               5                  10                  15

Val Asp Gly Asp Gly Ser Ile Tyr Ala Ser Ile Thr Pro Cys Gln Ser
            20                  25                  30

Tyr Lys Phe Lys His Arg Leu Leu Lys Phe Ser Val Ala Gln Lys
        35                  40                  45

Thr Gln Arg Arg Trp Phe Leu Asp Lys Leu Val Asp Glu Ile Gly Val
    50                  55                  60

Gly Tyr Val Thr Asp Ser Gly Ser Val Ser Glu Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
        180                 185                 190

Gly Thr Gly Tyr Asn Lys Glu Phe Leu Leu Tyr Leu Ala Gly Phe Val
    195                 200                 205

Asp Gly Asp Gly Ser Ile Tyr Ala Arg Ile Glu Pro Arg Gln Thr Ala
    210                 215                 220

Lys Phe Lys His Tyr Leu Arg Leu Thr Phe His Val Ser Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Gln Tyr Phe Leu Ser Gln Ile
        260                 265                 270

Lys Pro Leu His Asn Phe Leu Thr Gln Leu Gln Pro Phe Leu Lys Leu
    275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
```

```
                340                 345                 350

Ser Pro

<210> SEQ ID NO 75
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 75

Met Asn Thr Lys Tyr Asn Lys Glu Phe Leu Leu Tyr Leu Ala Gly Phe
1               5                   10                  15

Val Asp Gly Asp Gly Ser Ile Tyr Ala Thr Ile Met Pro Glu Gln Thr
            20                  25                  30

Val Lys Phe Lys His Arg Leu Arg Leu Phe Phe Glu Val Ala Gln Lys
        35                  40                  45

Thr Gln Arg Arg Trp Phe Leu Asp Lys Leu Val Asp Glu Ile Gly Val
    50                  55                  60

Gly Tyr Val Tyr Asp Gln Gly Ser Val Ser Ser Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Arg Ile Glu Pro Arg Gln Thr Ala
    210                 215                 220

Lys Phe Lys His Tyr Leu Arg Leu Thr Phe His Val Ser Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Gln Tyr Phe Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350
```

Ser Pro

<210> SEQ ID NO 76
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 76

```
Met Asn Thr Lys Tyr Asn Lys Glu Phe Leu Leu Tyr Leu Ala Gly Phe
1               5                   10                  15

Val Asp Gly Asp Gly Ser Ile Tyr Ala Thr Ile Gln Pro Glu Gln Ala
            20                  25                  30

Pro Lys Phe Lys His Arg Leu Arg Leu His Phe Thr Val His Gln Lys
        35                  40                  45

Thr Gln Arg Arg Trp Phe Leu Asp Lys Leu Val Asp Glu Ile Gly Val
    50                  55                  60

Gly Tyr Val Tyr Asp Gln Gly Ser Val Ser Glu Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Arg Ile Glu Pro Arg Gln Thr Ala
    210                 215                 220

Lys Phe Lys His Tyr Leu Arg Leu Thr Phe His Val Ser Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Gln Tyr Phe Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350
```

Ser Pro

<210> SEQ ID NO 77
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 77

```
Met Asn Thr Lys Tyr Asn Lys Glu Phe Leu Leu Tyr Leu Ala Gly Phe
1               5                   10                  15

Val Asp Gly Asp Gly Ser Ile Trp Ala Thr Ile Glu Pro Ser Gln Thr
            20                  25                  30

Leu Lys Phe Lys His Arg Leu Arg Leu His Phe Ser Val Tyr Gln Lys
        35                  40                  45

Thr Gln Arg Arg Trp Phe Leu Asp Lys Leu Val Asp Glu Ile Gly Val
    50                  55                  60

Gly Tyr Val Tyr Asp Asp Gly Ser Val Ser Arg Tyr Gln Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Arg Ile Glu Pro Arg Gln Thr Ala
    210                 215                 220

Lys Phe Lys His Tyr Leu Arg Leu Thr Phe His Val Ser Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Gln Tyr Phe Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro
```

```
<210> SEQ ID NO 78
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 78

Met Asn Thr Lys Tyr Asn Lys Glu Phe Leu Leu Tyr Leu Ala Gly Phe
1               5                   10                  15

Val Asp Gly Asp Gly Ser Ile Tyr Ala Ser Ile Thr Pro Cys Gln Ser
            20                  25                  30

Tyr Lys Phe Lys His Arg Leu Leu Lys Phe Ser Val Ala Gln Lys
        35                  40                  45

Thr Gln Arg Arg Trp Phe Leu Asp Lys Leu Val Asp Glu Ile Gly Val
    50                  55                  60

Gly Tyr Val Thr Asp Ser Gly Ser Val Ser Glu Tyr Arg Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Arg Ile Glu Pro Arg Gln Thr Ala
    210                 215                 220

Lys Phe Lys His Tyr Leu Arg Leu Thr Phe His Val Ser Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Gln Tyr Phe Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Ser
            340                 345                 350

Ser Pro
```

<210> SEQ ID NO 79
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 79

```
Met Asn Thr Lys Tyr Asn Lys Glu Phe Leu Leu Tyr Leu Ala Gly Phe
1               5                   10                  15

Val Asp Gly Asp Gly Ser Ile Tyr Ala Thr Ile Ile Pro Ser Gln Asn
            20                  25                  30

Leu Lys Phe Lys His Arg Leu Arg Leu Tyr Phe Glu Val Cys Gln Lys
        35                  40                  45

Thr Gln Arg Arg Trp Phe Leu Asp Lys Leu Val Asp Glu Ile Gly Val
    50                  55                  60

Gly Tyr Val Tyr Asp Gln Gly Ser Val Ser Ser Tyr Arg Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Arg Ile Glu Pro Arg Gln Thr Ala
    210                 215                 220

Lys Phe Lys His Tyr Leu Arg Leu Thr Phe His Val Ser Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Gln Tyr Phe Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro
```

<210> SEQ ID NO 80
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 80

```
Met Asn Thr Lys Tyr Asn Lys Glu Phe Leu Leu Tyr Leu Ala Gly Phe
1               5                   10                  15

Val Asp Gly Asp Gly Ser Ile Tyr Ala Ser Ile Cys Pro Thr Gln Ala
            20                  25                  30

Ala Lys Phe Lys His Arg Leu Arg Leu His Phe Ala Val Phe Gln Lys
        35                  40                  45

Thr Gln Arg Arg Trp Phe Leu Asp Lys Leu Val Asp Glu Ile Gly Val
    50                  55                  60

Gly Tyr Val Thr Asp Cys Gly Ser Val Ser Glu Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Arg Ile Glu Pro Arg Gln Thr Ala
    210                 215                 220

Lys Phe Lys His Tyr Leu Arg Leu Thr Phe His Val Ser Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Gln Tyr Phe Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro
```

<210> SEQ ID NO 81

```
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 81

Met Asn Thr Lys Tyr Asn Lys Glu Phe Leu Leu Tyr Leu Ala Gly Phe
1               5                   10                  15

Val Asp Gly Asp Gly Ser Ile Tyr Ala Ser Ile Glu Pro Ala Gln Ser
            20                  25                  30

Tyr Lys Phe Lys His Arg Leu Gln Leu Lys Phe Ala Val Ala Gln Lys
        35                  40                  45

Thr Gln Arg Arg Trp Phe Leu Asp Lys Leu Val Asp Glu Ile Gly Val
    50                  55                  60

Gly Tyr Val Cys Asp Ile Gly Ser Val Ser Glu Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Arg Ile Glu Pro Arg Gln Thr Ala
    210                 215                 220

Lys Phe Lys His Tyr Leu Arg Leu Thr Phe His Val Ser Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Gln Tyr Phe Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 82
<211> LENGTH: 354
```

<212> TYPE: PRT
<213> ORGANISM: Artificial Sequence
<220> FEATURE:
<223> OTHER INFORMATION: Synthetic Polypeptide

<400> SEQUENCE: 82

Met Asn Thr Lys Tyr Asn Lys Glu Phe Leu Leu Tyr Leu Ala Gly Phe
1               5                   10                  15

Val Asp Gly Asp Gly Ser Ile Tyr Ala Ala Ile Met Pro Thr Gln Ser
            20                  25                  30

Tyr Lys Phe Lys His Arg Leu Arg Leu Ala Phe Ser Val Ser Gln Lys
        35                  40                  45

Thr Gln Arg Arg Trp Phe Leu Asp Lys Leu Val Asp Glu Ile Gly Val
    50                  55                  60

Gly Tyr Val Thr Asp Ala Gly Ser Val Ser Glu Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
            195                 200                 205

Asp Gly Asp Gly Ser Ile Tyr Ala Arg Ile Glu Pro Arg Gln Thr Ala
        210                 215                 220

Lys Phe Lys His Tyr Leu Arg Leu Thr Phe His Val Ser Gln Lys Thr
225                 230                 235                 240

Gln Arg Arg Trp Phe Leu Asp Lys Leu Val Asp Glu Ile Gly Val Gly
            245                 250                 255

Tyr Val Val Asp Gln Gly Ser Val Ser Gln Tyr Phe Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 83
<211> LENGTH: 354
<212> TYPE: PRT

<213> ORGANISM: Artificial Sequence
<220> FEATURE:
<223> OTHER INFORMATION: Synthetic Polypeptide

<400> SEQUENCE: 83

```
Met Asn Thr Lys Tyr Asn Lys Glu Phe Leu Leu Tyr Leu Ala Gly Phe
1               5                   10                  15

Val Asp Gly Asp Gly Ser Ile Tyr Ala Thr Ile Thr Pro Asn Gln Arg
            20                  25                  30

Thr Lys Phe Lys His Gln Leu Lys Leu Ala Phe Ala Val Tyr Gln Lys
        35                  40                  45

Thr Gln Arg Arg Trp Phe Leu Asp Lys Leu Val Asp Glu Ile Gly Val
50                  55                  60

Gly Tyr Val Tyr Asp Gln Gly Ser Val Ser Cys Tyr Arg Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Arg Ile Glu Pro Arg Gln Thr Ala
    210                 215                 220

Lys Phe Lys His Tyr Leu Arg Leu Thr Phe His Val Ser Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Gln Tyr Phe Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Ser
            340                 345                 350

Ser Pro
```

<210> SEQ ID NO 84
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 84

Met Asn Thr Lys Tyr Asn Lys Glu Phe Leu Leu Tyr Leu Ala Gly Phe
1               5                   10                  15

Val Asp Gly Asp Gly Ser Ile Tyr Ala Ala Ile Val Pro Val Gln Ser
            20                  25                  30

Thr Lys Phe Lys His Arg Leu Arg Leu Tyr Phe Thr Val His Gln Lys
        35                  40                  45

Thr Gln Arg Arg Trp Phe Leu Asp Lys Leu Val Asp Glu Ile Gly Val
    50                  55                  60

Gly Tyr Val Tyr Asp Gln Gly Ser Val Ser Glu Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Arg Ile Glu Pro Arg Gln Thr Ala
    210                 215                 220

Lys Phe Lys His Tyr Leu Arg Leu Thr Phe His Val Ser Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Gln Tyr Phe Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 85
<211> LENGTH: 354
<212> TYPE: PRT
<213> ORGANISM: Artificial Sequence
<220> FEATURE:

<223> OTHER INFORMATION: Synthetic Polypeptide

<400> SEQUENCE: 85

```
Met Asn Thr Lys Tyr Asn Lys Glu Phe Leu Leu Tyr Leu Ala Gly Phe
1               5                   10                  15

Val Asp Gly Asp Gly Ser Ile Tyr Ala Thr Ile Cys Pro Val Gln Ser
            20                  25                  30

Leu Lys Phe Lys His Arg Leu Arg Leu Phe Phe Ala Val Cys Gln Lys
        35                  40                  45

Thr Gln Arg Arg Trp Phe Leu Asp Lys Leu Val Asp Glu Ile Gly Val
    50                  55                  60

Gly Tyr Val Val Asp His Gly Ser Val Ser Tyr Arg Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Val Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Arg Ile Glu Pro Arg Gln Thr Ala
    210                 215                 220

Lys Phe Lys His Tyr Leu Arg Leu Thr Phe His Val Ser Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Gln Tyr Phe Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro
```

<210> SEQ ID NO 86
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 86

Met Asn Thr Lys Tyr Asn Lys Glu Phe Leu Leu Tyr Leu Ala Gly Phe
1               5                   10                  15

Val Asp Gly Asp Gly Ser Ile Trp Ala Ser Ile Leu Pro Glu Gln Arg
            20                  25                  30

Asn Lys Phe Lys His Arg Leu Lys Leu Gly Phe Ser Val Ser Gln Lys
        35                  40                  45

Thr Gln Arg Arg Trp Phe Leu Asp Lys Leu Val Asp Glu Ile Gly Val
    50                  55                  60

Gly Tyr Val Val Asp Gln Gly Ser Val Ser Glu Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
        180                 185                 190

Gly Thr Gly Tyr Asn Lys Glu Phe Leu Leu Tyr Leu Ala Gly Phe Val
            195                 200                 205

Asp Gly Asp Gly Ser Ile Tyr Ala Arg Ile Glu Pro Arg Gln Thr Ala
        210                 215                 220

Lys Phe Lys His Tyr Leu Arg Leu Thr Phe His Val Ser Gln Lys Thr
225                 230                 235                 240

Gln Arg Arg Trp Phe Leu Asp Lys Leu Val Asp Glu Ile Gly Val Gly
            245                 250                 255

Tyr Val Val Asp Gln Gly Ser Val Ser Gln Tyr Phe Leu Ser Gln Ile
        260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 87
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 87

```
Met Asn Thr Lys Tyr Asn Lys Glu Phe Leu Leu Tyr Leu Ala Gly Phe
1               5                   10                  15

Val Asp Gly Asp Gly Ser Ile Tyr Ala Thr Ile His Pro Cys Gln Cys
            20                  25                  30

Thr Lys Phe Lys His Arg Leu Arg Leu Tyr Phe Glu Val Tyr Gln Lys
        35                  40                  45

Thr Gln Arg Arg Trp Phe Leu Asp Lys Leu Val Asp Glu Ile Gly Val
    50                  55                  60

Gly Tyr Val Tyr Asp Gln Gly Ser Val Ser Ser Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Arg Ile Glu Pro Arg Gln Thr Ala
    210                 215                 220

Lys Phe Lys His Tyr Leu Arg Leu Thr Phe His Val Ser Gln Lys Thr
225                 230                 235                 240

Gln Arg Arg Trp Phe Leu Asp Lys Leu Val Asp Glu Ile Gly Val Gly
                245                 250                 255

Tyr Val Thr Asp Trp Gly Ser Val Ser Gly Tyr Tyr Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro
```

<210> SEQ ID NO 88
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 88

```
Met Asn Thr Lys Tyr Asn Lys Glu Phe Leu Leu Tyr Leu Ala Gly Phe
1               5                   10                  15

Val Asp Gly Asp Gly Ser Ile Tyr Ala Thr Ile Asp Pro Asp Gln Arg
            20                  25                  30

Gln Lys Phe Lys His Arg Leu Arg Leu Lys Phe Ser Val Ser Gln Lys
        35                  40                  45

Thr Gln Arg Arg Trp Phe Leu Asp Lys Leu Val Asp Glu Ile Gly Val
    50                  55                  60

Gly Tyr Val Val Asp Gly Gly Ser Val Ser Glu Tyr Arg Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Cys Ile Glu Pro Lys Gln Thr Ser
    210                 215                 220

Lys Phe Lys His Arg Leu Cys Leu Arg Phe His Val Ser Gln Lys Thr
225                 230                 235                 240

Gln Arg Arg Trp Phe Leu Asp Lys Leu Val Asp Glu Ile Gly Val Gly
                245                 250                 255

Tyr Val His Asp Asn Gly Ser Val Ser Gln Tyr Tyr Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 89
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 89
```

| | | | | | | | | | | | | | | |
|---|---|---|---|---|---|---|---|---|---|---|---|---|---|---|
|Met|Asn|Thr|Lys|Tyr|Asn|Lys|Glu|Phe|Leu|Leu|Tyr|Leu|Ala|Gly|Phe|
|1| | | |5| | | |10| | | |15| | |

Val Asp Gly Asp Gly Ser Ile Tyr Ala Ala Ile Val Pro Asp Gln Ala
          20                  25                  30

Pro Lys Phe Lys His Arg Leu Arg Leu Phe Phe Ala Val Ser Gln Lys
              35                  40                  45

Thr Gln Arg Arg Trp Phe Leu Asp Lys Leu Val Asp Glu Ile Gly Val
 50                  55                  60

Gly Tyr Val Ala Asp Gln Gly Ser Val Ser Glu Tyr Arg Leu Ser Gln
 65                  70                  75                  80

Ile Lys Pro Leu His Asn Phe Leu Thr Gln Leu Gln Pro Phe Leu Lys
                  85                  90                  95

Leu Lys Gln Lys Gln Ala Asn Leu Val Leu Lys Ile Ile Glu Gln Leu
              100                 105                 110

Pro Ser Ala Lys Glu Ser Pro Asp Lys Phe Leu Glu Val Cys Thr Trp
              115                 120                 125

Val Asp Gln Ile Ala Ala Leu Asn Asp Ser Lys Thr Arg Lys Thr Thr
 130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                  165                 170                 175

Ser Pro Gly Ser Gly Ile Ser Glu Ala Leu Arg Ala Gly Ala Gly Ser
              180                 185                 190

Gly Thr Gly Tyr Asn Lys Glu Phe Leu Leu Tyr Leu Ala Gly Phe Val
              195                 200                 205

Asp Gly Asp Gly Ser Ile Tyr Ala Arg Ile Tyr Pro Gly Gln His Tyr
 210                 215                 220

Lys Phe Lys His Tyr Leu Arg Leu Thr Phe His Val Ser Gln Lys Thr
225                 230                 235                 240

Gln Arg Arg Trp Phe Leu Asp Lys Leu Val Asp Glu Ile Gly Val Gly
                  245                 250                 255

Tyr Val Thr Asp Ala Gly Ser Val Ser Gln Tyr Phe Leu Ser Gln Ile
              260                 265                 270

Lys Pro Leu His Asn Phe Leu Thr Gln Leu Gln Pro Phe Leu Lys Leu
              275                 280                 285

Lys Gln Lys Gln Ala Asn Leu Val Leu Lys Ile Ile Glu Gln Leu Pro
              290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                  325                 330                 335

Glu Thr Val Arg Ala Val Leu Asp Ser Leu Ser Glu Lys Lys Lys Ser
              340                 345                 350

Ser Pro

<210> SEQ ID NO 90
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 90

Met Asn Thr Lys Tyr Asn Lys Glu Phe Leu Leu Tyr Leu Ala Gly Phe

```
                1               5                   10                  15
            Val Asp Gly Asp Gly Ser Ile Tyr Ala Ser Ile Leu Pro Glu Gln Arg
                                20                  25                  30
            Asn Lys Phe Lys His Arg Leu Lys Leu Ser Phe Ser Val Cys Gln Lys
                                35                  40                  45
            Thr Gln Arg Arg Trp Phe Leu Asp Lys Leu Val Asp Glu Ile Gly Val
                50                              55                  60
            Gly Tyr Val Val Asp Gln Gly Ser Val Ser Glu Tyr Arg Leu Ser Glu
            65                              70                  75              80
            Ile Lys Pro Leu His Asn Phe Leu Thr Gln Leu Gln Pro Phe Leu Lys
                                85                  90                  95
            Leu Lys Gln Lys Gln Ala Asn Leu Val Leu Lys Ile Ile Glu Gln Leu
                            100                 105                 110
            Pro Ser Ala Lys Glu Ser Pro Asp Lys Phe Leu Glu Val Cys Thr Trp
                            115                 120                 125
            Val Asp Gln Ile Ala Ala Leu Asn Asp Ser Lys Thr Arg Lys Thr Thr
            130                             135                 140
            Ser Glu Thr Val Arg Ala Val Leu Asp Ser Leu Pro Gly Ser Val Gly
            145                 150                 155                 160
            Gly Leu Ser Pro Ser Gln Ala Ser Ser Ala Ser Ser Ala Ser Ser Ser
                            165                 170                 175
            Ser Pro Gly Ser Gly Ile Ser Glu Ala Leu Arg Ala Gly Ala Gly Ser
                            180                 185                 190
            Gly Thr Gly Tyr Asn Lys Glu Phe Leu Leu Tyr Leu Ala Gly Phe Val
                            195                 200                 205
            Asp Gly Asp Gly Ser Ile Tyr Ala Arg Ile Glu Pro Arg Gln Thr Ala
                210                             215                 220
            Lys Phe Lys His Tyr Leu Arg Leu Thr Phe His Val Ser Gln Lys Thr
            225                 230                 235                 240
            Gln Arg Arg Trp Phe Leu Asp Lys Leu Val Asp Glu Ile Gly Val Gly
                            245                 250                 255
            Tyr Val Ile Asp Ala Gly Ser Val Ser Gly Tyr Tyr Leu Ser Glu Ile
                            260                 265                 270
            Lys Pro Leu His Asn Phe Leu Thr Gln Leu Gln Pro Phe Leu Lys Leu
                            275                 280                 285
            Lys Gln Lys Gln Ala Asn Leu Val Leu Lys Ile Ile Glu Gln Leu Pro
                            290                 295                 300
            Ser Ala Lys Glu Ser Pro Asp Lys Phe Leu Glu Val Cys Thr Trp Val
            305                 310                 315                 320
            Asp Gln Ile Ala Ala Leu Asn Asp Ser Lys Thr Arg Lys Thr Thr Ser
                                325                 330                 335
            Glu Thr Val Arg Ala Val Leu Asp Ser Leu Ser Glu Lys Lys Lys Ser
                            340                 345                 350
            Ser Pro
```

<210> SEQ ID NO 91
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 91

```
            Met Asn Thr Lys Tyr Asn Lys Glu Phe Leu Leu Tyr Leu Ala Gly Phe
            1               5                   10                  15
```

-continued

Val Asp Gly Asp Gly Ser Ile Tyr Ala Ala Ile Val Pro Asp Gln Ala
            20                  25                  30

Pro Lys Phe Lys His Arg Leu Arg Leu Phe Phe Ala Val Ser Gln Lys
        35                  40                  45

Thr Gln Arg Arg Trp Phe Leu Asp Lys Leu Val Asp Glu Ile Gly Val
 50                  55                  60

Gly Tyr Val Ala Asp Gln Gly Ser Val Ser Glu Tyr Arg Leu Ser Glu
 65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Cys Ile Glu Pro Lys Gln Thr Ser
210                 215                 220

Lys Phe Lys His Arg Leu Cys Leu Arg Phe His Val Ser Gln Lys Thr
225                 230                 235                 240

Gln Arg Arg Trp Phe Leu Asp Lys Leu Val Asp Glu Ile Gly Val Gly
                245                 250                 255

Tyr Val His Asp Asn Gly Ser Val Ser Gln Tyr Tyr Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 92
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 92

Met Asn Thr Lys Tyr Asn Lys Glu Phe Leu Leu Tyr Leu Ala Gly Phe
1               5                   10                  15

Val Asp Gly Asp Gly Ser Ile Tyr Ala Cys Ile Cys Pro Asp Gln Gly
            20                  25                  30

Tyr Lys Phe Lys His Arg Leu Thr Leu Lys Phe Ser Val Ala Gln Lys
        35                  40                  45

Thr Gln Arg Arg Trp Phe Leu Asp Lys Leu Val Asp Glu Ile Gly Val
    50                  55                  60

Gly Tyr Val Leu Asp Gln Gly Ser Val Ser Glu Tyr Arg Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Arg Ile Glu Pro Arg Gln Thr Ala
    210                 215                 220

Lys Phe Lys His Gln Leu Arg Leu Thr Phe His Val Ser Gln Lys Thr
225                 230                 235                 240

Gln Arg Arg Trp Phe Leu Asp Lys Leu Val Asp Glu Ile Gly Val Gly
                245                 250                 255

Tyr Val Thr Asp Trp Gly Ser Val Ser Gly Tyr Tyr Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 93
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 93

Met Asn Thr Lys Tyr Asn Lys Glu Phe Leu Leu Tyr Leu Ala Gly Phe
1               5                   10                  15

Val Asp Gly Asp Gly Ser Ile Tyr Ala Cys Ile Leu Pro Glu Gln Lys

```
            20                  25                  30
Thr Lys Phe Lys His Arg Leu Lys Leu Ser Phe Thr Val Cys Gln Lys
        35                  40                  45

Thr Gln Arg Arg Trp Phe Leu Asp Lys Leu Val Asp Glu Ile Gly Val
    50                  55                  60

Gly Tyr Val Val Asp Gln Gly Ser Val Ser Glu Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Arg Ile Glu Pro Arg Gln Thr Val
    210                 215                 220

Lys Phe Lys His Met Leu Arg Leu Thr Phe His Val Ser Gln Lys Thr
225                 230                 235                 240

Gln Arg Arg Trp Phe Leu Asp Lys Leu Val Asp Glu Ile Gly Val Gly
                245                 250                 255

Tyr Val His Asp Asn Gly Ser Val Ser Gln Tyr Tyr Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 94
<211> LENGTH: 163
<212> TYPE: PRT
<213> ORGANISM: Artificial Sequence
<220> FEATURE:
<223> OTHER INFORMATION: Synthetic Polypeptide

<400> SEQUENCE: 94

Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Lys Pro Asn Gln Ser
            20                  25                  30
```

Tyr Lys Phe Lys His Gln Leu Ser Leu Ala Phe Gln Val Thr Gln Lys
            35                  40                  45

Thr Gln Arg Arg Trp Phe Leu Asp Lys Leu Val Asp Glu Ile Gly Val
    50                  55                  60

Gly Tyr Val Arg Asp Arg Gly Ser Val Ser Asp Tyr Ile Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Trp Arg Leu
            100                 105                 110

Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Ser Glu Lys Lys Lys
145                 150                 155                 160

Ser Ser Pro

<210> SEQ ID NO 95
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 95

Leu Ala Gly Leu Ile Asp Ala Asp Gly
1               5

<210> SEQ ID NO 96
<211> LENGTH: 1047
<212> TYPE: DNA
<213> ORGANISM: Artificial Sequence
<220> FEATURE:
<223> OTHER INFORMATION: Synthetic Polynucleotide

<400> SEQUENCE: 96
atgaatggca cagaaggccc taacttctac gtgcccttct ccaatgcgac gggtgtggta      60
cgcagcccct tcgagtaccc acagtactac ctggctgagc catggcagtt ctccatgctg     120
gccgcctaca tgtttctgct gatcgtgctg ggcttcccca tcaacttcct cacgctctac     180
gtcaccgtcc agcacaagaa gctgcgcacg cctctcaact catcctgct caacctagcc     240
gtggctgacc tcttcatggt cctaggtggc ttcaccagca ccctctacac ctctctgcat     300
ggatacttcg tcttcgggcc cacaggatgc aatttggagg gcttctttgc caccctgggc     360
ggtgaaattg ccctgtggtc cttggtggtc ctggccatcg agcggtacgt ggtggtgtgt     420
aagcccatga gcaacttccg cttcggggag aaccatgcca tcatgggcgt tgccttcacc     480
tgggtcatgg cgctggcctg cgccgcaccc ccactcgccg gctggtccag gtacatcccc     540
gagggcctgc agtgctcgtg tggaatcgac tactacacgc tcaagccgga ggtcaacaac     600
gagtcttttg tcatctacat gttcgtggtc cacttcacca tccccatgat tatcatcttt     660
ttctgctatg gcagctcgt cttcaccgtc aaggaggccg ctgcccagca gcaggagtca     720
gccaccacac agaaggcaga gaaggaggtc acccgcatgg tcatcatcat ggtcatcgct     780
ttcctgatct gctgggtgcc ctacgccagc gtggcattct acatcttcac ccaccagggc     840
tccaacttcg gtcccatctt catgaccatc ccagcgttct tgccaagag cgccgccatc     900

| | |
|---|---|
| tacaaccctg tcatctatat catgatgaac aagcagttcc ggaactgcat gctcaccacc | 960 |
| atctgctgcg gcaagaaccc actgggtgac gatgaggcct ctgctaccgt gtccaagacg | 1020 |
| gagacgagcc aggtggcccc ggcctaa | 1047 |

<210> SEQ ID NO 97
<211> LENGTH: 1047
<212> TYPE: DNA
<213> ORGANISM: Artificial Sequence
<220> FEATURE:
<223> OTHER INFORMATION: Synthetic Polynucleotide

<400> SEQUENCE: 97

| | |
|---|---|
| atgaatggca cagaaggccc taacttctac gtgcccttct ccaatgcgac gggtgtggta | 60 |
| cgcagccact tcgagtaccc acagtactac ctggctgagc catggcagtt ctccatgctg | 120 |
| gccgcctaca tgtttctgct gatcgtgctg ggcttcccca tcaacttcct cacgctctac | 180 |
| gtcaccgtcc agcacaagaa gctgcgcacg cctctcaact acatcctgct caacctagcc | 240 |
| gtggctgacc tcttcatggt cctaggtggc ttcaccagca ccctctacac ctctctgcat | 300 |
| ggatacttcg tcttcgggcc cacaggatgc aatttggagg gcttctttgc caccctgggc | 360 |
| ggtgaaattg ccctgtggtc cttggtggtc ctggccatcg agcggtacgt ggtggtgtgt | 420 |
| aagcccatga gcaacttccg cttcggggag aaccatgcca tcatgggcgt tgccttcacc | 480 |
| tgggtcatgg cgctggcctg cgccgcaccc ccactcgccg gctggtccag gtacatcccc | 540 |
| gagggcctgc agtgctcgtg tggaatcgac tactacacgc tcaagccgga ggtcaacaac | 600 |
| gagtcttttg tcatctacat gttcgtggtc cacttcacca tccccatgat tatcatcttt | 660 |
| ttctgctatg ggcagctcgt cttcaccgtc aaggaggccg ctgcccagca gcaggagtca | 720 |
| gccaccacac agaaggcaga aaggaggtc accogcatgg tcatcatcat ggtcatcgct | 780 |
| ttcctgatct gctgggtgcc ctacgccagc gtggcattct acatcttcac ccaccagggc | 840 |
| tccaacttcg gtcccatctt catgaccatc ccagcgttct tgccaagag cgccgccatc | 900 |
| tacaaccctg tcatctatat catgatgaac aagcagttcc ggaactgcat gctcaccacc | 960 |
| atctgctgcg gcaagaaccc actgggtgac gatgaggcct ctgctaccgt gtccaagacg | 1020 |
| gagacgagcc aggtggcccc ggcctaa | 1047 |

<210> SEQ ID NO 98
<211> LENGTH: 13706
<212> TYPE: DNA
<213> ORGANISM: Artificial Sequence
<220> FEATURE:
<223> OTHER INFORMATION: Synthetic Polynucleotide

<400> SEQUENCE: 98

| | |
|---|---|
| gtgggggacc aggagaaaga aagccaagga agaggaggag gaggaggaga aggaggagaa | 60 |
| ggatgctgac ctagcagctc ctctcacagc agctcctctc ttgcagaggc tgaagagcga | 120 |
| tttgtgccct gcaagctaag cccctaatcc accgaggcaa aggcaaagcc cctagccggg | 180 |
| ctcccgaggg ctgggactcg ggtgccccaa gatggctgca tccagccatc ttggcttaga | 240 |
| aagccccca catgccagct tggccaacac ccacaccatg ggtttctctg gactgccga | 300 |
| cacaaggtgt gggtgctggc caggcctgtg ttcaaatccc agctctgcag aggaactttg | 360 |
| accctgcata ccccagattc ctcagtggtc agtggggagt tagaccctct tcatagggg | 420 |
| caggaggagt tgttcattca ttcaacaaat gtttattgaa cacctcctat gggttgtgag | 480 |

```
ctcagaggca gcgatgaaca ggccaggctg gtcctgcatt ctagaaatag atgggaagtc    540
agtcaataag tagacaaatg aggccaggtg tggtggcatg cctgtagacc cagttactcg    600
ggatgctgag gtaggaggat cacttgagcc taggacagga attcaaggct gcagtaagct    660
atgattgcgc cactgcactc cagcctgggc aacagagcaa gactcatctc taaaaaacat    720
ttaaaaattg ttttaagaag acaaatgaga tagtcgctga tggtaatgac tgtgtaaaaa    780
ctgaacatgg ctgggtgtgg ttgctcacac ctataatctc agcactttgg gaggctgaga    840
ttacagcctc ccaagtggct cccaaggcag gaggatcact tgagcctggg agttagagaa    900
cagcttggac aatatagga gagcccaact ctacaaaaat gaaataaat tagccaggca    960 tggtggcaca caccaatggt cccagctact caggggttga ggtggtggac cgcttgagcc    1020
caggaggttg aggctgcagt gagccatgat catgccgctg cactccaacc tgagtcacag    1080
agtgataccc tgtctcaaaa aacaataggc caggtgtggt ggctcacgcc tgtaacccca    1140
gcactttggg aggccgaggc ggatggatca cttgagatca ggagttagag accagcctgg    1200
ctaacatggc aaaatcctgt ctgtactaaa aatataaaaa ttagccaggc atggcagtac    1260
atgcctgtag tcctggttac ttgggaggct aaggcaggag aatcgcttga acccaggaag    1320
aggaggttgc agtgagccaa gatcacacca ctgcactcca gcttgggtga cagagtgaga    1380
ccctgtctca aaacagctaa acctggtggg ggtgcctggt gtgtaggatg gtcaggggtg    1440
gtctctccaa ggacatgagt gtgagcgag acctgaagga gactcaggaa gagattaata    1500
ctgtcagcaa caaatatatt gatcacttac aagcactccc aataatccta ttaggtaggc    1560
actattatca ttcccatttt acagagtgga gaaccgaagc acactctcgg gagggcgggg    1620
tagctggctg cacccaggct gtgtagcctc agtccagatg taagggtggg tggaaaagag    1680
ccttgcccaa tgagggagaa cagtgaaacc aaggccatag ggtctaaaga ttcacgaacc    1740
aggctctcat ggagaaagca ggtgaggttt actgtataga tgggtgtgcc cctaccccac    1800
actgaggctt cctcgtctga gcaaactgag gcccagagag gggaaggaag caggactacc    1860
atggtgactc aaagaccagc tagaatccag cctcctctcc tcgaggcttc cactgcccca    1920
cgccaggcct gtgtgactca gtctagggcc tttccattac cccagctaaa cctttctttt    1980
gtcatttata ccatggtgtg aatggctggc tggtcttttcc tgagagctat ctttgatgag    2040
gggagggagg catagccagg tttgggaagc tgataccccca ggaagcccag ttgactgtgt    2100
gggttatagc ccaggctgtc actgattttgt aacgggacct gagcaactct gcagagctag    2160
gcctcagtct tttcatctgc aaaatggata tagcagagat ggtcagagta ggtgacttcg    2220 aatgacccctt ccagctcact atgagtctgt tttcctgaac aaagagcatt ttttgtttaa    2280
aaaaaatttt cttgggccgg acacggtggt tcactcctat aatcctggca ctttgggagg    2340
ccgaggaggg tggatcgctt gagccaggag ttcaggacca gcctgggcaa catagcgaga    2400
ctccacccct acaaaaaata caaaaactag tggtgtgcac ttgtggtccc agctactcag    2460
gaggctgagg tgagaggatc gcttgagccc aggaggcaga ggctacagtg agctatgatt    2520
gtggcactgc actccagcct gggcgacaga gaccttgtct caaaactttt tttttcttcg    2580
tcaagcttta cagaataaag agcactgtca cctcagtgat ggctgttagt tccccatcac    2640
cagggctcca tgaggttgca attgtgaaac tcacaaagga ggaacctgag acagagaggg    2700
gaagtactga gatcatctag gtccattccc ccactcactc gttcattcaa caaatattca    2760
ggagcacctt ctaggtgcca ggccctggag acacatcagt gaacaaaaca gacatcatcc    2820
cacctctttc cactacaggc caagcaccat gctggtctct gggaaccctg ttgtgagcaa    2880
```

```
gacagaccca ggcttaccct tgtggactca tgttacaggc agggagacgg gcacaaaaca   2940
caaataaaaa gcttccatgc tgtcagaagc actatgcaaa aagcaagatg ctgaggtact   3000
gctaagctgt gtgggatggg ggctcagccc ggccagggag gggccagttg tgggtcagtc   3060
ttgacccaag gcatccagga caccctcctt ctggccatga gggtccacgt cagaatcaaa   3120
ccctcacctt aacctcatta gcgttgggca taatcaccag gccaagcgcc ttaaactacg   3180
agaggcccca tcccacccgc cctgccttag ccctgccacg tgtgccaaac gctgttagac   3240
ccaacaccac ccaggccagg taggggctg gagcccaggt gggctgcagg aaggggca     3300 ctcttctgag cagacagatc tgggaatcct gggtgggaag agagacagtg agagagagat   3360
taagggatat tcccaggca tcagggcttt gcactctcag gggtccttcc gcctggatgt    3420
ccttcccctg aagcttcctc ctgttgttcc gttctcagct caagtccag cttctcagag    3480 aagcctcctg tgttgggagt ggctgcgact gaactgtccc tactgttatt cgctcttcta   3540
tttgtttgtg gtccctgtgc cccctcaccc cacaaaaaca ctggcttctt gtgagcagga   3600
gcttgctctt tcgtgtaccc tgtgtgtccc caaggaccaa gcaccttgtc tgggccacag   3660
taggtgctca atacacatgt tggctggaca gtggtcactg agcggccgca cgtcgggcac   3720
tctcagcact tgcacaggcc gccccagaca ccccacttca ttcctgggag gtgtcatcat   3780
gttgcttgga cgacggggag agggggacct gccagtgttg gcctccattt tcccccagtc   3840
atctgccccc aaggctctga ctactttctt tctcacggta catcctgcta ttctggaatc   3900
ggccctcgtg gggccacctg gtacatggca tttgaggccc tcgtggctga ttaggcctcc   3960
cccaacagtg ccctgtctgc tgcctccagg gccagcctcc ccttcagact ggagtcccct   4020
gaagggttct gccctcccc tgctctggta gccccctcca tcctccctcc ctccactcca    4080
tctttggggg catttgagtc acctttctac accagtgatc tgcccaagcc actgctcact   4140
ttcctctgga taaagccagg ttccccggcc tagcgttcaa gacccattac aactgccccc   4200
agcccagatc ttccccacct agccacctgg caaactgctc cttctctcaa aggcccaaac   4260
atggcctccc agactgcaac ccccaggcag tcaggccctg tctccacaac ctcacagcca   4320
ccctggacgg aatctgcttc ttcccacatt tgagtcctcc tcagccctg agctcctctg    4380 ggcagggctg tttctttcca tctttgtatt cccaggggcc tgcaaataaa tgtttaatga   4440
acgaacaaga gagtgaattc caattccatg caacaaggat tgggctcctg ggccctaggc   4500
tatgtgtctg gcaccagaaa cggaagctgc aggttgcagc ccctgccctc atggagctcc   4560
tcctgtcaga ggagtgtggg gactggatga ctccagaggt aacttgtggg ggaacgaaca   4620 ggtaagggc tgtgtgacga gatgagagac tgggagaata aaccagaaag tctctagctg    4680
tccagaggac atagcacaga ggcccatggt ccctatttca aacccaggcc accagactga   4740
gctgggacct tgggacagac aagtcatgca gaagttaggg gaccttctcc tccctttcc    4800 tggatcctga gtacctctcc tccctgacct caggcttcct cctagtgtca ccttggcccc   4860
tcttagaagc caattaggcc ctcagttct gcagcgggga ttaatatgat tatgaacacc    4920
cccaatctcc cagatgctga ttcagccagg agcttaggag ggggaggtca ctttataagg   4980
gtctgggggg gtcagaaccc agagtcatcc agctggagcc ctgagtggct gagctcaggc   5040
cttcgcagca ttcttgggtg ggagcagcca cgggtcagcc acaagggcca cagccatgaa   5100
tggcacagaa ggccctaact tctacgtgcc cttctccaat gcgacgggtg tggtacgcag   5160 cccccttcgag tacccacagt actacctggc tgagccatgg cagttctcca tgctggccgc   5220
```

```
ctacatgttt ctgctgatcg tgctgggctt ccccatcaac ttcctcacgc tctacgtcac    5280
cgtccagcac aagaagctgc gcacgcctct caactacatc ctgctcaacc tagccgtggc    5340
tgacctcttc atggtcctag gtggcttcac cagcaccctc tacacctctc tgcatggata    5400
cttcgtcttc gggcccacag gatgcaattt ggagggcttc tttgccaccc tgggcggtat    5460
gagccgggtg tgggtggggt gtgcaggagc ccgggagcat ggaggggtct gggagagtcc    5520
cgggcttggc ggtggtggct gagaggcctt ctcccttctc ctgtcctgtc aatgttatcc    5580
aaagccctca tatattcagt caacaaacac cattcatggt gatagccggg ctgctgtttg    5640
tgcagggctg gcactgaaca ctgccttgat cttatttgga gcaatatgcg cttgtctaat    5700
ttcacagcaa gaaaactgag ctgaggctca aagaagtcaa gcgccctgct ggggcgtcac    5760
acagggacgg gtgcagagtt gagttggaag cccgcatcta tctcgggcca tgtttgcagc    5820
accaagcctc tgtttcccTT ggagcagctg tgctgagtca gacccaggct gggcactgag    5880
ggagagctgg gcaagccaga cccctcctct ctggggccc aagctcaggg tgggaagtgg    5940
attttccatt ctccagtcat tgggtcttcc ctgtgctggg caatgggctc ggtcccctct    6000
ggcatcctct gcctcccctc tcagcccctg tcctcaggtg cccctccagc ctccctgccg    6060
cgttccaagt ctcctggtgt tgagaaccgc aagcagccgc tctgaagcag ttccttttg    6120
ctttagaata atgtcttgca tttaacagga aaacagatgg ggtgctgcag ggataacaga    6180
tcccacttaa cagagaggaa aactgaggca gggagagggg aagagactca tttagggatg    6240
tggccaggca gcaacaagag cctaggtctc ctggctgtga tccaggaata tctctgctga    6300
gatgcaggag gagacgctag aagcagccat tgcaaagctg ggtgacgggg agagcttacc    6360
gccagccaca agcgtctctc tgccagcctt gccctgtctc ccccatgtcc aggctgctgc    6420
ctcggtccca ttctcaggga atctctggcc attgttgggt gtttgttgca ttcaataatc    6480
acagatcact cagttctggc cagaaggtgg gtgtgccact tacgggtggt tgttctctgc    6540
agggtcagtc ccagtttaca aatattgtcc cttttcactgt taggaatgtc ccagtttggt    6600
tgattaacta tatggccact ctccctatgg aacttcatgg ggtggtgagc aggacagatg    6660
tctgaattcc atcatttcct tcttcttcct ctgggcaaaa cattgcacat tgcttcatgg    6720
ctcctaggag aggcccccac atgtccgggt tatttcattt cccgagaagg gagagggagg    6780
aaggactgcc aattctgggt ttccaccacc tctgcattcc ttcccaacaa ggaactctgc    6840
cccacattag gatgcattct tctgctaaac acacacacac acacacacac acacaacaca    6900
cacacacaca cacacacaca cacacacaca aaactcccta ccgggttccc agttcaatcc    6960
tgacccctg atctgattcg tgtcccttat gggcccagag cgctaagcaa ataacttccc    7020
ccattcctg gaatttcttt gcccagctct cctcagcgtg tggtccctct gcccttccc    7080
cctcctccca gcaccaagct ctctccttcc ccaaggcctc ctcaaatccc tctcccactc    7140
ctggttgcct tcctagctac cctctcctg tctagggggg agtgcaccct ccttaggcag    7200
tggggtctgt gctgaccgcc tgctgactgc cttgcaggtg aaattgccct gtggtccttg    7260
gtggtcctgg ccatcgagcg gtacgtggtg gtgtgtaagc ccatgagcaa cttccgcttc    7320
ggggagaacc atgccatcat gggcgttgcc ttcacctggg tcatgcgct ggcctgcgcc    7380
gcaccccac tcgccggctg gtccaggtaa tggcactgag cagaagggaa gaagctccgg    7440
gggctctttg tagggtcctc cagtcaggac tcaaacccag tagtgtctgg ttccaggcac    7500
tgaccttgta tgtctcctgg cccaaatgcc cactcagggg aggggtgtag ggcagaagaa    7560
gaaacagact ctaatgttgc tacaagggct ggtcccatct cctgagcccc atgtcaaaca    7620
```

```
gaatccaaga catcccaacc cttcaccttg gctgtgcccc taatcctcaa ctaagctagg    7680
cgcaaattcc aatcctcttt ggtctagtac cccggggca gcccctcta accttgggcc     7740
tcagcagcag gggaggccac accttcctag tgcaggtggc catattgtgg cccttggaa    7800
ctgggtccca ctcagcctct aggcgattgt ctcctaatgg ggctgagatg agacacagtg   7860
gggacagtgg tttggacaat aggactggtg actctggtcc ccagaggcct catgtccctc   7920
tgtctccaga aaattcccac tctcacttcc ctttcctcct cagtcttgct agggtccatt   7980
tcttacccct tgctgaattt gagcccaccc cctggacttt ttccccatct tctccaatct   8040
ggcctagttc tatcctctgg aagcagagcc gctggacgct ctgggtttcc tgaggcccgt   8100
ccactgtcac caatatcagg aaccattgcc acgtcctaat gacgtgcgct ggaagcctct   8160
agtttccaga agctgcacaa agatcccta gatactctgt gtgtccatct ttggcctgga    8220
aaatactctc accctggggc taggaagacc tcggtttgta caaacttcct caaatgcaga   8280
gcctgagggc tctccccacc tcctcaccaa ccctctgcgt ggcatagccc tagcctcagc   8340
gggcagtgga tgctggggct gggcatgcag ggagaggctg ggtggtgtca tctggtaacg   8400
cagccaccaa acaatgaagc gacactgatt ccacaaggtg catctgcatc ccatctgat    8460
ccattccatc ctgtcaccca gccatgcaga cgtttatgat ccccttttcc agggagggaa   8520
tgtgaagccc cagaaagggc cagcgctcgg cagccacctt ggctgttccc aagtccctca   8580
caggcagggt ctccctacct gcctgtcctc aggtacatcc ccgagggcct gcagtgctcg   8640
tgtggaatcg actactacac gctcaagccg gaggtcaaca acgagtcttt tgtcatctac   8700
atgttcgtgg tccacttcac catccccatg attatcatct ttttctgcta tgggcagctc   8760
gtcttcaccg tcaaggaggt acgggccggg ggtgggcgg cctcacggct ctgagggtcc    8820
agcccccagc atgcatctgc ggctcctgct ccctggagga gccatggtct ggacccgggt   8880
cccgtgtcct gcaggccgct gcccagcagc aggagtcagc caccacacag aaggcagaga   8940
aggaggtcac ccgcatggtc atcatcatgg tcatcgcttt cctgatctgc tgggtgccct   9000
acgccagcgt ggcattctac atcttcaccc accagggctc caacttcggt cccatcttca   9060
tgaccatccc agcgttcttt gccaagagcg ccgccatcta caacccgtc atctatatca    9120
tgatgaacaa gcaggtgcct actgcgggtg ggagggcccc agtgcccag gccacaggcg    9180
ctgcctgcca aggacaagct acttcccagg gcaggggagg gggctccatc agggttactg   9240
gcagcagtct tgggtcagca gtcccaatgg ggagtgtgtg agaaatgcag attcctggcc   9300
ccactcagaa ctgctgaatc tcagggtggg cccaggaacc tgcatttcca gcaagccctc   9360
cacaggtggc tcagatgctc actcaggtgg gagaagctcc agtcagctag ttctggaagc   9420
ccaatgtcaa agtcagaagg acccaagtcg ggaatgggat gggccagtct ccataaagct   9480
gaataaggag ctaaaaagtc ttattctgag gggtaaaggg gtaaagggtt cctcggagag   9540
gtacctccga ggggtaaaca gttgggtaaa cagtctctga agtcagctct gccattttct   9600
agctgtatgg ccctgggcaa gtcaatttcc ttctctgtgc tttggtttcc tcatccatag   9660
aaaggtagaa agggcaaaac accaaactct tggattacaa gagataattt acagaacacc   9720
cttggcacac agagggcacc atgaaatgtc acgggtgaca cagccccctt gtgctcagtc   9780
cctggcatct ctaggggtga ggagcgtctg cctagcaggt tccctccagg aagctggatt   9840
tgagtggatg gggcgctgga atcgtgaggg cagaagcag gcaaagggtc ggggcgaacc    9900
tcactaacgt gccagttcca agcacactgt gggcagccct ggccctgact caagcctctt   9960
```

-continued

```
gccttccagt tccggaactg catgctcacc accatctgct gcggcaagaa cccactgggt   10020
gacgatgagg cctctgctac cgtgtccaag acggagacga gccaggtggc cccggcctaa   10080
gacctgccta ggactctgtg gccgactata ggcgtctccc atcccctaca ccttccccca   10140
gccacagcca tcccaccagg agcagcgcct gtgcagaatg aacgaagtca cataggctcc   10200 ttaattttt tttttttttt aagaaataat taatgaggct cctcactcac ctgggacagc   10260
ctgagaaggg acatccacca agacctactg atctggagtc ccacgttccc caaggccagc   10320
gggatgtgtg cccctcctcc tcccaactca tctttcagga acacgaggat tcttgctttc   10380
tggaaaagtg tcccagctta gggataagtg tctagcacag aatggggcac acagtaggtg   10440
cttaataaat gctggatgga tgcaggaagg aatggaggaa tgaatgggaa gggagaacat   10500
atctatcctc tcagaccctc gcagcagcag caactcatac ttggctaatg atatggagca   10560 gttgttttc cctccctggg cctcactttc ttctcctata aaatggaaat cccagatccc   10620
tggtcctgcc gacacgcagc tactgagaag accaaaagag gtgtgtgtgt gtctatgtgt   10680
gtgtttcagc actttgtaaa tagcaagaag ctgtacagat tctagttaat gttgtgaata   10740
acatcaatta atgtaactag ttaattacta tgattatcac ctcctgatag tgaacatttt   10800
gagattgggc attcagatga tggggtttca cccaaccttg gggcaggttt ttaaaaatta   10860
gctaggcatc aaggccagac cagggctggg ggttgggctg taggcaggga cagtcacagg   10920
aatgcagaat gcagtcatca gacctgaaaa acaacactg ggggaggggg acggtgaagg   10980
ccaagttccc aatgagggtg agattgggcc tggggtctca cccctagtgt ggggccccag   11040
gtcccgtgcc tccccttccc aatgtggcct atggagagac aggcctttct ctcagcctct   11100
ggaagccacc tgctcttttg ctctagcacc tgggtcccag catctagagc atggagcctc   11160
tagaagccat gctcacccgc ccacatttaa ttaacagctg agtccctgat gtcatcctta   11220
tctcgaagag cttagaaaca aagagtggga aattccactg gcctacctt ccttggggat   11280 gttcatgggc cccagtttcc agtttccctt gccagacaag cccatcttca gcagttgcta   11340
gtccattctc cattctggag aatctgctcc aaaaagctgg ccacatctct gaggtgtcag   11400
aattaagctg cctcagtaac tgctccccct tctccatata agcaaagcca gaagctctag   11460
ctttacccag ctctgcctgg agactaaggc aaattgggcc attaaaagct cagctcctat   11520
gttggtatta acgtggtgg gttttgttgc tttcacactc tatccacagg atagattgaa   11580
actgccagct tccacctgat ccctgaccct gggatggctg gattgagcaa tgagcagagc   11640
caagcagcac agagtcccct ggggctgagg gtggaggagg cagtcctggg aatgggaaaa   11700
accccaactt tggggtcata gaggcacagg taacccataa aactgcaaac aagctttgtc   11760
acctctcaga gcttccttat ctgcaaaaaa gaatcttaaa actgaccttg gctgggcaca   11820
gtggctcaca cctctaatcc cagcactttg ggaggccaag gtgggcagat cacgaggtca   11880
ggagtttgag accagcctga ccaacacggt gaaaccctgt ctctactaaa aatacaaaaa   11940
tcagctgggc atggtggcgc gtgcctgtaa tcccagctat tcagtgggct gaggcaggag   12000
aatcgcttga acctgggagg tggaggttgc agtgagccga gattgcgcca ctgcactcca   12060
gcctgagcaa cagagggaca gtctgtctcc aaacaaaaca aaacaaacaa acaaacaaac   12120
aaacaaacaa aaacaacaa caaaaaaacc acttgatcct aagggattta gatgcgactg   12180
tggactttaa gtggccagcc tactgcctgg catgcagcag atgagactat ggcaatactg   12240
ggcttcagct cagagctggc cttactagag accctgtccc aaaggggaaa aggatggagc   12300
taaagctccc gagagtcacc ccctcctccg aggtgagaaa ggagggcagg agcatgagat   12360
```

```
agccgatcct cggtgccttg gtgaggctgg ggcaaatcat gctgggatct ctatcattgt    12420
ccctctttac tgtgactcac tagataatat cagtcaggat acttttggtc acaagtgata    12480
ggaaatccaa ctcatttggg ctgaagcaaa agggacacat tgttggctca catgaacaaa    12540
aagcccgggg cttcaggcac agggtatcac catgactgag atggggatta attctgtgat    12600
tggccaagtc taggtcacct gatcatacgt aactcattta tgcctgaggt tgcaattttt    12660 tggattttttg caatcagacc ttggcgatga ccttgagcag taggatataa ataactccca    12720
catgcttagc gttccaataa tggaatacta ggcatacgca ggtctaactg catcaccatg    12780
gctggaatgg ggattcatcc tctgattggt cagacctagg tcacatgctc acccctgcagc    12840 ccaagcaggc tgaatgggga gaggtaggtt tcacaaagga aagcccaggt gctgttacct    12900
gaagtaggag ggcaggaggc agggtgagca gagccaacat caacccagag ggaatggaat    12960
ctaagttggt gttttctggg cacgtggctg gaccaggcct ccctccctca tcatctcagg    13020
gacatgaggg agaagattcc tatggtggt cccgaaggtc tcacccttttg ttttggatgc    13080 tgtgttgggc cagggtggca gtgggtggga cagtggcatc ttagctgccc tgacttgcag    13140
gcagcccatt ccagctcccc gccccaaccc caacccagcc cacttttttct gagaaatggt    13200 acatttgccc cagcctcatg tccagaggaa aatttttactc taacaccaga acattctctg    13260
gtttgtcctg atagacaaga aagcctccac ctccttaatt tacaaatgac ttgacagctg    13320
cttcgtgggc acttgcatac ataaagagaa ggagctgctg ccttaagttg cagcaagttt    13380
ggccccacct catctccagg cagccagcag atgtacagag tgcctcttgg gtacaatggc    13440
agctccattc aaccaaacct gagcaagctg acccccatgcc agaatgcact ggggactcgg    13500
agatgaattg gagcctagag accaagtctc taggctatga cctgggctgc ctcacggcca    13560
cagagctctg tcacgccaag ggagagatgc accccctgaaa gctgaggtg ccccataagg    13620 agagagtggg tgcccttccc aactatgtag cttcagggca agttctcttt cttttcttttt    13680 cttttctttct ctttctttct ttcttt                                        13706
```

<210> SEQ ID NO 99
<211> LENGTH: 13706
<212> TYPE: DNA
<213> ORGANISM: Artificial Sequence
<220> FEATURE:
<223> OTHER INFORMATION: Synthetic Polynucleotide

<400> SEQUENCE: 99

```
gtgggggacc aggagaaaga aagccaagga agaggaggag gaggaggaga aggaggagaa      60
ggatgctgac ctagcagctc ctctcacagc agctcctctc ttgcagaggc tgaagagcga     120
tttgtgccct gcaagctaag cccctaatcc accgaggcaa aggcaaagcc cctagccggg     180
ctcccgaggg ctgggactcg ggtgccccaa gatggctgca tccagccatc ttggcttaga     240
aagcccccca catgccagct tggccaacac ccacaccatg ggtttctctg gactgcccga     300
cacaaggtgt gggtgctggc caggcctgtg ttcaaatccc agctctgcag aggaactttg     360
accctgcata ccccagattc ctcagtggtc agtggggagt tagaccctct tcataggggg     420
caggaggagt tgttcattca ttcaacaaat gtttattgaa cacctcctat ggggttgtgag    480 ctcagaggca gcgatgaaca ggccaggctg gtcctgcatt ctagaaatag atgggaagtc    540
agtcaataag tagacaaatg aggccaggtg tggtggcatg cctgtagacc cagttactcg    600
ggatgctgag gtaggaggat cacttgagcc taggacagga attcaaggct gcagtaagct    660
```

```
atgattgcgc cactgcactc cagcctgggc aacagagcaa gactcatctc taaaaaacat    720
ttaaaaattg ttttaagaag acaaatgaga tagtcgctga tggtaatgac tgtgtaaaaa    780
ctgaacatgg ctgggtgtgg ttgctcacac ctataatctc agcactttgg gaggctgaga    840
ttacagcctc ccaagtggct cccaaggcag gaggatcact tgagcctggg agttagagaa    900
cagcttggac aatataggga gagcccaact ctacaaaaat gaaaataaat tagccaggca    960
tggtggcaca caccaatggt cccagctact caggggttga ggtggtggac cgcttgagcc    1020
caggaggttg aggctgcagt gagccatgat catgccgctg cactccaacc tgagtcacag    1080
agtgataccc tgtctcaaaa aacaataggc caggtgtggt ggctcacgcc tgtaacccca    1140
gcactttggg aggccgaggc ggatggatca cttgagatca ggagttagag accagcctgg    1200
ctaacatggc aaaatcctgt ctgtactaaa aatataaaaa ttagccaggc atggcagtac    1260
atgcctgtag tcctggttac ttgggaggct aaggcaggag aatcgcttga acccaggaag    1320
aggaggttgc agtgagccaa gatcacacca ctgcactcca gcttgggtga cagagtgaga    1380
ccctgtctca aaacagctaa acctggtggg ggtgcctggt gtgtaggatg gtcaggggtg    1440
gtctctccaa ggacatgagt gtgagcggag acctgaagga gactcaggaa gagattaata    1500
ctgtcagcaa caaatatatt gatcacttac aagcactccc aataatccta ttaggtaggc    1560
actattatca ttcccatttt acagagtgga gaaccgaagc acactctcgg gagggcgggg    1620
tagctggctg cacccaggct gtgtagcctc agtccagatg taagggtggg tggaaaagag    1680
ccttgcccaa tgagggagaa cagtgaaacc aaggccatag ggtctaaaga ttcacgaacc    1740
aggctctcat ggagaaagca ggtgaggttt actgtataga tgggtgtgcc cctaccccac    1800
actgaggctt cctcgtctga gcaaactgag gcccagagag gggaaggaag caggactacc    1860
atggtgactc aaagaccagc tagaatccag cctcctctcc tcgaggcttc cactgcccca    1920
cgccaggcct gtgtgactca gtctagggcc tttccattac cccagctaaa cctttcttta    1980
gtcatttata ccatggtgtg aatggctggc tggtctttcc tgagagctat ctttgatgag    2040
gggagggagg catagccagg tttgggaagc tgataccccca ggaagcccag ttgactgtgt    2100
gggttatagc ccaggctgtc actgatttgt aacgggacct gagcaactct gcagagctag    2160
gcctcagtct tttcatctgc aaaatggata tagcagagat ggtcagagta ggtgacttcg    2220
aatgaccctt ccagctcact atgagtctgt tttcctgaac aaagagcatt ttttgtttaa    2280 aaaaaattt cttgggccgg acacggtggt tcactcctat aatcctggca ctttgggagg    2340
ccgaggaggg tggatcgctt gagccaggag ttcaggacca gcctgggcaa catagcgaga    2400
ctccacccct acaaaaaata caaaaactag tggtgtgcac ttgtggtccc agctactcag    2460
gaggctgagg tgagaggatc gcttgagccc aggaggcaga ggctacagtg agctatgatt    2520
gtggcactgc actccagcct gggcgacaga gaccttgtct caaaactttt ttttcttcg    2580 tcaagcttta cagaataaag agcactgtca cctcagtgat ggctgttagt tcccatcac    2640 cagggctcca tgaggttgca attgtgaaac tcacaaagga ggaacctgag acagagaggg    2700
gaagtactga gatcatctag gtccattccc ccactcactc gttcattcaa caaatattca    2760
ggagcacctt ctaggtgcca ggccctggag acacatcagt gaacaaaaca gacatcatcc    2820
cacctctttc cactacaggc caagcaccat gctggtctct gggaaccctg ttgtgagcaa    2880
gacagaccca ggcttaccct tgtggactca tgttacaggc agggagacgg gcacaaaaca    2940
caaataaaaa gcttccatgc tgtcagaagc actatgcaaa aagcaagatg ctgaggtact    3000
gctaagctgt gtgggatggg ggctcagccc ggccagggag gggccagttg tgggtcagtc    3060
```

```
ttgacccaag gcatccagga caccctcctt ctggccatga gggtccacgt cagaatcaaa    3120
ccctcacctt aacctcatta gcgttgggca taatcaccag gccaagcgcc ttaaactacg    3180
agaggcccca tcccacccgc cctgccttag ccctgccacg tgtgccaaac gctgttagac    3240
ccaacaccac ccaggccagg taggggctg gagcccaggt gggctgcagg gaaggggca     3300 ctcttctgag cagacagatc tgggaatcct gggtgggaag agagacagtg agagagagat    3360
taagggatat ttcccaggca tcagggcttt gcactctcag gggtccttcc gcctggatgt    3420
ccttcccctg aagcttcctc ctgttgttcc gttctcagct caagctccag cttctcagag    3480
aagcctcctg tgttgggagt ggctgcgact gaactgtccc tactgttatt cgctcttcta    3540
tttgtttgtg gtccctgtgc cccctcaccc cacaaaaaca ctggcttctt gtgagcagga    3600
gcttgctctt tcgtgtaccc tgtgtgtccc caaggaccaa gcaccttgtc tgggccacag    3660
taggtgctca atacacatgt tggctggaca gtggtcactg agcggccgca cgtcgggcac    3720
tctcagcact tgcacaggcc gcccagaca ccccacttca ttcctgggag gtgtcatcat    3780
gttgcttgga cgacggggag agggggacct gccagtgttg gcctccattt tcccccagtc    3840
atctgccccc aaggctctga ctactttctt tctcacggta catcctgcta ttctggaatc    3900
ggccctcgtg gggccacctg gtacatggca tttgaggccc tcgtggctga ttaggcctcc    3960
cccaacagtg ccctgtctgc tgcctccagg gccagcctcc ccttcagact ggagtcccct    4020
gaagggttct gcccctcccc tgctctggta gcccctcca tcctccctcc ctccactcca    4080
tctttggggg catttgagtc acctttctac accagtgatc tgcccaagcc actgctcact    4140
ttcctctgga taaagccagg ttccccggcc tagcgttcaa gacccattac aactgccccc    4200
agcccagatc ttccccacct agccacctgg caaactgctc cttctctcaa aggcccaaac    4260
atggcctccc agactgcaac ccccaggcag tcaggccctg tctccacaac ctcacagcca    4320
ccctggacgg aatctgcttc ttcccacatt tgagtcctcc tcagccctg agctcctctg    4380 ggcagggctg tttctttcca tctttgtatt cccaggggcc tgcaaataaa tgtttaatga    4440
acgaacaaga gagtgaattc caattccatg caacaaggat tgggctcctg ggccctaggc    4500
tatgtgtctg gcaccagaaa cggaagctgc aggttgcagc ccctgccctc atggagctcc    4560
tcctgtcaga gggagtgtggg gactggatga ctccagaggt aacttgtggg ggaacgaaca    4620
ggtaaggggc tgtgtgacga gatgagagac tgggagaata aaccagaaag tctctagctg    4680
tccagaggac atagcacaga ggcccatggt ccctatttca aacccaggcc accagactga    4740
gctgggacct tgggacagac aagtcatgca gaagttaggg gaccttctcc tccctttcc    4800 tggatcctga gtacctctcc tccctgacct caggcttcct cctagtgtca ccttggcccc    4860
tcttagaagc caattaggcc ctcagtttct gcagcgggga ttaatatgat tatgaacacc    4920
cccaatctcc cagatgctga ttcagccagg agcttaggag ggggaggtca ctttataagg    4980
gtctgggggg gtcagaaccc agagtcatcc agctggagcc ctgagtggct gagctcaggc    5040
cttcgcagca ttcttgggtg ggagcagcca cgggtcagcc acaagggcca cagccatgaa    5100
tggcacagaa ggccctaact tctacgtgcc cttctccaat gcgacgggtg tggtacgcag    5160
ccacttcgag tacccacagt actacctggc tgagccatgg cagttctcca tgctggccgc    5220
ctacatgttt ctgctgatcg tgctgggctt ccccatcaac ttcctcacgc tctacgtcac    5280
cgtccagcac aagaagctgc gcacgcctct caactacatc ctgctcaacc tagccgtggc    5340
tgacctcttc atggtcctag gtggcttcac cagcacccct acacctctc tgcatggata    5400
```

```
cttcgtcttc gggcccacag gatgcaattt ggagggcttc tttgccaccc tgggcggtat    5460
gagccgggtg tgggtggggt gtgcaggagc ccgggagcat ggaggggtct gggagagtcc    5520
cgggcttggc ggtggtggct gagaggcctt ctcccttctc ctgtcctgtc aatgttatcc    5580
aaagccctca tatattcagt caacaaacac cattcatggt gatagccggg ctgctgtttg    5640
tgcagggctg gcactgaaca ctgccttgat cttatttgga gcaatatgcg cttgtctaat    5700
ttcacagcaa gaaaactgag ctgaggctca agaagtcaa cgccctgct ggggcgtcac     5760
acagggacgg gtgcagagtt gagttggaag cccgcatcta tctcgggcca tgtttgcagc    5820
accaagcctc tgtttccctt ggagcagctg tgctgagtca gacccaggct gggcactgag    5880
ggagagctgg gcaagccaga cccctcctct ctggggccc aagctcaggg tgggaagtgg     5940
attttccatt ctccagtcat tgggtcttcc ctgtgctggg caatgggctc ggtcccctct    6000
ggcatcctct gcctccctc tcagccctg tcctcaggtg cccctccagc ctccctgccg      6060
cgttccaagt ctcctggtgt tgagaaccgc aagcagccgc tctgaagcag ttccttttg     6120
ctttagaata atgtcttgca tttaacagga aaacagatgg ggtgctgcag ggataacaga    6180
tcccacttaa cagagaggaa aactgaggca gggagagggg aagagactca tttagggatg    6240
tggccaggca gcaacaagag cctaggtctc ctggctgtga tccaggaata tctctgctga    6300
gatgcaggag gagacgctag aagcagccat tgcaaagctg ggtgacgggg agagcttacc    6360
gccagccaca agcgtctctc tgccagcctt gccctgtctc ccccatgtcc aggctgctgc    6420
ctcggtccca ttctcaggga atctctggcc attgttgggt gtttgttgca ttcaataatc    6480
acagatcact cagttctggc cagaaggtgg gtgtgccact tacgggtggt tgttctctgc    6540
agggtcagtc ccagtttaca aatattgtcc ctttcactgt taggaatgtc ccagtttggt    6600
tgattaacta tatggccact ctccctatgg aacttcatgg ggtggtgagc aggacagatg    6660
tctgaattcc atcatttcct tcttcttcct ctgggcaaaa cattgcacat tgcttcatgg    6720
ctcctaggag aggcccccac atgtccgggt tatttcattt cccgagaagg gagagggagg    6780
aaggactgcc aattctgggt ttccaccacc tctgcattcc ttcccaacaa ggaactctgc    6840
cccacattag gatgcattct tctgctaaac acacacacac acacacacac acacaacaca    6900
cacacacaca cacacacaca cacacacaca aaactcccta ccgggttccc agttcaatcc    6960
tgaccccctg atctgattcg tgtcccttat gggcccagag cgctaagcaa ataacttccc    7020
ccattccctg gaatttcttt gcccagctct cctcagcgtg tggtccctct gccccttccc    7080
cctcctccca gcaccaagct ctctccttcc ccaaggcctc ctcaaatccc tctcccactc    7140
ctggttgcct tcctagctac cctctccctg tctaggggg agtgcaccct ccttaggcag    7200
tggggtctgt gctgaccgcc tgctgactgc cttgcaggtg aaattgccct gtggtccttg    7260
gtggtcctgg ccatcgagcg gtacgtggtg gtgtgtaagc ccatgagcaa cttccgcttc    7320
ggggagaacc atgccatcat gggcgttgcc ttcacctggg tcatggcgct ggcctgcgcc    7380
gcacccccac tcgccggctg gtccaggtaa tggcactgag cagaagggaa gaagctccgg    7440
gggctctttg tagggtcctc cagtcaggac tcaaacccag tagtgtctgg ttccaggcac    7500
tgaccttgta tgtctcctgg cccaaatgcc cactcagggt aggggtgtag ggcagaagaa    7560
gaaacagact ctaatgttgc tacaagggct ggtcccatct cctgagcccc atgtcaaaca    7620
gaatccaaga catcccaacc cttcaccttg gctgtgcccc taatcctcaa ctaagctagg    7680
cgcaaattcc aatcctcttt ggtctagtac cccgggggca gccccctcta accttgggcc    7740
tcagcagcag gggaggccac accttcctag tgcaggtggc catattgtgg cccccttggaa   7800
```

-continued

| | |
|---|---|
| ctgggtccca ctcagcctct aggcgattgt ctcctaatgg ggctgagatg agacacagtg | 7860 |
| gggacagtgg tttggacaat aggactggtg actctggtcc ccagaggcct catgtccctc | 7920 |
| tgtctccaga aaattcccac tctcacttcc ctttcctcct cagtcttgct agggtccatt | 7980 |
| tcttacccct tgctgaattt gagcccaccc cctggacttt ttccccatct tctccaatct | 8040 |
| ggcctagttc tatcctctgg aagcagagcc gctggacgct ctgggtttcc tgaggcccgt | 8100 |
| ccactgtcac caatatcagg aaccattgcc acgtcctaat gacgtgcgct ggaagcctct | 8160 |
| agtttccaga agctgcacaa agatccctta gatactctgt gtgtccatct ttggcctgga | 8220 |
| aaatactctc accctggggc taggaagacc tcggtttgta caaacttcct caaatgcaga | 8280 |
| gcctgagggc tctccccacc tcctcaccaa ccctctgcgt ggcatagccc tagcctcagc | 8340 |
| gggcagtgga tgctggggct gggcatgcag ggagaggctg ggtggtgtca tctggtaacg | 8400 |
| cagccaccaa acaatgaagc gacactgatt ccacaaggtg catctgcatc cccatctgat | 8460 |
| ccattccatc ctgtcaccca gccatgcaga cgtttatgat cccctttttcc agggagggaa | 8520 |
| tgtgaagccc cagaaagggc cagcgctcgg cagccacctt ggctgttccc aagtccctca | 8580 |
| caggcagggt ctccctacct gcctgtcctc aggtacatcc ccgagggcct gcagtgctcg | 8640 |
| tgtggaatcg actactacac gctcaagccg gaggtcaaca acgagtcttt tgtcatctac | 8700 |
| atgttcgtgg tccacttcac catccccatg attatcatct ttttctgcta tgggcagctc | 8760 |
| gtcttcaccg tcaaggaggt acgggccggg gggtgggcgg cctcacggct ctgagggtcc | 8820 |
| agccccagc atgcatctgc ggctcctgct ccctggagga gccatggtct ggacccgggt | 8880 |
| cccgtgtcct gcaggccgct gcccagcagc aggagtcagc caccacacag aaggcagaga | 8940 |
| aggaggtcac ccgcatggtc atcatcatgg tcatcgcttt cctgatctgc tgggtgccct | 9000 |
| acgccagcgt ggcattctac atcttcaccc accagggctc caacttcggt cccatcttca | 9060 |
| tgaccatccc agcgttcttt gccaagagcg ccgccatcta caaccctgtc atctatatca | 9120 |
| tgatgaacaa gcaggtgcct actgcgggtg ggagggcccc agtgccccag gccacaggcg | 9180 |
| ctgcctgcca aggacaagct acttcccagg gcagggagg gggctccatc agggttactg | 9240 |
| gcagcagtct tgggtcagca gtcccaatgg ggagtgtgtg agaaatgcag attcctggcc | 9300 |
| ccactcagaa ctgctgaatc tcagggtggg cccaggaacc tgcatttcca gcaagccctc | 9360 |
| cacaggtggc tcagatgctc actcaggtgg gagaagctcc agtcagctag ttctggaagc | 9420 |
| ccaatgtcaa agtcagaagg acccaagtcg ggaatgggat gggccagtct ccataaagct | 9480 |
| gaataaggag ctaaaaagtc ttattctgag gggtaaaggg gtaaagggtt cctcggagag | 9540 |
| gtacctccga ggggtaaaca gttgggtaaa cagtctctga agtcagctct gccattttct | 9600 |
| agctgtatgg ccctgggcaa gtcaatttcc ttctctgtgc tttggtttcc tcatccatag | 9660 |
| aaaggtagaa agggcaaaac accaaactct tggattacaa gagataattt acagaacacc | 9720 |
| cttggcacac agagggcacc atgaaatgtc acggtgaca cagccccctt gtgctcagtc | 9780 |
| cctggcatct ctaggggtga ggagcgtctg cctagcaggt tccctccagg aagctggatt | 9840 |
| tgagtggatg gggcgctgga atcgtgaggg gcagaagcag gcaaagggtc ggggcgaacc | 9900 |
| tcactaacgt gccagttcca agcacactgt gggcagccct ggccctgact caagcctctt | 9960 |
| gccttccagt tccggaactg catgctcacc accatctgct gcggcaagaa cccactgggt | 10020 |
| gacgatgagg cctctgctac cgtgtccaag acggagacga gccaggtggc cccggcctaa | 10080 |
| gacctgccta ggactctgtg gccgactata ggcgtctccc atcccctaca ccttccccca | 10140 |

```
gccacagcca tcccaccagg agcagcgcct gtgcagaatg aacgaagtca cataggctcc   10200 ttaattttt tttttttttt aagaaataat taatgaggct cctcactcac ctgggacagc    10260
ctgagaaggg acatccacca agacctactg atctggagtc ccacgttccc caaggccagc   10320
gggatgtgtg cccctcctcc tcccaactca tctttcagga acacgaggat tcttgctttc   10380
tggaaaagtg tcccagctta gggataagtg tctagcacag aatggggcac acagtaggtg   10440
cttaataaat gctggatgga tgcaggaagg aatggaggaa tgaatgggaa gggagaacat   10500
atctatcctc tcagaccctc gcagcagcag caactcatac ttggctaatg atatggagca   10560 gttgttttc cctccctggg cctcactttc ttctcctata aaatggaaat cccagatccc    10620
tggtcctgcc gacacgcagc tactgagaag accaaaagag gtgtgtgtgt gtctatgtgt   10680
gtgtttcagc actttgtaaa tagcaagaag ctgtacagat tctagttaat gttgtgaata   10740
acatcaatta atgtaactag ttaattacta tgattatcac ctcctgatag tgaacatttt   10800
gagattgggc attcagatga tggggtttca cccaaccttg gggcaggttt ttaaaaatta   10860
gctaggcatc aaggccagac cagggctggg ggttgggctg taggcaggga cagtcacagg   10920
aatgcagaat gcagtcatca gacctgaaaa acaacactg ggggagggggg acggtgaagg    10980 ccaagttccc aatgagggtg agattgggcc tggggtctca cccctagtgt ggggcccag    11040 gtcccgtgcc tccccttccc aatgtggcct atggagagac aggcctttct ctcagcctct   11100
ggaagccacc tgctcttttg ctctagcacc tgggtcccag catctagagc atggagcctc   11160
tagaagccat gctcacccgc ccacatttaa ttaacagctg agtccctgat gtcatcctta   11220
tctcgaagag cttagaaaca aagagtggga aattccactg gcctaccttt ccttggggat   11280
gttcatgggc cccagtttcc agtttccctt gccagacaag cccatcttca gcagttgcta   11340
gtccattctc cattctggag aatctgctcc aaaaagctgg ccacatctct gaggtgtcag   11400
aattaagctg cctcagtaac tgctcccccct tctccatata agcaaagcca gaagctctag   11460 cttttaccccag ctctgcctgg agactaaggc aaattgggcc attaaaagct cagctcctat  11520
gttggtatta acggtggtgg gttttgttgc tttcacactc tatccacagg atagattgaa   11580
actgccagct tccacctgat ccctgaccct gggatggctg gattgagcaa tgagcagagc   11640
caagcagcac agagtcccct ggggctagag gtggaggagg cagtcctggg aatgggaaaa   11700
accccaactt tggggtcata gaggcacagg taacccataa aactgcaaac aagctttgtc   11760
acctctcaga gcttccttat ctgcaaaaaa gaatcttaaa actgaccttg gctgggcaca   11820
gtggctcaca cctctaatcc cagcactttg ggaggcaag gtgggcagat cacgaggtca    11880
ggagtttgag accagcctga ccaacacggt gaaaccctgt ctctactaaa aatacaaaaa   11940
tcagctgggc atggtggcgc gtgcctgtaa tcccagctat tcagtgggct gaggcaggag   12000
aatcgcttga acctgggagg tggaggttgc agtgagccga gattgcgcca ctgcactcca   12060
gcctgagcaa cagagggaca gtctgtctcc aaacaaaaca aaacaaacaa acaaacaaac   12120
aaacaaacaa aaacaacaa caaaaaaacc acttgatcct aagggggatta gatgcgactg   12180 tggactttaa gtggccagcc tactgcctgg catgcagcag atgagactat ggcaatactg   12240
ggcttcagct cagagctggc cttactagag accctgtccc aaaggggaaa aggatggagc   12300
taaagctccc gagagtcacc ccctcctccg aggtgagaaa ggagggcagg agcatgagat   12360
agccgatcct cggtgccttg gtgaggctgg ggcaaatcat gctgggatct ctatcattgt   12420
ccctctttac tgtgactcac tagataatat cagtcaggat acttttggtc acaagtgata   12480
ggaaatccaa ctcatttggg ctgaagcaaa aggacacat tgttggctca catgaacaaa     12540
```

```
aagcccgggg cttcaggcac agggtatcac catgactgag atggggatta attctgtgat   12600
tggccaagtc taggtcacct gatcatacgt aactcattta tgcctgaggt tgcaattttt   12660 tggattttg caatcagacc ttggcgatga ccttgagcag taggatataa ataactccca    12720
catgcttagc gttccaataa tggaatacta ggcatacgca ggtctaactg catcaccatg   12780
gctggaatgg ggattcatcc tctgattggt cagacctagg tcacatgctc accctgcagc   12840
ccaagcaggt gaatgggga gaggtaggtt tcacaaagga aagcccaggt gctgttacct    12900
gaagtaggag ggcaggaggc agggtgagca gagccaacat caacccagag ggaatggaat   12960
ctaagttggt gttttctggg cacgtggctg gaccaggcct ccctccctca tcatctcagg   13020
gacatgaggg agaagattcc tatgggtggt cccgaaggtc tcacccttg ttttggatgc    13080 tgtgttgggc cagggtggca gtgggtggga cagtggcatc ttagctgccc tgacttgcag   13140
gcagcccatt ccagctcccc gccccaaccc caacccagcc cacttttct gagaaatggt    13200 acatttgccc cagcctcatg tccagaggaa aatttactc taacaccaga acattctctg    13260
gtttgtcctg atagacaaga aagcctccac ctccttaatt tacaaatgac ttgacagctg   13320
cttcgtgggc acttgcatac ataaagagaa ggagctgctg ccttaagttg cagcaagttt   13380
ggccccacct catctccagg cagccagcag atgtacagag tgcctcttgg gtacaatggc   13440
agctccattc aaccaaacct gagcaagctg accccatgcc agaatgcact ggggactcgg   13500
agatgaattg gagcctagag accaagtctc taggctatga cctgggctgc ctcacggcca   13560
cagagctctg tcacgccaag ggagagatgc accctgaaa gcctgaggtg ccccataagg    13620
agagagtggg tgcccttccc aactatgtag cttcagggca agttctcttt ctttcttttt   13680 ctttcttct ctttctttct ttcttt                                         13706
```

<210> SEQ ID NO 100
<211> LENGTH: 348
<212> TYPE: PRT
<213> ORGANISM: Artificial Sequence
<220> FEATURE:
<223> OTHER INFORMATION: Synthetic Polypeptide

<400> SEQUENCE: 100

```
Met Asn Gly Thr Glu Gly Pro Asn Phe Tyr Val Pro Phe Ser Asn Ala
1               5                   10                  15

Thr Gly Val Val Arg Ser Pro Phe Glu Tyr Pro Gln Tyr Tyr Leu Ala
                20                  25                  30

Glu Pro Trp Gln Phe Ser Met Leu Ala Ala Tyr Met Phe Leu Leu Ile
            35                  40                  45

Val Leu Gly Phe Pro Ile Asn Phe Leu Thr Leu Tyr Val Thr Val Gln
        50                  55                  60

His Lys Lys Leu Arg Thr Pro Leu Asn Tyr Ile Leu Leu Asn Leu Ala
65                  70                  75                  80

Val Ala Asp Leu Phe Met Val Leu Gly Gly Phe Thr Ser Thr Leu Tyr
                85                  90                  95

Thr Ser Leu His Gly Tyr Phe Val Phe Gly Pro Thr Gly Cys Asn Leu
            100                 105                 110

Glu Gly Phe Phe Ala Thr Leu Gly Gly Glu Ile Ala Leu Trp Ser Leu
        115                 120                 125

Val Val Leu Ala Ile Glu Arg Tyr Val Val Val Cys Lys Pro Met Ser
    130                 135                 140

Asn Phe Arg Phe Gly Glu Asn His Ala Ile Met Gly Val Ala Phe Thr
```

```
                145                 150                 155                 160
Trp Val Met Ala Leu Ala Cys Ala Ala Pro Pro Leu Ala Gly Trp Ser
                165                 170                 175

Arg Tyr Ile Pro Glu Gly Leu Gln Cys Ser Cys Gly Ile Asp Tyr Tyr
            180                 185                 190

Thr Leu Lys Pro Glu Val Asn Asn Glu Ser Phe Val Ile Tyr Met Phe
            195                 200                 205

Val Val His Phe Thr Ile Pro Met Ile Ile Ile Phe Phe Cys Tyr Gly
        210                 215                 220

Gln Leu Val Phe Thr Val Lys Glu Ala Ala Gln Gln Gln Glu Ser
225                 230                 235                 240

Ala Thr Thr Gln Lys Ala Glu Lys Glu Val Thr Arg Met Val Ile Ile
                245                 250                 255

Met Val Ile Ala Phe Leu Ile Cys Trp Val Pro Tyr Ala Ser Val Ala
                260                 265                 270

Phe Tyr Ile Phe Thr His Gln Gly Ser Asn Phe Gly Pro Ile Phe Met
            275                 280                 285

Thr Ile Pro Ala Phe Phe Ala Lys Ser Ala Ala Ile Tyr Asn Pro Val
        290                 295                 300

Ile Tyr Ile Met Met Asn Lys Gln Phe Arg Asn Cys Met Leu Thr Thr
305                 310                 315                 320

Ile Cys Cys Gly Lys Asn Pro Leu Gly Asp Asp Glu Ala Ser Ala Thr
                325                 330                 335

Val Ser Lys Thr Glu Thr Ser Gln Val Ala Pro Ala
            340                 345

<210> SEQ ID NO 101
<211> LENGTH: 348
<212> TYPE: PRT
<213> ORGANISM: Artificial Sequence
<220> FEATURE:
<223> OTHER INFORMATION: Synthetic Polypeptide

<400> SEQUENCE: 101

Met Asn Gly Thr Glu Gly Pro Asn Phe Tyr Val Pro Phe Ser Asn Ala
1               5                   10                  15

Thr Gly Val Val Arg Ser His Phe Glu Tyr Pro Gln Tyr Tyr Leu Ala
            20                  25                  30

Glu Pro Trp Gln Phe Ser Met Leu Ala Ala Tyr Met Phe Leu Leu Ile
        35                  40                  45

Val Leu Gly Phe Pro Ile Asn Phe Leu Thr Leu Tyr Val Thr Val Gln
    50                  55                  60

His Lys Lys Leu Arg Thr Pro Leu Asn Tyr Ile Leu Leu Asn Leu Ala
65                  70                  75                  80

Val Ala Asp Leu Phe Met Val Leu Gly Gly Phe Thr Ser Thr Leu Tyr
                85                  90                  95

Thr Ser Leu His Gly Tyr Phe Val Phe Gly Pro Thr Gly Cys Asn Leu
            100                 105                 110

Glu Gly Phe Phe Ala Thr Leu Gly Gly Glu Ile Ala Leu Trp Ser Leu
        115                 120                 125

Val Val Leu Ala Ile Glu Arg Tyr Val Val Cys Lys Pro Met Ser
    130                 135                 140

Asn Phe Arg Phe Gly Glu Asn His Ala Ile Met Gly Val Ala Phe Thr
145                 150                 155                 160

Trp Val Met Ala Leu Ala Cys Ala Ala Pro Pro Leu Ala Gly Trp Ser
```

-continued

```
                165                 170                 175
Arg Tyr Ile Pro Glu Gly Leu Gln Cys Ser Cys Gly Ile Asp Tyr Tyr
            180                 185                 190

Thr Leu Lys Pro Glu Val Asn Asn Glu Ser Phe Val Ile Tyr Met Phe
            195                 200                 205

Val Val His Phe Thr Ile Pro Met Ile Ile Phe Phe Cys Tyr Gly
            210                 215                 220

Gln Leu Val Phe Thr Val Lys Glu Ala Ala Gln Gln Glu Ser
225                 230                 235                 240

Ala Thr Thr Gln Lys Ala Glu Lys Glu Val Thr Arg Met Val Ile Ile
            245                 250                 255

Met Val Ile Ala Phe Leu Ile Cys Trp Val Pro Tyr Ala Ser Val Ala
            260                 265                 270

Phe Tyr Ile Phe Thr His Gln Gly Ser Asn Phe Gly Pro Ile Phe Met
            275                 280                 285

Thr Ile Pro Ala Phe Phe Ala Lys Ser Ala Ala Ile Tyr Asn Pro Val
            290                 295                 300

Ile Tyr Ile Met Met Asn Lys Gln Phe Arg Asn Cys Met Leu Thr Thr
305                 310                 315                 320

Ile Cys Cys Gly Lys Asn Pro Leu Gly Asp Asp Glu Ala Ser Ala Thr
            325                 330                 335

Val Ser Lys Thr Glu Thr Ser Gln Val Ala Pro Ala
            340                 345
```

<210> SEQ ID NO 102
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 102

```
Lys Glu Phe Leu Leu Tyr Leu Ala Gly Phe Val Asp Gly Asp Gly Ser
1               5                   10                  15

Ile Trp Ala Ser Ile Ile Pro Glu Gln Gly Tyr Lys Phe Lys His Arg
            20                  25                  30

Leu Arg Leu Ser Phe Thr Val Ala Gln Lys Thr Gln Arg Arg Trp Phe
            35                  40                  45

Leu Asp Lys Leu Val Asp Glu Ile Gly Val Gly Tyr Val Val Asp Gln
            50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
            85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
            130                 135                 140

Val Leu Asp
145
```

<210> SEQ ID NO 103
<211> LENGTH: 147
<212> TYPE: PRT

<213> ORGANISM: Artificial Sequence
<220> FEATURE:
<223> OTHER INFORMATION: Synthetic Polypeptide

<400> SEQUENCE: 103

```
Lys Glu Phe Leu Leu Tyr Leu Ala Gly Phe Val Asp Gly Asp Gly Ser
1               5                   10                  15
Ile Trp Ala Ser Ile Ile Pro Glu Gln Gly Tyr Lys Phe Lys His Arg
            20                  25                  30
Leu Arg Leu Ser Phe Thr Val Ala Gln Lys Thr Gln Arg Arg Trp Phe
        35                  40                  45
Leu Asp Lys Leu Val Asp Glu Ile Gly Val Gly Tyr Val Val Asp Gln
    50                  55                  60
Gly Ser Val Ser Glu Tyr Arg Leu Ser Glu Ile Lys Pro Leu His Asn
65                  70                  75                  80
Phe Leu Thr Gln Leu Gln Pro Phe Leu Lys Leu Lys Gln Lys Gln Ala
                85                  90                  95
Asn Leu Val Leu Lys Ile Ile Glu Gln Leu Pro Ser Ala Lys Glu Ser
            100                 105                 110
Pro Asp Lys Phe Leu Glu Val Cys Thr Trp Val Asp Gln Ile Ala Ala
        115                 120                 125
Leu Asn Asp Ser Lys Thr Arg Lys Thr Thr Ser Glu Thr Val Arg Ala
    130                 135                 140
Val Leu Asp
145
```

<210> SEQ ID NO 104
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 104

```
Lys Glu Phe Leu Leu Tyr Leu Ala Gly Phe Val Asp Gly Asp Gly Ser
1               5                   10                  15
Ile Trp Ala Ser Ile Ile Pro Glu Gln Gly Tyr Lys Phe Lys His Arg
            20                  25                  30
Leu Arg Leu Ser Phe Thr Val Ala Gln Lys Thr Gln Arg Arg Trp Phe
        35                  40                  45
Leu Asp Lys Leu Val Asp Glu Ile Gly Val Gly Tyr Val Val Asp Gln
    50                  55                  60
Gly Ser Val Ser Glu Tyr Arg Leu Ser Glu Ile Lys Pro Leu His Asn
65                  70                  75                  80
Phe Leu Thr Gln Leu Gln Pro Phe Leu Lys Leu Lys Gln Lys Gln Ala
                85                  90                  95
Asn Leu Val Leu Lys Ile Ile Glu Gln Leu Pro Ser Ala Lys Glu Ser
            100                 105                 110
Pro Asp Lys Phe Leu Glu Val Cys Thr Trp Val Asp Gln Ile Ala Ala
        115                 120                 125
Leu Asn Asp Ser Lys Thr Arg Lys Thr Thr Ser Glu Thr Val Arg Ala
    130                 135                 140
Val Leu Asp
145
```

<210> SEQ ID NO 105
<211> LENGTH: 147

```
<212> TYPE: PRT
<213> ORGANISM: Artificial Sequence
<220> FEATURE:
<223> OTHER INFORMATION: Synthetic Polypeptide

<400> SEQUENCE: 105

Lys Glu Phe Leu Leu Tyr Leu Ala Gly Phe Val Asp Gly Asp Gly Ser
1               5                   10                  15

Ile Trp Ala Ser Ile Ile Pro Glu Gln Gly Tyr Lys Phe Lys His Arg
            20                  25                  30

Leu Arg Leu Ser Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 106
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 106

Lys Glu Phe Leu Leu Tyr Leu Ala Gly Phe Val Asp Gly Asp Gly Ser
1               5                   10                  15

Ile Tyr Ala Thr Ile Met Pro Glu Gln Arg Gln Lys Phe Lys His Arg
            20                  25                  30

Leu Arg Leu Tyr Phe Glu Val Cys Gln Lys Thr Gln Arg Arg Trp Phe
        35                  40                  45

Leu Asp Lys Leu Val Asp Glu Ile Gly Val Gly Tyr Val Tyr Asp Gln
    50                  55                  60

Gly Ser Val Ser Thr Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 107
```

```
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 107

Lys Glu Phe Leu Leu Tyr Leu Ala Gly Phe Val Asp Gly Asp Gly Ser
1               5                   10                  15

Ile Tyr Ala Thr Ile Ile Pro Ser Gln Thr Asp Lys Phe Lys His Arg
            20                  25                  30

Leu Arg Leu Tyr Phe Ala Val Ser Gln Lys Thr Gln Arg Arg Trp Phe
        35                  40                  45

Leu Asp Lys Leu Val Asp Glu Ile Gly Val Gly Tyr Val Ile Asp Ser
50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
            85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
        130                 135                 140

Val Leu Asp
145

<210> SEQ ID NO 108
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 108

Lys Glu Phe Leu Leu Tyr Leu Ala Gly Phe Val Asp Gly Asp Gly Ser
1               5                   10                  15

Ile Tyr Ala Ser Ile Gln Pro Asp Gln Val Tyr Lys Phe Lys His Arg
            20                  25                  30

Leu Arg Leu Arg Phe Ala Val Phe Gln Lys Thr Gln Arg Arg Trp Phe
        35                  40                  45

Leu Asp Lys Leu Val Asp Glu Ile Gly Val Gly Tyr Val Tyr Asp His
50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
            85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
        130                 135                 140

Val Leu Asp
145
```

<210> SEQ ID NO 109
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 109

```
Lys Glu Phe Leu Leu Tyr Leu Ala Gly Phe Val Asp Gly Asp Gly Ser
1               5                   10                  15

Ile Tyr Ala Ser Ile Glu Pro Val Gln Thr Tyr Lys Phe Lys His Arg
            20                  25                  30

Leu Arg Leu Ser Phe Ala Val Ser Gln Lys Thr Gln Arg Arg Trp Phe
        35                  40                  45

Leu Asp Lys Leu Val Asp Glu Ile Gly Val Gly Tyr Val Cys Asp Val
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145
```

<210> SEQ ID NO 110
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 110

```
Lys Glu Phe Leu Leu Tyr Leu Ala Gly Phe Val Asp Gly Asp Gly Ser
1               5                   10                  15

Ile Tyr Ala Ser Ile Thr Pro Ser Gln Ala Gly Lys Phe Lys His Arg
            20                  25                  30

Leu Arg Leu Tyr Phe Glu Val Ser Gln Lys Thr Gln Arg Arg Trp Phe
        35                  40                  45

Leu Asp Lys Leu Val Asp Glu Ile Gly Val Gly Tyr Val Tyr Asp Gln
    50                  55                  60

Gly Ser Val Ser Cys Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145
```

```
<210> SEQ ID NO 111
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 111

Lys Glu Phe Leu Leu Tyr Leu Ala Gly Phe Val Asp Gly Asp Gly Ser
1               5                   10                  15

Ile Tyr Ala Thr Ile Glu Pro Ala Gln Arg Tyr Lys Phe Lys His Arg
            20                  25                  30

Leu Arg Leu Lys Phe Ala Val Ser Gln Lys Thr Gln Arg Arg Trp Phe
        35                  40                  45

Leu Asp Lys Leu Val Asp Glu Ile Gly Val Gly Tyr Val Ala Asp Gln
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 112
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 112

Lys Glu Phe Leu Leu Tyr Leu Ala Gly Phe Val Asp Gly Asp Gly Ser
1               5                   10                  15

Ile Tyr Ala Thr Ile Glu Pro Gln Gln Pro Gly Lys Phe Lys His Arg
            20                  25                  30

Leu Ser Leu Arg Phe Ala Val Tyr Gln Lys Thr Gln Arg Arg Trp Phe
        35                  40                  45

Leu Asp Lys Leu Val Asp Glu Ile Gly Val Gly Tyr Val Tyr Asp Pro
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145
```

```
<210> SEQ ID NO 113
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 113

Lys Glu Phe Leu Leu Tyr Leu Ala Gly Phe Val Asp Gly Asp Gly Ser
1               5                   10                  15

Ile Tyr Ala Ser Ile Gly Pro Glu Gln Ser Ser Lys Phe Lys His Arg
            20                  25                  30

Leu Arg Leu Leu Phe Ala Val Ala Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 114
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 114

Lys Glu Phe Leu Leu Tyr Leu Ala Gly Phe Val Asp Gly Asp Gly Ser
1               5                   10                  15

Ile Tyr Ala Thr Ile Gln Pro Asp Gln Asn Gln Lys Phe Lys His Arg
            20                  25                  30

Leu Arg Leu Tyr Phe Ala Val Tyr Gln Lys Thr Gln Arg Arg Trp Phe
        35                  40                  45

Leu Asp Lys Leu Val Asp Glu Ile Gly Val Gly Tyr Val Tyr Asp Thr
    50                  55                  60

Gly Ser Val Ser Arg Tyr Gln Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
```

<210> SEQ ID NO 115
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 115

Lys Glu Phe Leu Leu Tyr Leu Ala Gly Phe Val Asp Gly Asp Gly Ser
1               5                   10                  15

Ile Trp Ala Ser Ile Ile Pro Glu Gln Gly Tyr Lys Phe Lys His Arg
            20                  25                  30

Leu Arg Leu Ser Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 116
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 116

Lys Glu Phe Leu Leu Tyr Leu Ala Gly Phe Val Asp Gly Asp Gly Ser
1               5                   10                  15

Ile Trp Ala Ser Ile Ile Pro Glu Gln Gly Tyr Lys Phe Lys His Arg
            20                  25                  30

Leu Arg Leu Ser Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 117
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 117

Lys Glu Phe Leu Leu Tyr Leu Ala Gly Phe Val Asp Gly Asp Gly Ser
1               5                   10                  15

Ile Trp Ala Ser Ile Ile Pro Glu Gln Gly Tyr Lys Phe Lys His Arg
            20                  25                  30

Leu Arg Leu Ser Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 118
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 118

Lys Glu Phe Leu Leu Tyr Leu Ala Gly Phe Val Asp Gly Asp Gly Ser
1               5                   10                  15

Ile Trp Ala Ser Ile Ile Pro Glu Gln Gly Tyr Lys Phe Lys His Arg
            20                  25                  30

Leu Arg Leu Ser Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 119
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 119

Lys Glu Phe Leu Leu Tyr Leu Ala Gly Phe Val Asp Gly Asp Gly Ser
1               5                   10                  15

Ile Trp Ala Ser Ile Ile Pro Glu Gln Gly Tyr Lys Phe Lys His Arg
            20                  25                  30

Leu Arg Leu Ser Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 120
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 120

Lys Glu Phe Leu Leu Tyr Leu Ala Gly Phe Val Asp Gly Asp Gly Ser
1               5                   10                  15

Ile Trp Ala Ser Ile Ile Pro Glu Gln Gly Tyr Lys Phe Lys His Arg
            20                  25                  30

Leu Arg Leu Ser Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala

```
            130                 135                 140

Val Leu Asp
145

<210> SEQ ID NO 121
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 121

Lys Glu Phe Leu Leu Tyr Leu Ala Gly Phe Val Asp Gly Asp Gly Ser
1               5                   10                  15

Ile Trp Ala Ser Ile Ile Pro Glu Gln Gly Tyr Lys Phe Lys His Arg
            20                  25                  30

Leu Arg Leu Ser Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 122
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 122

Lys Glu Phe Leu Leu Tyr Leu Ala Gly Phe Val Asp Gly Asp Gly Ser
1               5                   10                  15

Ile Trp Ala Ser Ile Ile Pro Glu Gln Gly Tyr Lys Phe Lys His Arg
            20                  25                  30

Leu Arg Leu Ser Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125
```

Leu Asn Asp Ser Lys Thr Arg Lys Thr Thr Ser Glu Thr Val Arg Ala
            130                 135                 140

Val Leu Asp
145

<210> SEQ ID NO 123
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 123

Lys Glu Phe Leu Leu Tyr Leu Ala Gly Phe Val Asp Gly Asp Gly Ser
1               5                   10                  15

Ile Trp Ala Ser Ile Ile Pro Glu Gln Gly Tyr Lys Phe Lys His Arg
            20                  25                  30

Leu Arg Leu Ser Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 124
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 124

Lys Glu Phe Leu Leu Tyr Leu Ala Gly Phe Val Asp Gly Asp Gly Ser
1               5                   10                  15

Ile Trp Ala Ser Ile Ile Pro Glu Gln Gly Tyr Lys Phe Lys His Arg
            20                  25                  30

Leu Arg Leu Ser Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

```
Leu Asn Asp Ser Lys Thr Arg Lys Thr Thr Ser Glu Thr Val Arg Ala
        130                 135                 140

Val Leu Asp
145

<210> SEQ ID NO 125
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 125

Lys Glu Phe Leu Leu Tyr Leu Ala Gly Phe Val Asp Gly Asp Gly Ser
1               5                   10                  15

Ile Trp Ala Ser Ile Ile Pro Glu Gln Gly Tyr Lys Phe Lys His Arg
            20                  25                  30

Leu Arg Leu Ser Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 126
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 126

Lys Glu Phe Leu Leu Tyr Leu Ala Gly Phe Val Asp Gly Asp Gly Ser
1               5                   10                  15

Ile Trp Ala Ser Ile Ile Pro Glu Gln Gly Tyr Lys Phe Lys His Arg
            20                  25                  30

Leu Arg Leu Ser Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
```

```
                115                 120                 125
Leu Asn Asp Ser Lys Thr Arg Lys Thr Thr Ser Glu Thr Val Arg Ala
    130                 135                 140
Val Leu Asp
145

<210> SEQ ID NO 127
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 127

Lys Glu Phe Leu Leu Tyr Leu Ala Gly Phe Val Asp Gly Asp Gly Ser
1               5                   10                  15

Ile Trp Ala Ser Ile Ile Pro Glu Gln Gly Tyr Lys Phe Lys His Arg
            20                  25                  30

Leu Arg Leu Ser Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 128
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 128

Lys Glu Phe Leu Leu Tyr Leu Ala Gly Phe Val Asp Gly Asp Gly Ser
1               5                   10                  15

Ile Trp Ala Ser Ile Ile Pro Glu Gln Gly Tyr Lys Phe Lys His Arg
            20                  25                  30

Leu Arg Leu Ser Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110
```

```
Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 129
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 129

Lys Glu Phe Leu Leu Tyr Leu Ala Gly Phe Val Asp Gly Asp Gly Ser
1               5                   10                  15

Ile Trp Ala Ser Ile Ile Pro Glu Gln Gly Tyr Lys Phe Lys His Arg
            20                  25                  30

Leu Arg Leu Ser Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 130
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 130

Lys Glu Phe Leu Leu Tyr Leu Ala Gly Phe Val Asp Gly Asp Gly Ser
1               5                   10                  15

Ile Trp Ala Ser Ile Ile Pro Glu Gln Gly Tyr Lys Phe Lys His Arg
            20                  25                  30

Leu Arg Leu Ser Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110
```

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
        130                 135                 140

Val Leu Asp
145

<210> SEQ ID NO 131
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 131

Lys Glu Phe Leu Leu Tyr Leu Ala Gly Phe Val Asp Gly Asp Gly Ser
1               5                   10                  15

Ile Trp Ala Ser Ile Ile Pro Glu Gln Gly Tyr Lys Phe Lys His Arg
            20                  25                  30

Leu Arg Leu Ser Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
            85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
        130                 135                 140

Val Leu Asp
145

<210> SEQ ID NO 132
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 132

Lys Glu Phe Leu Leu Tyr Leu Ala Gly Phe Val Asp Gly Asp Gly Ser
1               5                   10                  15

Ile Trp Ala Ser Ile Ile Pro Glu Gln Gly Tyr Lys Phe Lys His Arg
            20                  25                  30

Leu Arg Leu Ser Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
            85                  90                  95

Asn Leu Val Leu Lys Ile Ile Glu Gln Leu Pro Ser Ala Lys Glu Ser

```
                100                 105                 110
Pro Asp Lys Phe Leu Glu Val Cys Thr Trp Val Asp Gln Ile Ala Ala
        115                 120                 125
Leu Asn Asp Ser Lys Thr Arg Lys Thr Thr Ser Glu Thr Val Arg Ala
    130                 135                 140
Val Leu Asp
145

<210> SEQ ID NO 133
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 133

Lys Glu Phe Leu Leu Tyr Leu Ala Gly Phe Val Asp Gly Asp Gly Ser
1               5                   10                  15
Ile Trp Ala Ser Ile Ile Pro Glu Gln Gly Tyr Lys Phe Lys His Arg
            20                  25                  30
Leu Arg Leu Ser Phe Thr Val Ala Gln Lys Thr Gln Arg Arg Trp Phe
        35                  40                  45
Leu Asp Lys Leu Val Asp Glu Ile Gly Val Gly Tyr Val Val Asp Gln
    50                  55                  60
Gly Ser Val Ser Glu Tyr Arg Leu Ser Glu Ile Lys Pro Leu His Asn
65                  70                  75                  80
Phe Leu Thr Gln Leu Gln Pro Phe Leu Lys Leu Lys Gln Lys Gln Ala
                85                  90                  95
Asn Leu Val Leu Lys Ile Ile Glu Gln Leu Pro Ser Ala Lys Glu Ser
            100                 105                 110
Pro Asp Lys Phe Leu Glu Val Cys Thr Trp Val Asp Gln Ile Ala Ala
        115                 120                 125
Leu Asn Asp Ser Lys Thr Arg Lys Thr Thr Ser Glu Thr Val Arg Ala
    130                 135                 140
Val Leu Asp
145

<210> SEQ ID NO 134
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 134

Lys Glu Phe Leu Leu Tyr Leu Ala Gly Phe Val Asp Gly Asp Gly Ser
1               5                   10                  15
Ile Trp Ala Ser Ile Ile Pro Glu Gln Gly Tyr Lys Phe Lys His Arg
            20                  25                  30
Leu Arg Leu Ser Phe Thr Val Ala Gln Lys Thr Gln Arg Arg Trp Phe
        35                  40                  45
Leu Asp Lys Leu Val Asp Glu Ile Gly Val Gly Tyr Val Val Asp Gln
    50                  55                  60
Gly Ser Val Ser Glu Tyr Arg Leu Ser Glu Ile Lys Pro Leu His Asn
65                  70                  75                  80
Phe Leu Thr Gln Leu Gln Pro Phe Leu Lys Leu Lys Gln Lys Gln Ala
                85                  90                  95
```

```
Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 135
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 135

Lys Glu Phe Leu Leu Tyr Leu Ala Gly Phe Val Asp Gly Asp Gly Ser
1               5                   10                  15

Ile Trp Ala Ser Ile Ile Pro Glu Gln Gly Tyr Lys Phe Lys His Arg
            20                  25                  30

Leu Arg Leu Ser Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 136
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 136

Lys Glu Phe Leu Leu Tyr Leu Ala Gly Phe Val Asp Gly Asp Gly Ser
1               5                   10                  15

Ile Trp Ala Ser Ile Ile Pro Glu Gln Gly Tyr Lys Phe Lys His Arg
            20                  25                  30

Leu Arg Leu Ser Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95
```

-continued

```
Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 137
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 137

Lys Glu Phe Leu Leu Tyr Leu Ala Gly Phe Val Asp Gly Asp Gly Ser
1               5                   10                  15

Ile Trp Ala Ser Ile Ile Pro Glu Gln Gly Tyr Lys Phe Lys His Arg
            20                  25                  30

Leu Arg Leu Ser Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
            85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 138
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 138

Lys Glu Phe Leu Leu Tyr Leu Ala Gly Phe Val Asp Gly Asp Gly Ser
1               5                   10                  15

Ile Trp Ala Ser Ile Ile Pro Glu Gln Gly Tyr Lys Phe Lys His Arg
            20                  25                  30

Leu Arg Leu Ser Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
```

```
                    85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
        130                 135                 140

Val Leu Asp
145

<210> SEQ ID NO 139
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 139

Lys Glu Phe Leu Leu Tyr Leu Ala Gly Phe Val Asp Gly Asp Gly Ser
1               5                   10                  15

Ile Trp Ala Ser Ile Ile Pro Glu Gln Gly Tyr Lys Phe Lys His Arg
            20                  25                  30

Leu Arg Leu Ser Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
        130                 135                 140

Val Leu Asp
145

<210> SEQ ID NO 140
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 140

Lys Glu Phe Leu Leu Tyr Leu Ala Gly Phe Val Asp Gly Asp Gly Ser
1               5                   10                  15

Ile Trp Ala Ser Ile Ile Pro Glu Gln Gly Tyr Lys Phe Lys His Arg
            20                  25                  30

Leu Arg Leu Ser Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Glu Ile Lys Pro Leu His Asn
65                  70                  75                  80
```

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 141
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 141

Lys Glu Phe Leu Leu Tyr Leu Ala Gly Phe Val Asp Gly Asp Gly Ser
1               5                   10                  15

Ile Trp Ala Ser Ile Ile Pro Glu Gln Gly Tyr Lys Phe Lys His Arg
            20                  25                  30

Leu Arg Leu Ser Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 142
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 142

Lys Glu Phe Leu Leu Tyr Leu Ala Gly Phe Val Asp Gly Asp Gly Ser
1               5                   10                  15

Ile Trp Ala Ser Ile Ile Pro Glu Gln Gly Tyr Lys Phe Lys His Arg
            20                  25                  30

Leu Arg Leu Ser Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Glu Ile Lys Pro Leu His Asn
65                  70                  75                  80

```
Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 143
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 143

Lys Glu Phe Leu Leu Tyr Leu Ala Gly Phe Val Asp Gly Asp Gly Ser
1               5                   10                  15

Ile Trp Ala Ser Ile Ile Pro Glu Gln Gly Tyr Lys Phe Lys His Arg
            20                  25                  30

Leu Arg Leu Ser Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 144
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 144

Lys Glu Phe Leu Leu Tyr Leu Ala Gly Phe Val Asp Gly Asp Gly Ser
1               5                   10                  15

Ile Trp Ala Ser Ile Ile Pro Glu Gln Gly Tyr Lys Phe Lys His Arg
            20                  25                  30

Leu Arg Leu Ser Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Glu Ile Lys Pro Leu His Asn
```

65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 145
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 145

Lys Glu Phe Leu Leu Tyr Leu Ala Gly Phe Val Asp Gly Asp Gly Ser
1               5                   10                  15

Ile Trp Ala Ser Ile Ile Pro Glu Gln Gly Tyr Lys Phe Lys His Arg
            20                  25                  30

Leu Arg Leu Ser Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 146
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 146

Lys Glu Phe Leu Leu Tyr Leu Ala Gly Phe Val Asp Gly Asp Gly Ser
1               5                   10                  15

Ile Trp Ala Ser Ile Ile Pro Glu Gln Gly Tyr Lys Phe Lys His Arg
            20                  25                  30

Leu Arg Leu Ser Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
    50                  55                  60

```
Gly Ser Val Ser Glu Tyr Arg Leu Ser Glu Ile Lys Pro Leu His Asn
 65                  70                  75                  80

Phe Leu Thr Gln Leu Gln Pro Phe Leu Lys Leu Lys Gln Lys Gln Ala
                 85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 147
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 147

Lys Glu Phe Leu Leu Tyr Leu Ala Gly Phe Val Asp Gly Asp Gly Ser
  1               5                  10                  15

Ile Trp Ala Ser Ile Ile Pro Glu Gln Gly Tyr Lys Phe Lys His Arg
            20                  25                  30

Leu Arg Leu Ser Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
 50                  55                  60

Gly Ser Val Ser Glu Tyr Arg Leu Ser Glu Ile Lys Pro Leu His Asn
 65                  70                  75                  80

Phe Leu Thr Gln Leu Gln Pro Phe Leu Lys Leu Lys Gln Lys Gln Ala
                 85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 148
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 148

Lys Glu Phe Leu Leu Tyr Leu Ala Gly Phe Val Asp Gly Asp Gly Ser
  1               5                  10                  15

Ile Trp Ala Ser Ile Ile Pro Glu Gln Gly Tyr Lys Phe Lys His Arg
            20                  25                  30

Leu Arg Leu Ser Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
 50                  55                  60
```

```
Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 149
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 149

Lys Glu Phe Leu Leu Tyr Leu Ala Gly Phe Val Asp Gly Asp Gly Ser
1               5                   10                  15

Ile Trp Ala Ser Ile Ile Pro Glu Gln Gly Tyr Lys Phe Lys His Arg
            20                  25                  30

Leu Arg Leu Ser Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 150
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 150

Lys Glu Phe Leu Leu Tyr Leu Ala Gly Phe Val Asp Gly Asp Gly Ser
1               5                   10                  15

Ile Trp Ala Ser Ile Leu Pro Glu Ser Arg Met Lys Phe Lys His Arg
            20                  25                  30

Leu Arg Leu Gly Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
```

-continued

```
                    50                  55                  60
Gly Ser Val Ser Glu Tyr Arg Leu Ser Glu Ile Lys Pro Leu His Asn
 65                  70                  75                  80

Phe Leu Thr Gln Leu Gln Pro Phe Leu Lys Leu Lys Gln Lys Gln Ala
                 85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 151
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 151

Lys Glu Phe Leu Leu Tyr Leu Ala Gly Phe Val Asp Gly Asp Gly Ser
 1               5                  10                  15

Ile Trp Ala Gln Ile Leu Pro Glu Lys Lys Cys Ala Phe Lys His Arg
                20                  25                  30

Leu Arg Leu Trp Phe Thr Val Ala Gln Lys Thr Gln Arg Arg Trp Phe
            35                  40                  45

Leu Asp Lys Leu Val Asp Glu Ile Gly Val Gly Tyr Val Val Asp Gln
        50                  55                  60

Gly Ser Val Ser Glu Tyr Arg Leu Ser Glu Ile Lys Pro Leu His Asn
 65                  70                  75                  80

Phe Leu Thr Gln Leu Gln Pro Phe Leu Lys Leu Lys Gln Lys Gln Ala
                 85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 152
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 152

Lys Glu Phe Leu Leu Tyr Leu Ala Gly Phe Val Asp Gly Asp Gly Ser
 1               5                  10                  15

Ile Trp Ala Cys Ile Val Pro Glu Lys Ala Ser Arg Phe Lys His Arg
                20                  25                  30

Leu Arg Leu Ala Phe Thr Val Ala Gln Lys Thr Gln Arg Arg Trp Phe
            35                  40                  45
```

Leu Asp Lys Leu Val Asp Glu Ile Gly Val Gly Tyr Val Val Asp Gln
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 153
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 153

Lys Glu Phe Leu Leu Tyr Leu Ala Gly Phe Val Asp Gly Asp Gly Ser
1               5                   10                  15

Ile Trp Ala Thr Ile Val Pro Glu Lys Ser Ser Ile Phe Lys His Arg
            20                  25                  30

Leu Arg Leu Tyr Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 154
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 154

Lys Glu Phe Leu Leu Tyr Leu Ala Gly Phe Val Asp Gly Asp Gly Ser
1               5                   10                  15

Ile Trp Ala Ser Ile Val Pro Glu Glu Arg Thr Arg Phe Lys His Arg
            20                  25                  30

Leu Arg Leu Tyr Phe Thr Val Ala Gln Lys Thr Gln Arg Arg Trp Phe
        35                  40                  45

```
Leu Asp Lys Leu Val Asp Glu Ile Gly Val Gly Tyr Val Val Asp Gln
         50                  55                  60

Gly Ser Val Ser Glu Tyr Arg Leu Ser Glu Ile Lys Pro Leu His Asn
 65                  70                  75                  80

Phe Leu Thr Gln Leu Gln Pro Phe Leu Lys Leu Lys Gln Lys Gln Ala
                 85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
        130                 135                 140

Val Leu Asp
145

<210> SEQ ID NO 155
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 155

Lys Glu Phe Leu Leu Tyr Leu Ala Gly Phe Val Asp Gly Asp Gly Ser
 1               5                  10                  15

Ile Trp Ala Arg Ile Glu Pro Glu Lys Gly Gly Arg Phe Lys His Arg
                 20                  25                  30

Leu Arg Leu Tyr Phe Thr Val Ala Gln Lys Thr Gln Arg Arg Trp Phe
             35                  40                  45

Leu Asp Lys Leu Val Asp Glu Ile Gly Val Gly Tyr Val Val Asp Gln
         50                  55                  60

Gly Ser Val Ser Glu Tyr Arg Leu Ser Glu Ile Lys Pro Leu His Asn
 65                  70                  75                  80

Phe Leu Thr Gln Leu Gln Pro Phe Leu Lys Leu Lys Gln Lys Gln Ala
                 85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
        130                 135                 140

Val Leu Asp
145

<210> SEQ ID NO 156
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 156

Lys Glu Phe Leu Leu Tyr Leu Ala Gly Phe Val Asp Gly Asp Gly Ser
 1               5                  10                  15

Ile Trp Ala Ser Ile Ser Pro Glu Val Arg Ala Pro Phe Lys His Arg
                 20                  25                  30

Leu Arg Leu Tyr Phe Thr Val Ala Gln Lys Thr Gln Arg Arg Trp Phe
```

```
                35                  40                  45

Leu Asp Lys Leu Val Asp Glu Ile Gly Val Gly Tyr Val Val Asp Gln
        50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
        130                 135                 140

Val Leu Asp
145

<210> SEQ ID NO 157
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 157

Lys Glu Phe Leu Leu Tyr Leu Ala Gly Phe Val Asp Gly Asp Gly Ser
1               5                   10                  15

Ile Trp Ala Ser Ile Leu Pro Glu Thr Ser Ala Arg Phe Lys His Arg
            20                  25                  30

Leu Arg Leu Phe Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
        50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
        130                 135                 140

Val Leu Asp
145

<210> SEQ ID NO 158
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 158

Lys Glu Phe Leu Leu Tyr Leu Ala Gly Phe Val Asp Gly Asp Gly Ser
1               5                   10                  15

Ile Trp Ala Ala Ile Leu Pro Gln Ser Tyr Arg Phe Lys His Arg
            20                  25                  30
```

```
Leu Arg Leu Ala Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
 50                  55                  60

Gly Ser Val Ser Glu Tyr Arg Leu Ser Glu Ile Lys Pro Leu His Asn
 65                  70                  75                  80

Phe Leu Thr Gln Leu Gln Pro Phe Leu Lys Leu Lys Gln Lys Gln Ala
                 85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
                115                 120                 125

Leu Asn Asp Ser Lys Thr Arg Lys Thr Thr Ser Glu Thr Val Arg Ala
                130                 135                 140

Val Leu Asp
145

<210> SEQ ID NO 159
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 159

Lys Glu Phe Leu Leu Tyr Leu Ala Gly Phe Val Asp Gly Asp Gly Ser
 1               5                  10                  15

Ile Trp Ala Ser Ile Leu Pro Glu Arg Lys Thr Lys Phe Lys His Arg
                20                  25                  30

Leu Arg Leu Ala Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
 50                  55                  60

Gly Ser Val Ser Glu Tyr Arg Leu Ser Glu Ile Lys Pro Leu His Asn
 65                  70                  75                  80

Phe Leu Thr Gln Leu Gln Pro Phe Leu Lys Leu Lys Gln Lys Gln Ala
                 85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
                115                 120                 125

Leu Asn Asp Ser Lys Thr Arg Lys Thr Thr Ser Glu Thr Val Arg Ala
                130                 135                 140

Val Leu Asp
145

<210> SEQ ID NO 160
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 160

Lys Glu Phe Leu Leu Tyr Leu Ala Gly Phe Val Asp Gly Asp Gly Ser
 1               5                  10                  15

Ile Trp Ala Cys Ile Glu Pro Glu Arg Gly Tyr Arg Phe Lys His Arg
                20                  25                  30
```

```
Leu Arg Leu Ala Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
                115                 120                 125

Leu Asn Asp Ser Lys Thr Arg Lys Thr Thr Ser Glu Thr Val Arg Ala
        130                 135                 140

Val Leu Asp
145

<210> SEQ ID NO 161
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 161

Lys Glu Phe Leu Leu Tyr Leu Ala Gly Phe Val Asp Gly Asp Gly Ser
1               5                   10                  15

Ile Trp Ala Arg Ile Glu Pro Glu Leu Arg Leu Arg Phe Lys His Arg
                20                  25                  30

Leu Arg Leu Phe Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
                115                 120                 125

Leu Asn Asp Ser Lys Thr Arg Lys Thr Thr Ser Glu Thr Val Arg Ala
        130                 135                 140

Val Leu Asp
145

<210> SEQ ID NO 162
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 162

Lys Glu Phe Leu Leu Tyr Leu Ala Gly Phe Val Asp Gly Asp Gly Ser
1               5                   10                  15

Ile Trp Ala Gln Ile Val Pro Glu Arg Ala Gly Arg Phe Lys His Arg
```

```
                20                  25                  30
Leu Arg Leu Tyr Phe Thr Val Ala Gln Lys Thr Gln Arg Arg Trp Phe
            35                  40                  45

Leu Asp Lys Leu Val Asp Glu Ile Gly Val Gly Tyr Val Val Asp Gln
        50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 163
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 163

Lys Glu Phe Leu Leu Tyr Leu Ala Gly Phe Val Asp Gly Asp Gly Ser
1               5                   10                  15

Ile Trp Ala Ser Ile Thr Pro Glu Pro Thr Ala Ser Phe Lys His Arg
            20                  25                  30

Leu Arg Leu Tyr Phe Thr Val Ala Gln Lys Thr Gln Arg Arg Trp Phe
            35                  40                  45

Leu Asp Lys Leu Val Asp Glu Ile Gly Val Gly Tyr Val Val Asp Gln
        50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 164
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 164

Lys Glu Phe Leu Leu Tyr Leu Ala Gly Phe Val Asp Gly Asp Gly Ser
1               5                   10                  15
```

```
Ile Trp Ala Ser Ile Asn Pro Glu Pro Ser Tyr Arg Phe Lys His Arg
            20                  25                  30

Leu Arg Leu Ser Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 165
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 165

Lys Glu Phe Leu Leu Tyr Leu Ala Gly Phe Val Asp Gly Asp Gly Ser
1               5                   10                  15

Ile Trp Ala Ser Ile Leu Pro Glu His Gln Tyr Arg Phe Lys His Arg
            20                  25                  30

Leu Arg Leu Gly Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 166
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 166

Lys Glu Phe Leu Leu Tyr Leu Ala Gly Phe Val Asp Gly Asp Gly Ser
1               5                   10                  15
```

```
Ile Tyr Ala Ala Ile Asp Pro Asp Gln Lys Tyr Lys Phe Lys His Arg
            20                  25                  30

Leu Arg Leu Ile Phe Ala Val Cys Gln Lys Thr Gln Arg Arg Trp Phe
        35                  40                  45

Leu Asp Lys Leu Val Asp Glu Ile Gly Val Gly Tyr Val Val Asp His
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 167
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 167

Lys Glu Phe Leu Leu Tyr Leu Ala Gly Phe Val Asp Gly Asp Gly Ser
1               5                   10                  15

Ile Tyr Ala Thr Ile Glu Pro Ala Gln Arg Tyr Lys Phe Lys His Arg
            20                  25                  30

Leu Arg Leu Lys Phe Ala Val Ser Gln Lys Thr Gln Arg Arg Trp Phe
        35                  40                  45

Leu Asp Lys Leu Val Asp Glu Ile Gly Val Gly Tyr Val Ala Asp Gln
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 168
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 168

Lys Glu Phe Leu Leu Tyr Leu Ala Gly Phe Val Asp Gly Asp Gly Ser
```

```
1               5                   10                  15
Ile Tyr Ala Thr Ile Asn Pro Asp Gln Thr Asn Lys Phe Lys His Arg
            20                  25                  30

Leu Arg Leu Trp Phe Ala Val Cys Gln Lys Thr Gln Arg Arg Trp Phe
            35                  40                  45

Leu Asp Lys Leu Val Asp Glu Ile Gly Val Gly Tyr Val Ala Asp Thr
            50                  55                  60

Gly Ser Val Ser Glu Tyr Arg Leu Ser Gln Ile Lys Pro Leu His Asn
65                      70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
                115                 120                 125

Leu Asn Asp Ser Lys Thr Arg Lys Thr Thr Ser Glu Thr Val Arg Ala
            130                 135                 140

Val Leu Asp
145

<210> SEQ ID NO 169
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 169

Lys Glu Phe Leu Leu Tyr Leu Ala Gly Phe Val Asp Gly Asp Gly Ser
1               5                   10                  15

Ile Tyr Ala Cys Ile Glu Pro Ala Gln Asn Ser Lys Phe Lys His Tyr
            20                  25                  30

Leu Arg Leu Arg Phe Glu Val Ser Gln Lys Thr Gln Arg Arg Trp Phe
            35                  40                  45

Leu Asp Lys Leu Val Asp Glu Ile Gly Val Gly Tyr Val Tyr Asp Gln
            50                  55                  60

Gly Ser Val Ser Ser Tyr Arg Leu Ser Gln Ile Lys Pro Leu His Asn
65                      70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
                115                 120                 125

Leu Asn Asp Ser Lys Thr Arg Lys Thr Thr Ser Glu Thr Val Arg Ala
            130                 135                 140

Val Leu Asp
145

<210> SEQ ID NO 170
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 170
```

Lys Glu Phe Leu Leu Tyr Leu Ala Gly Phe Val Asp Gly Asp Gly Ser
1               5                   10                  15

Ile Tyr Ala Ser Ile Thr Pro Cys Gln Ser Tyr Lys Phe Lys His Arg
            20                  25                  30

Leu Leu Leu Lys Phe Ser Val Ala Gln Lys Thr Gln Arg Arg Trp Phe
        35                  40                  45

Leu Asp Lys Leu Val Asp Glu Ile Gly Val Gly Tyr Val Thr Asp Ser
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
            85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
            130                 135                 140

Val Leu Asp
145

<210> SEQ ID NO 171
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 171

Lys Glu Phe Leu Leu Tyr Leu Ala Gly Phe Val Asp Gly Asp Gly Ser
1               5                   10                  15

Ile Tyr Ala Thr Ile Met Pro Glu Gln Thr Val Lys Phe Lys His Arg
            20                  25                  30

Leu Arg Leu Phe Phe Glu Val Ala Gln Lys Thr Gln Arg Arg Trp Phe
        35                  40                  45

Leu Asp Lys Leu Val Asp Glu Ile Gly Val Gly Tyr Val Tyr Asp Gln
    50                  55                  60

Gly Ser Val Ser Ser Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
            85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
            130                 135                 140

Val Leu Asp
145

<210> SEQ ID NO 172
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 172

```
Lys Glu Phe Leu Leu Tyr Leu Ala Gly Phe Val Asp Gly Asp Gly Ser
1               5                   10                  15

Ile Tyr Ala Thr Ile Gln Pro Glu Gln Ala Pro Lys Phe Lys His Arg
                20                  25                  30

Leu Arg Leu His Phe Thr Val His Gln Lys Thr Gln Arg Arg Trp Phe
            35                  40                  45

Leu Asp Lys Leu Val Asp Glu Ile Gly Val Gly Tyr Val Tyr Asp Gln
        50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
        130                 135                 140

Val Leu Asp
145

<210> SEQ ID NO 173
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 173

Lys Glu Phe Leu Leu Tyr Leu Ala Gly Phe Val Asp Gly Asp Gly Ser
1               5                   10                  15

Ile Trp Ala Thr Ile Glu Pro Ser Gln Thr Leu Lys Phe Lys His Arg
                20                  25                  30

Leu Arg Leu His Phe Ser Val Tyr Gln Lys Thr Gln Arg Arg Trp Phe
            35                  40                  45

Leu Asp Lys Leu Val Asp Glu Ile Gly Val Gly Tyr Val Tyr Asp Asp
        50                  55                  60

Gly Ser Val Ser Arg Tyr Gln Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
        130                 135                 140

Val Leu Asp
145

<210> SEQ ID NO 174
<211> LENGTH: 147
<212> TYPE: PRT
<213> ORGANISM: Artificial Sequence
<220> FEATURE:
<223> OTHER INFORMATION: Synthetic Polypeptide
```

-continued

```
<400> SEQUENCE: 174

Lys Glu Phe Leu Leu Tyr Leu Ala Gly Phe Val Asp Gly Asp Gly Ser
1               5                   10                  15

Ile Tyr Ala Ser Ile Thr Pro Cys Gln Ser Tyr Lys Phe Lys His Arg
            20                  25                  30

Leu Leu Leu Lys Phe Ser Val Ala Gln Lys Thr Gln Arg Arg Trp Phe
        35                  40                  45

Leu Asp Lys Leu Val Asp Glu Ile Gly Val Gly Tyr Val Thr Asp Ser
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 175
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 175

Lys Glu Phe Leu Leu Tyr Leu Ala Gly Phe Val Asp Gly Asp Gly Ser
1               5                   10                  15

Ile Tyr Ala Thr Ile Ile Pro Ser Gln Asn Leu Lys Phe Lys His Arg
            20                  25                  30

Leu Arg Leu Tyr Phe Glu Val Cys Gln Lys Thr Gln Arg Arg Trp Phe
        35                  40                  45

Leu Asp Lys Leu Val Asp Glu Ile Gly Val Gly Tyr Val Tyr Asp Gln
    50                  55                  60

Gly Ser Val Ser Ser Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 176
<211> LENGTH: 147
<212> TYPE: PRT
<213> ORGANISM: Artificial Sequence
<220> FEATURE:
<223> OTHER INFORMATION: Synthetic Polypeptide
```

<400> SEQUENCE: 176

Lys Glu Phe Leu Leu Tyr Leu Ala Gly Phe Val Asp Gly Asp Gly Ser
1               5                   10                  15

Ile Tyr Ala Ser Ile Cys Pro Thr Gln Ala Ala Lys Phe Lys His Arg
            20                  25                  30

Leu Arg Leu His Phe Ala Val Phe Gln Lys Thr Gln Arg Arg Trp Phe
        35                  40                  45

Leu Asp Lys Leu Val Asp Glu Ile Gly Val Gly Tyr Val Thr Asp Cys
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 177
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 177

Lys Glu Phe Leu Leu Tyr Leu Ala Gly Phe Val Asp Gly Asp Gly Ser
1               5                   10                  15

Ile Tyr Ala Ser Ile Glu Pro Ala Gln Ser Tyr Lys Phe Lys His Arg
            20                  25                  30

Leu Gln Leu Lys Phe Ala Val Ala Gln Lys Thr Gln Arg Arg Trp Phe
        35                  40                  45

Leu Asp Lys Leu Val Asp Glu Ile Gly Val Gly Tyr Val Cys Asp Ile
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 178
<211> LENGTH: 147
<212> TYPE: PRT
<213> ORGANISM: Artificial Sequence
<220> FEATURE:

<223> OTHER INFORMATION: Synthetic Polypeptide

<400> SEQUENCE: 178

Lys Glu Phe Leu Leu Tyr Leu Ala Gly Phe Val Asp Gly Asp Gly Ser
1               5                   10                  15

Ile Tyr Ala Ala Ile Met Pro Thr Gln Ser Tyr Lys Phe Lys His Arg
            20                  25                  30

Leu Arg Leu Ala Phe Ser Val Ser Gln Lys Thr Gln Arg Arg Trp Phe
        35                  40                  45

Leu Asp Lys Leu Val Asp Glu Ile Gly Val Gly Tyr Val Thr Asp Ala
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 179
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 179

Lys Glu Phe Leu Leu Tyr Leu Ala Gly Phe Val Asp Gly Asp Gly Ser
1               5                   10                  15

Ile Tyr Ala Thr Ile Thr Pro Asn Gln Arg Thr Lys Phe Lys His Gln
            20                  25                  30

Leu Lys Leu Ala Phe Ala Val Tyr Gln Lys Thr Gln Arg Arg Trp Phe
        35                  40                  45

Leu Asp Lys Leu Val Asp Glu Ile Gly Val Gly Tyr Val Tyr Asp Gln
    50                  55                  60

Gly Ser Val Ser Cys Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 180
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 180

Lys Glu Phe Leu Leu Tyr Leu Ala Gly Phe Val Asp Gly Asp Gly Ser
1               5                   10                  15

Ile Tyr Ala Ala Ile Val Pro Val Gln Ser Thr Lys Phe Lys His Arg
            20                  25                  30

Leu Arg Leu Tyr Phe Thr Val His Gln Lys Thr Gln Arg Arg Trp Phe
        35                  40                  45

Leu Asp Lys Leu Val Asp Glu Ile Gly Val Gly Tyr Val Tyr Asp Gln
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Gln Lys Gln Ala
                85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
    130                 135                 140

Val Leu Asp
145

<210> SEQ ID NO 181
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 181

Lys Glu Phe Leu Leu Tyr Leu Ala Gly Phe Val Asp Gly Asp Gly Ser
1               5                   10                  15

Ile Tyr Ala Thr Ile Cys Pro Val Gln Ser Leu Lys Phe Lys His Arg
            20                  25                  30

Leu Arg Leu Phe Phe Ala Val Cys Gln Lys Thr Gln Arg Arg Trp Phe
        35                  40                  45

Leu Asp Lys Leu Val Asp Glu Ile Gly Val Gly Tyr Val Val Asp His
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
    130                 135                 140

Val Leu Asp
145

<210> SEQ ID NO 182
<211> LENGTH: 147
<212> TYPE: PRT

<213> ORGANISM: Artificial Sequence
<220> FEATURE:
<223> OTHER INFORMATION: Synthetic Polypeptide

<400> SEQUENCE: 182

```
Lys Glu Phe Leu Leu Tyr Leu Ala Gly Phe Val Asp Gly Asp Gly Ser
1               5                   10                  15

Ile Trp Ala Ser Ile Leu Pro Glu Gln Arg Asn Lys Phe Lys His Arg
            20                  25                  30

Leu Lys Leu Gly Phe Ser Val Ser Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145
```

<210> SEQ ID NO 183
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 183

```
Lys Glu Phe Leu Leu Tyr Leu Ala Gly Phe Val Asp Gly Asp Gly Ser
1               5                   10                  15

Ile Tyr Ala Thr Ile His Pro Cys Gln Cys Thr Lys Phe Lys His Arg
            20                  25                  30

Leu Arg Leu Tyr Phe Glu Val Tyr Gln Lys Thr Gln Arg Arg Trp Phe
        35                  40                  45

Leu Asp Lys Leu Val Asp Glu Ile Gly Val Gly Tyr Val Tyr Asp Gln
    50                  55                  60

Gly Ser Val Ser Ser Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145
```

<210> SEQ ID NO 184
<211> LENGTH: 147

```
<212> TYPE: PRT
<213> ORGANISM: Artificial Sequence
<220> FEATURE:
<223> OTHER INFORMATION: Synthetic Polypeptide

<400> SEQUENCE: 184

Lys Glu Phe Leu Leu Tyr Leu Ala Gly Phe Val Asp Gly Asp Gly Ser
1               5                   10                  15

Ile Tyr Ala Thr Ile Asp Pro Asp Gln Arg Gln Lys Phe Lys His Arg
            20                  25                  30

Leu Arg Leu Lys Phe Ser Val Ser Gln Lys Thr Gln Arg Arg Trp Phe
        35                  40                  45

Leu Asp Lys Leu Val Asp Glu Ile Gly Val Gly Tyr Val Val Asp Gly
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 185
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 185

Lys Glu Phe Leu Leu Tyr Leu Ala Gly Phe Val Asp Gly Asp Gly Ser
1               5                   10                  15

Ile Tyr Ala Ala Ile Val Pro Asp Gln Ala Pro Lys Phe Lys His Arg
            20                  25                  30

Leu Arg Leu Phe Phe Ala Val Ser Gln Lys Thr Gln Arg Arg Trp Phe
        35                  40                  45

Leu Asp Lys Leu Val Asp Glu Ile Gly Val Gly Tyr Val Ala Asp Gln
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 186
```

```
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 186

Lys Glu Phe Leu Leu Tyr Leu Ala Gly Phe Val Asp Gly Asp Gly Ser
1               5                   10                  15

Ile Tyr Ala Ser Ile Leu Pro Glu Gln Arg Asn Lys Phe Lys His Arg
            20                  25                  30

Leu Lys Leu Ser Phe Ser Val Cys Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 187
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 187

Lys Glu Phe Leu Leu Tyr Leu Ala Gly Phe Val Asp Gly Asp Gly Ser
1               5                   10                  15

Ile Tyr Ala Ala Ile Val Pro Asp Gln Ala Pro Lys Phe Lys His Arg
            20                  25                  30

Leu Arg Leu Phe Phe Ala Val Ser Gln Lys Thr Gln Arg Arg Trp Phe
        35                  40                  45

Leu Asp Lys Leu Val Asp Glu Ile Gly Val Gly Tyr Val Ala Asp Gln
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145
```

```
<210> SEQ ID NO 188
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 188

Lys Glu Phe Leu Leu Tyr Leu Ala Gly Phe Val Asp Gly Asp Gly Ser
1               5                   10                  15

Ile Tyr Ala Cys Ile Cys Pro Asp Gln Gly Tyr Lys Phe Lys His Arg
            20                  25                  30

Leu Thr Leu Lys Phe Ser Val Ala Gln Lys Thr Gln Arg Arg Trp Phe
        35                  40                  45

Leu Asp Lys Leu Val Asp Glu Ile Gly Val Gly Tyr Val Leu Asp Gln
50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Gln Lys Gln Ala
            85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
            130                 135                 140

Val Leu Asp
145

<210> SEQ ID NO 189
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 189

Lys Glu Phe Leu Leu Tyr Leu Ala Gly Phe Val Asp Gly Asp Gly Ser
1               5                   10                  15

Ile Tyr Ala Cys Ile Leu Pro Glu Gln Lys Thr Lys Phe Lys His Arg
            20                  25                  30

Leu Lys Leu Ser Phe Thr Val Cys Gln Lys Thr Gln Arg Arg Trp Phe
        35                  40                  45

Leu Asp Lys Leu Val Asp Glu Ile Gly Val Gly Tyr Val Val Asp Gln
50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
            85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
            130                 135                 140

Val Leu Asp
145
```

```
<210> SEQ ID NO 190
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 190

Lys Glu Phe Leu Leu Tyr Leu Ala Gly Phe Val Asp Gly Asp Gly Ser
1               5                   10                  15

Ile Phe Ala Arg Ile Phe Lys Gly Gln His Trp Lys Phe Lys His Tyr
            20                  25                  30

Ile Arg Leu Thr Phe Thr Val Ala Gln Lys Thr Gln Arg Arg Trp Phe
        35                  40                  45

Leu Asp Lys Leu Val Asp Glu Ile Gly Val Gly Tyr Val Thr Asp Trp
    50                  55                  60

Gly Ser Val Ser His Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 191
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 191

Lys Glu Phe Leu Leu Tyr Leu Ala Gly Phe Val Asp Gly Asp Gly Ser
1               5                   10                  15

Ile Tyr Ala Arg Ile Phe Lys Gly Gln His Trp Lys Phe Lys His Tyr
            20                  25                  30

Ile Arg Leu Thr Phe Cys Val Arg Gln Lys Thr Gln Arg Arg Trp Phe
        35                  40                  45

Leu Asp Lys Leu Val Asp Glu Ile Gly Val Gly Tyr Val Thr Asp Ser
    50                  55                  60

Gly Ser Val Ser Ala Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145
```

<210> SEQ ID NO 192
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 192

Lys Glu Phe Leu Leu Tyr Leu Ala Gly Phe Val Asp Gly Asp Gly Ser
1               5                   10                  15

Ile Tyr Ala Arg Ile Phe Lys Gly Gln His Trp Lys Phe Lys His His
            20                  25                  30

Ile Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Thr Asp Trp
    50                  55                  60

Gly Ser Val Ser Gly Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 193
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 193

Lys Glu Phe Leu Leu Tyr Leu Ala Gly Phe Val Asp Gly Asp Gly Ser
1               5                   10                  15

Ile Tyr Ala Arg Ile Glu Pro Arg Gln Thr Ala Lys Phe Lys His Tyr
            20                  25                  30

Leu Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Thr Asp Trp
    50                  55                  60

Gly Ser Val Ser Gly Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp

```
<210> SEQ ID NO 194
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 194

Lys Glu Phe Leu Leu Tyr Leu Ala Gly Phe Val Asp Gly Asp Gly Ser
1               5                   10                  15

Ile Tyr Ala Arg Ile Glu Pro Arg Gln Thr Ala Lys Phe Lys His Tyr
            20                  25                  30

Leu Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Gln Tyr Phe Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 195
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 195

Lys Glu Phe Leu Leu Tyr Leu Ala Gly Phe Val Asp Gly Asp Gly Ser
1               5                   10                  15

Ile Tyr Ala Arg Ile Glu Pro Arg Gln Asn Phe Lys Phe Lys His Thr
            20                  25                  30

Leu Arg Leu Thr Phe Phe Val Ser Gln Lys Thr Gln Arg Arg Trp Phe
        35                  40                  45

Leu Asp Lys Leu Val Asp Glu Ile Gly Val Gly Tyr Val Thr Asp Trp
    50                  55                  60

Gly Ser Val Ser Gly Tyr Tyr Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140
```

Val Leu Asp
145

<210> SEQ ID NO 196
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 196

Lys Glu Phe Leu Leu Tyr Leu Ala Gly Phe Val Asp Gly Asp Gly Ser
1               5                   10                  15

Ile Tyr Ala Arg Ile Glu Pro Arg Gln Gly Asn Lys Phe Lys His Tyr
            20                  25                  30

Leu Arg Leu Thr Phe Asn Val Cys Gln Lys Thr Gln Arg Arg Trp Phe
        35                  40                  45

Leu Asp Lys Leu Val Asp Glu Ile Gly Val Gly Tyr Val Ile Asp Arg
    50                  55                  60

Gly Ser Val Ser Asp Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
            85                  90                  95

Asn Leu Val Leu Lys Ile Ile Glu Gln Leu Pro Ser Ala Lys Glu Ser
        100                 105                 110

Pro Asp Lys Phe Leu Glu Val Cys Thr Trp Val Asp Gln Ile Ala Ala
    115                 120                 125

Leu Asn Asp Ser Lys Thr Arg Lys Thr Thr Ser Glu Thr Val Arg Ala
130                 135                 140

Val Leu Asp
145

<210> SEQ ID NO 197
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 197

Lys Glu Phe Leu Leu Tyr Leu Ala Gly Phe Val Asp Gly Asp Gly Ser
1               5                   10                  15

Ile Tyr Ala Arg Ile Glu Pro Arg Gln Thr Ala Lys Phe Lys His Tyr
            20                  25                  30

Leu Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Gln Tyr Phe Leu Ser Gln Ile Lys Pro Leu His Asn
65                  70                  75                  80

Phe Leu Thr Gln Leu Gln Pro Phe Leu Lys Leu Lys Gln Lys Gln Ala
            85                  90                  95

Asn Leu Val Leu Lys Ile Ile Glu Gln Leu Pro Ser Ala Lys Glu Ser
        100                 105                 110

Pro Asp Lys Phe Leu Glu Val Cys Thr Trp Val Asp Gln Ile Ala Ala
    115                 120                 125

Leu Asn Asp Ser Lys Thr Arg Lys Thr Thr Ser Glu Thr Val Arg Ala
130                 135                 140

Val Leu Asp
145

<210> SEQ ID NO 198
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 198

Lys Glu Phe Leu Leu Tyr Leu Ala Gly Phe Val Asp Gly Asp Gly Ser
1               5                   10                  15

Ile Tyr Ala Arg Ile Glu Pro Arg Gln Thr Ala Lys Phe Lys His Tyr
            20                  25                  30

Leu Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Gln Tyr Tyr Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 199
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 199

Lys Glu Phe Leu Leu Tyr Leu Ala Gly Phe Val Asp Gly Asp Gly Ser
1               5                   10                  15

Ile Tyr Ala Arg Ile Tyr Pro Lys Gln Ser Ser Lys Phe Lys His His
            20                  25                  30

Leu Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Tyr Asp Ser
    50                  55                  60

Gly Ser Val Ser Gln Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala

```
            130                 135                 140

Val Leu Asp
145

<210> SEQ ID NO 200
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 200

Lys Glu Phe Leu Leu Tyr Leu Ala Gly Phe Val Asp Gly Asp Gly Ser
1               5                   10                  15

Ile Tyr Ala Arg Ile Glu Pro Glu Gln Thr Ala Lys Phe Lys His Met
            20                  25                  30

Leu Arg Leu Thr Phe Arg Val Ser Gln Lys Thr Gln Arg Arg Trp Phe
        35                  40                  45

Leu Asp Lys Leu Val Asp Glu Ile Gly Val Gly Tyr Val Asn Asp Ser
    50                  55                  60

Gly Ser Val Ser Gly Tyr Tyr Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 201
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 201

Lys Glu Phe Leu Leu Tyr Leu Ala Gly Phe Val Asp Gly Asp Gly Ser
1               5                   10                  15

Ile Tyr Ala Arg Ile Glu Pro Arg Gln Thr Ala Lys Phe Lys His Tyr
            20                  25                  30

Leu Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Gln Tyr Phe Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125
```

```
Leu Asn Asp Ser Lys Thr Arg Lys Thr Thr Ser Glu Thr Val Arg Ala
            130                 135                 140

Val Leu Asp
145

<210> SEQ ID NO 202
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 202

Lys Glu Phe Leu Leu Tyr Leu Ala Gly Phe Val Asp Gly Asp Gly Ser
1               5                   10                  15

Ile Tyr Ala Arg Ile Glu Pro Lys Gln Thr Ala Lys Phe Lys His His
            20                  25                  30

Leu Cys Leu Arg Phe His Val Ser Gln Lys Thr Gln Arg Arg Trp Phe
        35                  40                  45

Leu Asp Lys Leu Val Asp Glu Ile Gly Val Gly Tyr Val Val Asp His
    50                  55                  60

Gly Ser Val Ser Gln Tyr Phe Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 203
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 203

Lys Glu Phe Leu Leu Tyr Leu Ala Gly Phe Val Asp Gly Asp Gly Ser
1               5                   10                  15

Ile Tyr Ala Arg Ile Glu Pro Arg Gln Thr Ala Lys Phe Lys His Tyr
            20                  25                  30

Leu Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Thr Asp Trp
    50                  55                  60

Gly Ser Val Ser Gly Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125
```

```
Leu Asn Asp Ser Lys Thr Arg Lys Thr Thr Ser Glu Thr Val Arg Ala
            130                 135                 140

Val Leu Asp
145

<210> SEQ ID NO 204
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 204

Lys Glu Phe Leu Leu Tyr Leu Ala Gly Phe Val Asp Gly Asp Gly Ser
1               5                   10                  15

Ile Tyr Ala Arg Ile Glu Pro Arg Gln Arg Val Lys Phe Lys His Phe
            20                  25                  30

Leu Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Thr Asp Trp
    50                  55                  60

Gly Ser Val Ser Gly Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 205
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 205

Lys Glu Phe Leu Leu Tyr Leu Ala Gly Phe Val Asp Gly Asp Gly Ser
1               5                   10                  15

Ile Tyr Ala Arg Ile Glu Pro Arg Gln Gly Cys Lys Phe Lys His Val
            20                  25                  30

Leu Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Thr Asp Trp
    50                  55                  60

Gly Ser Val Ser Gly Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
```

```
            115                 120                 125
Leu Asn Asp Ser Lys Thr Arg Lys Thr Thr Ser Glu Thr Val Arg Ala
    130                 135                 140

Val Leu Asp
145

<210> SEQ ID NO 206
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 206

Lys Glu Phe Leu Leu Tyr Leu Ala Gly Phe Val Asp Gly Asp Gly Ser
1               5                   10                  15

Ile Tyr Ala Arg Ile Glu Pro Arg Gln Val Cys Lys Phe Lys His Ile
            20                  25                  30

Leu Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Thr Asp Trp
    50                  55                  60

Gly Ser Val Ser Gly Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 207
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 207

Lys Glu Phe Leu Leu Tyr Leu Ala Gly Phe Val Asp Gly Asp Gly Ser
1               5                   10                  15

Ile Tyr Ala Arg Ile Glu Pro Arg Gln Cys Phe Lys Phe Lys His Cys
            20                  25                  30

Leu Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Thr Asp Trp
    50                  55                  60

Gly Ser Val Ser Gly Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110
```

```
Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 208
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 208

Lys Glu Phe Leu Leu Tyr Leu Ala Gly Phe Val Asp Gly Asp Gly Ser
1               5                   10                  15

Ile Tyr Ala Arg Ile Glu Pro Arg Gln Arg Phe Lys Phe Lys His Cys
            20                  25                  30

Leu Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Thr Asp Trp
    50                  55                  60

Gly Ser Val Ser Gly Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 209
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 209

Lys Glu Phe Leu Leu Tyr Leu Ala Gly Phe Val Asp Gly Asp Gly Ser
1               5                   10                  15

Ile Tyr Ala Arg Ile Glu Pro Arg Gln Phe Cys Lys Phe Lys His Ile
            20                  25                  30

Leu Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Thr Asp Trp
    50                  55                  60

Gly Ser Val Ser Gly Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110
```

```
Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 210
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 210

Lys Glu Phe Leu Leu Tyr Leu Ala Gly Phe Val Asp Gly Asp Gly Ser
1               5                   10                  15

Ile Tyr Ala Arg Ile Glu Pro Arg Gln Ala Phe Lys Phe Lys His Ala
            20                  25                  30

Leu Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Thr Asp Trp
    50                  55                  60

Gly Ser Val Ser Gly Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 211
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 211

Lys Glu Phe Leu Leu Tyr Leu Ala Gly Phe Val Asp Gly Asp Gly Ser
1               5                   10                  15

Ile Tyr Ala Arg Ile Glu Pro Arg Gln Thr Cys Lys Phe Lys His Ile
            20                  25                  30

Leu Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Thr Asp Trp
    50                  55                  60

Gly Ser Val Ser Gly Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
```

```
                        100                 105                 110
Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 212
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 212

Lys Glu Phe Leu Leu Tyr Leu Ala Gly Phe Val Asp Gly Asp Gly Ser
1               5                   10                  15

Ile Tyr Ala Arg Ile Glu Pro Arg Gln Cys Phe Lys Phe Lys His Gly
            20                  25                  30

Leu Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Thr Asp Trp
    50                  55                  60

Gly Ser Val Ser Gly Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 213
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 213

Lys Glu Phe Leu Leu Tyr Leu Ala Gly Phe Val Asp Gly Asp Gly Ser
1               5                   10                  15

Ile Tyr Ala Arg Ile Glu Pro Arg Gln Ser Ser Lys Phe Lys His Leu
            20                  25                  30

Leu Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Thr Asp Trp
    50                  55                  60

Gly Ser Val Ser Gly Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95
```

```
Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 214
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 214

Lys Glu Phe Leu Leu Tyr Leu Ala Gly Phe Val Asp Gly Asp Gly Ser
1               5                   10                  15

Ile Tyr Ala Arg Ile Tyr Leu Gly Gln His Trp Lys Phe Lys His Tyr
            20                  25                  30

Val Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Thr Asp Trp
    50                  55                  60

Gly Ser Val Ser Gly Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 215
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 215

Lys Glu Phe Leu Leu Tyr Leu Ala Gly Phe Val Asp Gly Asp Gly Ser
1               5                   10                  15

Ile Tyr Ala Arg Ile Tyr Leu Gly Gln His Tyr Lys Phe Lys His Tyr
            20                  25                  30

Ile Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Thr Asp Trp
    50                  55                  60

Gly Ser Val Ser Gly Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95
```

```
Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 216
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 216

Lys Glu Phe Leu Leu Tyr Leu Ala Gly Phe Val Asp Gly Asp Gly Ser
1               5                   10                  15

Ile Tyr Ala Arg Ile Tyr Asn Ala Gln Tyr Tyr Lys Phe Lys His Tyr
            20                  25                  30

Ile Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Thr Asp Trp
    50                  55                  60

Gly Ser Val Ser Gly Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
            85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 217
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 217

Lys Glu Phe Leu Leu Tyr Leu Ala Gly Phe Val Asp Gly Asp Gly Ser
1               5                   10                  15

Ile Tyr Ala Arg Ile Glu Arg Gln Asn Phe Lys Phe Lys His His
            20                  25                  30

Ile Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Thr Asp Trp
    50                  55                  60

Gly Ser Val Ser Gly Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
```

Asn Leu Val Leu Lys Ile Ile Glu Gln Leu Pro Ser Ala Lys Glu Ser
            100                 105                 110
Pro Asp Lys Phe Leu Glu Val Cys Thr Trp Val Asp Gln Ile Ala Ala
            115                 120                 125
Leu Asn Asp Ser Lys Thr Arg Lys Thr Thr Ser Glu Thr Val Arg Ala
            130                 135                 140
Val Leu Asp
145

<210> SEQ ID NO 218
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 218

Lys Glu Phe Leu Leu Tyr Leu Ala Gly Phe Val Asp Gly Asp Gly Ser
1               5                   10                  15
Ile Tyr Ala Arg Ile Glu Arg Arg Gln Cys Val Lys Phe Lys His Tyr
            20                  25                  30
Leu Arg Leu Thr Phe His Val Ser Gln Lys Thr Gln Arg Arg Trp Phe
        35                  40                  45
Leu Asp Lys Leu Val Asp Glu Ile Gly Val Gly Tyr Val Thr Asp Trp
    50                  55                  60
Gly Ser Val Ser Gly Tyr Tyr Leu Ser Glu Ile Lys Pro Leu His Asn
65                  70                  75                  80
Phe Leu Thr Gln Leu Gln Pro Phe Leu Lys Leu Lys Gln Lys Gln Ala
                85                  90                  95
Asn Leu Val Leu Lys Ile Ile Glu Gln Leu Pro Ser Ala Lys Glu Ser
            100                 105                 110
Pro Asp Lys Phe Leu Glu Val Cys Thr Trp Val Asp Gln Ile Ala Ala
            115                 120                 125
Leu Asn Asp Ser Lys Thr Arg Lys Thr Thr Ser Glu Thr Val Arg Ala
            130                 135                 140
Val Leu Asp
145

<210> SEQ ID NO 219
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 219

Lys Glu Phe Leu Leu Tyr Leu Ala Gly Phe Val Asp Gly Asp Gly Ser
1               5                   10                  15
Ile Tyr Ala Arg Ile Glu Tyr Arg Gln Gly Ala Lys Phe Lys His Tyr
            20                  25                  30
Leu Arg Leu Thr Phe His Val Ser Gln Lys Thr Gln Arg Arg Trp Phe
        35                  40                  45
Leu Asp Lys Leu Val Asp Glu Ile Gly Val Gly Tyr Val Thr Asp Trp
    50                  55                  60
Gly Ser Val Ser Gly Tyr Tyr Leu Ser Glu Ile Lys Pro Leu His Asn
65                  70                  75                  80

```
Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 220
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 220

Lys Glu Phe Leu Leu Tyr Leu Ala Gly Phe Val Asp Gly Asp Gly Ser
1               5                   10                  15

Ile Tyr Ala Arg Ile Glu Pro Arg Gln Ser Gly Lys Phe Lys His Tyr
            20                  25                  30

Ile Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Thr Asp Trp
    50                  55                  60

Gly Ser Val Ser Gly Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 221
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 221

Lys Glu Phe Leu Leu Tyr Leu Ala Gly Phe Val Asp Gly Asp Gly Ser
1               5                   10                  15

Ile Tyr Ala Arg Ile Phe Lys Gly Gln His Trp Lys Phe Lys His His
            20                  25                  30

Ile Arg Leu Thr Phe Asn Val Ser Gln Lys Thr Gln Arg Arg Trp Phe
        35                  40                  45

Leu Asp Lys Leu Val Asp Glu Ile Gly Val Gly Tyr Val Ser Asp Thr
    50                  55                  60

Gly Ser Gln Ser Asn Tyr Tyr Leu Ser Glu Ile Lys Pro Leu His Asn
65                  70                  75                  80
```

```
Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 222
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 222

Lys Glu Phe Leu Leu Tyr Leu Ala Gly Phe Val Asp Gly Asp Gly Ser
1               5                   10                  15

Ile Phe Ala Arg Ile Phe Lys Gly Gln His Trp Lys Phe Lys His His
            20                  25                  30

Ile Arg Leu Thr Phe Asn Val Ser Gln Lys Thr Gln Arg Arg Trp Phe
        35                  40                  45

Leu Asp Lys Leu Val Asp Glu Ile Gly Val Gly Tyr Val Asn Asp Tyr
    50                  55                  60

Gly Ser Thr Ser Asn Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 223
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 223

Lys Glu Phe Leu Leu Tyr Leu Ala Gly Phe Val Asp Gly Asp Gly Ser
1               5                   10                  15

Ile Phe Ala Arg Ile Phe Lys Gly Gln His Trp Lys Phe Lys His His
            20                  25                  30

Ile Arg Leu Thr Phe Asn Val Ala Gln Lys Thr Gln Arg Arg Trp Phe
        35                  40                  45

Leu Asp Lys Leu Val Asp Glu Ile Gly Val Gly Tyr Val Thr Asp His
    50                  55                  60

Gly Ser Asn Ser Asn Tyr Tyr Leu Ser Glu Ile Lys Pro Leu His Asn
```

```
                65                  70                  75                  80
Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
    130                 135                 140

Val Leu Asp
145

<210> SEQ ID NO 224
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 224

Lys Glu Phe Leu Leu Tyr Leu Ala Gly Phe Val Asp Gly Asp Gly Ser
1               5                   10                  15

Ile Tyr Ala Arg Ile Phe Lys Gly Gln His Trp Lys Phe Lys His His
                20                  25                  30

Ile Arg Leu Thr Phe Asn Val Thr Gln Lys Thr Gln Arg Arg Trp Phe
            35                  40                  45

Leu Asp Lys Leu Val Asp Glu Ile Gly Val Gly Tyr Val Ser Asp Tyr
    50                  55                  60

Gly Ser Met Ser Asn Tyr Tyr Leu Ser Glu Ile Lys Pro Leu His Asn
65              70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
    130                 135                 140

Val Leu Asp
145

<210> SEQ ID NO 225
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 225

Lys Glu Phe Leu Leu Tyr Leu Ala Gly Phe Val Asp Gly Asp Gly Ser
1               5                   10                  15

Ile Tyr Ala Arg Ile Phe Lys Gly Gln His Trp Lys Phe Lys His His
                20                  25                  30

Ile Arg Leu Thr Phe Ala Val Thr Gln Lys Thr Gln Arg Arg Trp Phe
            35                  40                  45

Leu Asp Lys Leu Val Asp Glu Ile Gly Val Gly Tyr Val Thr Asp His
    50                  55                  60
```

```
Gly Ser Cys Ser Asn Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 226
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 226

Lys Glu Phe Leu Leu Tyr Leu Ala Gly Phe Val Asp Gly Asp Gly Ser
1               5                   10                  15

Ile Tyr Ala Arg Ile Phe Lys Gly Gln His Trp Lys Phe Lys His His
            20                  25                  30

Ile Arg Leu Thr Phe Asn Val Ser Gln Lys Thr Gln Arg Arg Trp Phe
        35                  40                  45

Leu Asp Lys Leu Val Asp Glu Ile Gly Val Gly Tyr Val Gly Asp Tyr
    50                  55                  60

Gly Ser Met Ser His Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 227
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 227

Lys Glu Phe Leu Leu Tyr Leu Ala Gly Phe Val Asp Gly Asp Gly Ser
1               5                   10                  15

Ile Tyr Ala Arg Ile Phe Lys Gly Gln His Trp Lys Phe Lys His His
            20                  25                  30

Ile Arg Leu Thr Phe Asn Val Ser Gln Lys Thr Gln Arg Arg Trp Phe
        35                  40                  45

Leu Asp Lys Leu Val Asp Glu Ile Gly Val Gly Tyr Val Thr Asp Phe
    50                  55                  60
```

Gly Ser Gln Ser Gln Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 228
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 228

Lys Glu Phe Leu Leu Tyr Leu Ala Gly Phe Val Asp Gly Asp Gly Ser
1               5                   10                  15

Ile Phe Ala Arg Ile Phe Lys Gly Gln His Trp Lys Phe Lys His His
            20                  25                  30

Ile Arg Leu Thr Phe Asn Val Thr Gln Lys Thr Gln Arg Arg Trp Phe
        35                  40                  45

Leu Asp Lys Leu Val Asp Glu Ile Gly Val Gly Tyr Val Ser Asp Tyr
    50                  55                  60

Gly Ser Ile Ser Asn Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 229
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 229

Lys Glu Phe Leu Leu Tyr Leu Ala Gly Phe Val Asp Gly Asp Gly Ser
1               5                   10                  15

Ile Tyr Ala Arg Ile Phe Lys Gly Gln His Trp Lys Phe Lys His His
            20                  25                  30

Ile Arg Leu Thr Phe Asn Val Thr Gln Lys Thr Gln Arg Arg Trp Phe
        35                  40                  45

Leu Asp Lys Leu Val Asp Glu Ile Gly Val Gly Tyr Val Ile Asp Tyr

```
                    50                  55                  60
Gly Ser Ile Ser Asn Tyr Tyr Leu Ser Glu Ile Lys Pro Leu His Asn
 65                  70                  75                  80

Phe Leu Thr Gln Leu Gln Pro Phe Leu Lys Leu Lys Gln Lys Gln Ala
                     85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
                115                 120                 125

Leu Asn Asp Ser Lys Thr Arg Lys Thr Thr Ser Glu Thr Val Arg Ala
                130                 135                 140

Val Leu Asp
145

<210> SEQ ID NO 230
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 230

Lys Glu Phe Leu Leu Tyr Leu Ala Gly Phe Val Asp Gly Asp Gly Ser
 1                5                  10                  15

Ile Tyr Ala Arg Ile Phe Lys Gly Gln His Trp Lys Phe Lys His His
                 20                  25                  30

Ile Arg Leu Thr Phe Asn Val Thr Gln Lys Thr Gln Arg Arg Trp Phe
             35                  40                  45

Leu Asp Lys Leu Val Asp Glu Ile Gly Val Gly Tyr Val Thr Asp Tyr
 50                  55                  60

Gly Ser Ser Ser Asn Tyr Tyr Leu Ser Glu Ile Lys Pro Leu His Asn
 65                  70                  75                  80

Phe Leu Thr Gln Leu Gln Pro Phe Leu Lys Leu Lys Gln Lys Gln Ala
                     85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
                115                 120                 125

Leu Asn Asp Ser Lys Thr Arg Lys Thr Thr Ser Glu Thr Val Arg Ala
                130                 135                 140

Val Leu Asp
145

<210> SEQ ID NO 231
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 231

Lys Glu Phe Leu Leu Tyr Leu Ala Gly Phe Val Asp Gly Asp Gly Ser
 1                5                  10                  15

Ile Phe Ala Arg Ile Phe Lys Gly Gln His Trp Lys Phe Lys His His
                 20                  25                  30

Ile Arg Leu Thr Phe Asn Val Ser Gln Lys Thr Gln Arg Arg Trp Phe
             35                  40                  45
```

```
Leu Asp Lys Leu Val Asp Glu Ile Gly Val Gly Tyr Val Thr Asp Gly
    50                  55                  60

Gly Ser Ser Ser Asn Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
            130                 135                 140

Val Leu Asp
145

<210> SEQ ID NO 232
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 232

Lys Glu Phe Leu Leu Tyr Leu Ala Gly Phe Val Asp Gly Asp Gly Ser
1               5                   10                  15

Ile Phe Ala Arg Ile Phe Lys Gly Gln His Trp Lys Phe Lys His His
            20                  25                  30

Ile Arg Leu Thr Phe Asn Val Ser Gln Lys Thr Gln Arg Arg Trp Phe
        35                  40                  45

Leu Asp Lys Leu Val Asp Glu Ile Gly Val Gly Tyr Val Tyr Asp His
    50                  55                  60

Gly Ser Gln Ser Asn Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
            130                 135                 140

Val Leu Asp
145

<210> SEQ ID NO 233
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 233

Lys Glu Phe Leu Leu Tyr Leu Ala Gly Phe Val Asp Gly Asp Gly Ser
1               5                   10                  15

Ile Tyr Ala Arg Ile Phe Lys Gly Gln His Trp Lys Phe Lys His His
            20                  25                  30

Ile Arg Leu Thr Phe Asn Val Ser Gln Lys Thr Gln Arg Arg Trp Phe
        35                  40                  45
```

```
Leu Asp Lys Leu Val Asp Glu Ile Gly Val Gly Tyr Val Cys Asp Asn
    50                  55                  60

Gly Ser Asn Ser Asn Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
        130                 135                 140

Val Leu Asp
145

<210> SEQ ID NO 234
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 234

Lys Glu Phe Leu Leu Tyr Leu Ala Gly Phe Val Asp Gly Asp Gly Ser
1               5                   10                  15

Ile Phe Ala Arg Ile Phe Lys Gly Gln His Trp Lys Phe Lys His His
            20                  25                  30

Ile Arg Leu Thr Phe Asn Val Ser Gln Lys Thr Gln Arg Arg Trp Phe
        35                  40                  45

Leu Asp Lys Leu Val Asp Glu Ile Gly Val Gly Tyr Val Ala Asp Tyr
    50                  55                  60

Gly Ser Thr Ser Asn Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
        130                 135                 140

Val Leu Asp
145

<210> SEQ ID NO 235
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 235

Lys Glu Phe Leu Leu Tyr Leu Ala Gly Phe Val Asp Gly Asp Gly Ser
1               5                   10                  15

Ile Tyr Ala Arg Ile Phe Lys Gly Gln His Trp Lys Phe Lys His His
            20                  25                  30

Ile Arg Leu Thr Phe Cys Val Ser Gln Lys Thr Gln Arg Arg Trp Phe
```

```
                     35                  40                  45
Leu Asp Lys Leu Val Asp Glu Ile Gly Val Gly Tyr Val Ala Asp Tyr
         50                  55                  60

Gly Ser Met Ser Asn Tyr Tyr Leu Ser Glu Ile Lys Pro Leu His Asn
 65                  70                  75                  80

Phe Leu Thr Gln Leu Gln Pro Phe Leu Lys Leu Lys Gln Lys Gln Ala
                 85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 236
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 236

Lys Glu Phe Leu Leu Tyr Leu Ala Gly Phe Val Asp Gly Asp Gly Ser
 1               5                  10                  15

Ile Met Ala Arg Ile Phe Lys Gly Gln His Trp Lys Phe Lys His Tyr
                20                  25                  30

Ile Arg Leu Thr Leu Cys Val Arg Gln Lys Thr Gln Arg Arg Trp Phe
            35                  40                  45

Leu Asp Lys Leu Val Asp Glu Ile Gly Val Gly Tyr Val Cys Asp Ser
        50                  55                  60

Gly Ser Met Ser Ala Tyr Tyr Leu Ser Glu Ile Lys Pro Leu His Asn
 65                  70                  75                  80

Phe Leu Thr Gln Leu Gln Pro Phe Leu Lys Leu Lys Gln Lys Gln Ala
                 85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 237
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 237

Lys Glu Phe Leu Leu Tyr Leu Ala Gly Phe Val Asp Gly Asp Gly Ser
 1               5                  10                  15

Ile Phe Ala Arg Ile Phe Lys Gly Gln His Trp Lys Phe Lys His His
                20                  25                  30
```

Ile Arg Leu Thr Phe Asn Val Ser Gln Lys Thr Gln Arg Arg Trp Phe
            35                  40                  45

Leu Asp Lys Leu Val Asp Glu Ile Gly Val Gly Tyr Val Thr Asp Gly
 50                  55                  60

Gly Ser Ser Asn Tyr Tyr Leu Ser Glu Ile Lys Pro Leu His Asn
 65                  70                  75                  80

Phe Leu Thr Gln Leu Gln Pro Phe Leu Lys Leu Lys Gln Ala
                85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
                115                 120                 125

Leu Asn Asp Ser Lys Thr Arg Lys Thr Thr Ser Glu Thr Val Arg Ala
            130                 135                 140

Val Leu Asp
145

<210> SEQ ID NO 238
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 238

Lys Glu Phe Leu Leu Tyr Leu Ala Gly Phe Val Asp Gly Asp Gly Ser
1               5                   10                  15

Ile Tyr Ala Arg Ile Phe Lys Gly Gln His Trp Lys Phe Lys His His
                20                  25                  30

Ile Arg Leu Thr Phe His Val Ser Gln Lys Thr Gln Arg Arg Trp Phe
            35                  40                  45

Leu Asp Lys Leu Val Asp Glu Ile Gly Val Gly Tyr Val Thr Asp Trp
 50                  55                  60

Gly Ser Val Ser Gly Tyr Tyr Leu Ser Glu Ile Lys Pro Leu His Asn
 65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
                115                 120                 125

Leu Asn Asp Ser Lys Thr Arg Lys Thr Thr Ser Glu Thr Val Arg Ala
            130                 135                 140

Val Leu Asp
145

<210> SEQ ID NO 239
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 239

Lys Glu Phe Leu Leu Tyr Leu Ala Gly Phe Val Asp Gly Asp Gly Ser
1               5                   10                  15

Ile Tyr Ala Arg Ile Phe Lys Gly Gln His Trp Lys Phe Lys His His
                20                  25                  30

```
Ile Arg Leu Thr Phe His Val Ser Gln Lys Thr Gln Arg Arg Trp Phe
            35                  40                  45

Leu Asp Lys Leu Val Asp Glu Ile Gly Val Gly Tyr Val Thr Asp Trp
 50                  55                  60

Gly Ser Val Ser Gly Tyr Tyr Leu Ser Glu Ile Lys Pro Leu His Asn
 65                  70                  75                  80

Phe Leu Thr Gln Leu Gln Pro Phe Leu Lys Leu Lys Gln Lys Gln Ala
                 85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
130                 135                 140

Val Leu Asp
145

<210> SEQ ID NO 240
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 240

Lys Glu Phe Leu Leu Tyr Leu Ala Gly Phe Val Asp Gly Asp Gly Ser
 1               5                  10                  15

Ile Tyr Ala Arg Ile Phe Lys Gly Gln His Trp Lys Phe Lys His His
                20                  25                  30

Ile Arg Leu Thr Phe His Val Ser Gln Lys Thr Gln Arg Arg Trp Phe
            35                  40                  45

Leu Asp Lys Leu Val Asp Glu Ile Gly Val Gly Tyr Val Thr Asp Trp
 50                  55                  60

Gly Ser Val Ser Gly Tyr Tyr Leu Ser Glu Ile Lys Pro Leu His Asn
 65                  70                  75                  80

Phe Leu Thr Gln Leu Gln Pro Phe Leu Lys Leu Lys Gln Lys Gln Ala
                 85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
130                 135                 140

Val Leu Asp
145

<210> SEQ ID NO 241
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 241

Lys Glu Phe Leu Leu Tyr Leu Ala Gly Phe Val Asp Gly Asp Gly Ser
 1               5                  10                  15

Ile Tyr Ala Arg Ile Phe Lys Gly Gln His Trp Lys Phe Lys His His
```

```
                 20                  25                  30

Ile Arg Leu Thr Phe His Val Ser Gln Lys Thr Gln Arg Arg Trp Phe
             35                  40                  45

Leu Asp Lys Leu Val Asp Glu Ile Gly Val Gly Tyr Val Thr Asp Trp
         50                  55                  60

Gly Ser Val Ser Gly Tyr Tyr Leu Ser Glu Ile Lys Pro Leu His Asn
 65                  70                  75                  80

Phe Leu Thr Gln Leu Gln Pro Phe Leu Lys Leu Lys Gln Lys Gln Ala
                 85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
            130                 135                 140

Val Leu Asp
145

<210> SEQ ID NO 242
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 242

Lys Glu Phe Leu Leu Tyr Leu Ala Gly Phe Val Asp Gly Asp Gly Ser
 1               5                  10                  15

Ile Tyr Ala Arg Ile Phe Lys Gly Gln His Trp Lys Phe Lys His His
             20                  25                  30

Ile Arg Leu Thr Phe His Val Ser Gln Lys Thr Gln Arg Arg Trp Phe
             35                  40                  45

Leu Asp Lys Leu Val Asp Glu Ile Gly Val Gly Tyr Val Thr Asp Trp
         50                  55                  60

Gly Ser Val Ser Gly Tyr Tyr Leu Ser Glu Ile Lys Pro Leu His Asn
 65                  70                  75                  80

Phe Leu Thr Gln Leu Gln Pro Phe Leu Lys Leu Lys Gln Lys Gln Ala
                 85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
            130                 135                 140

Val Leu Asp
145

<210> SEQ ID NO 243
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 243

Lys Glu Phe Leu Leu Tyr Leu Ala Gly Phe Val Asp Gly Asp Gly Ser
 1               5                  10                  15
```

Ile Tyr Ala Arg Ile Phe Lys Gly Gln His Trp Lys Phe Lys His His
        20                  25                  30

Ile Arg Leu Thr Phe His Val Ser Gln Lys Thr Gln Arg Arg Trp Phe
            35                  40                  45

Leu Asp Lys Leu Val Asp Glu Ile Gly Val Gly Tyr Val Thr Asp Trp
    50                  55                  60

Gly Ser Val Ser Gly Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 244
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 244

Lys Glu Phe Leu Leu Tyr Leu Ala Gly Phe Val Asp Gly Asp Gly Ser
1               5                   10                  15

Ile Tyr Ala Arg Ile Phe Lys Gly Gln His Trp Lys Phe Lys His His
        20                  25                  30

Ile Arg Leu Thr Phe His Val Ser Gln Lys Thr Gln Arg Arg Trp Phe
            35                  40                  45

Leu Asp Lys Leu Val Asp Glu Ile Gly Val Gly Tyr Val Thr Asp Trp
    50                  55                  60

Gly Ser Val Ser Gly Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 245
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 245

Lys Glu Phe Leu Leu Tyr Leu Ala Gly Phe Val Asp Gly Asp Gly Ser
1               5                   10                  15

```
Ile Tyr Ala Arg Ile Phe Lys Gly Gln His Trp Lys Phe Lys His His
            20                  25                  30

Ile Arg Leu Thr Phe His Val Ser Gln Lys Thr Gln Arg Arg Trp Phe
            35                  40                  45

Leu Asp Lys Leu Val Asp Glu Ile Gly Val Gly Tyr Val Thr Asp Trp
 50                  55                  60

Gly Ser Val Ser Gly Tyr Tyr Leu Ser Glu Ile Lys Pro Leu His Asn
 65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
            130                 135                 140

Val Leu Asp
145

<210> SEQ ID NO 246
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 246

Lys Glu Phe Leu Leu Tyr Leu Ala Gly Phe Val Asp Gly Asp Gly Ser
 1               5                  10                  15

Ile Tyr Ala Arg Ile Phe Lys Gly Gln His Trp Lys Phe Lys His His
            20                  25                  30

Ile Arg Leu Thr Phe His Val Ser Gln Lys Thr Gln Arg Arg Trp Phe
            35                  40                  45

Leu Asp Lys Leu Val Asp Glu Ile Gly Val Gly Tyr Val Thr Asp Trp
 50                  55                  60

Gly Ser Val Ser Gly Tyr Tyr Leu Ser Glu Ile Lys Pro Leu His Asn
 65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
            130                 135                 140

Val Leu Asp
145

<210> SEQ ID NO 247
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 247

Lys Glu Phe Leu Leu Tyr Leu Ala Gly Phe Val Asp Gly Asp Gly Ser
```

```
                1               5                  10                 15
            Ile Tyr Ala Arg Ile Phe Lys Gly Gln His Trp Lys Phe Lys His His
                            20                 25                 30

Ile Arg Leu Thr Phe His Val Ser Gln Lys Thr Gln Arg Arg Trp Phe
                            35                 40                 45

Leu Asp Lys Leu Val Asp Glu Ile Gly Val Gly Tyr Val Thr Asp Trp
                        50                 55                 60

Gly Ser Val Ser Gly Tyr Tyr Leu Ser Glu Ile Lys Pro Leu His Asn
             65                 70                 75                 80

Phe Leu Thr Gln Leu Gln Pro Phe Leu Lys Leu Lys Gln Lys Gln Ala
                            85                 90                 95

Asn Leu Val Leu Lys Ile Ile Glu Gln Leu Pro Ser Ala Lys Glu Ser
                           100                105                110

Pro Asp Lys Phe Leu Glu Val Cys Thr Trp Val Asp Gln Ile Ala Ala
                           115                120                125

Leu Asn Asp Ser Lys Thr Arg Lys Thr Thr Ser Glu Thr Val Arg Ala
                       130                135                140

Val Leu Asp
            145

<210> SEQ ID NO 248
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 248

Lys Glu Phe Leu Leu Tyr Leu Ala Gly Phe Val Asp Gly Asp Gly Ser
            1               5                  10                 15

Ile Tyr Ala Arg Ile Phe Lys Gly Gln His Trp Lys Phe Lys His His
                            20                 25                 30

Ile Arg Leu Thr Phe His Val Ser Gln Lys Thr Gln Arg Arg Trp Phe
                            35                 40                 45

Leu Asp Lys Leu Val Asp Glu Ile Gly Val Gly Tyr Val Thr Asp Trp
                        50                 55                 60

Gly Ser Val Ser Gly Tyr Tyr Leu Ser Glu Ile Lys Pro Leu His Asn
             65                 70                 75                 80

Phe Leu Thr Gln Leu Gln Pro Phe Leu Lys Leu Lys Gln Lys Gln Ala
                            85                 90                 95

Asn Leu Val Leu Lys Ile Ile Glu Gln Leu Pro Ser Ala Lys Glu Ser
                           100                105                110

Pro Asp Lys Phe Leu Glu Val Cys Thr Trp Val Asp Gln Ile Ala Ala
                           115                120                125

Leu Asn Asp Ser Lys Thr Arg Lys Thr Thr Ser Glu Thr Val Arg Ala
                       130                135                140

Val Leu Asp
            145

<210> SEQ ID NO 249
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 249
```

```
Lys Glu Phe Leu Leu Tyr Leu Ala Gly Phe Val Asp Gly Asp Gly Ser
1               5                   10                  15

Ile Tyr Ala Arg Ile Phe Lys Gly Gln His Trp Lys Phe Lys His Tyr
            20                  25                  30

Ile Arg Leu Thr Phe Cys Val Ser Gln Lys Thr Gln Arg Arg Trp Phe
            35                  40                  45

Leu Asp Lys Leu Val Asp Glu Ile Gly Val Gly Tyr Val Asn Asp Ser
            50                  55                  60

Gly Ser Cys Ser Asn Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
                115                 120                 125

Leu Asn Asp Ser Lys Thr Arg Lys Thr Thr Ser Glu Thr Val Arg Ala
            130                 135                 140

Val Leu Asp
145

<210> SEQ ID NO 250
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 250

Lys Glu Phe Leu Leu Tyr Leu Ala Gly Phe Val Asp Gly Asp Gly Ser
1               5                   10                  15

Ile Tyr Ala Arg Ile Phe Lys Gly Gln His Trp Lys Phe Lys His Tyr
            20                  25                  30

Ile Arg Leu Thr Phe Cys Val Ser Gln Lys Thr Gln Arg Arg Trp Phe
            35                  40                  45

Leu Asp Lys Leu Val Asp Glu Ile Gly Val Gly Tyr Val Asn Asp Ser
            50                  55                  60

Gly Ser Cys Ser Asn Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
                115                 120                 125

Leu Asn Asp Ser Lys Thr Arg Lys Thr Thr Ser Glu Thr Val Arg Ala
            130                 135                 140

Val Leu Asp
145

<210> SEQ ID NO 251
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 251
```

Lys Glu Phe Leu Leu Tyr Leu Ala Gly Phe Val Asp Gly Asp Gly Ser
1               5                   10                  15

Ile Tyr Ala Arg Ile Phe Lys Gly Gln His Trp Lys Phe Lys His His
                20                  25                  30

Ile Arg Leu Thr Phe Asn Val Ser Gln Lys Thr Gln Arg Arg Trp Phe
                35                  40                  45

Leu Asp Lys Leu Val Asp Glu Ile Gly Val Gly Tyr Val Cys Asp Ser
            50                  55                  60

Gly Ser Gln Ser Asn Tyr Tyr Leu Ser Glu Ile Lys Pro Leu His Asn
65                  70                  75                  80

Phe Leu Thr Gln Leu Gln Pro Phe Leu Lys Leu Gln Lys Gln Ala
                85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
                115                 120                 125

Leu Asn Asp Ser Lys Thr Arg Lys Thr Thr Ser Glu Thr Val Arg Ala
                130                 135                 140

Val Leu Asp
145

<210> SEQ ID NO 252
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 252

Lys Glu Phe Leu Leu Tyr Leu Ala Gly Phe Val Asp Gly Asp Gly Ser
1               5                   10                  15

Ile Phe Ala Arg Ile Phe Lys Gly Gln His Trp Lys Phe Lys His His
                20                  25                  30

Ile Arg Leu Thr Phe Cys Val Ser Gln Lys Thr Gln Arg Arg Trp Phe
                35                  40                  45

Leu Asp Lys Leu Val Asp Glu Ile Gly Val Gly Tyr Val Val Asp Asn
            50                  55                  60

Gly Ser Met Ser Asn Tyr Tyr Leu Ser Glu Ile Lys Pro Leu His Asn
65                  70                  75                  80

Phe Leu Thr Gln Leu Gln Pro Phe Leu Lys Leu Gln Lys Gln Ala
                85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
                115                 120                 125

Leu Asn Asp Ser Lys Thr Arg Lys Thr Thr Ser Glu Thr Val Arg Ala
                130                 135                 140

Val Leu Asp
145

<210> SEQ ID NO 253
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 253

Lys Glu Phe Leu Leu Tyr Leu Ala Gly Phe Val Asp Gly Asp Gly Ser
1               5                   10                  15

Ile Tyr Ala Arg Ile Phe Lys Gly Gln His Trp Lys Phe Lys His His
            20                  25                  30

Ile Arg Leu Thr Phe Cys Val Thr Gln Lys Thr Gln Arg Arg Trp Phe
        35                  40                  45

Leu Asp Lys Leu Val Asp Glu Ile Gly Val Gly Tyr Val His Asp Tyr
    50                  55                  60

Gly Ser Cys Ser Asn Tyr Tyr Leu Ser Glu Ile Lys Pro Leu His Asn
65              70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 254
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 254

Lys Glu Phe Leu Leu Tyr Leu Ala Gly Phe Val Asp Gly Asp Gly Ser
1               5                   10                  15

Ile Tyr Ala Arg Ile Glu Pro Arg Gln Thr Ala Lys Phe Lys His Tyr
            20                  25                  30

Leu Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Gln Tyr Phe Leu Ser Glu Ile Lys Pro Leu His Asn
65              70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 255
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 255

Lys Glu Phe Leu Leu Tyr Leu Ala Gly Phe Val Asp Gly Asp Gly Ser
1               5                   10                  15

Ile Tyr Ala Arg Ile Glu Pro Arg Gln Thr Ala Lys Phe Lys His Tyr
            20                  25                  30

Leu Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Gln Tyr Phe Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 256
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 256

Lys Glu Phe Leu Leu Tyr Leu Ala Gly Phe Val Asp Gly Asp Gly Ser
1               5                   10                  15

Ile Tyr Ala Arg Ile Glu Pro Arg Gln Thr Ala Lys Phe Lys His Tyr
            20                  25                  30

Leu Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Gln Tyr Phe Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 257
<211> LENGTH: 147
<212> TYPE: PRT
<213> ORGANISM: Artificial Sequence
<220> FEATURE:

<223> OTHER INFORMATION: Synthetic Polypeptide

<400> SEQUENCE: 257

```
Lys Glu Phe Leu Leu Tyr Leu Ala Gly Phe Val Asp Gly Asp Gly Ser
1               5                   10                  15

Ile Tyr Ala Arg Ile Glu Pro Arg Gln Thr Ala Lys Phe Lys His Tyr
            20                  25                  30

Leu Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Gln Tyr Phe Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145
```

<210> SEQ ID NO 258
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 258

```
Lys Glu Phe Leu Leu Tyr Leu Ala Gly Phe Val Asp Gly Asp Gly Ser
1               5                   10                  15

Ile Tyr Ala Arg Ile Glu Pro Arg Gln Thr Ala Lys Phe Lys His Tyr
            20                  25                  30

Leu Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Gln Tyr Phe Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145
```

<210> SEQ ID NO 259
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 259

Lys Glu Phe Leu Leu Tyr Leu Ala Gly Phe Val Asp Gly Asp Gly Ser
1               5                   10                  15

Ile Tyr Ala Arg Ile Glu Pro Arg Gln Thr Ala Lys Phe Lys His Tyr
            20                  25                  30

Leu Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Gln Tyr Phe Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 260
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 260

Lys Glu Phe Leu Leu Tyr Leu Ala Gly Phe Val Asp Gly Asp Gly Ser
1               5                   10                  15

Ile Tyr Ala Arg Ile Glu Pro Arg Gln Thr Ala Lys Phe Lys His Tyr
            20                  25                  30

Leu Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Gln Tyr Phe Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 261
<211> LENGTH: 147
<212> TYPE: PRT

<213> ORGANISM: Artificial Sequence
<220> FEATURE:
<223> OTHER INFORMATION: Synthetic Polypeptide

<400> SEQUENCE: 261

Lys Glu Phe Leu Leu Tyr Leu Ala Gly Phe Val Asp Gly Asp Gly Ser
1               5                   10                  15

Ile Tyr Ala Arg Ile Glu Pro Arg Gln Thr Ala Lys Phe Lys His Tyr
            20                  25                  30

Leu Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Gln Tyr Phe Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 262
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 262

Lys Glu Phe Leu Leu Tyr Leu Ala Gly Phe Val Asp Gly Asp Gly Ser
1               5                   10                  15

Ile Tyr Ala Arg Ile Glu Pro Arg Gln Thr Ala Lys Phe Lys His Tyr
            20                  25                  30

Leu Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Gln Tyr Phe Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 263
<211> LENGTH: 147

```
<212> TYPE: PRT
<213> ORGANISM: Artificial Sequence
<220> FEATURE:
<223> OTHER INFORMATION: Synthetic Polypeptide

<400> SEQUENCE: 263

Lys Glu Phe Leu Leu Tyr Leu Ala Gly Phe Val Asp Gly Asp Gly Ser
1               5                   10                  15

Ile Tyr Ala Arg Ile Glu Pro Arg Gln Thr Ala Lys Phe Lys His Tyr
            20                  25                  30

Leu Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Gln Tyr Phe Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 264
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 264

Lys Glu Phe Leu Leu Tyr Leu Ala Gly Phe Val Asp Gly Asp Gly Ser
1               5                   10                  15

Ile Tyr Ala Arg Ile Glu Pro Arg Gln Thr Ala Lys Phe Lys His Tyr
            20                  25                  30

Leu Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Gln Tyr Phe Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 265
```

<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 265

Lys Glu Phe Leu Leu Tyr Leu Ala Gly Phe Val Asp Gly Asp Gly Ser
1               5                   10                  15

Ile Tyr Ala Arg Ile Glu Pro Arg Gln Thr Ala Lys Phe Lys His Tyr
            20                  25                  30

Leu Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Gln Tyr Phe Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 266
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 266

Lys Glu Phe Leu Leu Tyr Leu Ala Gly Phe Val Asp Gly Asp Gly Ser
1               5                   10                  15

Ile Tyr Ala Arg Ile Glu Pro Arg Gln Thr Ala Lys Phe Lys His Tyr
            20                  25                  30

Leu Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Gln Tyr Phe Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

```
<210> SEQ ID NO 267
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 267

Lys Glu Phe Leu Leu Tyr Leu Ala Gly Phe Val Asp Gly Asp Gly Ser
1               5                   10                  15

Ile Tyr Ala Arg Ile Glu Pro Arg Gln Thr Ala Lys Phe Lys His Tyr
            20                  25                  30

Leu Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Val Asp Gln
50                  55                  60

Gly Ser Val Ser Gln Tyr Phe Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
130                 135                 140

Val Leu Asp
145

<210> SEQ ID NO 268
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 268

Lys Glu Phe Leu Leu Tyr Leu Ala Gly Phe Val Asp Gly Asp Gly Ser
1               5                   10                  15

Ile Tyr Ala Arg Ile Glu Pro Arg Gln Thr Ala Lys Phe Lys His Tyr
            20                  25                  30

Leu Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Val Asp Gln
50                  55                  60

Gly Ser Val Ser Gln Tyr Phe Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
130                 135                 140

Val Leu Asp
145
```

```
<210> SEQ ID NO 269
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 269

Lys Glu Phe Leu Leu Tyr Leu Ala Gly Phe Val Asp Gly Asp Gly Ser
1               5                   10                  15

Ile Tyr Ala Arg Ile Glu Pro Arg Gln Thr Ala Lys Phe Lys His Tyr
            20                  25                  30

Leu Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Gln Tyr Phe Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 270
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 270

Lys Glu Phe Leu Leu Tyr Leu Ala Gly Phe Val Asp Gly Asp Gly Ser
1               5                   10                  15

Ile Tyr Ala Arg Ile Glu Pro Arg Gln Thr Ala Lys Phe Lys His Tyr
            20                  25                  30

Leu Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Val Asp Gln
    50                  55                  60

Gly Ser Val Ser Gln Tyr Phe Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145
```

<210> SEQ ID NO 271
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 271

Lys Glu Phe Leu Leu Tyr Leu Ala Gly Phe Val Asp Gly Asp Gly Ser
1               5                   10                  15

Ile Tyr Ala Arg Ile Glu Pro Arg Gln Thr Ala Lys Phe Lys His Tyr
            20                  25                  30

Leu Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Thr Asp Trp
    50                  55                  60

Gly Ser Val Ser Gly Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 272
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 272

Lys Glu Phe Leu Leu Tyr Leu Ala Gly Phe Val Asp Gly Asp Gly Ser
1               5                   10                  15

Ile Tyr Ala Cys Ile Glu Pro Lys Gln Thr Ser Lys Phe Lys His Arg
            20                  25                  30

Leu Cys Leu Arg Phe His Val Ser Gln Lys Thr Gln Arg Arg Trp Phe
        35                  40                  45

Leu Asp Lys Leu Val Asp Glu Ile Gly Val Gly Tyr Val His Asp Asn
    50                  55                  60

Gly Ser Val Ser Gln Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp

<210> SEQ ID NO 273
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 273

```
Lys Glu Phe Leu Leu Tyr Leu Ala Gly Phe Val Asp Gly Asp Gly Ser
1               5                   10                  15

Ile Tyr Ala Arg Ile Tyr Pro Gly Gln His Tyr Lys Phe Lys His Tyr
            20                  25                  30

Leu Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Thr Asp Ala
    50                  55                  60

Gly Ser Val Ser Gln Tyr Phe Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145
```

<210> SEQ ID NO 274
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 274

```
Lys Glu Phe Leu Leu Tyr Leu Ala Gly Phe Val Asp Gly Asp Gly Ser
1               5                   10                  15

Ile Tyr Ala Arg Ile Glu Pro Arg Gln Thr Ala Lys Phe Lys His Tyr
            20                  25                  30

Leu Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Ile Asp Ala
    50                  55                  60

Gly Ser Val Ser Gly Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140
```

Val Leu Asp
145

<210> SEQ ID NO 275
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 275

Lys Glu Phe Leu Leu Tyr Leu Ala Gly Phe Val Asp Gly Asp Gly Ser
1               5                   10                  15

Ile Tyr Ala Cys Ile Glu Pro Lys Gln Thr Ser Lys Phe Lys His Arg
            20                  25                  30

Leu Cys Leu Arg Phe His Val Ser Gln Lys Thr Gln Arg Arg Trp Phe
        35                  40                  45

Leu Asp Lys Leu Val Asp Glu Ile Gly Val Gly Tyr Val His Asp Asn
    50                  55                  60

Gly Ser Val Ser Gln Tyr Tyr Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 276
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 276

Lys Glu Phe Leu Leu Tyr Leu Ala Gly Phe Val Asp Gly Asp Gly Ser
1               5                   10                  15

Ile Tyr Ala Arg Ile Glu Pro Arg Gln Thr Ala Lys Phe Lys His Gln
            20                  25                  30

Leu Arg Leu Thr Phe His Val Ser Gln Lys Thr Gln Arg Arg Trp Phe
        35                  40                  45

Leu Asp Lys Leu Val Asp Glu Ile Gly Val Gly Tyr Val Thr Asp Trp
    50                  55                  60

Gly Ser Val Ser Gly Tyr Tyr Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 277
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 277

Lys Glu Phe Leu Leu Tyr Leu Ala Gly Phe Val Asp Gly Asp Gly Ser
1               5                   10                  15

Ile Tyr Ala Arg Ile Glu Pro Arg Gln Thr Val Lys Phe Lys His Met
            20                  25                  30

Leu Arg Leu Thr Phe His Val Ser Gln Lys Thr Gln Arg Arg Trp Phe
        35                  40                  45

Leu Asp Lys Leu Val Asp Glu Ile Gly Val Gly Tyr Val His Asp Asn
    50                  55                  60

Gly Ser Val Ser Gln Tyr Tyr Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 278
<211> LENGTH: 6214
<212> TYPE: DNA
<213> ORGANISM: Artificial Sequence
<220> FEATURE:
<223> OTHER INFORMATION: Synthetic Polynucleotide

<400> SEQUENCE: 278
cagcagctgg cgtaatagcg aagaggcccg caccgatcgc ccttcccaac agttgcgcag    60
cctgaatggc gaatggaatt ccagacgatt gagcgtcaaa atgtaggtat tccatgagc   120 gttttttcctg ttgcaatggc tggcggtaat attgttctgg atattaccag caaggccgat  180
agtttgagtt cttctactca ggcaagtgat gttattacta atcaaagaag tattgcgaca   240
acggttaatt tgcgtgatgg acagactctt ttactcggtg gcctcactga ttataaaaac   300
acttctcagg attctggcgt accgttcctg tctaaaatcc ctttaatcgg cctcctgttt   360
agctcccgct ctgattctaa cgaggaaagc acgttatacg tgctcgtcaa agcaaccata   420
gtacgcgccc tgtagcggcg cattaagcgc ggcgggtgtg gtggttacgc gcagcgtgac   480
cgctacactt gccagcgccc tagcgcccgc tcctttcgct ttcttccctt cctttctcgc   540
cacgttcgcc ggctttcccc gtcaagctct aaatcggggg ctcccttag ggttccgatt   600 tagtgcttta cggcacctcg accccaaaaa acttgattag ggtgatggtt cacgtagtgg   660
gccatcgccc tgatagacgg ttttcgccc tttgacgttg gagtccacgt tctttaatag   720
tggactcttg ttccaaactg gaacaacact caaccctatc tcggtctatt cttttgattt   780

```
ataagggatt tgccgatttt cggcctattg gttaaaaaat gagctgattt aacaaaaatt      840
taacgcgaat tttaacaaaa tattaacgct tacaatttaa atatttgctt atacaatctt      900
cctgtttttg gggcttttct gattatcaac cggggtacat atgattgaca tgctagtttt      960
acgattaccg ttcatcgccc tgcgcgctcg ctcgctcact gaggccgccc gggcaaagcc     1020
cgggcgtcgg gcgacctttg gtcgcccggc ctcagtgagc gagcgagcgc gcagagaggg     1080
agtggaattc acgcgtggat ctaatagtaa tcaattacgg ggtcattagt tcatagccca     1140
tatatggagt tccgcgttac ataacttacg gtaaatggcc cgcctggctg accgcccaac     1200
gacccccgcc cattgacgtc aataatgacg tatgttccca tagtaacgcc aatagggact     1260
ttccattgac gtcaatgggt ggagtattta cggtaaactg cccacttggc agtacatcaa     1320
gtgtatcata tgccaagtcc gcccctatt gacgtcaatg acggtaaatg gcccgcctgg      1380
cattatgccc agtacatgac cttacgggac tttcctactt ggcagtacat ctacgtatta     1440
gtcatcgcta ttaccatgtt gatgcggttt tggcagtaca ccaatgggcg tggatagcgg     1500
tttgactcac ggggatttcc aagtctccac cccattgacg tcaatgggag tttgtttggc     1560
accaaaatca acgggacttt ccaaaatgtc gtaataaccc cgccccgttg acgcaaatgg     1620
gcggtaggcg tgtacggtgg gaggtctata taagcagagc tcgtttagtg aaccgtcaga     1680
tcactagaag cttttattgcg gtagtttatc acagttaaat tgctaacgca gtcagtgctt     1740
ctgacacaac agtctcgaac ttaagctgca gaagttggtc gtgaggcact gggcaggtaa     1800
gtatcaaggt tacaagacag gtttaaggag accaatagaa actgggcttg tcgagacaga     1860
gaagactctt gcgtttctga taggcaccta ttggtcttac tgacatccac tttgcctttc     1920
tctccacagg tgtccactcc cagttcaatt acagctctta aggctagagt acttaatacg     1980
actcactata ggctagccac catggcaccg aagaagaagc gcaaggtgca tatgaataca     2040
aaatataata aagagttctt actctactta gcagggtttg tagacggtga cggttccatc     2100
tttgcccgta tctttaaggg tcaacattgg aagttcaagc actatattcg tttgaccttc     2160
acggtggctc agaagacaca gcgccgttgg ttcctcgaca agctggtgga cgagatcggt     2220
gtgggttacg tgactgactg gggcagcgtg tcccattact atctgtccga gatcaagcct     2280
ttgcataatt ttttaacaca actacaacct tttctaaaac taaaacaaaa acaagcaaat     2340
ttagttttaa aaattattga acaacttccg tcagcaaaag aatccccgga caaattctta     2400
gaagtttgta catgggtgga tcaaattgca gctctgaatg attcgaagac gcgtaaaaca     2460
acttctgaaa ccgttcgtgc tgtgctagac agtttaccag gatccgtggg aggtctatcg     2520
ccatctcagg catccagcgc cgcatcctcg gcttcctcaa gcccgggttc agggatctcc     2580
gaagcactca gagctggagc aggttccggc actggataca caaggaatt cctgctctac     2640
ctggcgggct tcgtcgacgg ggacggctcc atctgggcct cgatcattcc tgagcaaggt     2700
tataagttca gcacaggct gcgtctctct ttcactgtcg ctcagaagac acagcgccgt     2760
tggttcctcg acaagctggt ggacgagatc ggtgtgggtt acgtggttga ccagggcagc     2820
gtctccgagt acaggctgtc cgagatcaag cctctgcaca acttcctgac ccagctccag     2880
cccttcctga agctcaagca gaagcaggcc aactcgtgc tgaagatcat cgagcagctg     2940
ccctccgcca aggaatcccc ggacaagttc ctggaggtgt gcacctgggt ggaccagatc     3000
gccgctctga acgactccaa gacccgcaag accacttccg aaaccgtccg cgccgttcta     3060
gacagtctct ccgagaagaa gaagtcgtcc ccctaaggta ccagcggccg cgactctaga     3120
```

```
tcataatcag ccataccaca tttgtagagg ttttacttgc tttaaaaaac ctcccacacc    3180
tcccctgaa cctgaaacat aaaatgaatg caattgttgt tgttaacttg tttattgcag    3240
cttataatgg ttacaaataa agcaatagca tcacaaattt cacaaataaa gcatttttt    3300
cactgcattc tagttgtggt ttgtccaaac tcatcaatgt atcttaaggc gggaattgat    3360
ctgaggaacc cctagtgatg gagttggcca ctccctctct gcgcgctcgc tcgctcactg    3420
aggccgggcg accaaaggtc gcccgacgcc cgggcaaagc ccgggcgtcg ggcgaccttt    3480
ggtcgcccgg cctcagtgag cgagcgagcg cgcagagagg gagtggccaa ccccccccc    3540
cccccccgg cgattctctt gtttgctcca gactctcagg caatgacctg atagcctttg    3600
tagagacctc tcaaaaatag ctaccctctc cggcatgaat ttatcagcta gaacggttga    3660
atatcatatt gatggtgatt tgactgtctc cggcctttct cacccgtttg aatctttacc    3720
tacacattac tcaggcattg catttaaaat atatgagggt tctaaaaatt tttatccttg    3780
cgttgaaata aaggcttctc ccgcaaaagt attacagggt cataatgttt ttggtacaac    3840
cgatttagct ttatgctctg aggctttatt gcttaatttt gctaattctt tgccttgcct    3900
gtatgattta ttggatgttg gaattcctga tgcggtattt tctccttacg catctgtgcg    3960
gtatttcaca ccgcatatgg tgcactctca gtacaatctg ctctgatgcc gcatagttaa    4020
gccagccccg acaccgcca acaccgctg acgcgccctg acgggcttgt ctgctcccgg    4080
catccgctta cagacaagct gtgaccgtct ccggagctg catgtgtcag aggttttcac    4140
cgtcatcacc gaaacgcgcg agacgaaagg gcctcgtgat acgcctattt ttataggtta    4200
atgtcatgat aataatggtt tcttagacgt caggtggcac ttttcgggga atgtgcgcg    4260
gaaccctat ttgtttattt ttctaaatac attcaaatat gtatccgctc atgagacaat    4320
aaccctgata aatgcttcaa taatattgaa aaaggaagag tatgagtatt caacatttcc    4380
gtgtcgccct tattccctt tttgcggcat tttgccttcc tgtttttgct cacccagaaa    4440
cgctggtgaa agtaaaagat gctgaagatc agttgggtgc acgagtgggt tacatcgaac    4500
tggatctcaa cagcggtaag atccttgaga gttttcgccc cgaagaacgt tttccaatga    4560
tgagcacttt taaagttctg ctatgtggcg cggtattatc ccgtattgac gccgggcaag    4620
agcaactcgg tcgccgcata cactattctc agaatgactt ggttgagtac tcaccagtca    4680
cagaaaagca tcttacggat ggcatgacag taagagaatt atgcagtgct gccataacca    4740
tgagtgataa cactgcggcc aacttacttc tgacaacgat cggaggaccg aaggagctaa    4800
ccgcttttt gcacaacatg ggggatcatg taactcgcct tgatcgttgg gaaccggagc    4860
tgaatgaagc cataccaaac gacgagcgtg acaccacgat gcctgtagca atggcaacaa    4920
cgttgcgcaa actattaact ggcgaactac ttactctagc ttcccggcaa caattaatag    4980
actggatgga ggcggataaa gttgcaggac cacttctgcg ctcggccctt ccggctggct    5040
ggtttattgc tgataaatct ggagccggtg agcgtgggtc tcgcggtatc attgcagcac    5100
tggggccaga tggtaagccc tcccgtatcg tagttatcta cacgacgggg agtcaggcaa    5160
ctatggatga acgaaataga cagatcgctg agataggtgc ctcactgatt aagcattggt    5220
aactgtcaga ccaagtttac tcatatatac tttagattga tttaaaactt catttttaat    5280
ttaaaaggat ctaggtgaag atcctttttg ataatctcat gaccaaaatc ccttaacgtg    5340
agttttcgtt ccactgagcg tcagacccg tagaaaagat caaaggatct tcttgagatc    5400
cttttttct gcgcgtaatc tgctgcttgc aaacaaaaaa accaccgcta ccagcggtgg    5460
tttgtttgcc ggatcaagag ctaccaactc tttttccgaa ggtaactggc ttcagcagag    5520
```

```
cgcagatacc aaatactgtc cttctagtgt agccgtagtt aggccaccac ttcaagaact    5580
ctgtagcacc gcctacatac ctcgctctgc taatcctgtt accagtggct gctgccagtg    5640
gcgataagtc gtgtcttacc gggttggact caagacgata gttaccggat aaggcgcagc    5700
ggtcgggctg aacgggggt tcgtgcacac agcccagctt ggagcgaacg acctacaccg     5760
aactgagata cctacagcgt gagctatgag aaagcgccac gcttcccgaa gggagaaagg    5820
cggacaggta tccggtaagc ggcagggtcg aacaggaga gcgcacgagg gagcttccag     5880
ggggaaacgc ctggtatctt tatagtcctg tcgggtttcg ccacctctga cttgagcgtc    5940
gatttttgtg atgctcgtca ggggggcgga gcctatggaa aaacgccagc aacgcggcct    6000
ttttacggtt cctggccttt tgctggcctt ttgctcacat gttctttcct gcgttatccc    6060
ctgattctgt ggataaccgt attaccgcct ttgagtgagc tgataccgct cgccgcagcc    6120
gaacgaccga gcgcagcgag tcagtgagcg aggaagcgga agagcgccca atacgcaaac    6180
cgcctctccc cgcgcgttgg ccgattcatt aatg                                6214
```

<210> SEQ ID NO 279
<211> LENGTH: 6214
<212> TYPE: DNA
<213> ORGANISM: Artificial Sequence
<220> FEATURE:
<223> OTHER INFORMATION: Synthetic Polynucleotide

<400> SEQUENCE: 279

```
cagcagctgg cgtaatagcg aagaggcccg caccgatcgc ccttcccaac agttgcgcag      60
cctgaatggc gaatggaatt ccagacgatt gagcgtcaaa atgtaggtat ttccatgagc     120
gtttttcctg ttgcaatggc tggcggtaat attgttctgg atattaccag caaggccgat     180
agtttgagtt cttctactca ggcaagtgat gttattacta atcaaagaag tattgcgaca     240
acggttaatt tgcgtgatgg acagactctt ttactcggtg gcctcactga ttataaaaac     300
acttctcagg attctggcgt accgttcctg tctaaaatcc ctttaatcgg cctcctgttt     360
agctcccgct ctgattctaa cgaggaaagc acgttatacg tgctcgtcaa agcaaccata     420
gtacgcgccc tgtagcggcg cattaagcgc ggcgggtgtg tggttacgc gcagcgtgac      480 cgctacactt gccagcgccc tagcgcccgc tcctttcgct ttcttccctt cctttctcgc     540
cacgttcgcc ggctttcccc gtcaagctct aaatcggggg ctcccttag ggttccgatt      600 tagtgcttta cggcacctcg accccaaaaa acttgattag ggtgatggtt cacgtagtgg     660
gccatcgccc tgatagacgg ttttcgccc tttgacgttg gagtccacgt tctttaatag     720
tggactcttg ttccaaactg gaacaacact caaccctatc tcggtctatt cttttgattt     780
ataagggatt ttgccgattt cggcctattg gttaaaaaat gagctgattt aacaaaaatt     840
taacgcgaat tttaacaaaa tattaacgct tacaatttaa atatttgctt atacaatctt     900
cctgtttttg gggcttttct gattatcaac cggggtacat atgattgaca tgctagtttt     960
acgattaccg ttcatcgccc tgcgcgctcg ctcgctcact gaggccgccc gggcaaagcc    1020
cgggcgtcgg gcgacctttg gtcgcccggc ctcagtgagc gagcgagcgc gcagagaggg    1080
agtggaattc acgcgtggat ctaatagtaa tcaattacgg ggtcattagt tcatagccca    1140
tatatggagt tccgcgttac ataacttacg gtaaatggcc cgcctggctg accgcccaac    1200
gacccccgcc cattgacgtc aataatgacg tatgttccca tagtaacgcc aatagggact    1260
ttccattgac gtcaatgggt ggagtattta cggtaaactg cccacttggc agtacatcaa    1320
```

-continued

```
gtgtatcata tgccaagtcc gcccsctatt gacgtcaatg acggtaaatg gcccgcctgg      1380
cattatgccc agtacatgac cttacgggac tttcctactt ggcagtacat ctacgtatta      1440
gtcatcgcta ttaccatgtt gatgcggttt tggcagtaca ccaatgggcg tggatagcgg      1500
tttgactcac ggggatttcc aagtctccac cccattgacg tcaatgggag tttgtttggc      1560
accaaaatca acgggacttt ccaaaatgtc gtaataaccc cgccccgttg acgcaaatgg      1620
gcggtaggcg tgtacggtgg gaggtctata agcagagc tcgtttagtg aaccgtcaga      1680
tcactagaag ctttattgcg gtagtttatc acagttaaat tgctaacgca gtcagtgctt      1740
ctgacacaac agtctcgaac ttaagctgca aagttggtc gtgaggcact gggcaggtaa      1800
gtatcaaggt tacaagacag gtttaaggag accaatagaa actgggcttg tcgagacaga      1860
gaagactctt gcgtttctga taggcaccta ttggtcttac tgacatccac tttgccttc      1920 tctccacagg tgtccactcc cagttcaatt acagctctta aggctagagt acttaatacg      1980
actcactata ggctagccac catggcaccg aagaagaagc gcaaggtgca tatgaataca      2040
aaatataata aagagttctt actctactta gcagggtttg tagacggtga cggttccatc      2100
tatgcccgta tctttaaggg tcaacattgg aagttcaagc actatattcg tttgaccttc      2160
tgtgtgcggc agaagacaca gcgccgttgg ttcctcgaca agctggtgga cgagatcggt      2220
gtgggttacg tgactgactc tggcagcgtt ccgcttact atctgtccga gatcaagcct      2280
ttgcataatt ttttaacaca actacaacct tttctaaaac taaacaaaa acaagcaaat      2340 ttagttttaa aaattattga acaacttccg tcagcaaaag aatccccgga caaattctta      2400 gaagttttgta catgggtgga tcaaattgca gctctgaatg attcgaagac gcgtaaaaca      2460
acttctgaaa ccgttcgtgc tgtgctagac agtttaccag gatccgtggg aggtctatcg      2520
ccatctcagg catccagcgc cgcatcctcg gcttcctcaa gcccgggttc agggatctcc      2580
gaagcactca gagctggagc aggttccggc actggataca caaggaatt cctgctctac      2640 ctggcgggct tcgtcgacgg ggacggctcc atctgggcct cgatcattcc tgagcaaggt      2700
tataagttca agcacaggct gcgtctctct ttcactgtcg ctcagaagac acagcgccgt      2760
tggttcctcg acaagctggt ggacgagatc ggtgtgggtt acgtggttga ccagggcagc      2820
gtctccgagt acaggctgtc cgagatcaag cctctgcaca acttcctgac ccagctccag      2880 ccctcctga agctcaagca gaagcaggcc aacctcgtgc tgaagatcat cgagcagctg      2940
ccctccgcca aggaatcccc ggacaagttc ctggaggtgt gcacctgggt ggaccagatc      3000
gccgctctga acgactccaa gacccgcaag accacttccg aaaccgtccg cgccgttcta      3060
gacagtctct ccgagaagaa gaagtcgtcc ccctaaggta ccagcggccg cgactctaga      3120
tcataatcag ccataccaca tttgtagagg ttttacttgc tttaaaaaac ctcccacacc      3180
tccccctgaa cctgaaacat aaaatgaatg caattgttgt tgttaacttg tttattgcag      3240
cttataatgg ttacaaataa agcaatagca tcacaaattt cacaaataaa gcatttttt      3300 cactgcattc tagttgtggt ttgtccaaac tcatcaatgt atcttaaggc gggaattgat      3360
ctgaggaacc cctagtgatg gagttggcca ctccctctct gcgcgctcgc tcgctcactg      3420
aggccgggcg accaaaggtc gcccgacgcc cgggcaaagc ccgggcgtcg ggcgaccttt      3480
ggtcgcccgg cctcagtgag cgagcgagcg cgcagagagg gagtggccaa ccccccccc       3540 cccccccggg cgattctctt gtttgctcca gactctcagg caatgacctg atagcctttg      3600
tagagacctc tcaaaaatag ctaccctctc cggcatgaat ttatcagcta gaacggttga      3660
atatcatatt gatggtgatt tgactgtctc cggcctttct cacccgtttg aatctttacc      3720
```

```
tacacattac tcaggcattg catttaaaat atatgagggt tctaaaaatt tttatccttg    3780
cgttgaaata aaggcttctc ccgcaaaagt attacagggt cataatgttt ttggtacaac    3840
cgatttagct ttatgctctg aggctttatt gcttaatttt gctaattctt tgccttgcct    3900
gtatgattta ttggatgttg gaattcctga tgcggtattt tctccttacg catctgtgcg    3960
gtatttcaca ccgcatatgg tgcactctca gtacaatctg ctctgatgcc gcatagttaa    4020
gccagccccg acaccgcca acaccgctg acgcgcctg acgggcttgt ctgctcccgg       4080
catccgctta cagacaagct gtgaccgtct ccgggagctg catgtgtcag aggttttcac    4140
cgtcatcacc gaaacgcgcg agacgaaagg gcctcgtgat acgcctattt ttataggtta    4200
atgtcatgat aataatggtt tcttagacgt caggtggcac ttttcgggga atgtgcgcg     4260 gaaccctat ttgtttattt ttctaaatac attcaaatat gtatccgctc atgagacaat     4320
aaccctgata aatgcttcaa taatattgaa aaggaagag tatgagtatt caacatttcc     4380
gtgtcgccct tattccctt tttgcggcat tttgccttcc tgtttttgct cacccagaaa     4440
cgctggtgaa agtaaaagat gctgaagatc agttgggtgc acgagtgggt tacatcgaac    4500
tggatctcaa cagcggtaag atccttgaga gttttcgccc cgaagaacgt tttccaatga    4560
tgagcacttt taaagttctg ctatgtggcg cggtattatc ccgtattgac gccgggcaag    4620
agcaactcgg tcgccgcata cactattctc agaatgactt ggttgagtac tcaccagtca    4680
cagaaaagca tcttacggat ggcatgacag taagagaatt atgcagtgct gccataacca    4740
tgagtgataa cactgcggcc aacttacttc tgacaacgat cggaggaccg aaggagctaa    4800 ccgcttttt gcacaacatg gggatcatg taactcgcct tgatcgttgg gaaccggagc      4860
tgaatgaagc cataccaaac gacgagcgtg acaccacgat gcctgtagca atggcaacaa    4920
cgttgcgcaa actattaact ggcgaactac ttactctagc ttcccggcaa caattaatag    4980
actggatgga ggcggataaa gttgcaggac cacttctgcg ctcggccctt ccggctggct    5040
ggtttattgc tgataaatct ggagccggtg agcgtgggtc tcgcggtatc attgcagcac    5100
tggggccaga tggtaagccc tcccgtatcg tagttatcta cacgacgggg agtcaggcaa    5160
ctatggatga acgaaataga cagatcgctg agataggtgc ctcactgatt aagcattggt    5220
aactgtcaga ccaagtttac tcatatatac tttagattga tttaaaactt cattttaat    5280 ttaaaggat ctaggtgaag atccttttg ataatctcat gaccaaaatc ccttaacgtg     5340
agttttcgtt ccactgagcg tcagaccccg tagaaaagat caaaggatct tcttgagatc    5400 cttttttct gcgcgtaatc tgctgcttgc aaacaaaaaa accaccgcta ccagcggtgg    5460
tttgtttgcc ggatcaagag ctaccaactc tttttccgaa ggtaactggc ttcagcagag    5520
cgcagatacc aaatactgtc cttctagtgt agccgtagtt aggccaccac ttcaagaact    5580
ctgtagcacc gcctacatac ctcgctctgc taatcctgtt accagtggct gctgccagtg    5640
gcgataagtc gtgtcttacc gggttggact caagacgata gttaccggat aaggcgcagc    5700
ggtcgggctg aacggggggt tcgtgcacac agcccagctt ggagcgaacg acctacaccg    5760
aactgagata cctacagcgt gagctatgag aaagcgccac gcttcccgaa gggagaaagg    5820
cggacaggta tccggtaagc ggcagggtcg gaacaggaga gcgcacgagg gagcttccag    5880
ggggaaacgc ctggtatctt tatagtcctg tcgggtttcg ccacctctga cttgagcgtc    5940
gatttttgtg atgctcgtca ggggggcgga gcctatggaa aaacgccagc aacgcggcct    6000
ttttacggtt cctggccttt tgctggcctt ttgctcacat gttctttcct gcgttatccc    6060
```

```
ctgattctgt ggataaccgt attaccgcct tgagtgagc tgataccgct cgccgcagcc    6120
gaacgaccga gcgcagcgag tcagtgagcg aggaagcgga agagcgccca atacgcaaac    6180
cgcctctccc cgcgcgttgg ccgattcatt aatg                                6214

<210> SEQ ID NO 280
<211> LENGTH: 5888
<212> TYPE: DNA
<213> ORGANISM: Artificial Sequence
<220> FEATURE:
<223> OTHER INFORMATION: Synthetic Polynucleotide

<400> SEQUENCE: 280
cagcagctgg cgtaatagcg aagaggcccg caccgatcgc ccttcccaac agttgcgcag      60
cctgaatggc gaatggaatt ccagacgatt gagcgtcaaa atgtaggtat ttccatgagc     120 gttttttcctg ttgcaatggc tggcggtaat attgttctgg atattaccag caaggccgat    180
agtttgagtt cttctactca ggcaagtgat gttattacta atcaaagaag tattgcgaca     240
acggttaatt tgcgtgatgg acagactctt ttactcggtg gcctcactga ttataaaaac     300
acttctcagg attctggcgt accgttcctg tctaaaatcc ctttaatcgg cctcctgttt     360
agctcccgct ctgattctaa cgaggaaagc acgttatacg tgctcgtcaa agcaaccata     420
gtacgcgccc tgtagcggcg cattaagcgc ggcgggtgtg gtggttacgc gcagcgtgac     480
cgctacactt gccagcgccc tagcgcccgc tcctttcgct ttcttccctt cctttctcgc     540
cacgttcgcc ggctttcccc gtcaagctct aaatcggggg ctccctttag ggttccgatt     600
tagtgcttta cggcacctcg accccaaaaa acttgattag ggtgatggtt cacgtagtgg     660
gccatcgccc tgatagacgg ttttcgccc tttgacgttg gagtccacgt tctttaatag      720
tggactcttg ttccaaactg gaacaacact caaccctatc tcggtctatt cttttgattt     780
ataagggatt tgccgatttt cggcctattg gttaaaaaat gagctgattt aacaaaaatt     840
taacgcgaat tttaacaaaa tattaacgtt tacaatttaa atatttgctt atacaatctt     900 cctgttttttg gggcttttct gattatcaac cggggtacat atgattgaca tgctagtttt    960
acgattaccg ttcatcgccc tgcgcgctcg ctcgctcact gaggccgccc gggcaaagcc    1020
cgggcgtcgg cgaccttttg gtcgcccggc ctcagtgagc gagcgagcgc gcagagaggg    1080
agtggaattc acgcgtgggc cccagaaagcc tggtggttgt ttgtccttct caggggaaaa    1140
gtgaggcggc cccttggagg aagggggcgg gcagaatgat ctaatcggat tccaagcagc    1200 tcagggggatt gtcttttttct agcaccttct tgccactcct aagcgtcctc cgtgaccccg    1260
gctgggattt agcctggtgc tgtgtcagcc ccgggctccc agggggcttcc cagtggtccc    1320 caggaaccct cgacagggcc agggcgtctc tctcgtccag caaggcagg acgggccac       1380 aggccaaggg caagctttat tgcggtagtt tatcacagtt aaattgctaa cgcagtcagt    1440
gcttctgaca caacagtctc gaacttaagc tgcagaagtt ggtcgtgagg cactgggcag    1500
gtaagtatca aggttacaag acaggtttaa ggagaccaat agaaactggg cttgtcgaga    1560
cagagaagac tcttgcgttt ctgataggca cctattggtc ttactgacat ccactttgcc    1620
tttctctcca caggtgtcca ctcccagttc aattacagct cttaaggcta gagtacttaa    1680
tacgactcac tataggctag ccaccatggc accgaagaag aagcgcaagg tgcatatgaa    1740
tacaaaatat aataaagagt tcttactcta cttagcaggg tttgtagacg gtgacggttc    1800
catctttgcc cgtatcttta agggtcaaca ttggaagttc aagcactata ttcgtttgac    1860
cttcacggtg gctcagaaga cacagcgccg ttggttcctc gacaagctgg tggacgagat    1920
```

-continued

```
cggtgtgggt tacgtgactg actggggcag cgtgtcccat tactatctgt ccgagatcaa   1980
gcctttgcat aatttttttaa cacaactaca accttttcta aaactaaaac aaaaacaagc   2040
aaatttagtt ttaaaaatta ttgaacaact tccgtcagca aaagaatccc cggacaaatt   2100
cttagaagtt tgtacatggg tggatcaaat tgcagctctg aatgattcga agacgcgtaa   2160
aacaacttct gaaaccgttc gtgctgtgct agacagttta ccaggatccg tgggaggtct   2220
atcgccatct caggcatcca cgccgcatc ctcggcttcc tcaagcccgg gttcagggat   2280
ctccgaagca ctcagagctg agcaggttc cggcactgga tacaacaagg aattcctgct   2340
ctacctggcg ggcttcgtcg acggggacgg ctccatctgg gcctcgatca ttcctgagca   2400
aggttataag ttcaagcaca ggctgcgtct ctctttcact gtcgctcaga agacacagcg   2460
ccgttggttc ctcgacaagc tggtggacga gatcggtgtg ggttacgtgg ttgaccaggg   2520
cagcgtctcc gagtacaggc tgtccgagat caagcctctg cacaacttcc tgacccagct   2580
ccagccccttc ctgaagctca agcagaagca ggccaacctc gtgctgaaga tcatcgagca   2640
gctgccctcc gccaaggaat ccccggacaa gttcctggag gtgtgcacct gggtggacca   2700
gatcgccgct ctgaacgact ccaagaccg caagaccact tccgaaaccg tccgcgccgt   2760
tctagacagt ctctccgaga agaagaagtc gtcccctaa gcggccgcga ctctagatca   2820
taatcagcca taccacattt gtagaggttt tacttgcttt aaaaaacctc ccacacctcc   2880
ccctgaacct gaaacataaa atgaatgcaa ttgttgttgt taacttgttt attgcagctt   2940
ataatggtta caaataaagc aatagcatca caaatttcac aaataaagca ttttttttcac   3000
tgcattctag ttgtggtttg tccaaactca tcaatgtatc ttaaggcggg aattgatcta   3060
ggaaccccta gtgatggagt tggccactcc ctctctgcgc gctcgctcgc tcactgaggc   3120
cgccccgggca aagcccgggc gtcgggcgac ctttggtcgc ccggcctcag tgagcgagcg   3180
agcgcgcaga gagggagtgg ccaacccccc ccccccccc ccggcgattc tcttgtttgc   3240
tccagactct caggcaatga cctgatagcc tttgtagaga cctctcaaaa atagctaccc   3300
tctccggcat gaatttatca gctagaacgg ttgaatatca tattgatggt gatttgactg   3360
tctccggcct ttctcacccg tttgaatctt tacctacaca ttactcaggc attgcattta   3420
aaatatatga gggttctaaa atttttttatc cttgcgttga ataaaaggct tctcccgcaa   3480
aagtattaca gggtcataat gttttttggta caaccgattt agctttatgc tctgaggctt   3540
tattgcttaa ttttgctaat tctttgcctt gcctgtatga tttattggat gttggaattc   3600
ctgatgcggt atttttctcct tacgcatctg tgcggtattt cacaccgcat atggtgcact   3660
ctcagtacaa tctgctctga tgccgcatag ttaagccagc cccgacaccc gccaacaccc   3720
gctgacgcgc cctgacgggc ttgtctgctc ccggcatccg cttacagaca agctgtgacc   3780
gtctccggga gctgcatgtg tcagaggttt tcaccgtcat caccgaaacg cgcgagacga   3840
aagggcctcg tgatacgcct atttttatag gttaatgtca tgataataat ggtttcttag   3900
acgtcaggtg gcacttttcg gggaaatgtg cgcggaaccc ctatttgttt atttttctaa   3960
atacattcaa atatgtatcc gctcatgaga caataaccct gataaatgct tcaataatat   4020
tgaaaaagga agagtatgag tattcaacat ttccgtgtcg cccttattcc ctttttttgcg   4080
gcattttgcc ttcctgtttt tgctcaccca gaaacgctgg tgaaagtaaa agatgctgaa   4140
gatcagttgg gtgcacgagt gggttacatc gaactggatc tcaacagcgg taagatcctt   4200
gagagttttc gccccgaaga acgttttcca atgatgagca cttttaaagt tctgctatgt   4260
```

```
ggcgcggtat tatcccgtat tgacgccggg caagagcaac tcggtcgccg catacactat    4320
tctcagaatg acttggttga gtactcacca gtcacagaaa agcatcttac ggatggcatg    4380
acagtaagag aattatgcag tgctgccata accatgagtg ataacactgc ggccaactta    4440
cttctgacaa cgatcggagg accgaaggag ctaaccgctt ttttgcacaa catgggggat    4500
catgtaactc gccttgatcg ttgggaaccg gagctgaatg aagccatacc aaacgacgag    4560
cgtgacacca cgatgcctgt agcaatggca acaacgttgc gcaaactatt aactggcgaa    4620
ctacttactc tagcttcccg gcaacaatta atagactgga tggaggcgga taaagttgca    4680
ggaccacttc tgcgctcggc ccttccggct ggctggttta ttgctgataa atctggagcc    4740
ggtgagcgtg gtctcgcgg tatcattgca gcactggggc cagatggtaa gccctcccgt    4800
atcgtagtta tctacacgac ggggagtcag gcaactatgg atgaacgaaa tagacagatc    4860
gctgagatag gtgcctcact gattaagcat tggtaactgt cagaccaagt ttactcatat    4920
atactttaga ttgatttaaa acttcatttt taatttaaaa ggatctaggt gaagatcctt    4980
tttgataatc tcatgaccaa aatcccttaa cgtgagtttt cgttccactg agcgtcagac    5040
cccgtagaaa agatcaaagg atcttcttga gatcctttttt ttctgcgcgt aatctgctgc    5100
ttgcaaacaa aaaaaccacc gctaccagcg gtggtttgtt tgccggatca agagctacca    5160 actcttttc cgaaggtaac tggcttcagc agagcgcaga taccaaatac tgtccttcta    5220
gtgtagccgt agttaggcca ccacttcaag aactctgtag caccgcctac atacctcgct    5280
ctgctaatcc tgttaccagt ggctgctgcc agtggcgata agtcgtgtct taccgggttg    5340
gactcaagac gatagttacc ggataaggcg cagcggtcgg gctgaacggg gggttcgtgc    5400
acacagccca gcttggagcg aacgacctac accgaactga gatacctaca gcgtgagcta    5460
tgagaaagcg ccacgcttcc cgaagggaga aaggcggaca ggtatccggt aagcggcagg    5520
gtcggaacag gagagcgcac gagggagctt ccaggggaa acgcctggta tctttatagt    5580
cctgtcgggt ttcgccacct ctgacttgag cgtcgatttt tgtgatgctc gtcaggggg    5640 cggagcctat ggaaaaacgc cagcaacgcg gcctttttac ggttcctggc cttttgctgg    5700 cctttttgctc acatgttctt tcctgcgtta tcccctgatt ctgtggataa ccgtattacc    5760
gcctttgagt gagctgatac cgctcgccgc agccgaacga ccgagcgcag cgagtcagtg    5820
agcgaggaag cggaagagcg cccaatacgc aaaccgcctc tccccgcgcg ttggccgatt    5880
cattaatg                                                              5888

<210> SEQ ID NO 281
<211> LENGTH: 5888
<212> TYPE: DNA
<213> ORGANISM: Artificial Sequence
<220> FEATURE:
<223> OTHER INFORMATION: Synthetic Polynucleotide

<400> SEQUENCE: 281
cagcagctgg cgtaatagcg aagaggcccg caccgatcgc ccttcccaac agttgcgcag      60
cctgaatggc gaatggaatt ccagacgatt gagcgtcaaa atgtaggtat ttccatgagc     120
gtttttcctg ttgcaatggc tggcggtaat attgttctgg atattaccag caaggccgat     180
agtttgagtt cttctactca ggcaagtgat gttattacta atcaaagaag tattgcgaca     240
acggttaatt tgcgtgatgg acagactctt ttactcggtg gcctcactga ttataaaaac     300
acttctcagg attctggcgt accgttcctg tctaaaatcc ctttaatcgg cctcctgttt     360
agctcccgct ctgattctaa cgaggaaagc acgttatacg tgctcgtcaa agcaaccata     420
```

```
gtacgcgccc tgtagcggcg cattaagcgc ggcgggtgtg gtggttacgc gcagcgtgac    480
cgctacactt gccagcgccc tagcgcccgc tcctttcgct ttcttccctt cctttctcgc    540
cacgttcgcc ggctttcccc gtcaagctct aaatcggggg ctccctttag ggttccgatt    600
tagtgcttta cggcacctcg accccaaaaa acttgattag ggtgatggtt cacgtagtgg    660
gccatcgccc tgatagacgg ttttcgccc tttgacgttg gagtccacgt tctttaatag    720
tggactcttg ttccaaactg gaacaacact caacccatc tcggtctatt cttttgattt    780
ataagggatt ttgccgattt cggcctattg gttaaaaaat gagctgattt aacaaaaatt    840
taacgcgaat tttaacaaaa tattaacgtt tacaatttaa atatttgctt atacaatctt    900 cctgttttg gggcttttct gattatcaac cggggtacat atgattgaca tgctagtttt    960
acgattaccg ttcatcgccc tgcgcgctcg ctcgctcact gaggccgccc gggcaaagcc   1020
cgggcgtcgg gcgacctttg gtcgcccggc ctcagtgagc gagcgagcgc gcagagaggg   1080
agtggaattc acgcgtgggc cccagaagcc tggtggttgt ttgtccttct caggggaaaa   1140
gtgaggcggc cccttggagg aaggggccgg gcagaatgat ctaatcggat ccaagcagc   1200 tcagggggatt gtcttttttct agcaccttct tgccactcct aagcgtcctc cgtgaccccg   1260
gctgggattt agcctggtgc tgtgtcagcc ccgggctccc aggggcttcc cagtggtccc   1320
caggaaccct cgacagggcc agggcgtctc tctcgtccag caagggcagg gacgggccac   1380
aggccaaggg caagctttat tgcggtagtt tatcacagtt aaattgctaa cgcagtcagt   1440
gcttctgaca caacagtctc gaacttaagc tgcagaagtt ggtcgtgagg cactgggcag   1500
gtaagtatca aggttacaag acaggtttaa ggagaccaat agaaactggg cttgtcgaga   1560
cagagaagac tcttgcgttt ctgataggca cctattggtc ttactgacat ccactttgcc   1620
tttctctcca caggtgtcca ctcccagttc aattacagct cttaaggcta gagtacttaa   1680
tacgactcac tataggctag ccaccatggc accgaagaag aagcgcaagg tgcatatgaa   1740
tacaaaatat aataaagagt tcttactcta cttagcaggg tttgtagacg gtgacggttc   1800
catctatgcc cgtatcttta agggtcaaca ttggaagttc aagcactata ttcgtttgac   1860
cttctgtgtg cggcagaaga cacagcgccg ttggttcctc gacaagctgg tggacagat   1920 cggtgtgggt tacgtgactg actctggcag cgtttccgct tactatctgt ccgagatcaa   1980
gcctttgcat aatttttttaa cacaactaca acctttctta aaactaaaac aaaaacaagc   2040
aaatttagtt ttaaaaatta ttgaacaact tccgtcagca aaagaatccc cggacaaatt   2100
cttagaagtt tgtacatggg tggatcaaat tgcagctctg aatgattcga agacgcgtaa   2160
aacaacttct gaaaccgttc gtgctgtgct agacagttta ccaggatccg tgggaggtct   2220
atcgccatct caggcatcca cgccgcatc tcggcttcc tcaagcccgg gttcagggat   2280
ctccgaagca ctcagagctg gagcaggttc cggcactgga tacaacaagg aattcctgct   2340
ctacctggcg ggcttcgtcg acggggacg ctccatctgg gcctcgatca ttcctgagca   2400
aggttataag ttcaagcaca ggctgcgtct ctctttcact gtcgctcaga agacacagcg   2460
ccgttggttc ctcgacaagc tggtggacga gatcggtgtg ggttacgtgg ttgaccaggg   2520
cagcgtctcc gagtacaggc tgtccgagat caagcctctg cacaacttcc tgacccagct   2580
ccagcccttc ctgaagctca agcagaagca ggccaacctc gtgctgaaga tcatcgagca   2640
gctgccctcc gccaaggaat ccccggacaa gttcctggag gtgtgcacct gggtggacca   2700
gatcgccgct ctgaacgact ccaagacccg caagaccact tccgaaaccg tccgcgccgt   2760
```

```
tctagacagt ctctccgaga agaagaagtc gtcccccταa gcggccgcga ctctagatca    2820
taatcagcca taccacattt gtagaggttt tacttgcttt aaaaaacctc ccacacctcc    2880
ccctgaacct gaaacataaa atgaatgcaa ttgttgttgt taacttgttt attgcagctt    2940
ataatggtta caaataaagc aatagcatca caaatttcac aaataaagca ttttttttcac   3000
tgcattctag ttgtggtttg tccaaactca tcaatgtatc ttaaggcggg aattgatcta    3060
ggaacccccta gtgatggagt tggccactcc ctctctgcgc gctcgctcgc tcactgaggc   3120
cgcccgggca agcccgggc gtcgggcgac ctttggtcgc ccggcctcag tgagcgagcg     3180
agcgcgcaga gagggagtgg ccaaccccc ccccccccc ccggcgattc tcttgtttgc      3240
tccagactct caggcaatga cctgatagcc tttgtagaga cctctcaaaa atagctaccc    3300
tctccggcat gaatttatca gctagaacgg ttgaatatca tattgatggt gatttgactg    3360
tctccggcct ttctcacccg tttgaatctt tacctacaca ttactcaggc attgcattta    3420
aaatatatga gggttctaaa aattttatc cttgcgttga aataaaggct tctcccgcaa     3480
aagtattaca gggtcataat gtttttggta caaccgattt agctttatgc tctgaggctt    3540
tattgcttaa ttttgctaat tctttgcctt gcctgtatga tttattggat gttggaattc    3600
ctgatgcggt attttctcct tacgcatctg tgcggtattt cacaccgcat atggtgcact    3660
ctcagtacaa tctgctctga tgccgcatag ttaagccagc cccgacaccc gccaacaccc    3720
gctgacgcgc cctgacgggc ttgtctgctc ccggcatccg cttacagaca agctgtgacc    3780
gtctccggga gctgcatgtg tcagaggttt tcaccgtcat caccgaaacg cgcgagacga    3840
aagggcctcg tgatacgcct atttttatag gttaatgtca tgataataat ggtttcttag    3900
acgtcaggtg cacttttcg gggaaatgtg cgcggaaccc ctatttgttt attttttctaa    3960
atacattcaa atatgtatcc gctcatgaga caataaccct gataaatgct tcaataatat    4020
tgaaaaagga agagtatgag tattcaacat ttccgtgtcg cccttattcc cttttttgcg    4080
gcattttgcc ttcctgtttt tgctcaccca gaaacgctgg tgaaagtaaa agatgctgaa    4140
gatcagttgg gtgcacgagt gggttacatc gaactggatc tcaacagcgg taagatcctt    4200
gagagttttc gccccgaaga acgttttcca atgatgagca cttttaaagt tctgctatgt    4260
ggcgcggtat tatcccgtat tgacgccggg caagagcaac tcggtcgccg catacactat    4320
tctcagaatg acttggttga gtactcacca gtcacagaaa agcatcttac ggatggcatg    4380
acagtaagag aattatgcag tgctgccata accatgagtg ataacactgc ggccaactta    4440
cttctgacaa cgatcggagg accgaaggag ctaaccgctt ttttgcacaa catgggggat    4500
catgtaactc gccttgatcg ttgggaaccg gagctgaatg aagccatacc aaacgacgag    4560
cgtgacacca cgatgcctgt agcaatggca acaacgttgc gcaaactatt aactggcgaa    4620
ctacttactc tagcttcccg gcaacaatta atagactgga tggaggcgga taaagttgca    4680
ggaccacttc tgcgctcggc ccttccggct ggctggttta ttgctgataa atctggagcc    4740
ggtgagcgtg ggtctcgcgg tatcattgca gcactggggc cagatggtaa gccctcccgt    4800
atcgtagtta tctacacgac ggggagtcag gcaactatgg atgaacgaaa tagacagatc    4860
gctgagatag gtgcctcact gattaagcat tggtaactgt cagaccaagt ttactcatat    4920
atactttaga ttgatttaaa acttcatttt taatttaaaa ggatctaggt gaagatcctt    4980
tttgataatc tcatgaccaa aatcccttaa cgtgagtttt cgttccactg agcgtcagac    5040
cccgtagaaa agatcaaagg atcttcttga gatccttttt ttctgcgcgt aatctgctgc    5100
ttgcaaacaa aaaaaccacc gctaccagcg gtggtttgtt tgccggatca agagctacca    5160
```

```
actcttttc  cgaaggtaac  tggcttcagc  agagcgcaga  taccaaatac  tgtccttcta      5220
gtgtagccgt  agttaggcca  ccacttcaag  aactctgtag  caccgcctac  atacctcgct     5280
ctgctaatcc  tgttaccagt  ggctgctgcc  agtggcgata  agtcgtgtct  taccgggttg     5340
gactcaagac  gatagttacc  ggataaggcg  cagcggtcgg  gctgaacggg  gggttcgtgc     5400
acacagccca  gcttggagcg  aacgacctac  accgaactga  gatacctaca  gcgtgagcta     5460
tgagaaagcg  ccacgcttcc  cgaagggaga  aaggcggaca  ggtatccggt  aagcggcagg     5520
gtcggaacag  gagagcgcac  gagggagctt  ccaggggaa   acgcctggta  tctttatagt     5580
cctgtcgggt  ttcgccacct  ctgacttgag  cgtcgatttt  tgtgatgctc  gtcagggggg     5640
cggagcctat  ggaaaaacgc  cagcaacgcg  gccttttac   ggttcctggc  cttttgctgg     5700
ccttttgctc  acatgttctt  tcctgcgtta  tcccctgatt  ctgtggataa  ccgtattacc     5760
gcctttgagt  gagctgatac  cgctcgccgc  agccgaacga  ccgagcgcag  cgagtcagtg     5820
agcgaggaag  cggaagagcg  cccaatacgc  aaaccgcctc  tccccgcgcg  ttggccgatt     5880
cattaatg                                                                   5888
```

TREATMENT OF RETINITIS PIGMENTOSA USING ENGINEERED MEGANUCLEASES

CROSS REFERENCE TO RELATED APPLICATIONS

The application is a national stage filing under 35 U.S.C. § 371 of international application number PCT/US2016/050809, filed Sep. 8, 2016, which was published under PCT Article 21(2) in English and claims the benefit of priority under 35 U.S.C. § 119(e) to U.S. provisional application Ser. No. 62/215,460, filed Sep. 8, 2015, the contents of each of which are incorporated in their entirety by reference.

FIELD OF THE INVENTION

The invention relates to the field of molecular biology and recombinant nucleic acid technology. In particular, the invention relates to recombinant meganucleases engineered to recognize and cleave a recognition sequence found in a human rhodopsin gene allele. The invention further relates to the use of such recombinant meganucleases in methods for treating retinitis pigmentosa.

BACKGROUND OF THE INVENTION

Retinitis pigmentosa (RP) is an inherited degenerative eye disease that causes severe vision impairment due to the progressive degeneration of photoreceptor cells in the retina. RP is characterized by an initial decline in rod photoreceptor cells, resulting in compromised peripheral and dim light vision. Progressive rod degeneration is followed by abnormalities in the retinal pigment epithelium and deterioration of cone photoreceptor cells. As the disease advances, patients experience nyctalopia, progressive tunnel vision, and eventual blindness. RP affects approximately 1 in 3000 people and can occur alone or together with other systemic disorders. Currently, RP has no effective treatment.

The genetic causes of RP have been identified as autosomal dominant, autosomal recessive, X-linked, or maternally acquired. The autosomal dominant form of RP represents 30-40% of cases (Ma et al. (2105), *Scientific Reports.* 18(5:9236):1-6), and has been associated with mutations in genes expressed in rod photoreceptor cells and the retinal pigment epithelium. The human rhodopsin gene (RHO) was the first gene shown to contribute to the pathogenesis of autosomal dominant RP and remains the most common gene associated with this form of the disease (McWilliam et al. (1989) *Genomics.* 5:619-622; Dryja et al. (1990) *Nature.* 343:364-366; Farrar et al. (1990) *EMBO Journal.* 21:857-864). Indeed, RHO mutations are associated with 30-40% of autosomal dominant RP cases worldwide, and are observed in approximately 26.5% of cases in the United States (Illing et al. (2002) *Journal of Bio. Chem.* 277(37):34150-34160).

Rhodopsin is an essential photopigment expressed in retinal rod photoreceptor cells that is responsible for the conversion of light stimuli into electrical signals in the first step of phototransduction. Rhodopsin is expressed as a light-sensitive G-protein-coupled receptor that consists of an opsin protein moiety bound to an 11-cis-retinal chromophore, and represents the main component of the disk membranes of rod photoreceptor cell outer segments.

The first RHO mutation shown to contribute to autosomal dominant RP was a C to A mutation at position 68 of the RHO gene coding sequence, which confers a proline to histidine substitution at position 23 (P23H) of the encoded protein. This mutation is referred to herein as the "RHO P23H mutation," and a RHO allele comprising the mutation is referred to herein as a "mutant RHO P23H allele." The RHO P23H mutation is the most frequently reported RHO mutation in autosomal dominant RP cases in North America (Mao et al. (2011) *Human Gene Therapy.* 22:567-575), and patients having a single mutant RHO P23H allele can develop RP despite the presence of a functional wild-type RHO allele.

Rhodopsin proteins that comprise the P23H substitution fold improperly, accumulate in the endoplasmic reticulum of rod photoreceptor cells, and do not reconstitute with the 11-cis-retinal chromophore. In many cases of autosomal dominant RP, misfolded P23H rhodopsin contributes to rod photoreceptor cell degeneration and death. Accumulated P23H rhodopsin undergoes proteasomal and lysosomal degradation and has been shown to stimulate the ER-associated unfolded protein response, which can induce ER stress and cellular apoptosis (Lin et al. (2007), *Science.* 318:944-949; Gorbatyuk et al. (2010) *PNAS U.S.A.* 107(13):5961-5966). Misfolding of P23H rhodopsin may also contribute to cell death by interfering with the transport or function of wild-type rhodopsin (Illing et al., 2002, Lin et al., 2007). Furthermore, P23H rhodopsin has been shown to exhibit delayed dephosphorylation, and cell death may result from abnormal cytosolic $Ca^{2+}$ levels (Saito et al. (2008) *Clin. Opthamol.* 2:821-828).

Multiple strategies have been pursued to treat autosomal dominant RP, including nutritional therapies, pharmaceuticals, and gene therapy. Gene therapy approaches have adopted either an indirect or a direct strategy for treating autosomal dominant RP. Indirect approaches have aimed to promote the survival of rod photoreceptor cells without directly affecting the expression of pathogenic mutant proteins. For example, gene therapy has been used to introduce neurotrophic factors, such as GDNF, and anti-apoptotic proteins, such as XIAP, in retinal cells in order to inhibit apoptosis in rod photoreceptor cells.

By contrast, direct approaches in gene therapy have sought to modulate the levels of proteins that directly contribute to the pathogenesis of autosomal dominant RP. In the context of RHO-associated autosomal dominant RP, one strategy has been to enhance the proteasomal degradation of P23H rhodopsin, though no significant success has been made in animal models. Another strategy has utilized targeted RNA-based therapy to silence a mutant RHO allele while maintaining expression of the functional wild-type allele. Such approaches have used ribozymes and RNA interference (RNAi) to target specific mRNA transcripts produced by a mutant RHO P23H transgene in rats.

Further strategies have pursued a "suppression and replacement" approach by non-specifically silencing both the wild-type RHO allele and the mutant RHO allele, while concurrently delivering a replacement copy of wild-type RHO to express the wild-type protein. For example, O'Reilly et al. utilized adeno-associated virus (AAV) vectors to deliver and express short hairpin RNAs designed to target and suppress both the wild-type and mutant RHO alleles in heterozygous Pro23His$^{+/-}$ mice, while also delivering and expressing a RHO replacement gene (O'Reilly et al. (2007) *Amer. J. of Human Genetics.* 81:127-135). Palfi et al. similarly demonstrated the use of AAV vectors to deliver a RHO replacement gene to Rho$^{-/-}$ knockout mice (Palfi et al. (2010) *Human Gene Therapy.* 21:311-323). However, in such approaches, toxicity and off-target effects may be induced if RHO replacement levels are too high. Furthermore, off-target effects of RNAi approaches are a known complication, and it has been shown that siRNAs greater than 21 base pairs in length can induce retinal degeneration in animal models (Kleinman et al. (2012) *Mol. Ther.* 20(1): 101-108).

The use of engineered nucleases for cleaving DNA targets in the human RHO gene was previously disclosed in U.S. Patent Publication No. US 2012/0204282 A1 by Zhang ("the Zhang application"). The Zhang application disclosed several approaches for targeting and modulating the expression of mutant RHO alleles. Specifically, the Zhang application discussed the use of engineered DNA binding domains, such as zinc finger proteins (ZFP) and TAL effector (TALE) proteins, as repressors of RHO gene expression. The Zhang application also described fusion proteins comprising a ZFP or TALE binding domain operably linked to a regulatory or functional domain. The functional domain could be a transcriptional repressor domain that downregulates RHO gene expression. Alternatively, the functional domain could be a transcriptional activation domain. Further, the functional domain could comprise a nuclease domain. When linked to a nuclease domain, the resulting fusion proteins include zinc finger nucleases (ZFNs) and TALE-nucleases (TALENs).

In addition to ZFNs and TALENs, the Zhang application discusses the use of meganucleases for targeting and inhibiting the expression of wild-type and/or mutant RHO alleles. The Zhang application describes the use of such meganucleases for disrupting RHO gene expression via non-homologous end joining (NHEJ) at the recognition sequence, and for introducing a replacement wild-type RHO gene sequence to express the wild-type rhodopsin protein. However, the recognition sequences in the RHO gene that are identified by the Zhang application are limited to three pairs of ZFN target sites found in the wild-type RHO gene (see, Zhang application at Table 2).

The use of engineered meganucleases for cleaving DNA targets in the RHO gene was also disclosed in U.S. Patent Publication No. US 2013/0183282 by Lemaire and Arnould ("the Lemaire application"). The Lemaire application disclosed meganucleases designed to target various regions of the RHO gene for use in one of three gene therapy strategies. The first strategy is gene correction, wherein the engineered meganucleases are specific for a recognition sequence in the vicinity of a specified mutation, induce a double-strand break at that site, and rely on homologous recombination of a corresponding non-mutant allelic sequence into the genome. The second strategy disclosed in the Lemaire application is exon knock-in, wherein a functional protein is reconstituted by using a meganuclease to introduce a synthetic wild-type coding sequence into the genome while preventing the expression of the pathologic mutation. The third strategy disclosed in the Lemaire application is gene inactivation by mutagenesis, which relies a meganuclease to induce a double-strand break at a target recognition sequence in the genome, and NHEJ at the cleavage site to induce a mutation.

Accordingly, there is still a need in the art for methods that can preferentially target and inactivate the RHO P23H allele for treatment of RP.

SUMMARY OF THE INVENTION

The present invention provides recombinant meganucleases that are engineered to recognize and cleave P23H recognition sequences. The present invention further provides methods comprising the delivery of such a recombinant meganuclease, or genes encoding such a recombinant meganuclease, to the cells of a patient having RP, such that the recombinant meganuclease (or encoded recombinant meganuclease) preferentially targets and cleaves a P23H recognition sequence present on the mutant RHO P23H allele. NHEJ occurs at the cleavage site, resulting in mutagenesis and disruption of the mutant RHO P23H allele, while the functional wild-type RHO allele remains intact to express wild-type rhodopsin in rod photoreceptor cells of the retina. Preferential inactivation of the mutant RHO P23H allele, and disruption of P23H rhodopsin expression, is expected to delay, prevent, or reverse the progression of RP in patients.

Thus, in some embodiments, the present invention provides recombinant meganucleases that are engineered to recognize and cleave a P23H recognition sequence, which is present in the mutant RHO P23H allele but not in the wild-type RHO allele. The present invention further provides the use of such a recombinant meganuclease in a method for treating RP, preferably autosomal dominant RP, wherein the mutant RHO P23H allele is preferentially targeted and cleaved. In this manner, expression of P23H rhodopsin is suppressed due to NHEJ at the meganuclease cleavage site, while the functional wild-type RHO allele remains intact to express wild-type rhodopsin in rod photoreceptor cells of the retina.

Thus, the invention includes the use of site-specific, rare-cutting, homing endonucleases (also called "meganucleases") that are engineered to recognize specific DNA sequences in a locus of interest. Homing endonucleases are a group of naturally-occurring nucleases which recognize 15-40 base pair cleavage sites commonly found in the genomes of plants and fungi. They are frequently associated with parasitic DNA elements, such as group 1 self-splicing introns and inteins. They naturally promote homologous recombination or gene insertion at specific locations in the host genome by producing a double-stranded break in the chromosome, which recruits the cellular DNA-repair machinery (Stoddard (2006), *Q. Rev. Biophys.* 38:49-95). Homing endonucleases are commonly grouped into four families: the LAGLIDADG (SEQ ID NO:96) family, the GIY-YIG family, the His-Cys box family and the HNH family. These families are characterized by structural motifs, which affect catalytic activity and recognition sequence. For instance, members of the LAGLIDADG (SEQ ID NO:96) family are characterized by having either one or two copies of the conserved LAGLIDADG (SEQ ID NO:96) motif (Chevalier et al. (2001), *Nucleic Acids Res.* 29(18): 3757-3774). The LAGLIDADG (SEQ ID NO:96) homing endonucleases with a single copy of the LAGLIDADG (SEQ ID NO:96) motif form homodimers, whereas members with two copies of the LAGLIDADG (SEQ ID NO:96) motif are found as monomers.

Methods for producing engineered, site-specific recombinant meganucleases are known in the art. I-CreI (SEQ ID NO:95) is a member of the LAGLIDADG (SEQ ID NO:96) family of homing endonucleases which recognizes and cuts a 22 base pair recognition sequence in the chloroplast chromosome of the algae *Chlamydomonas reinhardtii*. Genetic selection techniques have been used to modify the wild-type I-CreI cleavage site preference (Sussman et al. (2004), *J. Mol. Biol.* 342: 31-41; Chames et al. (2005), *Nucleic Acids Res.* 33: e178; Seligman et al. (2002), *Nucleic Acids Res.* 30: 3870-9, Arnould et al. (2006), *J. Mol. Biol.* 355: 443-58). More recently, a method of rationally-designing mono-LAGLIDADG (SEQ ID NO:96) homing endonucleases was described which is capable of comprehensively redesigning I-CreI and other homing endonucleases to target widely-divergent DNA sites, including sites in mammalian, yeast, plant, bacterial, and viral genomes (WO 2007/047859).

As first described in WO 2009/059195, I-CreI and its engineered derivatives are normally dimeric but can be fused into a single polypeptide using a short peptide linker that joins the C-terminus of a first subunit to the N-terminus of a second subunit (see also Li, et al. (2009) *Nucleic Acids Res.* 37:1650-62; Grizot, et al. (2009) *Nucleic Acids Res.* 37:5405-19.) Thus, a functional "single-chain" meganuclease can be expressed from a single transcript. Such engineered meganucleases exhibit an extremely low frequency of off-target cutting. By delivering a gene encoding a single-chain meganuclease to retinal cells, and preferably to rod photoreceptor cells, it is possible to specifically and preferentially target, cleave, and inactivate the mutant RHO P23H allele, thus suppressing expression of P23H rhodopsin.

Thus, in one aspect, the invention provides a recombinant meganuclease that recognizes and cleaves a recognition sequence comprising the mutation which encodes P23H substitution in the P23H mutant allele. In some embodiments, the recognition sequence is selected from the SEQ ID NOs:1-4 (i.e., the P23H recognition sequences). The recombinant meganuclease comprises a first subunit and a second subunit, wherein the first subunit recognizes a first recognition half-site of one of the P23H recognition sequences and comprises an (a) an amino acid sequence having at least 80% sequence identity to residues 198-344 of any one of SEQ ID NOs:6-69 or residues 7-153 of any one of SEQ ID NOs:70-93; and (b) a first hypervariable (HVR1) region which determines specificity for the first recognition half-site. The recombinant meganuclease further comprises a second subunit that recognizes a second half-site of one of the P23H recognition sequences and comprises: (a) an amino acid sequence having at least 80% sequence identity to residues 7-153 of any one of SEQ ID NOs:6-69 or residues 198-344 of any one of SEQ ID NOs:70-93; and (b) a second hypervariable (HVR2) region which determines specificity for the second recognition half-site. In some embodiments, the P23H recognition sequence is SEQ ID NO:1 and the recombinant meganuclease comprises a first subunit and a second subunit, wherein the first subunit recognizes a first recognition half-site of one of SEQ ID NO:1 and comprises (a) an amino acid sequence having at least 80% sequence identity to residues 198-344 of any one of SEQ ID NOs:6-69 or residues 7-153 of any one of SEQ ID NOs:70-93; and (b) a first hypervariable (HVR1) region which determines specificity for the first recognition half-site. The recombinant meganuclease further comprises a second subunit that recognizes a second half-site of SEQ ID NO:1 and comprises: (a) an amino acid sequence having at least 80% sequence identity to residues 7-153 of any one of SEQ ID NOs:6-69 or residues 198-344 of any one of SEQ ID NOs:70-93; and (b) a second hypervariable (HVR2) region which determines specificity for the second recognition half-site.

In some embodiments, the P23H recognition sequence is SEQ ID NO:1 and the first subunit comprises an amino acid sequence having at least 85%, 90%, or 95% sequence identity to residues 198-344 of any one of SEQ ID NOs:6-69 or residues 7-153 of any one of SEQ ID NOs:70-93, and the second subunit comprises an amino acid sequence having at least 85%, 90%, or 95% sequence identity to residues 7-153 of any one of SEQ ID NOs:6-69 or residues 198-344 of any one of SEQ ID NOs:70-93.

In other embodiments, the P23H recognition sequence is SEQ ID NO:1 and the HVR1 region comprises W or Y at a position corresponding to: (a) position 215 of any one of SEQ ID NOs:6-69; or (b) position 24 of any one of SEQ ID NOs:70-93. In other embodiments, the P23H recognition sequence is SEQ ID NO:1 and the HVR1 region comprises I at a position corresponding to: (a) position 219 of any one of SEQ ID NOs:6-69; or (b) position 28 of any one of SEQ ID NOs:70-93. In other embodiments, the P23H recognition sequence is SEQ ID NO:1 and the HVR1 region comprises V at a position corresponding to: (a) position 259 of any one of SEQ ID NOs:6-69; or (b) position 68 of any one of SEQ ID NOs:70-93. In other embodiments, the P23H recognition sequence is SEQ ID NO:1 and the HVR1 region comprises one or more of W or Y, I, and V at positions corresponding to (a) positions 215, 219, and 259, respectively, of any one of SEQ ID NOs:6-69; or (b) positions 24, 28, and 68, respectively, of any one of SEQ ID NOs:70-93.

In other embodiments, the P23H recognition sequence is SEQ ID NO:1 and the HVR2 region comprises Y or M at a position corresponding to (a) position 24 of any one of SEQ ID NOs:6-69; or (b) position 215 of any one of SEQ ID NOs:70-93. In other embodiments, the P23H recognition sequence is SEQ ID NO:1 and the HVR2 region comprises F at a position corresponding to (a) position 28 of any one of SEQ ID NOs:6-69; or (b) position 219 of any one of SEQ ID NOs:70-93. In other embodiments, the P23H recognition sequence is SEQ ID NO:1 and the HVR2 region comprises H at a position corresponding to (a) position 44 of any one of SEQ ID NOs:6-69; or (b) position 235 of any one of SEQ ID NOs:70-93. In other embodiments, the P23H recognition sequence is SEQ ID NO:1 and the HVR2 region comprises S at a position corresponding to (a) position 46 of any one of SEQ ID NOs:6-69; or (b) position 237 of any one of SEQ ID NOs:70-93. In other embodiments, the P23H recognition sequence is SEQ ID NO:1 and the HVR2 region comprises W at a position corresponding to (a) position 70 of any one of SEQ ID NOs:6-69; or (b) position 261 of any one of SEQ ID NOs:70-93. In other embodiments, the P23H recognition sequence is SEQ ID NO:1 and the HVR2 region comprises one or more of Y or M, F, H, S, and W at positions corresponding to (a) positions 24, 28, 44, 46, and 70, respectively, of any one of SEQ ID NOs:6-69; or (b) positions 215, 219, 235, 237, and 261, respectively, of any one of SEQ ID NOs:70-93.

In some embodiments, the recombinant meganuclease is a single-chain meganuclease comprising a linker, wherein the linker covalently joins the first subunit and the second subunit.

In some embodiments, the P23H recognition sequence is SEQ ID NO:1 and the first subunit comprises residues 198-344 of any one of SEQ ID NOs:6-69 or residues 7-153 of any one of SEQ ID NOs:70-93. In some embodiments, the P23H recognition sequence is SEQ ID NO:1 and the second subunit comprises residues 7-153 of any one of SEQ ID NOs:6-69 or residues 198-344 of any one of SEQ ID NOs:70-93.

In some specific embodiments, the P23H recognition sequence is SEQ ID NO:1 and the meganuclease comprises the amino acid sequence of any one of SEQ ID NOs:6-93.

In some embodiments, the recombinant meganuclease preferentially recognizes and cleaves one of the P23H recognition sequences (SEQ ID NOs:1-4) relative to the corresponding 22 base pair recognition sequence present in the wild-type RHO allele (e.g., SE ID NO: 1 relative to SEQ ID NO:5).

In another aspect, the invention provides an isolated polynucleotide comprising a nucleic acid sequence encoding a recombinant meganuclease described herein.

In another aspect, the invention provides a recombinant DNA construct comprising an isolated polynucleotide, wherein the isolated polynucleotide comprises a nucleic acid sequence encoding a recombinant meganuclease described herein. In some embodiments, the recombinant DNA construct encodes a viral vector. In some such embodiments, the viral vector can be a retroviral vector, a lentiviral vector, an adenoviral vector, or an adeno-associated viral (AAV) vector. In some particular embodiment, the recombinant DNA construct encodes a recombinant AAV vector.

In another aspect, the invention provides a viral vector comprising an isolated polynucleotide, wherein the isolated polynucleotide comprises a nucleic acid sequence encoding a recombinant meganuclease described herein. In some embodiments, the viral vector can be a retroviral vector, a lentiviral vector, an adenoviral vector, or an AAV vector. In some particular embodiments, the viral vector can be a recombinant AAV vector.

In another aspect, the invention provides a pharmaceutical composition for treatment of a subject having RP, preferably autosomal dominant RP caused by the P23H mutation. The pharmaceutical composition can comprise a pharmaceutically acceptable carrier and: (a) a nucleic acid encoding a recombinant meganuclease described herein, wherein the recombinant meganuclease is expressed in a target cell in vivo; or (b) a recombinant meganuclease protein described herein; wherein the recombinant meganuclease has specificity for one of the P23H recognition sequences (SEQ ID NOs:1-4) in the target cell.

In some embodiments, the nucleic acid encoding the recombinant meganuclease can be an mRNA.

In other embodiments, the pharmaceutical composition comprises a recombinant DNA construct comprising the nucleic acid.

In some embodiments, the pharmaceutical composition comprises a viral vector comprising the nucleic acid. In one such embodiment, the viral vector can be a retroviral vector, a lentiviral vector, an adenoviral vector, or an AAV vector. In some particular embodiments, the viral vector can be a recombinant AAV vector.

In another aspect, the invention provides a recombinant meganuclease described herein for use as a medicament. The invention further provides the use of a recombinant meganuclease described herein in the manufacture of a medicament for treating RP, preferably autosomal dominant RP caused by the P23H mutation, and preferably for a subject that is heterozygous for the P23H mutant allele and a functional, normal or wild-type allele.

In another aspect, the invention provides an isolated polynucleotide for use as a medicament, wherein the isolated polynucleotide comprises a nucleic acid sequence encoding a recombinant meganuclease described herein. The invention further provides the use of an isolated polynucleotide in the manufacture of a medicament for treating RP, preferably autosomal dominant RP caused by the P23H mutation, and preferably for a subject that is heterozygous for the P23H mutant allele and a functional, normal or wild-type allele, wherein the isolated polynucleotide comprises a nucleic acid sequence encoding a recombinant meganuclease described herein.

In another aspect, the invention provides a recombinant AAV vector for use as a medicament, wherein the recombinant AAV vector comprises an isolated polynucleotide, and wherein the isolated polynucleotide comprises a nucleic acid sequence encoding a recombinant meganuclease described herein. The invention further provides the use of a recombinant AAV vector in the manufacture of a medicament for treating RP, preferably autosomal dominant RP caused by the P23H mutation, and preferably for a subject that is heterozygous for the P23H mutant allele and a functional, normal or wild-type allele wherein the recombinant AAV vector comprises an isolated polynucleotide, and wherein the isolated polynucleotide comprises a nucleic acid sequence encoding a recombinant meganuclease described herein.

In another aspect, the invention provides a method for treating RP caused by the P23H mutation in a subject in need thereof, and preferably for a subject that is heterozygous for the P23H mutant allele and a functional, normal or wild-type allele. The method comprises contacting the DNA of a target cell of said subject with a recombinant meganuclease described herein that recognizes and cleaves the a recognition sequence including the P23H mutation (e.g, SEQ ID NOs:1-4). The target cell of the subject comprises the P23H recognition sequence in a RHO gene allele, and cleavage of the recognition sequence inhibits expression of the RHO gene allele.

In some embodiments, the method is for treating autosomal dominant RP caused by the P23H mutation, and preferably for a subject that is heterozygous for the P23H mutant allele and a functional, normal or wild-type allele.

In some embodiments, the target cell in the subject is a retinal target cell. In preferred embodiments, the retinal cell is a rod photoreceptor cell.

In some embodiments of the method, a nucleic acid encoding the recombinant meganuclease is introduced into the target cell. In some such embodiments, the nucleic acid can be an mRNA. In other such embodiments, the nucleic acid can be introduced into the cell using a recombinant DNA construct. In yet other such embodiments, the nucleic acid can be introduced into the target cell using a viral vector such as a retroviral vector, a lentiviral vector, an adenoviral vector, or an AAV vector. In some particular embodiment, a gene encoding the recombinant meganuclease is delivered to the target cell using a recombinant AAV vector.

In other embodiments of the method, a recombinant meganuclease protein of the invention is introduced into the target cell.

In the various embodiments of the method, the recombinant meganuclease protein, or a nucleic acid encoding the recombinant meganuclease, can be administered to the subject in a pharmaceutical composition described herein.

In another aspect, the invention provides a method for producing a genetically-modified cell. The method comprises: (a) obtaining a cell comprising at least one P23H RHO allele; and (b) introducing into the cell: (i) a nucleic acid sequence encoding a recombinant meganuclease of the invention, wherein the recombinant meganuclease is expressed in the cell; or (ii) a recombinant meganuclease protein; wherein the recombinant meganuclease has specificity for a P23H recognition sequence present on the P23H RHO allele(s); and wherein the recombinant meganuclease recognizes and cleaves the P23H recognition sequence; and wherein expression of the P23H RHO allele is disrupted by non-homologous end joining at the cleavage site. Preferably the cell is heterozygous for the P23H mutant allele and a functional, normal or wild-type allele prior to the modification.

In some embodiments of the method, the cell can be a eukaryotic cell. In some such embodiments, the eukaryotic cell can be a pluripotent cell. In such embodiments, the pluripotent cell can be an induced pluripotent stem (iPS) cell. In some particular embodiments, the iPS cell can be a human iPS cell.

In other embodiments of the method, the nucleic acid can be an mRNA.

In some embodiment of the method, the nucleic acid can be introduced into the cell using a recombinant DNA construct.

In some embodiments of the method, the nucleic acid can be introduced into the cell using a viral vector. In some such embodiments, the viral vector can be a retroviral vector, a lentiviral vector, an adenoviral vector, or an AAV vector. In some particular embodiments, the viral vector can be a recombinant AAV vector.

In another aspect, the invention provides a genetically-modified cell, wherein the genetically-modified cell comprises a wild-type RHO allele and a disrupted P23H allele, wherein the genetically-modified cell expresses a wild-type RHO protein and does not express a P23H RHO protein, and wherein the genetically-modified cell is produced according to the methods of the invention described herein. In some embodiments, the disrupted P23H allele includes a deletion mutation caused by cleavage with the meganuclease and NHEJ. In some particular embodiments, the genetically-modified cell can be a pluripotent cell, an iPS cell, or a human iPS cell.

In another aspect, the invention provides a pharmaceutical composition for treatment of a subject having RP caused by the P23H mutation, and preferably for a subject that is heterozygous for the P23H mutant allele and a functional, normal or wild-type allele. In different embodiments, the pharmaceutical composition can comprise a pharmaceutically acceptable carrier and any genetically-modified cell of the invention, and/or any genetically-modified cell produced according to the methods of the invention, which comprises a wild-type RHO allele that expresses wild-type RHO protein and a disrupted P23H allele which does not express P23H RHO protein. In some embodiments, the disrupted P23H allele includes a deletion mutation caused by cleavage with the meganuclease and NHEJ.

In another aspect, the invention provides a method for treating RP caused by the P23H mutation in a subject in need thereof, and preferably for a subject that is heterozygous for the P23H mutant allele and a functional, normal or wild-type allele. The method comprises administering to the subject a pharmaceutical composition described herein which comprises a pharmaceutically acceptable carrier and a genetically-modified cell of the invention, which comprises a wild-type RHO allele that expresses wild-type RHO protein and a disrupted P23H allele which does not express P23H RHO protein. In some embodiments, the disrupted P23H allele includes a deletion mutation caused by cleavage with the meganuclease and NHEJ.

In some embodiments of the method, the genetically-modified cell can be delivered to a target tissue. Such target tissues can include the eye, and particularly the retina.

Further, in some embodiments of the method, the genetically-modified cell can be a genetically-modified iPS cell. In such embodiments, the genetically-modified iPS cell can differentiate into a cell which expresses wild-type RHO protein when it is delivered to the target tissue. In some particular embodiments, the genetically-modified iPS cell can differentiate into a retinal cell, and particularly into a rod photoreceptor cell, which expresses the wild-type rhodopsin protein but not the P23H rhodopsin protein.

BRIEF DESCRIPTION OF THE FIGURES

FIG. 1. P23H recognition sequence. A) Alignment of the 22 base pair P23H recognition sequence of SEQ ID NO:1 with the corresponding 22 base pair recognition sequence present in the wild-type human RHO gene allele (SEQ ID NO:5). These sequences span nucleotides 49 to 70 of the P23H mutant or wild-type RHO gene coding sequences (SEQ ID NOs:98 and 97, respectively). The C68A nucleotide substitution within the P23H recognition sequence is highlighted. B) The P23H recognition sequence of SEQ ID NO:1 comprises two recognition half-sites, referred to as RHO1 and RHO2. Each recognition half-site comprises 9 base pairs as shown. Half-sites in the recognition sequence are separated by a 4 base pair central region. C) The recombinant meganuclease of the invention comprises two subunits, wherein the first subunit binds to the a first half-site (e.g., RHO1) of a P23H recognition sequence (e.g., SEQ ID NO:1) and the second subunit binds to a second half-site (e.g., RHO2). In embodiments where the recombinant meganuclease is a single-chain meganuclease, the first subunit can be positioned as either the N-terminal or C-terminal subunit. Likewise, the second subunit can be positioned as either the N-terminal or C-terminal subunit.

FIGS. 2A-2F. Amino acid alignment of RHO1-binding subunits. A-F) Recombinant meganucleases encompassed by the invention comprise one subunit that binds the 9 base pair RHO1 recognition half-site of SEQ ID NO:1. Amino acid sequence alignments are provided for the RHO1-binding subunits (SEQ ID NOs:102-188) of the recombinant meganucleases set forth in SEQ ID NOs:6-93. As shown, the RHO1-binding subunit of SEQ ID NOs:6-69 comprises residues 198-344, whereas the RHO1-binding subunit of SEQ ID NOs:70-93 comprises residues 7-153. Each RHO1-binding subunit comprises a 56 amino acid hypervariable region as indicated. Variable residues within the hypervariable region are shaded, with the most frequent amino acids at each position further highlighted; the most prevalent residues are bolded, whereas the second most prevalent are bolded and italicized. Residues outside of the hypervariable region are identical in each subunit (but this is not required), with the exception of a Q or E residue at position 80 or position 271 (see, U.S. Pat. No. 8,021,867). Nearly all RHO1-binding subunits provided in FIG. 2A-2F share at least 90% sequence identity to the RHO1-binding subunit (residues 198-344) of the RHO2-L3-59 meganuclease (SEQ ID NO:102). Residue numbers shown are those of SEQ ID NOs:6-93.

FIGS. 3A-3F. Amino acid alignment of RHO2-binding subunits. A-F) Recombinant meganucleases encompassed by the invention comprise one subunit that binds the 9 base pair RHO2 recognition half-site of SEQ ID NO:1. Amino acid sequence alignments are provided for the RHO2-binding subunits (SEQ ID NOs:190-277) of the recombinant meganucleases set forth in SEQ ID NOs:6-93. As shown, the RHO2-binding subunit of SEQ ID NOs:6-69 comprises residues 7-153, whereas the RHO2-binding subunit of SEQ ID NOs:70-93 comprises residues 198-344. Each RHO2-binding subunit comprises a 56 amino acid hypervariable region as indicated. Variable residues within the hypervariable region are shaded, with the most frequent amino acids at each position further highlighted; the most prevalent residues are bolded, whereas the second most prevalent are bolded and italicized. Residues outside of the hypervariable region are identical in each subunit (but this is not required), with the exception of a Q or E residue at position 80 or position 271 (see, U.S. Pat. No. 8,021,867). Nearly all RHO2-binding subunits provided in FIGS. 3A-3F share at least 90% sequence identity to the RHO2-binding subunit (residues 7-153) of the RHO2-L3-59 meganuclease (SEQ ID NO:190). Residue numbers shown are those of SEQ ID NOs:6-93.

FIG. 8. Generation and expression of recombinant AAV vectors. A) Diagram of recombinant AAV vector genome shown with inverted terminal repeats (ITRs) at the 5' and 3' ends. The vector comprises the coding sequence for the recombinant meganuclease RHO-1/2-L2-49 (SEQ ID NO:8) operably linked to a cytomegalovirus-early (CMV) promoter. The nuclease expression cassette was incorporated into a "packaging" plasmid that was used in conjunction with an Ad helper plasmid to produce recombinant AAV capable of delivering genes encoding the RHO-1/2-L2-49 meganuclease. B) Immunoblot of RHO-1/2-L2-49 meganuclease expression in recombinant AAV-transduced CHO cells after 24 hours.

FIG. 15. Western blot analysis of meganuclease expression in mouse retinal cells following subretinal AAV injection. Wild-type mice were administered a recombinant AAV vector encoding the RHO2-L5-14 meganuclease (SEQ ID NO:7) by subretinal injection. Retinal cells were obtained from the left (OS) and right (OD) eye of five mice and cell lysates were analyzed by Western blot for the expression of the RHO2-L5-14 meganuclease and β-actin.

BRIEF DESCRIPTION OF THE SEQUENCES

Figure 4:
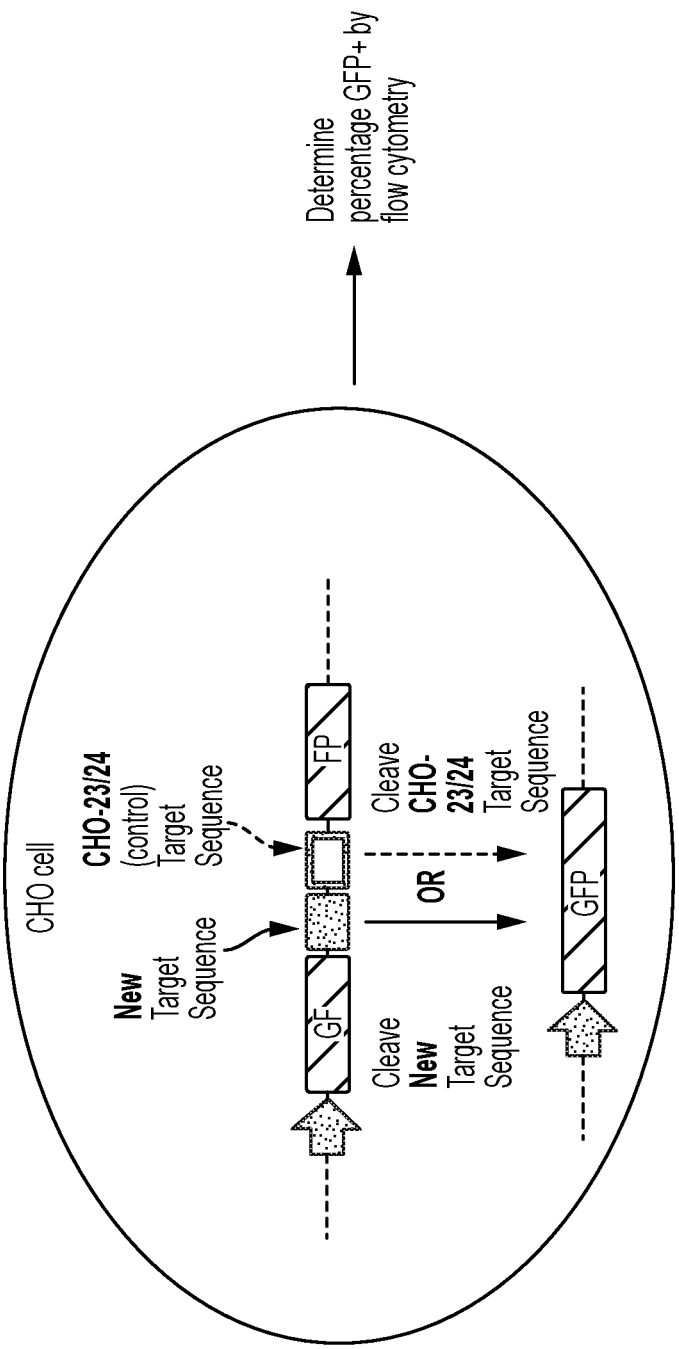
FIG. 4. Schematic of reporter assay in CHO cells for evaluating recombinant meganucleases targeting a P23H recognition sequence. For the recombinant meganucleases described herein, a CHO cell line was produced in which a reporter cassette was integrated stably into the genome of the cell. The reporter cassette comprised, in 5' to 3' order: an SV40 Early Promoter; the 5' 2/3 of the GFP gene; the recognition sequence for an engineered meganuclease of the invention, for example a P23H recognition sequence of any one of SEQ ID NOs:1-4; the recognition sequence for the CHO-23/24 meganuclease (WO 2012/167192); and the 3' 2/3 of the GFP gene. Cells stably transfected with this cassette did not express GFP in the absence of a DNA break-inducing agent. Meganucleases were introduced by transduction of plasmid DNA or mRNA encoding each meganuclease. When a DNA break was induced at either of the meganuclease recognition sequences, the duplicated regions of the GFP gene recombined with one another to produce a functional GFP gene. The percentage of GFP-expressing cells could then be determined by flow cytometry as an indirect measure of the frequency of genome cleavage by the meganucleases.

SEQ ID NO:1 sets forth the nucleotide sequence of one P23H recognition sequence (RHO-1/2).

SEQ ID NO:2 sets forth the nucleotide sequence of one P23H recognition sequence (RHO-9/10).

SEQ ID NO:3 sets forth the nucleotide sequence of one P23H recognition sequence (RHO-11/12).

SEQ ID NO:4 sets forth the nucleotide sequence of one P23H recognition sequence (RHO-13/14).

SEQ ID NO:5 sets forth the nucleotide sequence of the corresponding recognition sequence found in the wild-type RHO allele (i.e., the RHO 3-4 recognition sequence).

SEQ ID NO: 6 sets forth the amino acid sequence of the RHO2-L3-59 meganuclease.

SEQ ID NO: 7 sets forth the amino acid sequence of the RHO2-L5-14 meganuclease.
SEQ ID NO: 8 sets forth the amino acid sequence of the RHO-1/2-L2-49 meganuclease.
SEQ ID NO: 9 sets forth the amino acid sequence of the RHO 1-2x.179 meganuclease.
SEQ ID NO: 10 sets forth the amino acid sequence of the RHO 1-2x.4 meganuclease.
SEQ ID NO: 11 sets forth the amino acid sequence of the RHO 1-2x.207 meganuclease.
SEQ ID NO: 12 sets forth the amino acid sequence of the RHO 1-2x.277 meganuclease.
SEQ ID NO: 13 sets forth the amino acid sequence of the RHO 1-2x.292 meganuclease.
SEQ ID NO: 14 sets forth the amino acid sequence of the RHO 1-2x.324 meganuclease.
SEQ ID NO: 15 sets forth the amino acid sequence of the RHO 1-2x.371 meganuclease.
SEQ ID NO: 16 sets forth the amino acid sequence of the RHO 1-2x.164 meganuclease.
SEQ ID NO: 17 sets forth the amino acid sequence of the RHO 1-2x.181 meganuclease.
SEQ ID NO: 18 sets forth the amino acid sequence of the RHO 1-2x.184 meganuclease.
SEQ ID NO: 19 sets forth the amino acid sequence of the RHO-1/2-L1-21 meganuclease.
SEQ ID NO: 20 sets forth the amino acid sequence of the RHO-1/2-L1-43 meganuclease.
SEQ ID NO: 21 sets forth the amino acid sequence of the RHO-1/2-L1-45 meganuclease.
SEQ ID NO: 22 sets forth the amino acid sequence of the RHO-1/2-L1-60 meganuclease.
SEQ ID NO: 23 sets forth the amino acid sequence of the RHO-1/2-L1-61 meganuclease.
SEQ ID NO: 24 sets forth the amino acid sequence of the RHO-1/2-L1-58 meganuclease.
SEQ ID NO: 25 sets forth the amino acid sequence of the RHO-1/2-L1-7 meganuclease.
SEQ ID NO: 26 sets forth the amino acid sequence of the RHO-1/2-L1-13 meganuclease.
SEQ ID NO: 27 sets forth the amino acid sequence of the RHO-1/2-L1-18 meganuclease.
SEQ ID NO: 28 sets forth the amino acid sequence of the RHO-1/2-L1-70 meganuclease.
SEQ ID NO: 29 sets forth the amino acid sequence of the RHO-1/2-L1-86 meganuclease.
SEQ ID NO: 30 sets forth the amino acid sequence of the RHO-1/2-L2-13 meganuclease.
SEQ ID NO: 31 sets forth the amino acid sequence of the RHO-1/2-L2-24 meganuclease.
SEQ ID NO: 32 sets forth the amino acid sequence of the RHO-1/2-L2-37 meganuclease.
SEQ ID NO: 33 sets forth the amino acid sequence of the RHO-1/2-L2-58 meganuclease.
SEQ ID NO: 34 sets forth the amino acid sequence of the RHO-1/2-L2-31 meganuclease.
SEQ ID NO: 35 sets forth the amino acid sequence of the RHO-1/2-L2-29 meganuclease.
SEQ ID NO: 36 sets forth the amino acid sequence of the RHO-1/2-L2-61 meganuclease.
SEQ ID NO: 37 sets forth the amino acid sequence of the RHO2-L3-2 meganuclease.
SEQ ID NO: 38 sets forth the amino acid sequence of the RHO2-L3-3 meganuclease.
SEQ ID NO: 39 sets forth the amino acid sequence of the RHO2-L3-5 meganuclease.
SEQ ID NO: 40 sets forth the amino acid sequence of the RHO2-L3-10 meganuclease.
SEQ ID NO: 41 sets forth the amino acid sequence of the RHO2-L3-11 meganuclease.
SEQ ID NO: 42 sets forth the amino acid sequence of the RHO2-L3-12 meganuclease.
SEQ ID NO: 43 sets forth the amino acid sequence of the RHO2-L3-13 meganuclease.
SEQ ID NO: 44 sets forth the amino acid sequence of the RHO2-L3-28 meganuclease.
SEQ ID NO: 45 sets forth the amino acid sequence of the RHO2-L3-29 meganuclease.
SEQ ID NO: 46 sets forth the amino acid sequence of the RHO2-L3-57 meganuclease.
SEQ ID NO: 47 sets forth the amino acid sequence of the RHO2-L3-80 meganuclease.
SEQ ID NO: 48 sets forth the amino acid sequence of the RHO2-L3-85 meganuclease.
SEQ ID NO: 49 sets forth the amino acid sequence of the RHO2-L3-86 meganuclease.
SEQ ID NO: 50 sets forth the amino acid sequence of the RHO2-L3-92 meganuclease.
SEQ ID NO: 51 sets forth the amino acid sequence of the RHO2-L3-4 meganuclease.
SEQ ID NO: 52 sets forth the amino acid sequence of the RHO2-L3-20 meganuclease.
SEQ ID NO: 53 sets forth the amino acid sequence of the RHO2-L3-72 meganuclease.
SEQ ID NO: 54 sets forth the amino acid sequence of the RHO1-L1-4 meganuclease.
SEQ ID NO: 55 sets forth the amino acid sequence of the RHO1-L1-8 meganuclease.
SEQ ID NO: 56 sets forth the amino acid sequence of the RHO1-L1-13 meganuclease.
SEQ ID NO: 57 sets forth the amino acid sequence of the RHO1-L1-19 meganuclease.
SEQ ID NO: 58 sets forth the amino acid sequence of the RHO1-L1-58 meganuclease.
SEQ ID NO: 59 sets forth the amino acid sequence of the RHO1-L1-69 meganuclease.
SEQ ID NO: 60 sets forth the amino acid sequence of the RHO1-L1-80 meganuclease.
SEQ ID NO: 61 sets forth the amino acid sequence of the RHO1-L1-82 meganuclease.
SEQ ID NO: 62 sets forth the amino acid sequence of the RHO1-L1-73 meganuclease.
SEQ ID NO: 63 sets forth the amino acid sequence of the RHO1-L1-85 meganuclease.
SEQ ID NO: 64 sets forth the amino acid sequence of the RHO1-L1-86 meganuclease.
SEQ ID NO: 65 sets forth the amino acid sequence of the RHO-1/2-L4-10 meganuclease.
SEQ ID NO: 66 sets forth the amino acid sequence of the RHO-1/2-L4-29 meganuclease.
SEQ ID NO: 67 sets forth the amino acid sequence of the RHO-1/2-L4-65 meganuclease.
SEQ ID NO: 68 sets forth the amino acid sequence of the RHO-1/2-L4-66 meganuclease.
SEQ ID NO: 69 sets forth the amino acid sequence of the RHO-1/2-L4-85 meganuclease.
SEQ ID NO: 70 sets forth the amino acid sequence of the RHO 1-2x.216 meganuclease.
SEQ ID NO: 71 sets forth the amino acid sequence of the RHO 1-2x.241 meganuclease.
SEQ ID NO: 72 sets forth the amino acid sequence of the RHO 1-2x.94 meganuclease.

SEQ ID NO: 73 sets forth the amino acid sequence of the RHO 1-2x.95 meganuclease.

SEQ ID NO: 74 sets forth the amino acid sequence of the RHO 1-2x.1 meganuclease.

SEQ ID NO: 75 sets forth the amino acid sequence of the RHO 1-2x.60 meganuclease.

SEQ ID NO: 76 sets forth the amino acid sequence of the RHO 1-2x.74 meganuclease.

SEQ ID NO: 77 sets forth the amino acid sequence of the RHO 1-2x.88 meganuclease.

SEQ ID NO: 78 sets forth the amino acid sequence of the RHO 1-2x.294 meganuclease.

SEQ ID NO: 79 sets forth the amino acid sequence of the RHO 1-2x.302 meganuclease.

SEQ ID NO: 80 sets forth the amino acid sequence of the RHO 1-2x.306 meganuclease.

SEQ ID NO: 81 sets forth the amino acid sequence of the RHO 1-2x.338 meganuclease.

SEQ ID NO: 82 sets forth the amino acid sequence of the RHO 1-2x.348 meganuclease.

SEQ ID NO: 83 sets forth the amino acid sequence of the RHO 1-2x.356 meganuclease.

SEQ ID NO: 84 sets forth the amino acid sequence of the RHO 1-2x.364 meganuclease.

SEQ ID NO: 85 sets forth the amino acid sequence of the RHO 1-2x.142 meganuclease.

SEQ ID NO: 86 sets forth the amino acid sequence of the RHO 1-2x.177 meganuclease.

SEQ ID NO: 87 sets forth the amino acid sequence of the RHO 1-2x.148 meganuclease.

SEQ ID NO: 88 sets forth the amino acid sequence of the RHO 1-2x.20 meganuclease.

SEQ ID NO: 89 sets forth the amino acid sequence of the RHO 1-2x.55 meganuclease.

SEQ ID NO: 90 sets forth the amino acid sequence of the RHO 1-2x.197 meganuclease.

SEQ ID NO: 91 sets forth the amino acid sequence of the RHO 1-2x.252 meganuclease.

SEQ ID NO: 92 sets forth the amino acid sequence of the RHO 1-2x.372 meganuclease.

SEQ ID NO: 93 sets forth the amino acid sequence of the RHO 1-2x.151 meganuclease.

SEQ ID NO:94 sets forth the amino acid sequence of the wild-type I-CreI meganuclease.

SEQ ID NO:95 sets forth the amino acid sequence of the LAGLIDADG motif of the I-CreI meganuclease.

SEQ ID NO:96 sets forth the nucleic acid sequence of the coding region for wild-type human rhodopsin.

SEQ ID NO:97 sets forth the nucleic acid sequence of the coding region for mutant P23H rhodopsin.

SEQ ID NO:98 sets forth the nucleic acid sequence of the wild-type human rhodopsin gene.

SEQ ID NO:99 sets forth the nucleic acid sequence of the human rhodopsin gene comprising a C68A mutation that encodes a P23H substitution in rhodopsin.

SEQ ID NO:100 sets forth the amino acid sequence of wild-type human rhodopsin.

SEQ ID NO:101 sets for the amino acid sequence of mutant P23H rhodopsin.

SEQ ID NO: 102 sets forth residues 198-344 of the RHO2-L3-59 meganuclease.

SEQ ID NO: 103 sets forth residues 198-344 of the RHO-L5-14 meganuclease.

SEQ ID NO: 104 sets forth residues 198-344 of the RHO-1/2-L2-49 meganuclease.

SEQ ID NO: 105 sets forth residues 198-344 of the RHO 1-2x.179 meganuclease.

SEQ ID NO: 106 sets forth residues 198-344 of the RHO 1-2x.4 meganuclease.

SEQ ID NO: 107 sets forth residues 198-344 of the RHO 1-2x.207 meganuclease.

SEQ ID NO: 108 sets forth residues 198-344 of the RHO 1-2x.277 meganuclease.

SEQ ID NO: 109 sets forth residues 198-344 of the RHO 1-2x.292 meganuclease.

SEQ ID NO: 110 sets forth residues 198-344 of the RHO 1-2x.324 meganuclease.

SEQ ID NO: 111 sets forth residues 198-344 of the RHO 1-2x.371 meganuclease.

SEQ ID NO: 112 sets forth residues 198-344 of the RHO 1-2x.164 meganuclease.

SEQ ID NO: 113 sets forth residues 198-344 of the RHO 1-2x.181 meganuclease.

SEQ ID NO: 114 sets forth residues 198-344 of the RHO 1-2x.184 meganuclease.

SEQ ID NO: 115 sets forth residues 198-344 of the RHO-1/2-L1-21 meganuclease.

SEQ ID NO: 116 sets forth residues 198-344 of the RHO-1/2-L1-43 meganuclease.

SEQ ID NO: 117 sets forth residues 198-344 of the RHO-1/2-L1-45 meganuclease.

SEQ ID NO: 118 sets forth residues 198-344 of the RHO-1/2-L1-60 meganuclease.

SEQ ID NO: 119 sets forth residues 198-344 of the RHO-1/2-L1-61 meganuclease.

SEQ ID NO: 120 sets forth residues 198-344 of the RHO-1/2-L1-58 meganuclease.

SEQ ID NO: 121 sets forth residues 198-344 of the RHO-1/2-L1-7 meganuclease.

SEQ ID NO: 122 sets forth residues 198-344 of the RHO-1/2-L1-13 meganuclease.

SEQ ID NO: 123 sets forth residues 198-344 of the RHO-1/2-L1-18 meganuclease.

SEQ ID NO: 124 sets forth residues 198-344 of the RHO-1/2-L1-70 meganuclease.

SEQ ID NO: 125 sets forth residues 198-344 of the RHO-1/2-L1-86 meganuclease.

SEQ ID NO: 126 sets forth residues 198-344 of the RHO-1/2-L2-13 meganuclease.

SEQ ID NO: 127 sets forth residues 198-344 of the RHO-1/2-L2-24 meganuclease.

SEQ ID NO: 128 sets forth residues 198-344 of the RHO-1/2-L2-37 meganuclease.

SEQ ID NO: 129 sets forth residues 198-344 of the RHO-1/2-L2-58 meganuclease.

SEQ ID NO: 130 sets forth residues 198-344 of the RHO-1/2-L2-31 meganuclease.

SEQ ID NO: 131 sets forth residues 198-344 of the RHO-1/2-L2-29 meganuclease.

SEQ ID NO: 132 sets forth residues 198-344 of the RHO-1/2-L2-61 meganuclease.

SEQ ID NO: 133 sets forth residues 198-344 of the RHO2-L3-2 meganuclease.

SEQ ID NO: 134 sets forth residues 198-344 of the RHO2-L3-3 meganuclease.

SEQ ID NO: 135 sets forth residues 198-344 of the RHO2-L3-5 meganuclease.

SEQ ID NO: 136 sets forth residues 198-344 of the RHO2-L3-10 meganuclease.

SEQ ID NO: 137 sets forth residues 198-344 of the RHO2-L3-11 meganuclease.

SEQ ID NO: 138 sets forth residues 198-344 of the RHO2-L3-12 meganuclease.

SEQ ID NO: 139 sets forth residues 198-344 of the RHO2-L3-13 meganuclease.
SEQ ID NO: 140 sets forth residues 198-344 of the RHO2-L3-28 meganuclease.
SEQ ID NO: 141 sets forth residues 198-344 of the RHO2-L3-29 meganuclease.
SEQ ID NO: 142 sets forth residues 198-344 of the RHO2-L3-57 meganuclease.
SEQ ID NO: 143 sets forth residues 198-344 of the RHO2-L3-80 meganuclease.
SEQ ID NO: 144 sets forth residues 198-344 of the RHO2-L3-85 meganuclease.
SEQ ID NO: 145 sets forth residues 198-344 of the RHO2-L3-86 meganuclease.
SEQ ID NO: 146 sets forth residues 198-344 of the RHO2-L3-92 meganuclease.
SEQ ID NO: 147 sets forth residues 198-344 of the RHO2-L3-4 meganuclease.
SEQ ID NO: 148 sets forth residues 198-344 of the RHO2-L3-20 meganuclease.
SEQ ID NO: 149 sets forth residues 198-344 of the RHO2-L3-72 meganuclease.
SEQ ID NO: 150 sets forth residues 198-344 of the RHO1-L1-4 meganuclease.
SEQ ID NO: 151 sets forth residues 198-344 of the RHO1-L1-8 meganuclease.
SEQ ID NO: 152 sets forth residues 198-344 of the RHO1-L1-13 meganuclease.
SEQ ID NO: 153 sets forth residues 198-344 of the RHO1-L1-19 meganuclease.
SEQ ID NO: 154 sets forth residues 198-344 of the RHO1-L1-58 meganuclease.
SEQ ID NO: 155 sets forth residues 198-344 of the RHO1-L1-69 meganuclease.
SEQ ID NO: 156 sets forth residues 198-344 of the RHO1-L1-80 meganuclease.
SEQ ID NO: 157 sets forth residues 198-344 of the RHO1-L1-82 meganuclease.
SEQ ID NO: 158 sets forth residues 198-344 of the RHO1-L1-73 meganuclease.
SEQ ID NO: 159 sets forth residues 198-344 of the RHO1-L1-85 meganuclease.
SEQ ID NO: 160 sets forth residues 198-344 of the RHO1-L1-86 meganuclease.
SEQ ID NO: 161 sets forth residues 198-344 of the RHO-1/2-L4-10 meganuclease.
SEQ ID NO: 162 sets forth residues 198-344 of the RHO-1/2-L4-29 meganuclease.
SEQ ID NO: 163 sets forth residues 198-344 of the RHO-1/2-L4-65 meganuclease.
SEQ ID NO: 164 sets forth residues 198-344 of the RHO-1/2-L4-66 meganuclease.
SEQ ID NO: 165 sets forth residues 198-344 of the RHO-1/2-L4-85 meganuclease.
SEQ ID NO: 166 sets forth residues 7-153 of the RHO 1-2x.216 meganuclease.
SEQ ID NO: 167 sets forth residues 7-153 of the RHO 1-2x.241 meganuclease.
SEQ ID NO: 168 sets forth residues 7-153 of the RHO 1-2x.94 meganuclease.
SEQ ID NO: 169 sets forth residues 7-153 of the RHO 1-2x.95 meganuclease.
SEQ ID NO: 170 sets forth residues 7-153 of the RHO 1-2x.1 meganuclease.
SEQ ID NO: 171 sets forth residues 7-153 of the RHO 1-2x.60 meganuclease.
SEQ ID NO: 172 sets forth residues 7-153 of the RHO 1-2x.74 meganuclease.
SEQ ID NO: 173 sets forth residues 7-153 of the RHO 1-2x.88 meganuclease.
SEQ ID NO: 174 sets forth residues 7-153 of the RHO 1-2x.294 meganuclease.
SEQ ID NO: 175 sets forth residues 7-153 of the RHO 1-2x.302 meganuclease.
SEQ ID NO: 176 sets forth residues 7-153 of the RHO 1-2x.306 meganuclease.
SEQ ID NO: 177 sets forth residues 7-153 of the RHO 1-2x.338 meganuclease.
SEQ ID NO: 178 sets forth residues 7-153 of the RHO 1-2x.348 meganuclease.
SEQ ID NO: 179 sets forth residues 7-153 of the RHO 1-2x.356 meganuclease.
SEQ ID NO: 180 sets forth residues 7-153 of the RHO 1-2x.364 meganuclease.
SEQ ID NO: 181 sets forth residues 7-153 of the RHO 1-2x.142 meganuclease.
SEQ ID NO: 182 sets forth residues 7-153 of the RHO 1-2x.177 meganuclease.
SEQ ID NO: 183 sets forth residues 7-153 of the RHO 1-2x.148 meganuclease.
SEQ ID NO: 184 sets forth residues 7-153 of the RHO 1-2x.20 meganuclease.
SEQ ID NO: 185 sets forth residues 7-153 of the RHO 1-2x.55 meganuclease.
SEQ ID NO: 186 sets forth residues 7-153 of the RHO 1-2x.197 meganuclease.
SEQ ID NO: 187 sets forth residues 7-153 of the RHO 1-2x.252 meganuclease.
SEQ ID NO: 188 sets forth residues 7-153 of the RHO 1-2x.372 meganuclease.
SEQ ID NO: 189 sets forth residues 7-153 of the RHO 1-2x.151 meganuclease.
SEQ ID NO: 190 sets forth residues 7-153 of the RHO2-L3-59 meganuclease.
SEQ ID NO: 191 sets forth residues 7-153 of the RHO2-L5-14 meganuclease.
SEQ ID NO: 192 sets forth residues 7-153 of the RHO-1/2-L2-49 meganuclease.
SEQ ID NO: 193 sets forth residues 7-153 of the RHO 1-2x.179 meganuclease.
SEQ ID NO: 194 sets forth residues 7-153 of the RHO 1-2x.4 meganuclease.
SEQ ID NO: 195 sets forth residues 7-153 of the RHO 1-2x.207 meganuclease.
SEQ ID NO: 196 sets forth residues 7-153 of the RHO 1-2x.277 meganuclease.
SEQ ID NO: 197 sets forth residues 7-153 of the RHO 1-2x.292 meganuclease.
SEQ ID NO: 198 sets forth residues 7-153 of the RHO 1-2x.324 meganuclease.
SEQ ID NO: 199 sets forth residues 7-153 of the RHO 1-2x.371 meganuclease.
SEQ ID NO: 200 sets forth residues 7-153 of the RHO 1-2x.164 meganuclease.
SEQ ID NO: 201 sets forth residues 7-153 of the RHO 1-2x.181 meganuclease.
SEQ ID NO: 202 sets forth residues 7-153 of the RHO 1-2x.184 meganuclease.
SEQ ID NO: 203 sets forth residues 7-153 of the RHO-1/2-L1-21 meganuclease.
SEQ ID NO: 204 sets forth residues 7-153 of the RHO-1/2-L1-43 meganuclease.

SEQ ID NO: 205 sets forth residues 7-153 of the RHO-1/2-L1-45 meganuclease.
SEQ ID NO: 206 sets forth residues 7-153 of the RHO-1/2-L1-60 meganuclease.
SEQ ID NO: 207 sets forth residues 7-153 of the RHO-1/2-L1-61 meganuclease.
SEQ ID NO: 208 sets forth residues 7-153 of the RHO-1/2-L1-58 meganuclease.
SEQ ID NO: 209 sets forth residues 7-153 of the RHO-1/2-L1-7 meganuclease.
SEQ ID NO: 210 sets forth residues 7-153 of the RHO-1/2-L1-13 meganuclease.
SEQ ID NO: 211 sets forth residues 7-153 of the RHO-1/2-L1-18 meganuclease.
SEQ ID NO: 212 sets forth residues 7-153 of the RHO-1/2-L1-70 meganuclease.
SEQ ID NO: 213 sets forth residues 7-153 of the RHO-1/2-L1-86 meganuclease.
SEQ ID NO: 214 sets forth residues 7-153 of the RHO-1/2-L2-13 meganuclease.
SEQ ID NO: 215 sets forth residues 7-153 of the RHO-1/2-L2-24 meganuclease.
SEQ ID NO: 216 sets forth residues 7-153 of the RHO-1/2-L2-37 meganuclease.
SEQ ID NO: 217 sets forth residues 7-153 of the RHO-1/2-L2-58 meganuclease.
SEQ ID NO: 218 sets forth residues 7-153 of the RHO-1/2-L2-31 meganuclease.
SEQ ID NO: 219 sets forth residues 7-153 of the RHO-1/2-L2-29 meganuclease.
SEQ ID NO: 220 sets forth residues 7-153 of the RHO-1/2-L2-61 meganuclease.
SEQ ID NO: 221 sets forth residues 7-153 of the RHO2-L3-2 meganuclease.
SEQ ID NO: 222 sets forth residues 7-153 of the RHO2-L3-3 meganuclease.
SEQ ID NO: 223 sets forth residues 7-153 of the RHO2-L3-5 meganuclease.
SEQ ID NO: 224 sets forth residues 7-153 of the RHO2-L3-10 meganuclease.
SEQ ID NO: 225 sets forth residues 7-153 of the RHO2-L3-11 meganuclease.
SEQ ID NO: 226 sets forth residues 7-153 of the RHO2-L3-12 meganuclease.
SEQ ID NO: 227 sets forth residues 7-153 of the RHO2-L3-13 meganuclease.
SEQ ID NO: 228 sets forth residues 7-153 of the RHO2-L3-28 meganuclease.
SEQ ID NO: 229 sets forth residues 7-153 of the RHO2-L3-29 meganuclease.
SEQ ID NO: 230 sets forth residues 7-153 of the RHO2-L3-57 meganuclease.
SEQ ID NO: 231 sets forth residues 7-153 of the RHO2-L3-80 meganuclease.
SEQ ID NO: 232 sets forth residues 7-153 of the RHO2-L3-85 meganuclease.
SEQ ID NO: 233 sets forth residues 7-153 of the RHO2-L3-86 meganuclease.
SEQ ID NO: 234 sets forth residues 7-153 of the RHO2-L3-92 meganuclease.
SEQ ID NO: 235 sets forth residues 7-153 of the RHO2-L3-4 meganuclease.
SEQ ID NO: 236 sets forth residues 7-153 of the RHO2-L3-20 meganuclease.
SEQ ID NO: 237 sets forth residues 7-153 of the RHO2-L3-72 meganuclease.
SEQ ID NO: 238 sets forth residues 7-153 of the RHO1-L1-4 meganuclease.
SEQ ID NO: 239 sets forth residues 7-153 of the RHO1-L1-8 meganuclease.
SEQ ID NO: 240 sets forth residues 7-153 of the RHO1-L1-13 meganuclease.
SEQ ID NO: 241 sets forth residues 7-153 of the RHO1-L1-19 meganuclease.
SEQ ID NO: 242 sets forth residues 7-153 of the RHO1-L1-58 meganuclease.
SEQ ID NO: 243 sets forth residues 7-153 of the RHO1-L1-69 meganuclease.
SEQ ID NO: 244 sets forth residues 7-153 of the RHO1-L1-80 meganuclease.
SEQ ID NO: 245 sets forth residues 7-153 of the RHO1-L1-82 meganuclease.
SEQ ID NO: 246 sets forth residues 7-153 of the RHO1-L1-73 meganuclease.
SEQ ID NO: 244 sets forth residues 7-153 of the RHO1-L1-85 meganuclease.
SEQ ID NO: 248 sets forth residues 7-153 of the RHO1-L1-86 meganuclease.
SEQ ID NO: 249 sets forth residues 7-153 of the RHO-1/2-L4-10 meganuclease.
SEQ ID NO: 250 sets forth residues 7-153 of the RHO-1/2-L4-29 meganuclease.
SEQ ID NO: 251 sets forth residues 7-153 of the RHO-1/2-L4-65 meganuclease.
SEQ ID NO: 252 sets forth residues 7-153 of the RHO-1/2-L4-66 meganuclease.
SEQ ID NO: 253 sets forth residues 7-153 of the RHO-1/2-L4-85 meganuclease.
SEQ ID NO: 254 sets forth residues 198-344 of the RHO 1-2x.216 meganuclease.
SEQ ID NO: 255 sets forth residues 198-344 of the RHO 1-2x.241 meganuclease.
SEQ ID NO: 256 sets forth residues 198-344 of the RHO 1-2x.94 meganuclease.
SEQ ID NO: 257 sets forth residues 198-344 of the RHO 1-2x.95 meganuclease.
SEQ ID NO: 258 sets forth residues 198-344 of the RHO 1-2x.1 meganuclease.
SEQ ID NO: 259 sets forth residues 198-344 of the RHO 1-2x.60 meganuclease.
SEQ ID NO: 260 sets forth residues 198-344 of the RHO 1-2x.74 meganuclease.
SEQ ID NO: 261 sets forth residues 198-344 of the RHO 1-2x.88 meganuclease.
SEQ ID NO: 262 sets forth residues 198-344 of the RHO 1-2x.294 meganuclease.
SEQ ID NO: 263 sets forth residues 198-344 of the RHO 1-2x.302 meganuclease.
SEQ ID NO: 264 sets forth residues 198-344 of the RHO 1-2x.306 meganuclease.
SEQ ID NO: 265 sets forth residues 198-344 of the RHO 1-2x.338 meganuclease.
SEQ ID NO: 266 sets forth residues 198-344 of the RHO 1-2x.348 meganuclease.
SEQ ID NO: 267 sets forth residues 198-344 of the RHO 1-2x.356 meganuclease.
SEQ ID NO: 268 sets forth residues 198-344 of the RHO 1-2x.364 meganuclease.
SEQ ID NO: 269 sets forth residues 198-344 of the RHO 1-2x.142 meganuclease.
SEQ ID NO: 270 sets forth residues 198-344 of the RHO 1-2x.177 meganuclease.

SEQ ID NO: 271 sets forth residues 198-344 of the RHO 1-2x.148 meganuclease.

SEQ ID NO: 272 sets forth residues 198-344 of the RHO 1-2x.20 meganuclease.

SEQ ID NO: 273 sets forth residues 198-344 of the RHO 1-2x.55 meganuclease.

SEQ ID NO: 274 sets forth residues 198-344 of the RHO 1-2x.197 meganuclease.

SEQ ID NO: 275 sets forth residues 198-344 of the RHO 1-2x.252 meganuclease.

SEQ ID NO: 276 sets forth residues 198-344 of the RHO 1-2x.372 meganuclease.

SEQ ID NO: 277 sets forth residues 198-344 of the RHO 1-2x.151 meganuclease.

SEQ ID NO: 278 sets forth the nucleic acid sequence of the pDS CMV RHO2_L3_59 plasmid.

SEQ ID NO: 279 sets forth the nucleic acid sequence of the pDS CMV RHO2_L5_14 plasmid.

SEQ ID NO: 280 sets forth the nucleic acid sequence of the pDS GRK1 RHO2_L3_59 plasmid.

SEQ ID NO: 281 sets forth the nucleic acid sequence of the pDS GRK1 RHO2_L5_14 plasmid.

DETAILED DESCRIPTION OF THE INVENTION

1.1 References and Definitions

The patent and scientific literature referred to herein establishes knowledge that is available to those of skill in the art. The issued US patents, allowed applications, published foreign applications, and references, including GenBank database sequences, which are cited herein are hereby incorporated by reference to the same extent as if each was specifically and individually indicated to be incorporated by reference.

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference herein in their entirety.

As used herein, "a," "an," or "the" can mean one or more than one. For example, "a" cell can mean a single cell or a multiplicity of cells.

As used herein, unless specifically indicated otherwise, the word "or" is used in the inclusive sense of "and/or" and not the exclusive sense of "either/or."

As used herein, the term "meganuclease" refers to an endonuclease that binds double-stranded DNA at a recognition sequence that is greater than 12 base pairs. Preferably, the recognition sequence for a meganuclease of the invention is 22 base pairs. A meganuclease can be an endonuclease that is derived from I-CreI, and can refer to an engineered variant of I-CreI that has been modified relative to natural I-CreI with respect to, for example, DNA-binding specificity, DNA cleavage activity, DNA-binding affinity, or dimerization properties. Methods for producing such modified variants of I-CreI are known in the art (e.g. WO 2007/047859). A meganuclease as used herein binds to double-stranded DNA as a heterodimer. A meganuclease may also be a "single-chain meganuclease" in which a pair of DNA-binding domains are joined into a single polypeptide using a peptide linker.

As used herein, the term "single-chain meganuclease" refers to a polypeptide comprising a pair of meganuclease subunits joined by a linker. A single-chain meganuclease has the organization: N-terminal subunit-Linker-C-terminal subunit. The two meganuclease subunits will generally be non-identical in amino acid sequence and will recognize non-identical DNA sequences. Thus, single-chain meganucleases typically cleave pseudo-palindromic or non-palindromic recognition sequences. A single-chain meganuclease may be referred to as a "single-chain heterodimer" or "single-chain heterodimeric meganuclease" although it is not, in fact, dimeric. For clarity, unless otherwise specified, the term "meganuclease" can refer to a dimeric or single-chain meganuclease. Methods for producing single-chain meganuclease variants of I-CreI are known in the art (e.g., WO 2009/059195; Li, et al. (2009) *Nucleic Acids Res.* 37:1650-62; Grizot, et al. (2009) *Nucleic Acids Res.* 37:5405-19). The term "homing endonuclease" is synonymous with the term "meganuclease."

As used herein, the term "linker" refers to an exogenous peptide sequence used to join two meganuclease subunits into a single polypeptide. A linker may have a sequence that is found in natural proteins, or may be an artificial sequence that is not found in any natural protein. A linker may be flexible and lacking in secondary structure or may have a propensity to form a specific three-dimensional structure under physiological conditions. A linker can include, without limitation, those encompassed by U.S. Pat. No. 8,445,251. In some embodiments, a linker may have an amino acid sequence comprising residues 154-195 of any one of SEQ ID NOs:6-93.

As used herein, with respect to a protein, the term "recombinant" means having an altered amino acid sequence as a result of the application of genetic engineering techniques to nucleic acids which encode the protein, and cells or organisms which express the protein. With respect to a nucleic acid, the term "recombinant" means having an altered nucleic acid sequence as a result of the application of genetic engineering techniques. Genetic engineering techniques include, but are not limited to, PCR and DNA cloning technologies; transfection, transformation and other gene transfer technologies; homologous recombination; site-directed mutagenesis; and gene fusion. In accordance with this definition, a protein having an amino acid sequence identical to a naturally-occurring protein, but produced by cloning and expression in a heterologous host, is not considered recombinant.

As used herein, the term "wild-type" refers to the most common naturally occurring allele (i.e., polynucleotide sequence) in the allele population of the same type of gene, wherein a polypeptide encoded by the wild-type allele has its original functions. The term "wild-type" also refers a polypeptide encoded by a wild-type allele. Wild-type alleles (i.e., polynucleotides) and polypeptides are distinguishable from mutant or variant alleles and polypeptides, which comprise one or more mutations and/or substitutions relative to the wild-type sequence(s). Whereas a wild-type allele or polypeptide can confer a normal phenotype in an organism, a mutant or variant allele or polypeptide can, in some instances, confer an altered phenotype. The mutant RHO P23H allele and the P23H rhodopsin protein are distinguishable from the wild-type RHO allele and rhodopsin protein. Further, wild-type homing endonucleases are distinguishable from recombinant or non-naturally-occurring meganucleases.

As used herein with respect to recombinant proteins, the term "modification" means any insertion, deletion or substitution of an amino acid residue in the recombinant sequence relative to a reference sequence (e.g., a wild-type or a native sequence).

As used herein, the term "recognition sequence" refers to a DNA sequence that is bound and cleaved by a meganuclease. In the case of a recombinant meganuclease of the invention, a recognition sequence comprises a pair of inverted, 9 base pair "half-sites" or "recognition half-sites" which are separated by four base pairs. In the case of a single-chain meganuclease, the N-terminal subunit of the protein contacts a first half-site and the C-terminal subunit of the protein contacts a second half-site. Cleavage by a meganuclease produces four base pair 3' "overhangs". "Overhangs", or "sticky ends" are short, single-stranded DNA segments that can be produced by meganuclease cleavage of a double-stranded DNA sequence. In the case of meganucleases of the present invention, the overhang comprises bases 10-13 of the 22 base pair recognition sequence.

As used herein, the term "target site" or "target sequence" refers to a region of the chromosomal DNA of a cell comprising a recognition sequence for a meganuclease.

As used herein, the term "DNA-binding affinity" or "binding affinity" means the tendency of a meganuclease to non-covalently associate with a reference DNA molecule (e.g., a recognition sequence or an arbitrary sequence). Binding affinity is measured by a dissociation constant, $K_d$. As used herein, a meganuclease has "altered" binding affinity if the $K_d$ of the recombinant meganuclease for a reference recognition sequence is increased or decreased by a statistically significant ($p<0.05$) amount relative to a reference meganuclease.

As used herein, the term "homologous recombination" or "HR" refers to the natural, cellular process in which a double-stranded DNA-break is repaired using a homologous DNA sequence as the repair template (see, e.g. Cahill et al. (2006), *Front. Biosci.* 11:1958-1976). The homologous DNA sequence may be an endogenous chromosomal sequence or an exogenous nucleic acid that was delivered to the cell.

As used herein, the term "non-homologous end-joining" or "NHEJ" refers to the natural, cellular process in which a double-stranded DNA-break is repaired by the direct joining of two non-homologous DNA segments (see, e.g. Cahill et al. (2006), *Front. Biosci.* 11:1958-1976). DNA repair by non-homologous end-joining is error-prone and frequently results in the untemplated addition or deletion of DNA sequences at the site of repair. In some instances, cleavage at a target recognition sequence results in NHEJ at a target recognition site. Nuclease-induced cleavage of a target site in the coding sequence of a gene followed by DNA repair by NHEJ can introduce mutations into the coding sequence, such as frameshift mutations, that disrupt gene function. Thus, engineered nucleases such as meganucleases can be used to effectively knock-out a gene in a population of cells.

As used herein with respect to both amino acid sequences and nucleic acid sequences, the terms "percent identity," "sequence identity," "percentage similarity," "sequence similarity" and the like refer to a measure of the degree of similarity of two sequences based upon an alignment of the sequences which maximizes similarity between aligned amino acid residues or nucleotides, and which is a function of the number of identical or similar residues or nucleotides, the number of total residues or nucleotides, and the presence and length of gaps in the sequence alignment. A variety of algorithms and computer programs are available for determining sequence similarity using standard parameters. As used herein, sequence similarity is measured using the BLASTp program for amino acid sequences and the BLASTn program for nucleic acid sequences, both of which are available through the National Center for Biotechnology Information (www.ncbi.nlm.nih.gov/), and are described in, for example, Altschul et al. (1990), *J. Mol. Biol.* 215:403-410; Gish and States (1993), *Nature Genet.* 3:266-272; Madden et al. (1996), *Meth. Enzymol.* 266:131-141; Altschul et al. (1997), *Nucleic Acids Res.* 25:33 89-3402); Zhang et al. (2000), *J. Comput. Biol.* 7(1-2):203-14. As used herein, percent similarity of two amino acid sequences is the score based upon the following parameters for the BLASTp algorithm: word size=3; gap opening penalty=-11; gap extension penalty=-1; and scoring matrix=BLOSUM62. As used herein, percent similarity of two nucleic acid sequences is the score based upon the following parameters for the BLASTn algorithm: word size=11; gap opening penalty=-5; gap extension penalty=-2; match reward=1; and mismatch penalty=-3. Similarly, the percent identity can be established based upon an alignment of the sequences which maximizes identity between aligned amino acid residues or nucleotides, and which is a function of the number of identical residues or nucleotides divided by the number of total residues or nucleotides in the larger of the two sequences.

As used herein with respect to modifications of two proteins or amino acid sequences, the term "corresponding to" is used to indicate that a specified modification in the first protein is a substitution of the same amino acid residue as in the modification in the second protein, and that the amino acid position of the modification in the first proteins corresponds to or aligns with the amino acid position of the modification in the second protein when the two proteins are subjected to standard sequence alignments (e.g., using the BLASTp program). Thus, the modification of residue "X" to amino acid "A" in the first protein will correspond to the modification of residue "Y" to amino acid "A" in the second protein if residues X and Y correspond to each other in a sequence alignment, and despite the fact that X and Y may be different numbers.

As used herein, the term "recognition half-site," "recognition sequence half-site," or simply "half-site" means a nucleic acid sequence in a double-stranded DNA molecule which is recognized by a monomer of a homodimeric or heterodimeric meganuclease, or by one subunit of a single-chain meganuclease.

As used herein, the term "preferentially" refers to the specificity of a recombinant meganuclease for recognizing and cleaving a particular target recognition sequence in the genome relative to a second, reference recognition sequence. By way of example, a recombinant meganuclease of the invention may preferentially recognize and cleave a P23H recognition sequence (e.g., SEQ ID NO:1) with greater efficiency than it recognizes and cleaves the corresponding wild-type recognition sequence (e.g., SEQ ID NO:5), as determined by methods known in the art, including those methods provided in the examples herein. In some embodiments, a recombinant meganuclease of the invention may recognize and cleave a P23H recognition sequence with greater than about 5%, 10%, 15%, 20%, 25%, 30%, 40%, 50%, 60%, 70%, 80%, 90%, or 100% more efficiency than it recognizes and cleaves the corresponding wild-type recognition sequence. In other embodiments, a recombinant meganuclease of the invention may recognize and cleave a P23H recognition sequence with greater than about 1-fold, 2-fold, 5-fold, 10-fold, 50-fold, 100-fold, or 1000-fold more efficiency than it recognizes and cleaves the corresponding wild-type recognition sequence.

As used herein, the term "hypervariable region" refers to a localized sequence within a meganuclease monomer or subunit that comprises amino acids with relatively high variability. A hypervariable region can comprise about 50-60 contiguous residues, about 53-57 contiguous residues, or preferably about 56 residues. In some embodiments, the residues of a hypervariable region may correspond to positions 24-79 or positions 215-270 of any one of SEQ ID NOs:6-93. A hypervariable region can comprise one or more residues that contact DNA bases in a recognition sequence and can be modified to alter base preference of the monomer or subunit. A hypervariable region can also comprise one or more residues that bind to the DNA backbone when the meganuclease associates with a double-stranded DNA recognition sequence. Such residues can be modified to alter the binding affinity of the meganuclease for the DNA backbone and the target recognition sequence. In different embodiments of the invention, a hypervariable region may comprise between 1-20 residues that exhibit variability and can be modified to influence base preference and/or DNA-binding affinity. In particular embodiments, a hypervariable region comprises between about 15-18 residues that exhibit variability and can be modified to influence base preference and/or DNA-binding affinity. In some embodiments, variable residues within a hypervariable region correspond to one or more of positions 24, 26, 28, 29, 30, 32, 33, 38, 39, 40, 42, 44, 46, 68, 70, 73, 75, and 77 of any one of SEQ ID NOs:6-93. In other embodiments, variable residues within a hypervariable region correspond to one or more of positions 215, 217, 219, 220, 221, 223, 224, 229, 230, 231, 233, 235, 237, 259, 261, 264, 266, and 268 of any one of SEQ ID NOs:6-93.

As used herein, the terms "RHO," "RHO gene," "rhodopsin gene," and "wild-type RHO allele" are used interchangeably and refer to the human rhodopsin gene, preferably the gene identified by NCBI Reference Sequence NG 009115.1 (SEQ ID NO:98). The terms "mutant RHO allele" and "mutant RHO P23H allele" are used interchangeably and refer to a RHO allele sequence comprising a C68A mutation (SEQ ID NO:99), which results in a P23H substitution in the encoded protein. The terms "rhodopsin" and "wild-type rhodopsin" are used interchangeably and refer to the protein encoded by the wild-type rhodopsin gene, particularly the protein identified by *NCBI Reference Sequence* NP_000530.1 (SEQ ID NO:100). The term "P23H rhodopsin" refers to the mutant rhodopsin protein comprising a P23H substitution, particularly the protein set forth in SEQ ID NO:101.

The terms "recombinant DNA construct," "recombinant construct," "expression cassette," "expression construct," "chimeric construct," "construct," and "recombinant DNA fragment" are used interchangeably herein and are nucleic acid fragments. A recombinant construct comprises an artificial combination of nucleic acid fragments, including, without limitation, regulatory and coding sequences that are not found together in nature. For example, a recombinant DNA construct may comprise regulatory sequences and coding sequences that are derived from different sources, or regulatory sequences and coding sequences derived from the same source and arranged in a manner different than that found in nature. Such a construct may be used by itself or may be used in conjunction with a vector.

As used herein, a "vector" or "recombinant DNA vector" may be a construct that includes a replication system and sequences that are capable of transcription and translation of a polypeptide-encoding sequence in a given host cell. If a vector is used then the choice of vector is dependent upon the method that will be used to transform host cells as is well known to those skilled in the art. Vectors can include, without limitation, plasmid vectors and recombinant AAV vectors, or any other vector known in that art suitable for delivering a gene encoding a meganuclease of the invention to a target cell. The skilled artisan is well aware of the genetic elements that must be present on the vector in order to successfully transform, select and propagate host cells comprising any of the isolated nucleotides or nucleic acid sequences of the invention.

As used herein, a "vector" can also refer to a viral vector. Viral vectors can include, without limitation, retroviral vectors, lentiviral vectors, adenoviral vectors, and adeno-associated viral vectors (AAV).

As used herein, a "target cell" refers to a cell that comprises at least one RHO allele comprising a P23H recognition sequence (e.g., one of SEQ ID NOs:1-4). Such target cells can express mutant RHO P23H protein. Target cells can include, without limitation, cells of the eye, preferably cells in the posterior segment of the eye, and even more preferably cells of the retina, including rod photoreceptor cells comprising a P23H recognition sequence in at least one RHO gene allele.

As used herein, a "control" or "control cell" refers to a cell that provides a reference point for measuring changes in genotype or phenotype of a genetically-modified cell. A control cell may comprise, for example: (a) a wild-type cell, i.e., of the same genotype as the starting material for the genetic alteration which resulted in the genetically-modified cell; (b) a cell of the same genotype as the genetically-modified cell but which has been transformed with a null construct (i.e., with a construct which has no known effect on the trait of interest); or, (c) a cell genetically identical to the genetically-modified cell but which is not exposed to conditions or stimuli or further genetic modifications that would induce expression of altered genotype or phenotype.

As used herein with respect to modifications of two proteins or amino acid sequences, the term "corresponding to" is used to indicate that a specified modification in the first protein is a substitution of the same amino acid residue as in the modification in the second protein, and that the amino acid position of the modification in the first proteins corresponds to or aligns with the amino acid position of the modification in the second protein when the two proteins are subjected to standard sequence alignments (e.g., using the BLASTp program). Thus, the modification of residue "X" to amino acid "A" in the first protein will correspond to the modification of residue "Y" to amino acid "A" in the second protein if residues X and Y correspond to each other in a sequence alignment, and despite the fact that X and Y may be different numbers.

As used herein, the terms "treatment" or "treating a subject" refers to the administration of recombinant meganuclease of the invention, or a nucleic acid encoding recombinant meganuclease of the invention, to a subject having RP for the purpose of providing partial or complete relief of one or more symptoms of RP. In some aspects, recombinant meganuclease of the invention, or a nucleic acid encoding the same, is administered during treatment in the form of a pharmaceutical composition of the invention. Preferably the subject is heterozygous for the P23H mutant allele and a functional, normal or wild-type allele.

As used herein, the recitation of a numerical range for a variable is intended to convey that the invention may be practiced with the variable equal to any of the values within that range. Thus, for a variable which is inherently discrete, the variable can be equal to any integer value within the numerical range, including the end-points of the range. Similarly, for a variable which is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, or any other real values ≥0 and ≤2 if the variable is inherently continuous.

2.1 Principle of Targeting and Inactivating the Mutant RHO P23H Allele

The present invention is based, in part, on the hypothesis that autosomal dominant RP can be corrected or prevented by targeting, cleaving, and inactivating a mutant RHO P23H allele, which encodes the pathogenic P23H rhodopsin protein. Surprisingly, recombinant meganucleases can be engineered to recognize and cleave a P23H recognition sequence (e.g., one of SEQ ID NOs:1-4) present in the mutant RHO P23H allele. Such recombinant meganucleases can preferentially target and cleave the mutant RHO P23H allele relative to the corresponding wild-type allele (SEQ ID NO:96). NHEJ at the cleavage site results in mutagenesis and disruption of the mutant RHO P23H allele, while the functional wild-type RHO allele remains intact to express wild-type rhodopsin in rod photoreceptor cells of the retina. Preferential inactivation of the mutant RHO P23H allele, and disruption of P23H rhodopsin expression, is expected to prevent, delay, or reverse the progression of RP in patients.

2.2 Meganucleases for Recognizing and Cleaving the P23H Recognition Sequence Meganucleases can make a site-specific DNA break in the genome of a living cell, and such a DNA break can result in permanent modification of the genome via mutagenic NHEJ repair or via homologous recombination with a transgenic DNA sequence. NHEJ can produce mutagenesis at the cleavage site, resulting in inactivation of the allele. NHEJ-associated mutagenesis may inactivate an allele via generation of early stop codons, frameshift mutations producing aberrant non-functional proteins, or could trigger mechanisms such as nonsense-mediated mRNA decay. The use of meganucleases to induce mutagenesis via NHEJ can be used to target a specific mutation or a sequence present in a wild-type allele.

In preferred embodiments, the nucleases used to practice the invention are single-chain meganucleases. A single-chain meganuclease comprises an N-terminal subunit and a C-terminal subunit joined by a linker peptide. Each of the two domains recognizes half of the recognition sequence (i.e., a recognition half-site) and the site of DNA cleavage is at the middle of the recognition sequence near the interface of the two subunits. DNA strand breaks are offset by four base pairs such that DNA cleavage by a meganuclease generates a pair of four base pair, 3' single-strand overhangs.

Recombinant meganucleases of the invention have been engineered to recognize and cleave a P23H recognition sequence (e.g., one of SEQ ID NOs:1-4). Such meganucleases preferentially cleave the P23H recognition sequence on the mutant RHO P23H allele relative to the corresponding wild-type RHO recognition sequence (SEQ ID NO:96). Exemplary recombinant meganucleases of the invention are provided in SEQ ID NOs:6-93, which are collectively referred to herein as "RHO 1-2 meganucleases" or "RHO 1/2 meganucleases."

Recombinant meganucleases of the invention comprise a first subunit, comprising a first hypervariable (HVR1) region, and a second subunit, comprising a second hypervariable (HVR2) region. Further, the first subunit binds to a first recognition half-site in a P23H recognition sequence (e.g., the RHO1 half-site), and the second subunit binds to a second recognition half-site in the P23H recognition sequence (e.g., the RHO2 half-site). In embodiments where the recombinant meganuclease is a single-chain meganuclease, the first and second subunits can be oriented such that the first subunit is positioned as the N-terminal subunit, and the second subunit is positioned as the C-terminal subunit (e.g., SEQ ID NOs:70-93). In alternative embodiments, the first and second subunits can be oriented such that the first subunit is positioned as the C-terminal subunit, and the second subunit is positioned as the N-terminal subunit (e.g., SEQ ID NOs:6-69). Exemplary recombinant meganucleases of the invention are provided in Table 1.

TABLE 1

Exemplary recombinant meganucleases engineered to recognize and cleave the P23H recognition sequence (SEQ ID NO: 1)

| Meganuclease | AA SEQ ID | RHO1 Subunit Residues | RHO1 Subunit SEQ ID | *RHO1 Subunit % | RHO2 Subunit Residues | RHO2 Subunit SEQ ID | *RHO2 Subunit % |
|---|---|---|---|---|---|---|---|
| RHO2-L3-59 | 6 | 198-344 | 102 | 100 | 7-153 | 187 | 100 |
| RHO2-L5-14 | 7 | 198-344 | 103 | 100 | 7-153 | 188 | 96.6 |
| RHO-1/2-L2-49 | 8 | 198-344 | 104 | 100 | 7-153 | 189 | 96.6 |
| RHO 1-2x.179 | 9 | 198-344 | 105 | 100 | 7-153 | 190 | 93.2 |
| RHO 1-2x.4 | 10 | 198-344 | 106 | 92.52 | 7-153 | 191 | 91.16 |
| RHO 1-2x.207 | 11 | 198-344 | 107 | 93.2 | 7-153 | 192 | 91.84 |
| RHO 1-2x.277 | 12 | 198-344 | 108 | 93.2 | 7-153 | 193 | 91.84 |
| RHO 1-2x.292 | 13 | 198-344 | 109 | 94.56 | 7-153 | 194 | 90.48 |
| RHO 1-2x.324 | 14 | 198-344 | 110 | 92.52 | 7-153 | 195 | 91.16 |

TABLE 1-continued

Exemplary recombinant meganucleases engineered to recognize and cleave the
P23H recognition sequence (SEQ ID NO: 1)

| Meganuclease | AA SEQ ID | RHO1 Subunit Residues | RHO1 Subunit SEQ ID | *RHO1 Subunit % | RHO2 Subunit Residues | RHO2 Subunit SEQ ID | *RHO2 Subunit % |
|---|---|---|---|---|---|---|---|
| RHO 1-2x.371 | 15 | 198-344 | 111 | 93.2 | 7-153 | 196 | 91.16 |
| RHO 1-2x.164 | 16 | 198-344 | 112 | 91.16 | 7-153 | 197 | 90.48 |
| RHO 1-2x.181 | 17 | 198-344 | 113 | 95.24 | 7-153 | 198 | 90.48 |
| RHO 1-2x.184 | 18 | 198-344 | 114 | 90.48 | 7-153 | 199 | 88.44 |
| RHO-1/2-L1-21 | 19 | 198-344 | 115 | 100 | 7-153 | 200 | 93.2 |
| RHO-1/2-L1-43 | 20 | 198-344 | 116 | 100 | 7-153 | 201 | 92.52 |
| RHO-1/2-L1-45 | 21 | 198-344 | 117 | 100 | 7-153 | 202 | 92.52 |
| RHO-1/2-L1-60 | 22 | 198-344 | 118 | 100 | 7-153 | 203 | 92.52 |
| RHO-1/2-L1-61 | 23 | 198-344 | 119 | 100 | 7-153 | 204 | 92.52 |
| RHO-1/2-L1-58 | 24 | 198-344 | 120 | 100 | 7-153 | 205 | 92.52 |
| RHO-1/2-L1-7 | 25 | 198-344 | 121 | 100 | 7-153 | 206 | 92.52 |
| RHO-1/2-L1-13 | 26 | 198-344 | 122 | 100 | 7-153 | 207 | 92.52 |
| RHO-1/2-L1-18 | 27 | 198-344 | 123 | 100 | 7-153 | 208 | 92.52 |
| RHO-1/2-L1-70 | 28 | 198-344 | 124 | 100 | 7-153 | 209 | 92.52 |
| RHO-1/2-L1-86 | 29 | 198-344 | 125 | 100 | 7-153 | 210 | 92.52 |
| RHO-1/2-L2-13 | 30 | 198-344 | 126 | 100 | 7-153 | 211 | 95.24 |
| RHO-1/2-L2-24 | 31 | 198-344 | 127 | 100 | 7-153 | 212 | 95.24 |
| RHO-1/2-L2-37 | 32 | 198-344 | 128 | 100 | 7-153 | 213 | 93.88 |
| RHO-1/2-L2-58 | 33 | 198-344 | 129 | 100 | 7-153 | 214 | 93.2 |
| RHO-1/2-L2-31 | 34 | 198-344 | 130 | 100 | 7-153 | 215 | 93.2 |
| RHO-1/2-L2-29 | 35 | 198-344 | 131 | 100 | 7-153 | 216 | 93.2 |
| RHO-1/2-L2-61 | 36 | 198-344 | 132 | 100 | 7-153 | 217 | 93.88 |
| RHO2-L3-2 | 37 | 198-344 | 133 | 100 | 7-153 | 218 | 94.56 |
| RHO2-L3-3 | 38 | 198-344 | 134 | 100 | 7-153 | 219 | 95.24 |
| RHO2-L3-5 | 39 | 198-344 | 135 | 100 | 7-153 | 220 | 96.6 |
| RHO2-L3-10 | 40 | 198-344 | 136 | 100 | 7-153 | 221 | 94.56 |
| RHO2-L3-11 | 41 | 198-344 | 137 | 100 | 7-153 | 222 | 95.24 |
| RHO2-L3-12 | 42 | 198-344 | 138 | 100 | 7-153 | 223 | 95.24 |
| RHO2-L3-13 | 43 | 198-344 | 139 | 100 | 7-153 | 224 | 95.24 |
| RHO2-L3-28 | 44 | 198-344 | 140 | 100 | 7-153 | 225 | 95.24 |
| RHO2-L3-29 | 45 | 198-344 | 141 | 100 | 7-153 | 226 | 94.56 |
| RHO2-L3-57 | 46 | 198-344 | 142 | 100 | 7-153 | 227 | 95.24 |
| RHO2-L3-80 | 47 | 198-344 | 143 | 100 | 7-153 | 228 | 95.92 |
| RHO2-L3-85 | 48 | 198-344 | 144 | 100 | 7-153 | 229 | 95.24 |
| RHO2-L3-86 | 49 | 198-344 | 145 | 100 | 7-153 | 230 | 94.56 |
| RHO2-L3-92 | 50 | 198-344 | 146 | 100 | 7-153 | 231 | 95.24 |
| RHO2-L3-4 | 51 | 198-344 | 147 | 100 | 7-153 | 232 | 94.56 |
| RHO2-L3-20 | 52 | 198-344 | 148 | 100 | 7-153 | 233 | 94.56 |
| RHO2-L3-72 | 53 | 198-344 | 149 | 100 | 7-153 | 234 | 95.92 |
| RHO1-L1-4 | 54 | 198-344 | 150 | 96.6 | 7-153 | 235 | 96.6 |
| RHO1-L1-8 | 55 | 198-344 | 151 | 95.24 | 7-153 | 236 | 96.6 |
| RHO1-L1-13 | 56 | 198-344 | 152 | 95.24 | 7-153 | 237 | 96.6 |
| RHO1-L1-19 | 57 | 198-344 | 153 | 95.24 | 7-153 | 238 | 96.6 |
| RHO1-L1-58 | 58 | 198-344 | 154 | 95.92 | 7-153 | 239 | 96.6 |
| RHO1-L1-69 | 59 | 198-344 | 155 | 95.92 | 7-153 | 240 | 96.6 |
| RHO1-L1-80 | 60 | 198-344 | 156 | 95.92 | 7-153 | 241 | 96.6 |
| RHO1-L1-82 | 61 | 198-344 | 157 | 95.92 | 7-153 | 245 | 96.6 |
| RHO1-L1-73 | 62 | 198-344 | 158 | 96.6 | 7-153 | 246 | 96.6 |
| RHO1-L1-85 | 63 | 198-344 | 159 | 96.6 | 7-153 | 247 | 96.6 |
| RHO1-L1-86 | 64 | 198-344 | 160 | 96.6 | 7-153 | 248 | 96.6 |
| RHO-1/2-L4-10 | 65 | 198-344 | 161 | 95.24 | 7-153 | 249 | 95.24 |
| RHO-1/2-L4-29 | 66 | 198-344 | 162 | 95.24 | 7-153 | 250 | 95.24 |
| RHO-1/2-L4-65 | 67 | 198-344 | 163 | 95.92 | 7-153 | 251 | 94.56 |
| RHO-1/2-L4-66 | 68 | 198-344 | 164 | 97.28 | 7-153 | 252 | 95.24 |
| RHO-1/2-L4-85 | 69 | 198-344 | 165 | 96.6 | 7-153 | 253 | 94.56 |
| RHO 1-2x.216 | 70 | 7-153 | 166 | 93.2 | 198-344 | 254 | 91.16 |
| RHO 1-2x.241 | 71 | 7-153 | 167 | 93.88 | 198-344 | 255 | 91.16 |
| RHO 1-2x.94 | 72 | 7-153 | 168 | 91.84 | 198-344 | 256 | 91.16 |
| RHO 1-2x.95 | 73 | 7-153 | 169 | 91.16 | 198-344 | 257 | 91.16 |
| RHO 1-2x.1 | 74 | 7-153 | 170 | 93.2 | 198-344 | 258 | 90.48 |
| RHO 1-2x.60 | 75 | 7-153 | 171 | 93.2 | 198-344 | 259 | 90.48 |
| RHO 1-2x.74 | 76 | 7-153 | 172 | 93.88 | 198-344 | 260 | 90.48 |
| RHO 1-2x.88 | 77 | 7-153 | 173 | 91.16 | 198-344 | 261 | 90.48 |
| RHO 1-2x.294 | 78 | 7-153 | 174 | 93.88 | 198-344 | 262 | 90.48 |
| RHO 1-2x.302 | 79 | 7-153 | 175 | 93.2 | 198-344 | 263 | 90.48 |
| RHO 1-2x.306 | 80 | 7-153 | 176 | 92.52 | 198-344 | 264 | 90.48 |
| RHO 1-2x.338 | 81 | 7-153 | 177 | 93.2 | 198-344 | 265 | 90.48 |
| RHO 1-2x.348 | 82 | 7-153 | 178 | 92.52 | 198-344 | 266 | 90.48 |
| RHO 1-2x.356 | 83 | 7-153 | 179 | 91.16 | 198-344 | 267 | 90.48 |
| RHO 1-2x.364 | 84 | 7-153 | 180 | 93.2 | 198-344 | 268 | 90.48 |
| RHO 1-2x.142 | 85 | 7-153 | 181 | 93.2 | 198-344 | 269 | 90.48 |
| RHO 1-2x.177 | 86 | 7-153 | 182 | 94.56 | 198-344 | 270 | 90.48 |
| RHO 1-2x.148 | 87 | 7-153 | 183 | 91.84 | 198-344 | 271 | 93.2 |

TABLE 1-continued

Exemplary recombinant meganucleases engineered to recognize and cleave the P23H recognition sequence (SEQ ID NO: 1)

| Meganuclease | AA SEQ ID | RHO1 Subunit Residues | RHO1 Subunit SEQ ID | *RHO1 Subunit % | RHO2 Subunit Residues | RHO2 Subunit SEQ ID | *RHO2 Subunit % |
| --- | --- | --- | --- | --- | --- | --- | --- |
| RHO 1-2x.20  | 88 | 7-153 | 184 | 93.2  | 198-344 | 272 | 89.12 |
| RHO 1-2x.55  | 89 | 7-153 | 185 | 92.52 | 198-344 | 273 | 92.52 |
| RHO 1-2x.197 | 90 | 7-153 | 186 | 95.24 | 198-344 | 274 | 91.84 |
| RHO 1-2x.252 | 91 | 7-153 | 187 | 93.2  | 198-344 | 275 | 88.44 |
| RHO 1-2x.372 | 92 | 7-153 | 188 | 94.56 | 198-344 | 276 | 91.84 |
| RHO 1-2x.151 | 93 | 7-153 | 189 | 94.56 | 198-344 | 277 | 90.48 |

*"RHO1 Subunit %" and "RHO2 Subunit %" represent the amino acid sequence identity between the RHO1-binding and RHO2-binding subunit regions of each meganuclease and the RHO1-binding and RHO2-binding subunit regions, respectively, of the RHO2-L3-59 meganuclease.

2.3 Methods for Delivering and Expressing Recombinant Meganucleases

Treating RP using the invention requires that a recombinant meganuclease can be expressed in cells in the appropriate tissues. The target tissue(s) for delivery of recombinant meganucleases of the invention are cells of the eye, preferably cells in the posterior segment of the eye, and even more preferably cells of the retina, including rod photoreceptor cells. Recombinant meganucleases can be delivered as purified protein or as RNA or DNA encoding the meganucleases. In one embodiment, recombinant meganuclease proteins, or mRNA or vector encoding recombinant meganucleases, are supplied to target cells (e.g., cells in the retina) via injection directly to the target tissue. For example, delivery of RNA, DNA, or recombinant AAV vectors to the eye via subretinal or intravitreal injection is described in the art (see for example, Martin et al. (2002) *Methods.* 28:267-275; Hauswirth et al. (2008) *Human Gene Therapy.* 19(10): 979-990; Johnson et al. (2008) *Molecular Vision.* 14:2211-2226). Alternatively, meganuclease protein, mRNA, or DNA can be delivered systemically via the circulatory system.

In some embodiments, recombinant meganuclease proteins, or DNA/mRNA encoding recombinant meganucleases, are formulated for systemic administration, or administration to target tissues, in a pharmaceutical carrier in accordance with known techniques. See, e.g., Remington, *The Science And Practice of Pharmacy* ($21^{st}$ ed. 2005). In the manufacture of a pharmaceutical formulation according to the invention, proteins/RNA/mRNA are typically admixed with a pharmaceutically acceptable carrier. The carrier must, of course, be acceptable in the sense of being compatible with any other ingredients in the formulation and must not be deleterious to the patient. The carrier can be a solid or a liquid, or both, and can be formulated with the compound as a unit-dose formulation.

In some embodiments, recombinant meganuclease proteins, or DNA/mRNA encoding recombinant meganucleases, are coupled to a cell penetrating peptide or targeting ligand to facilitate cellular uptake. Examples of cell penetrating peptides known in the art include poly-arginine (Jearawiriyapaisarn, et al. (2008) *Mol Ther.* 16:1624-9), TAT peptide from the HIV virus (Hudecz et al. (2005), *Med. Res. Rev.* 25: 679-736), MPG (Simeoni, et al. (2003) *Nucleic Acids Res.* 31:2717-2724), Pep-1 (Deshayes et al. (2004) *Biochemistry* 43: 7698-7706, and HSV-1 VP-22 (Deshayes et al. (2005) *Cell Mot Life Sci.* 62:1839-49. In an alternative embodiment, recombinant meganucleases, or DNA/mRNA encoding recombinant meganucleases, are coupled covalently or non-covalently to an antibody that recognizes a specific cell-surface receptor expressed on target cells such that the meganuclease protein/DNA/mRNA binds to and is internalized by the target cells. Alternatively, recombinant meganuclease protein/DNA/mRNA can be coupled covalently or non-covalently to the natural ligand (or a portion of the natural ligand) for such a cell-surface receptor. (McCall, et al. (2014) *Tissue Barriers.* 2(4):e944449; Dinda, et al. (2013) *Curr Pharm Biotechnol.* 14:1264-74; Kang, et al. (2014) *Curr Pharm Biotechnol.* 15(3):220-30; Qian et al. (2014) *Expert Opin Drug Metab Toxicol.* 10(11):1491-508). Examples of targeting ligands to direct delivery to cells in the eye include RGD (Pollinger et al. (2013) *PNAS.* 110(15): 6115-6120), transferrin (Lajunen et al. (2014) *Eur J Pharm Sci.* 62: 23-32), and hyaluronic acid (Martens et al. (2015) *J Control Release.* 202: 83-92).

In some embodiments, recombinant meganuclease proteins, or DNA/mRNA encoding recombinant meganucleases, are encapsulated within biodegradable hydrogels for injection or implantation within the desired region of the eye (e.g., intravitreal or subconjunctival injection). Hydrogels can provide sustained and tunable release of the therapeutic payload to the desired region of the eye without the need for frequent injections, and stimuli-responsive materials (e.g., temperature- and pH-responsive hydrogels) can be designed to release the payload in response to environmental or externally applied cues (Kang Derwent et al. (2008) *Trans Am Ophthalmol Soc.* 106:206-214).

In some embodiments, recombinant meganuclease proteins, or DNA/mRNA encoding recombinant meganucleases, are coupled covalently or, preferably, non-covalently to a nanoparticle or encapsulated within such a nanoparticle using methods known in the art (Sharma, et al. (2014) *Biomed Res Int.* 2014). A nanoparticle is a nanoscale delivery system whose length scale is <1 µm, preferably <100 nm. Such nanoparticles may be designed using a core composed of metal, lipid, polymer, or biological macromolecule, and multiple copies of the recombinant meganuclease proteins, mRNA, or DNA can be attached to or encapsulated with the nanoparticle core. This increases the copy number of the protein/mRNA/DNA that is delivered to each cell and, so, increases the intracellular expression of each recombinant meganuclease to maximize the likelihood that the target recognition sequences will be cut. The surface of such nanoparticles may be further modified with polymers or lipids (e.g., chitosan, cationic polymers, or cationic lipids) to form a core-shell nanoparticle whose surface confers additional functionalities to enhance cellular delivery and uptake of the payload (Jian et al. (2012), *Biomaterials.* 33(30): 7621-30). Nanoparticles may additionally be advantageously coupled to targeting molecules to direct the nanoparticle to the appropriate cell type and/or increase the likelihood of cellular uptake. Examples of such targeting molecules include antibodies specific for cell-surface receptors and the natural ligands (or portions of the natural ligands) for cell surface receptors.

In some embodiments, the meganuclease proteins or DNA/mRNA encoding the meganucleases are encapsulated within liposomes or complexed using cationic lipids (see, e.g., Lipofectamine™, Life Technologies Corp., Carlsbad, Calif.; Zuris et al. (2015), *Nat Biotechnol.* 33: 73-80; Mishra et al. (2011), *J Drug Deliv.* 2011:863734). The liposome and lipoplex formulations can protect the payload from degradation, enhance accumulation and retention at the target site, and facilitate cellular uptake and delivery efficiency through fusion with and/or disruption of the cellular membranes of the target cells.

In some embodiments, recombinant meganuclease proteins, or DNA/mRNA encoding recombinant meganucleases, are encapsulated within polymeric scaffolds (e.g., PLGA) or complexed using cationic polymers (e.g., PEI, PLL) (Tamboli et al. (2011), *Ther Deliv.* 2(4): 523-536). Polymeric carriers can be designed to provide tunable drug release rates through control of polymer erosion and drug diffusion, and high drug encapsulation efficiencies can offer protection of the therapeutic payload until intracellular delivery to the desired target cell population.

In some embodiments, recombinant meganuclease proteins, or DNA/mRNA encoding recombinant meganucleases, are combined with amphiphilic molecules that self-assemble into micelles (Tong et al. (2007), *J Gene Med.* 9(11): 956-66). Polymeric micelles may include a micellar shell formed with a hydrophilic polymer (e.g., polyethyleneglycol) that can prevent aggregation, mask charge interactions, and reduce nonspecific interactions within the vitreous fluid.

In some embodiments, recombinant meganuclease proteins, or DNA/mRNA encoding recombinant meganucleases, are formulated into an emulsion or a nanoemulsion (i.e., having an average particle diameter of <1 nm) for administration and/or delivery to the target cell. The term "emulsion" refers to, without limitation, any oil-in-water, water-in-oil, water-in-oil-in-water, or oil-in-water-in-oil dispersions or droplets, including lipid structures that can form as a result of hydrophobic forces that drive apolar residues (e.g., long hydrocarbon chains) away from water and polar head groups toward water, when a water immiscible phase is mixed with an aqueous phase. These other lipid structures include, but are not limited to, unilamellar, paucilamellar, and multilamellar lipid vesicles, micelles, and lamellar phases. Emulsions are composed of an aqueous phase and a lipophilic phase (typically containing an oil and an organic solvent). Emulsions also frequently contain one or more surfactants. Nanoemulsion formulations are well known, e.g., as described in US Patent Application Nos. 2002/0045667 and 2004/0043041, and U.S. Pat. Nos. 6,015,832, 6,506,803, 6,635,676, and 6,559,189, each of which is incorporated herein by reference in its entirety.

In some embodiments, recombinant meganuclease proteins, or DNA/mRNA encoding recombinant meganucleases, are covalently attached to, or non-covalently associated with, multifunctional polymer conjugates, DNA dendrimers, and polymeric dendrimers (Mastorakos et al. (2015), *Nanoscale.* 7(9): 3845-56; Cheng et al. (2008), *J Pharm Sci.* 97(1): 123-43). The dendrimer generation can control the payload capacity and size, and can provide a high drug payload capacity. Moreover, display of multiple surface groups can be leveraged to improve stability, reduce nonspecific interactions, and enhance cell-specific targeting and drug release.

In some embodiments, genes encoding a recombinant meganuclease are delivered using a viral vector. Such vectors are known in the art and include lentiviral vectors, adenoviral vectors, and adeno-associated virus (AAV) vectors (reviewed in Vannucci, et al. (2013), *New Microbiol.* 36:1-22). In some embodiments, the viral vectors are injected directly into target tissues (Bosch, et al. (2000), *Mol Ther.* 1:63-70; Greig et al. (2014), *PLoS One.* November 13; 9(11):e112268). In alternative embodiments, the viral vectors are delivered systemically via the circulatory system. It is known in the art that different AAV vectors tend to localize to different tissues. In retinal target tissues, effective transduction of retinal photoreceptor cells has been shown, for example, with AAV serotypes 1, 2, 5, 8, and 9 (Petrs-Silva et al. (2014), *Clinical Ophthalmology.* 8:127-136). AAV vectors can also be self-complementary such that they do not require second-strand DNA synthesis in the host cell (McCarty et al. (2001), *Gene Ther.* 8:1248-54).

In one embodiment, a viral vector used for meganuclease gene delivery is a self-limiting viral vector. A self-limiting viral vector can have limited persistence time in a cell or organism due to the presence of a recognition sequence for a recombinant meganuclease within the vector. Thus, a self-limiting viral vector can be engineered to provide coding for a promoter, a recombinant meganuclease described herein, and a meganuclease recognition site within the ITRs. The self-limiting viral vector delivers the meganuclease gene to a cell, tissue, or organism, such that the meganuclease is expressed and able to cut the genome of the cell at an endogenous recognition sequence within the genome. The delivered meganuclease will also find its target site within the self-limiting viral vector itself, and cut the vector at this target site. Once cut, the 5' and 3' ends of the viral genome will be exposed and degraded by exonucleases, thus killing the virus and ceasing production of the recombinant meganuclease.

If the recombinant meganuclease genes are delivered in DNA form (e.g. plasmid) and/or via a viral vector (e.g. AAV) they must be operably linked to a promoter. In some embodiments, this can be a viral promoter such as endogenous promoters from the viral vector (e.g. the LTR of a lentiviral vector) or the well-known cytomegalovirus- or SV40 virus-early promoters. In a preferred embodiment, meganuclease genes are operably linked to a promoter that drives gene expression preferentially in the target cells. Examples of retina and/or rod photoreceptor cell-specific promoters include, without limitation, the human rhodopsin kinase promoter, the proximal mouse opsin promoter (mOP), the human G-protein-coupled receptor protein kinase 1 promoter (hGRK1), and the human interphotoreceptor retinoid-binding protein (IRBP) promoter (Khani et al. (2007), *Invest. Ophthamol. Vis. Sci.* 48(9):3954-3961); Beltran et al. (2010), *Gene Therapy.* 17(9):1162-1174); Yokoyama et al. (1992), *Exp. Eye Res.* 55(2):225-233), as well as rod photoreceptor cell-specific promoters disclosed in U.S. Patent Publication No. US 2014/0287510.

In some embodiments, the invention provides a pharmaceutical composition comprising a pharmaceutically acceptable carrier and a recombinant meganuclease of the invention, or a pharmaceutically acceptable carrier and an isolated polynucleotide comprising a nucleic acid encoding a recombinant meganuclease of the invention. Such pharmaceutical compositions can be prepared in accordance with known techniques. See, e.g., Remington, *The Science And Practice* of *Pharmacy* (21st ed. 2005). In the manufacture of a pharmaceutical formulation according to the invention, endonuclease polypeptides (or DNA/RNA encoding the same) are typically admixed with a pharmaceutically acceptable carrier and the resulting composition is administered to a subject. The carrier must, of course, be acceptable in the sense of being compatible with any other ingredients in the formulation and must not be deleterious to the subject. In some embodiments, pharmaceutical compositions of the invention can further comprise one or more additional agents or biological molecules useful in the treatment of a disease in the subject. Likewise, the additional agent(s) and/or biological molecule(s) can be co-administered as a separate composition.

It is envisioned that a single treatment will permanently inactivate the mutant P23H RHO allele in a percentage of patient target cells. If the frequency of P23H allele inactivation is low, however, or if a large percentage of target cells need to be corrected, it may be necessary to perform multiple treatments on each patient.

2.4 Recombinant Meganuclease Variants

Embodiments of the invention encompass the recombinant meganucleases described herein, and variants thereof. Further embodiments of the invention encompass isolated polynucleotides comprising a nucleic acid sequence encoding the recombinant meganucleases described herein, and variants of such polynucleotides.

In particular, the invention provides variants of the meganucleases of SEQ ID Nos:6-93 in which the hypervariable regions have been modified such that the meganucleases preferentially recognize and cleave one of SEQ ID NOs: 2-4 relative to the corresponding wild-type sequences in the wild-type RHO gene (SEQ ID NO: 98). Such additional variants meganucleases can be produced by routine experimentation according to the methods described in WO2007/047859, U.S. Pat. Nos. 8,021,867, 8,119,361, 8,119,381, 8,124,369, 8,129,134, 8,133,697, 8,143,015, 8,143,016, 8,148,098, 8,163,514, 8,304,222, 8,377,674 and 8,445,251, and discussed below.

As used herein, "variants" is intended to mean substantially similar sequences. A "variant" polypeptide is intended to mean a polypeptide derived from the "native" polypeptide by deletion or addition of one or more amino acids at one or more internal sites in the native protein and/or substitution of one or more amino acids at one or more sites in the native polypeptide. As used herein, a "native" polynucleotide or polypeptide comprises a parental sequence from which variants are derived. Variant polypeptides encompassed by the embodiments are biologically active. That is, they continue to possess the desired biological activity of the native protein; i.e., the ability to preferentially recognize and cleave a P23H recognition sequence (e.g., one of SEQ ID NOs:1-4), as described herein. Such variants may result, for example, from human manipulation. Biologically active variants of a native polypeptide of the embodiments (e.g., SEQ ID NOs:6-93), or biologically active variants of the RHO1- and RHO2-binding subunits described herein (e.g., SEQ ID NOs:99-274), will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about 99%, sequence identity to the amino acid sequence of the native polypeptide or native subunit, as determined by sequence alignment programs and parameters described elsewhere herein. A biologically active variant of a polypeptide or subunit of the embodiments may differ from that polypeptide or subunit by as few as about 1-40 amino acid residues, as few as about 1-20, as few as about 1-10, as few as about 5, as few as 4, 3, 2, or even 1 amino acid residue.

The polypeptides of the embodiments may be altered in various ways including amino acid substitutions, deletions, truncations, and insertions. Methods for such manipulations are generally known in the art. For example, amino acid sequence variants can be prepared by mutations in the DNA. Methods for mutagenesis and polynucleotide alterations are well known in the art. See, for example, Kunkel (1985), *Proc. Natl. Acad. Sci. USA* 82:488-492; Kunkel et al. (1987), *Methods in Enzymol.* 154:367-382; U.S. Pat. No. 4,873,192; Walker and Gaastra, eds. (1983), *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978), *Atlas of Protein Sequence and Structure* (Natl. Biomed. Res. Found., Washington, D.C.), herein incorporated by reference. Conservative substitutions, such as exchanging one amino acid with another having similar properties, may be optimal.

A substantial number of amino acid modifications to the DNA recognition domain of the wild-type I-CreI meganuclease have previously been identified (e.g., U.S. Pat. No. 8,021,867) which, singly or in combination, result in recombinant meganucleases with specificities altered at individual bases within the DNA recognition sequence half-site, such that the resulting rationally-designed meganucleases have half-site specificities different from the wild-type enzyme. Table 2 provides potential substitutions that can be made in a recombinant meganuclease monomer or subunit to enhance specificity based on the base present at each half-site position (−1 through −9) of a recognition half-site.

TABLE 2

| Posn. | A | C | G | T | A/T | A/C | A/G | C/T | G/T | A/G/T | A/C/G/T |
|---|---|---|---|---|---|---|---|---|---|---|---|
| −1 | Y75 | R70\* | K70 | Q70\* | | | | T46\* | | | G70 |
| | L75\* | H75\* | E70\* | C70 | | | | | | | A70 |
| | C75\* | R75\* | E75\* | L70 | | | | | | | S70 |
| | Y139\* | H46\* | E46\* | Y75\* | | | | | | | G46\* |
| | C46\* | K46\* | D46\* | Q75\* | | | | | | | |
| | A46\* | R46\* | | H75\* | | | | | | | |
| | | | | H139 | | | | | | | |
| | | | | Q46\* | | | | | | | |
| | | | | H46\* | | | | | | | |

TABLE 2-continued

| | | | | | Favored Sense-Strand Base | | | | | |
|---|---|---|---|---|---|---|---|---|---|---|
| Posn. | A | C | G | T | A/T | A/C | A/G | C/T | G/T | A/G/T | A/C/G/T |
| -2 | Q70<br>T44*<br>A44*<br>V44*<br>I44*<br>L44*<br>N44* | E70<br>D70<br>K44*<br>R44* | H70<br>D44*<br>E44* | Q44* | C44* | | | | | | |
| -3 | Q68<br>C24*<br>I24* | E68<br>F68<br>K24*<br>R24* | R68 | M68<br>C68<br>L68<br>F68 | | H68 | | | Y68 | K68 | |
| -4 | A26*<br>Q77 | E77<br>K26* | R77<br>E26* | | | | | S77<br>Q26* | | | S26* |
| -5 | | E42 | R42 | | | K28* | C28*<br>Q42 | | | | M66<br>K66 |
| -6 | Q40<br>C28* | E40<br>R28* | R40 | C40<br>I40<br>V40<br>C79<br>I79<br>V79<br>Q28* | A40<br>A79<br>A28*<br>H28* | | | | | S40<br>S28* | |
| -7 | N30*<br>Q38 | E38<br>K30*<br>R30* | K38<br>R38<br>E30* | I38<br>L38 | | | C38 | | | H38<br>N38<br>Q30* | |
| -8 | F33<br>Y33 | E33<br>D33 | F33<br>H33 | L33<br>V33<br>I33<br>F33<br>C33 | R32* | R33 | | | | | |
| -9 | | E32<br>K32 | R32<br>K32 | L32<br>V32<br>A32<br>C32 | | | | | D32<br>I32 | | S32<br>N32<br>H32<br>Q32<br>T32 |

For polynucleotides, a "variant" comprises a deletion and/or addition of one or more nucleotides at one or more sites within the native polynucleotide. One of skill in the art will recognize that variants of the nucleic acids of the embodiments will be constructed such that the open reading frame is maintained. For polynucleotides, conservative variants include those sequences that, because of the degeneracy of the genetic code, encode the amino acid sequence of one of the polypeptides of the embodiments. Variant polynucleotides include synthetically derived polynucleotides, such as those generated, for example, by using site-directed mutagenesis but which still encode a recombinant meganuclease of the embodiments. Generally, variants of a particular polynucleotide of the embodiments will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to that particular polynucleotide as determined by sequence alignment programs and parameters described elsewhere herein. Variants of a particular polynucleotide of the embodiments (i.e., the reference polynucleotide) can also be evaluated by comparison of the percent sequence identity between the polypeptide encoded by a variant polynucleotide and the polypeptide encoded by the reference polynucleotide.

The deletions, insertions, and substitutions of the protein sequences encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by screening the polypeptide for its ability to preferentially recognize and cleave a P23H recognition sequence (e.g., one of SEQ ID NOs:1-4).

EXAMPLES

This invention is further illustrated by the following examples, which should not be construed as limiting. Those skilled in the art will recognize, or be able to ascertain, using no more than routine experimentation, numerous equivalents to the specific substances and procedures described herein. Such equivalents are intended to be encompassed in the scope of the claims that follow the examples below.

Example 1

Evaluation of Meganucleases that Recognize and Cleave a P23H Recognition Sequence 1. Meganucleases that Recognize and Cleave a P23H Recognition Sequence Recombinant meganucleases (SEQ ID NOs:6-93), collectively referred to herein as "RHO 1-2 meganucleases," were engineered to recognize and cleave one of the P23H recognition sequences (i.e, SEQ ID NO:1), which is present in the mutant RHO P23H allele (see, FIG. 1A). Each RHO 1-2 recombinant meganuclease comprises an N-terminal nuclease-localization signal derived from SV40, a first meganuclease subunit, a linker sequence, and a second meganuclease subunit. A first subunit in each RHO 1-2 meganuclease binds to the RHO1 recognition half-site of SEQ ID NO:1, while a second subunit binds to the RHO2 recognition half-site (see, FIG. 1B).

Figure 2B:
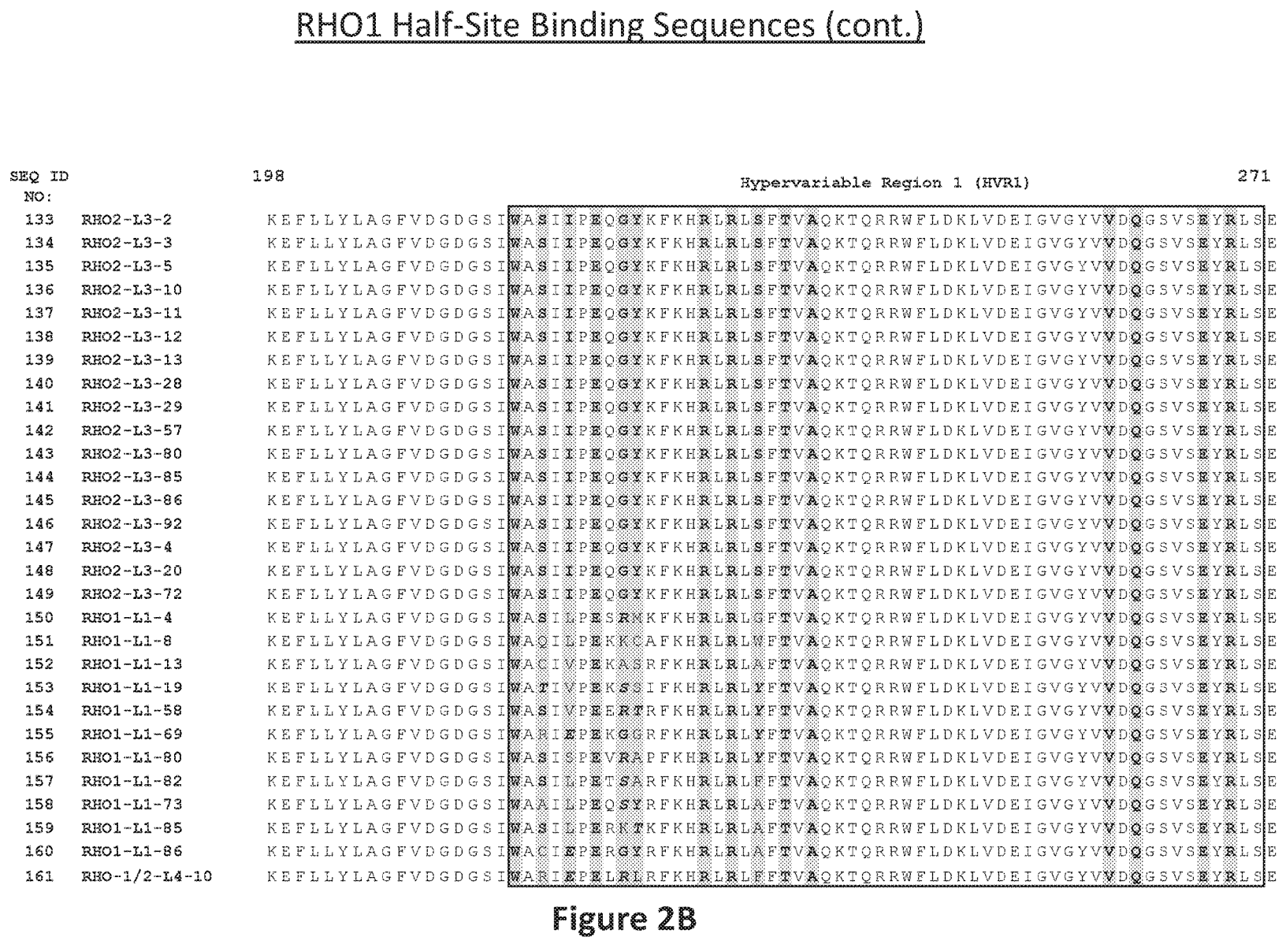
Figure 2C:
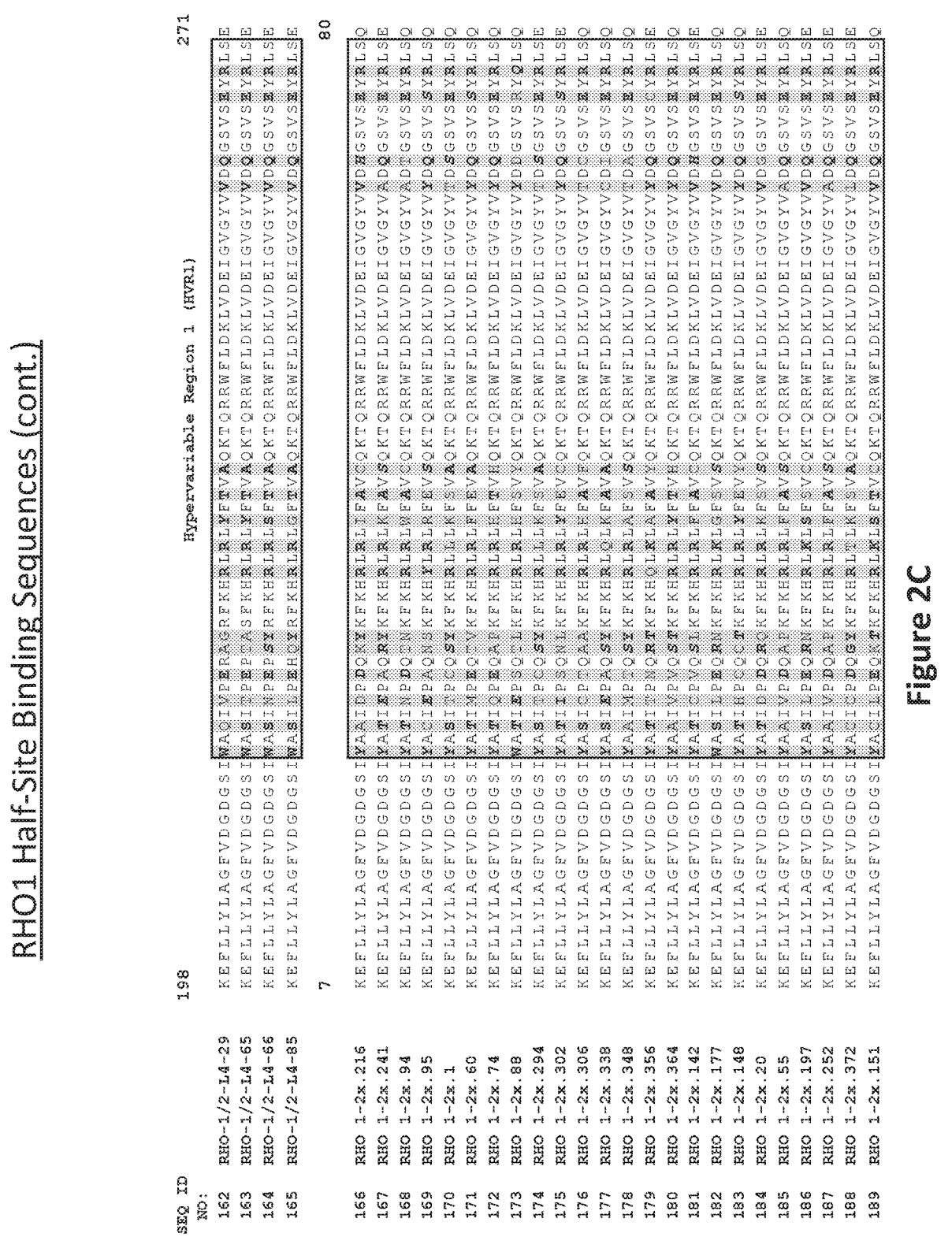
Figure 3A:
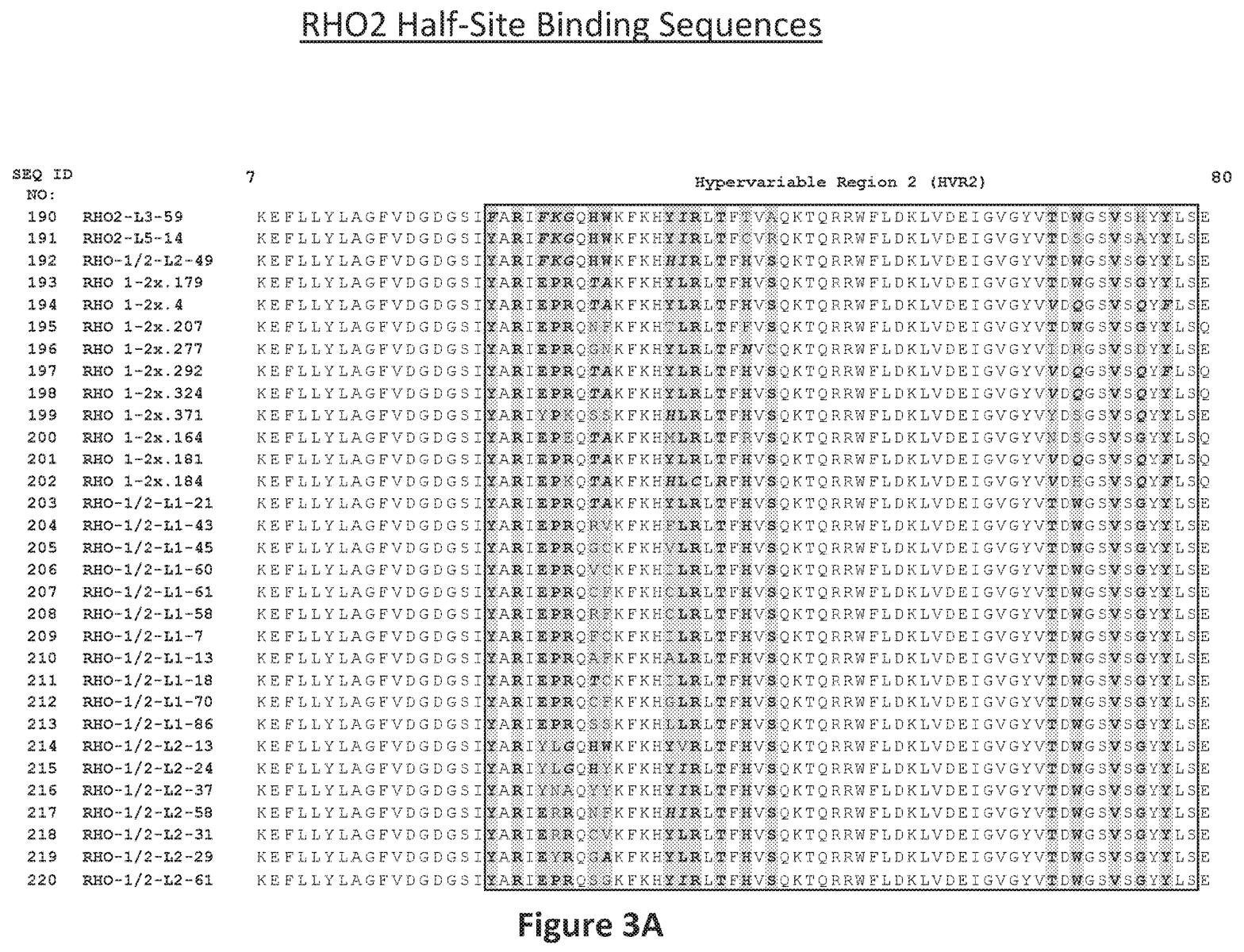

As illustrated in FIGS. 2 and 3, RHO1-binding subunits and RHO2-binding subunits each comprise a 56 base pair hypervariable region, referred to as HVR1 and HVR2, respectively. RHO1-binding subunits are identical outside of the HVR1 region except at position 80 or position 271 (comprising a Q or E residue), and are highly conserved within the HVR1 region. Similarly, RHO2-binding subunits are also identical outside of the HVR2 region except at position 80 or position 271 (comprising a Q or E residue), and are highly conserved within the HVR2 region.

The RHO1-binding regions of SEQ ID NOs:6-93 are illustrated in FIGS. 2A-2F and are provided as SEQ ID NOs:102-189, respectively. Nearly all of SEQ ID NOs:102-189 share at least 90% sequence identity to SEQ ID NO:102, which is the RHO1-binding region of the meganuclease RHO2-L3-59 (SEQ ID NO:6). RHO2-binding regions of SEQ ID NOs:6-93 are illustrated in FIGS. 3A-3F and are provided as SEQ ID NOs:190-277, respectively. Nearly all of SEQ ID NOs:190-277 share at least 90% sequence identity to SEQ ID NO:190, which is the RHO2-binding region of the meganuclease RHO2-L3-59 (SEQ ID NO:6).

2. Cleavage of a P23H Recognition Sequence in a CHO Cell Reporter Assay

Figure 5:
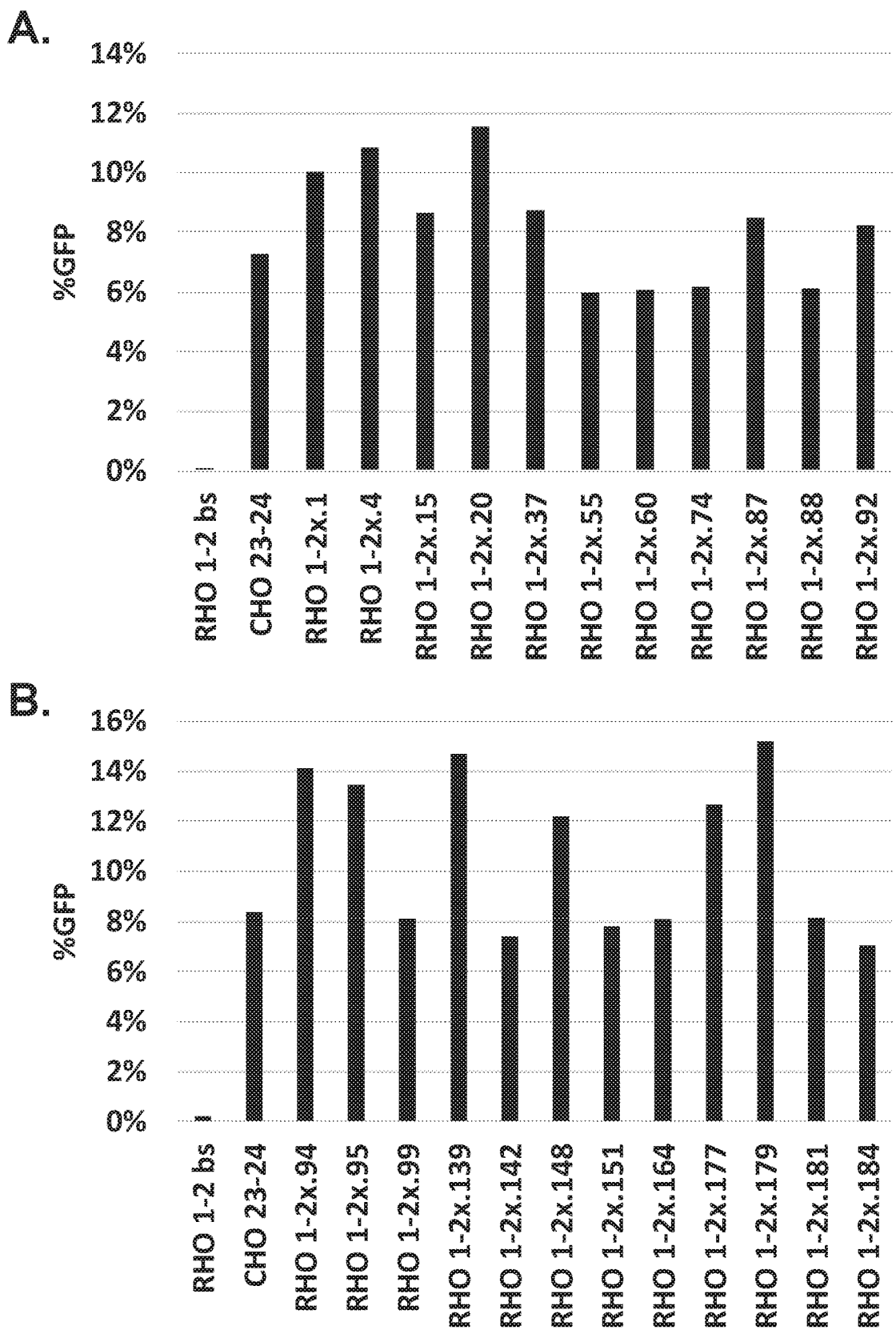
FIG. 5. Efficiency of recombinant meganucleases for recognizing and cleaving a P23H recognition sequence in a CHO cell reporter assay. A)-J) Each of the recombinant meganucleases set forth in SEQ ID NOs:6-93 were engineered to target a P23H recognition sequence and were screened for efficacy in the CHO cell reporter assay. The results shown provide the percentage of GFP-expressing cells observed in each assay, which indicates the efficacy of each meganuclease for cleaving the P23H recognition sequence or the CHO-23/24 recognition sequence. A negative control (RHO 1-2 bs) was further included in each assay.
Figure 5:
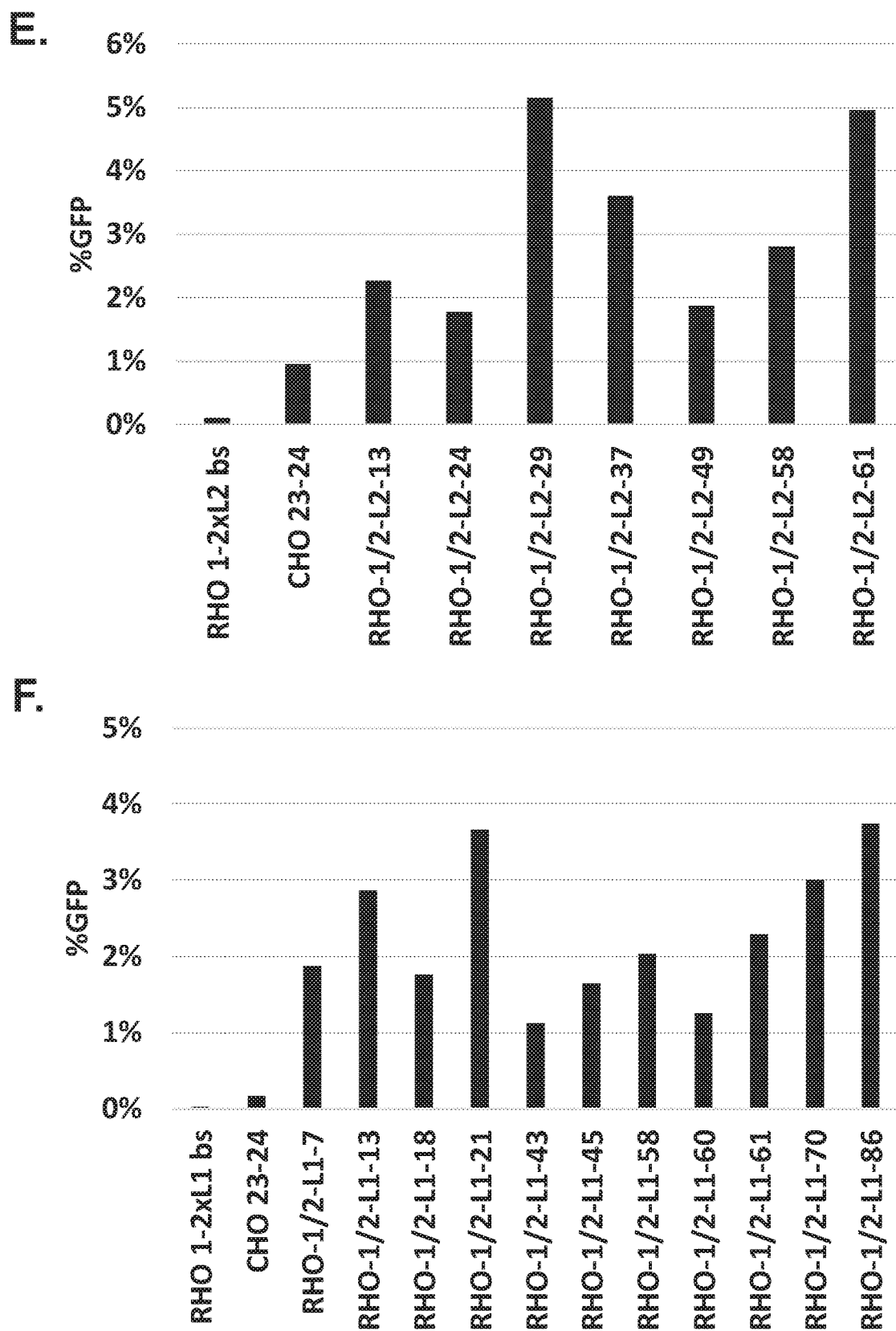
Figure 5:
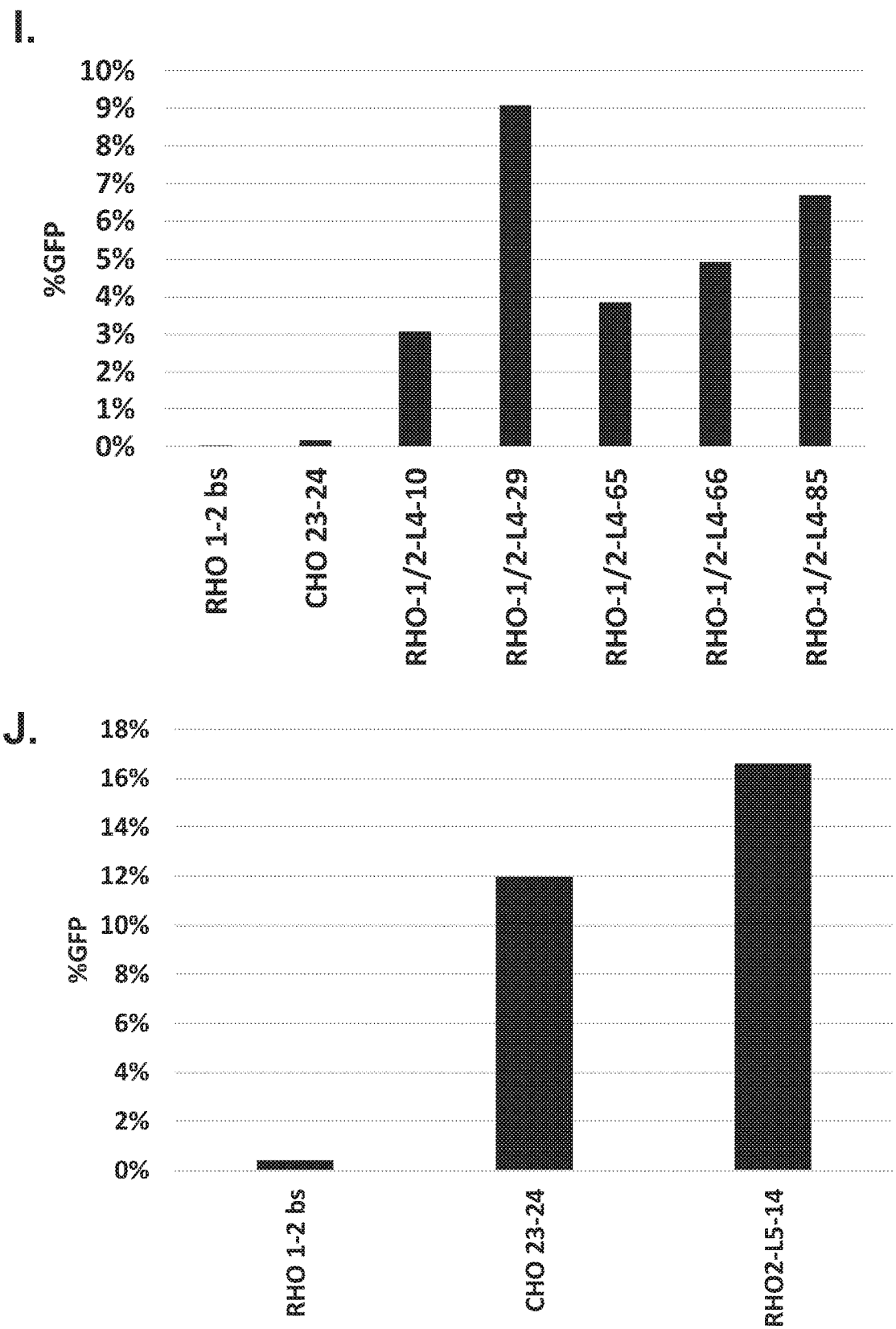

To determine whether RHO 1-2 meganucleases could recognize and cleave the P23H recognition sequence of SEQ ID NO:1, each RHO 1-2 meganuclease was evaluated using the CHO cell reporter assay previously described (see WO2012/167192, FIG. 4). To perform the assay, a pair of CHO cell reporter lines were produced which carried a non-functional Green Fluorescent Protein (GFP) gene expression cassette integrated into the genome of the cell. The GFP gene in each cell line was interrupted by a pair of recognition sequences such that intracellular cleavage of either recognition sequence by a meganuclease would stimulate a homologous recombination event resulting in a functional GFP gene. In both cell lines, one of the recognition sequences was derived from the RHO gene (either SEQ ID NO:1 or SEQ ID NO:5) and the second recognition sequence was specifically recognized by a control meganuclease called "CHO-23/24". CHO reporter cells comprising the P23H recognition sequence of SEQ ID NO:1 and the CHO-23/24 recognition sequence are referred to herein as "RHO 1-2 cells." RHO 1-2 cells were transfected with plasmid DNA encoding one of the RHO 1-2 meganucleases (SEQ ID NOs:6-93) or encoding the CHO-23/34 meganuclease. Approximately 4×10⁵ CHO cells were transfected with 50 ng of plasmid DNA in a 96-well plate using Lipofectamine 2000 (ThermoFisher) according to the manufacturer's instructions. At 48 hours post-transfection, cells were evaluated by flow cytometry to determine the percentage of GFP-positive cells compared to an untransfected negative control (RHO 1-2 bs). All RHO 1-2 meganucleases were found to produce GFP-positive cells in cell lines comprising the P23H recognition sequence at frequencies significantly exceeding the negative control and comparable to or exceeding the CHO-23/24 positive control, indicating that each RHO 1-2 meganuclease was able to efficiently recognize and cleave the intended P23H recognition sequence in a cell (see, FIG. 5).

Figure 6:
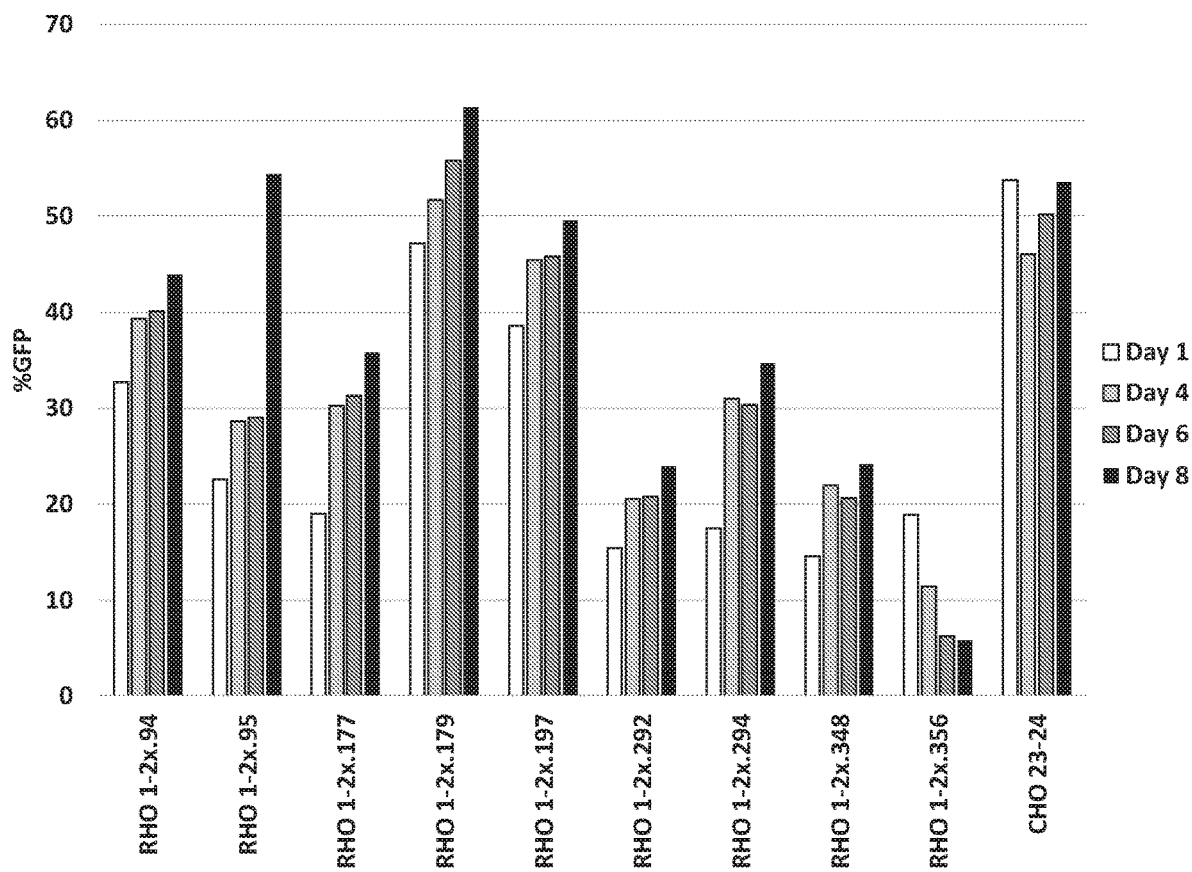
FIG. 6. Time course of recombinant meganuclease efficacy in CHO cell reporter assay. Recombinant meganucleases encompassed by the invention were evaluated in the CHO reporter assay, with the percentage of GFP-expressing cells determined 1, 4, 6, and 8 days after introduction of meganuclease-encoding mRNA into the CHO reporter cells. A CHO-23/24 meganuclease was included at each time point as a positive control.

The efficacy of RHO 1-2 recombinant meganucleases was also determined in a time-dependent manner 1, 4, 6, and 8 days after introduction of the meganucleases into RHO 1-2 cells. In this study, RHO 1-2 cells (1.0×10⁶) were electroporated with 1×10⁶ copies of meganuclease mRNA per cell using a BioRad Gene Pulser Xcell according to the manufacturer's instructions. At 48 hours post-transfection, cells were evaluated by flow cytometry to determine the percentage of GFP-positive cells. A CHO-23/24 meganuclease was also included at each time point as a positive control. As shown in FIG. 6, the efficacy of RHO 1-2 meganucleases persisted over the 8 day period evaluated.

3. Conclusions

These studies demonstrated that RHO 1-2 meganucleases (SEQ ID NOs:6-93) encompassed by the invention can target and cleave the P23H recognition sequence of SEQ ID NO:1 in cells.

Example 2

Specificity of Meganucleases for a P23H Recognition Sequence

1. CHO Reporter Cells Comprising a Corresponding Wild-Type RHO Sequence

To determine the specificity of RHO 1-2 meganucleases (SEQ ID NOs:6-93) for the P23H recognition sequence of SEQ ID NO:1, a CHO reporter cell line was generated as previously described that comprises the corresponding wild-type RHO recognition sequence (SEQ ID NO:5), referred to herein as the "RHO 3-4 recognition sequence," and the CHO-23/24 recognition sequence. The resulting cells are referred to herein as "RHO 3-4 cells."

2. Specificity of RHO 1-2 Meganucleases

Figure 7:
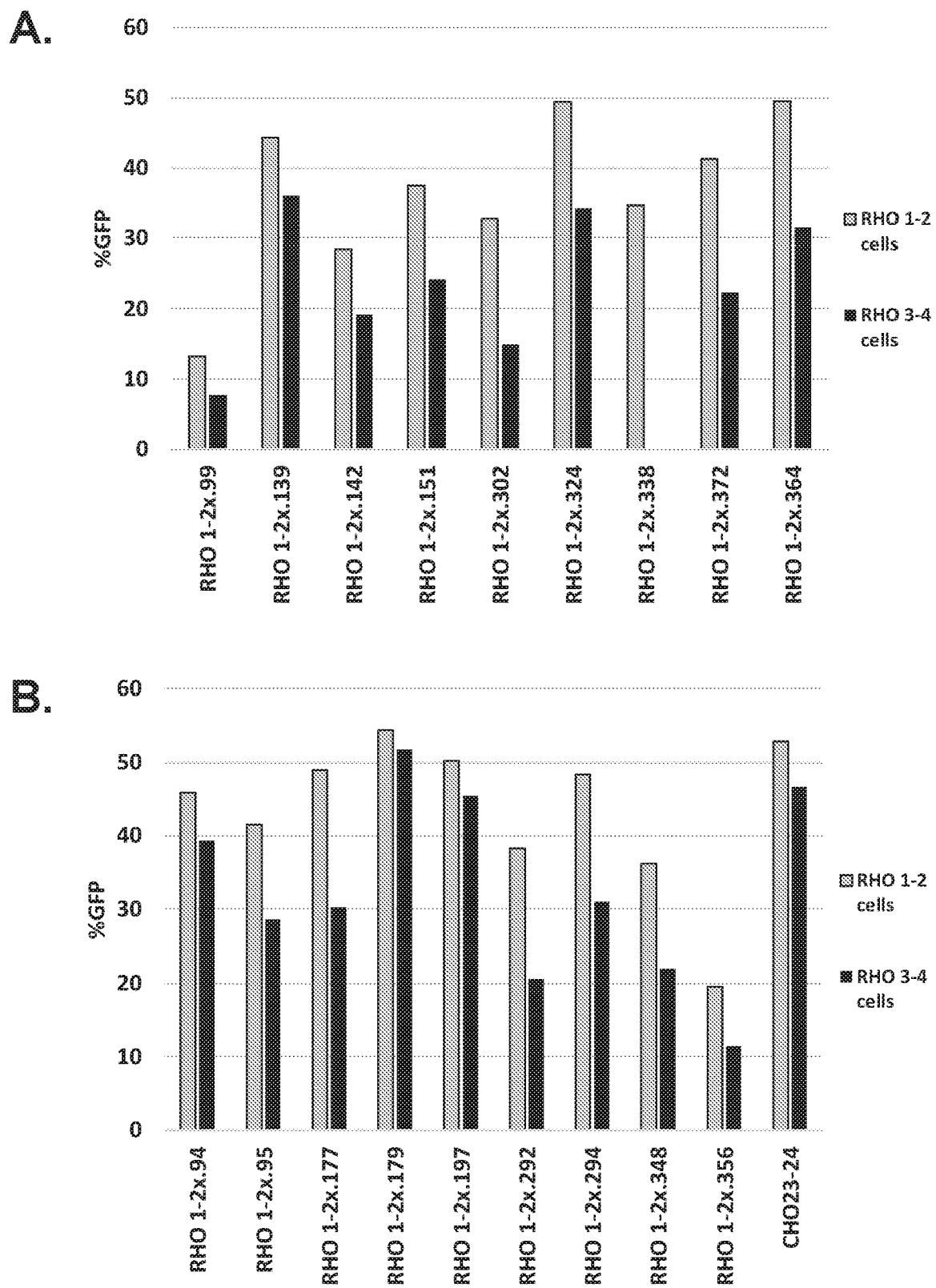
FIG. 7. Selectivity of recombinant meganucleases. A)-F) The selectivity of recombinant meganucleases for a P23H recognition sequence (SEQ ID NO:1) versus the corresponding wild-type RHO recognition sequence (SEQ ID NO:5) was determined using the CHO cell reporter assay. Recombinant meganucleases encompassed by the invention were introduced into cells comprising a P23H recognition sequence ("RHO 1-2 cells," gray bars) or the corresponding wild-type RHO recognition sequence ("RHO 3-4 cells," black bars) to determine if they could discriminate between the mutant and wild-type targets.

RHO 1-2 meganucleases were introduced into RHO 1-2 cells or RHO 3-4 cells to determine if the recombinant meganucleases could discriminate between the P23H recognition sequence of SEQ ID NO:1 and the corresponding wild-type recognition sequence (SEQ ID NO:5). RHO 1-2 meganuclease mRNA was introduced into RHO 1-2 cells or RHO 3-4 cells via electroporation of mRNA as previously described, and the percent GFP-positive cells was determined after 3-5 days. As shown in FIG. 7, each of the RHO 1-2 meganucleases tested preferentially cleaved the P23H recognition sequence relative to the RHO 3-4 recognition sequence, as evidenced by higher percentages of GFP-positive RHO 1-2 cells than RHO 3-4 cells (see, FIG. 7A-7E). In subsequent experiments, it was shown that recombinant meganucleases could be developed that preferentially target and cleave the wild-type RHO 3-4 recognition sequence (SEQ ID NO:5). This set of meganucleases, when evaluated using the CHO cell reporter assay described above, were found to yield a higher percentage of GFP-positive RHO 3-4 cells than RHO 1-2 cells (see, FIG. 7F).

3. Conclusions

We have demonstrated that RHO 1-2 meganucleases encompassed by the invention preferentially cleave the P23H recognition sequence of SEQ ID NO:1 relative to the corresponding wild-type RHO 3-4 recognition sequence (SEQ ID NO:5).

Example 3

Generation and Expression of Recombinant AAV Vectors for Expressing Recombinant Meganucleases 1. Recombinant AAV vectors for expressing RHO 1-2 meganucleases Recombinant AAV vectors were designed to express RHO 1-2 meganucleases in CHO reporter cells. As shown in FIG. 8A, the recombinant AAV vectors comprise, from 5' to 3', a first inverted terminal repeat (ITR), a CMV promoter operably linked to a nucleotide sequence encoding a meganuclease, and a second inverted terminal repeat. In this study, a coding sequence for the RHO-1/2-L2-49 meganuclease was incorporated into the recombinant AAV vector.

2. Expression of a RHO 1-2 Meganuclease Following Recombinant AAV Transduction

A recombinant AAV vector (rAAV-RHO-1/2) was prepared for expression of the RHO-1/2-L2-49 meganuclease in RHO 1-2 cells using a standard triple-transfection protocol in HEK-293 cells (Drittanti et al. (2001), *J Gene Med.* 3:59-71). RHO 1-2 CHO reporter cells were transduced with the rAAV-RHO-1/2 vector at three concentrations of virus. At 24 hours post-transduction, cells were lysed and analyzed by Western blot using a polyclonal meganuclease-specific antibody or a β-actin-specific control antibody. As shown in FIG. 8B, RHO-1/2-L2-49 expression was observed at all three concentrations of virus.

3. Specificity of AAV-Delivered RHO 1-2 Meganuclease

Figure 9:
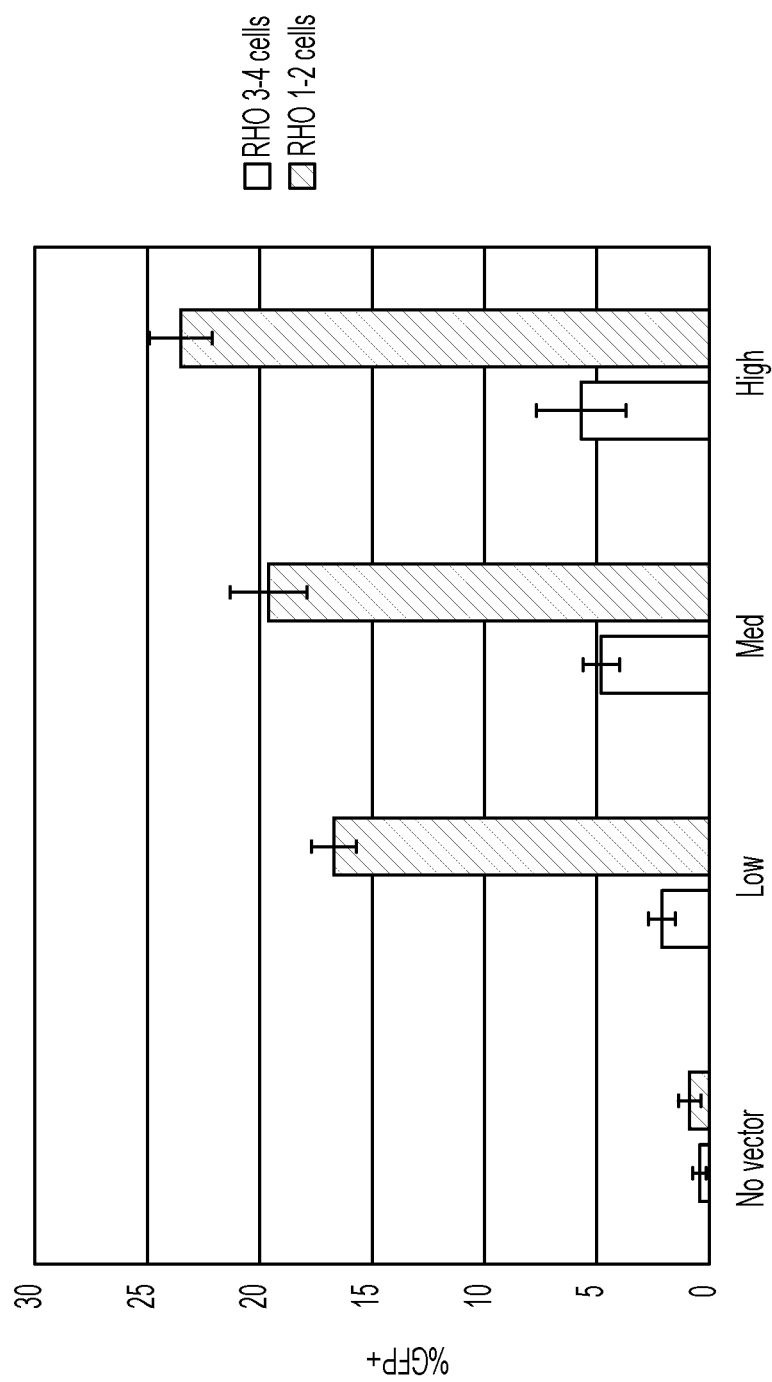
FIG. 9. Efficiency and selectivity of a RHO-1/2-L2-49 meganuclease for a P23H recognition sequence (SEQ ID NO:1) when expressed by recombinant AAV in a CHO cell reporter assay. CHO cells harboring the wild-type recognition sequence (SEQ ID NO:5; "RHO 3-4 cells", black bars) or the P23H recognition sequence (SEQ ID NO:1; "RHO 1-2 cells," gray bars) were transduced with three different doses of AAV2 vector encoding the RHO-1/2-L2-49 meganuclease operably linked to a CMV promoter.

The rAAV-RHO-1/2 vector was transduced into RHO 1-2 cells or RHO 3-4 cells to demonstrate the specificity of AAV-delivered RHO-1/2-L2-49 meganuclease for recognizing and cleaving the P23H recognition sequence of SEQ ID NO:1 relative to the corresponding wild-type RHO 3-4 recognition sequence (SEQ ID NO:5). As shown in FIG. 9, after three days post-transduction, the AAV-delivered RHO-1/2-L2-49 meganuclease induced a higher percentage of GFP-positive RHO 1-2 cells than RHO 3-4 cells at all concentrations of virus used, indicating that the meganuclease preferentially recognizes and cleaves the mutant sequence.

4. Persistence of AAV-Delivered RHO 1-2 Meganuclease Expression

Figure 10:
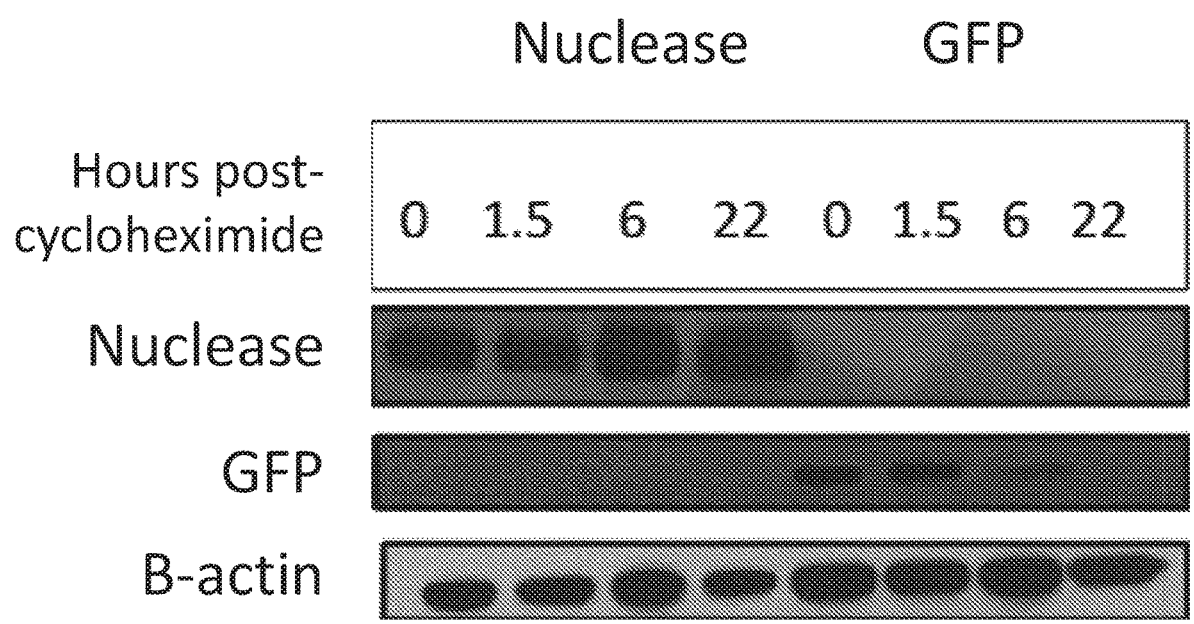
FIG. 10. RHO-1/2-L2-49 meganuclease stability in CHO reporter cells following treatment with cycloheximide.

RHO 1-2 cells, transduced with the recombinant AAV vector encoding the RHO-1/2-L2-49 meganuclease or GFP, were treated with cycloheximide to halt protein translation and determine the stability of the expressed proteins in cells. Cells were lysed at various times (0, 1.5, 6, and 22 hours) post-cycloheximide treatment, and protein levels of RHO-1/2-L2-49, GFP, and β-actin were determined by Western Blot analysis. As shown in FIG. 10, RHO-1/2-L2-49 protein persisted significantly longer than GFP, with no reduction in meganuclease protein apparent after 22 hours.

5. Conclusions

This study indicates that RHO 1-2 meganucleases encompassed by the invention can be expressed in cells using recombinant AAV vectors, and that such meganucleases can preferentially recognize and cleave the P23H recognition sequence of SEQ ID NO:1 relative to the corresponding wild-type RHO 3-4 sequence (SEQ ID NO:5). Furthermore, this study demonstrates that RHO 1-2 meganuclease proteins are stable in cells when expressed using recombinant AAV vectors.

Example 4

Cleavage of RHO 1-2 Recognition Sequence in Reporter Cells with RHO 1-2 Meganucleases Delivered by AAV 1. Production of Recombinant AAV Vectors The purpose of this study was to demonstrate that RHO 1-2 meganucleases could be expressed in mammalian cells by viral transduction, and to further demonstrate their ability to cleave the RHO 1-2 recognition sequence.

Figure 11:
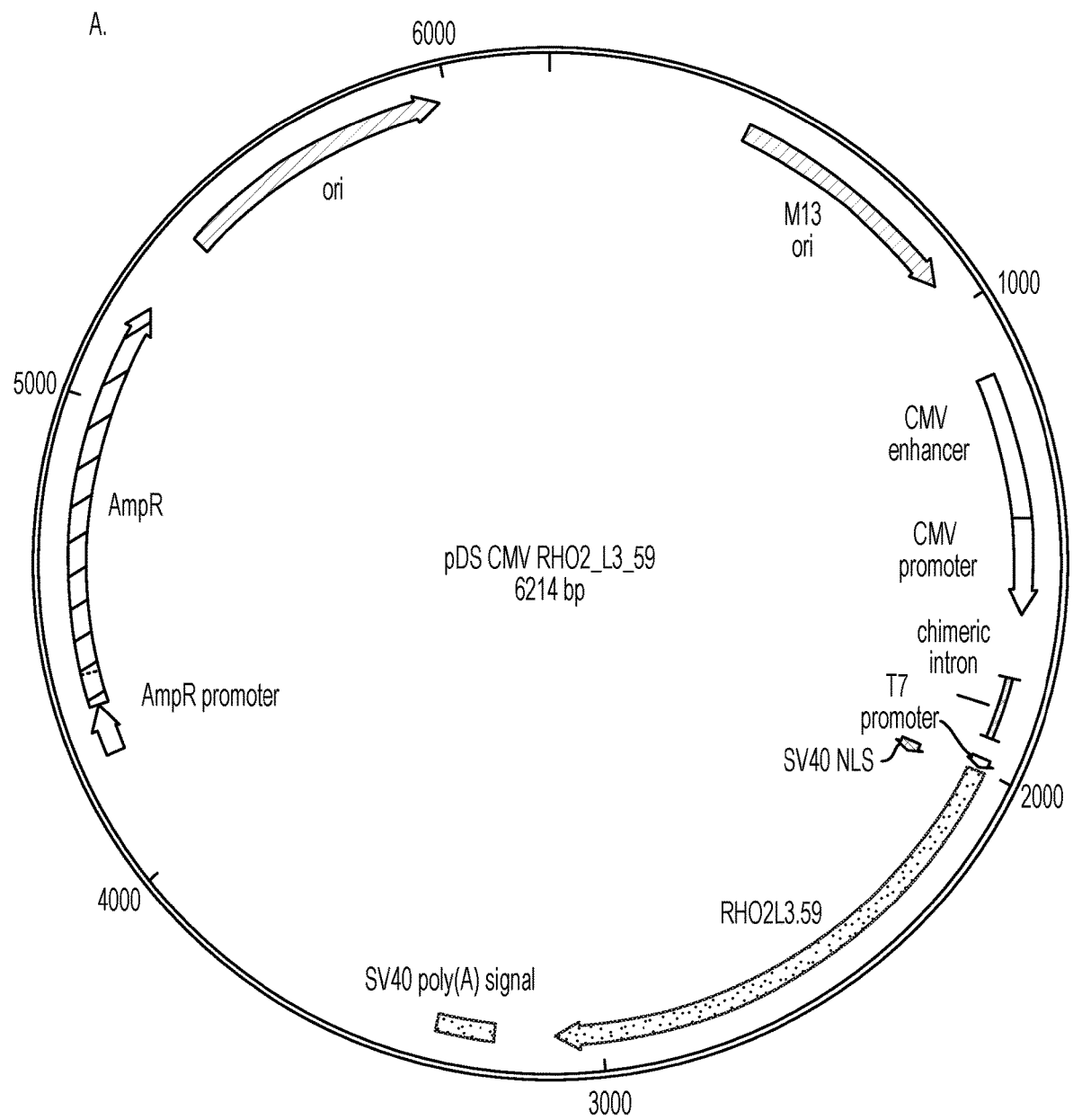
FIG. 11. A) Vector map of the pDS CMV RHO2_b 3_59 plasmid (SEQ ID NO:278). B) Vector map of the pDS CMV RHO2_L5_14 plasmid (SEQ ID NO:279).
Figure 11:
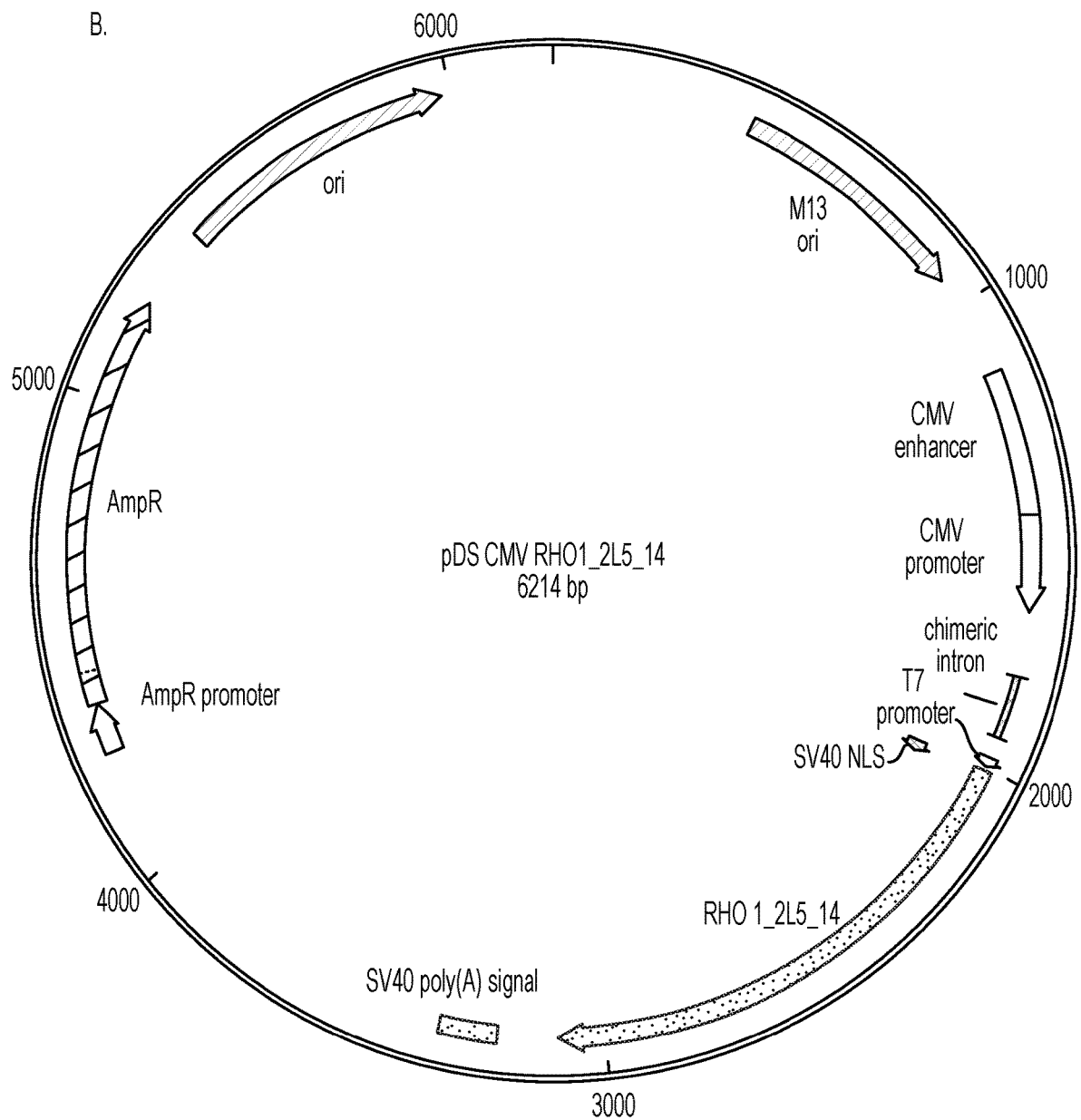

For this experiment, two recombinant AAV2 vectors were produced by the triple-transfection method previously described. The two donor plasmids were pDS CMV RHO2_L3_59 (SEQ ID NO:248) and pDS CMV RHO2_L5_14 (SEQ ID NO:249), which encoded the RHO2-L3-59 and RHO2-L5-14 meganucleases, respectively (FIG. 11). These plasmids comprise a CMV promoter and enhancer driving expression of the nuclease, an SV40 polyA sequence, AAV ITR (inverted terminal repeat) sequences required for genome replication, and are suitable for the production of self-complimentary AAV genomes (scAAV). The capsid from AAV serotype 2 was used to generate these vectors. Recombinant scAAV was produced using the triple-transfection method in HEK 293 cells and purified over a CsCl gradient. Viral titer was determined by RT-PCR and slot-blot methods.

2. Transduction of Reporter Cells and Analysis of Cleavage Efficiency

To determine whether these AAV particles could deliver functional RHO 1-2 meganucleases capable of recognizing and specifically cleaving the RHO 1-2 recognition sequence (SEQ ID NO:1) and not the RHO 3-4 recognition sequence (SEQ ID NO:5), they were tested in previously described CHO reporter lines (see WO2012/167192). To perform the assay, a pair of CHO cell reporter lines were produced which carried a non-functional Green Fluorescent Protein (GFP) gene expression cassette integrated into the genome of the cell. The GFP gene in each cell line was interrupted by either the RHO 1-2 or RHO 3-4 recognition sequence such that intracellular cleavage of the recognition sequence by a meganuclease would stimulate a homologous recombination event resulting in a functional GFP gene. CHO reporter cells comprising the RHO 1-2 recognition sequence are referred to in this experiment as "P23H RHO cells." CHO reporter cells comprising the RHO 3-4 recognition sequence are referred to in this experiment as "WT RHO cells." Wild-type control cells that do not harbor the GFP reporter cassette are referred to in this experiment as "CHO K cells."

Figure 12:
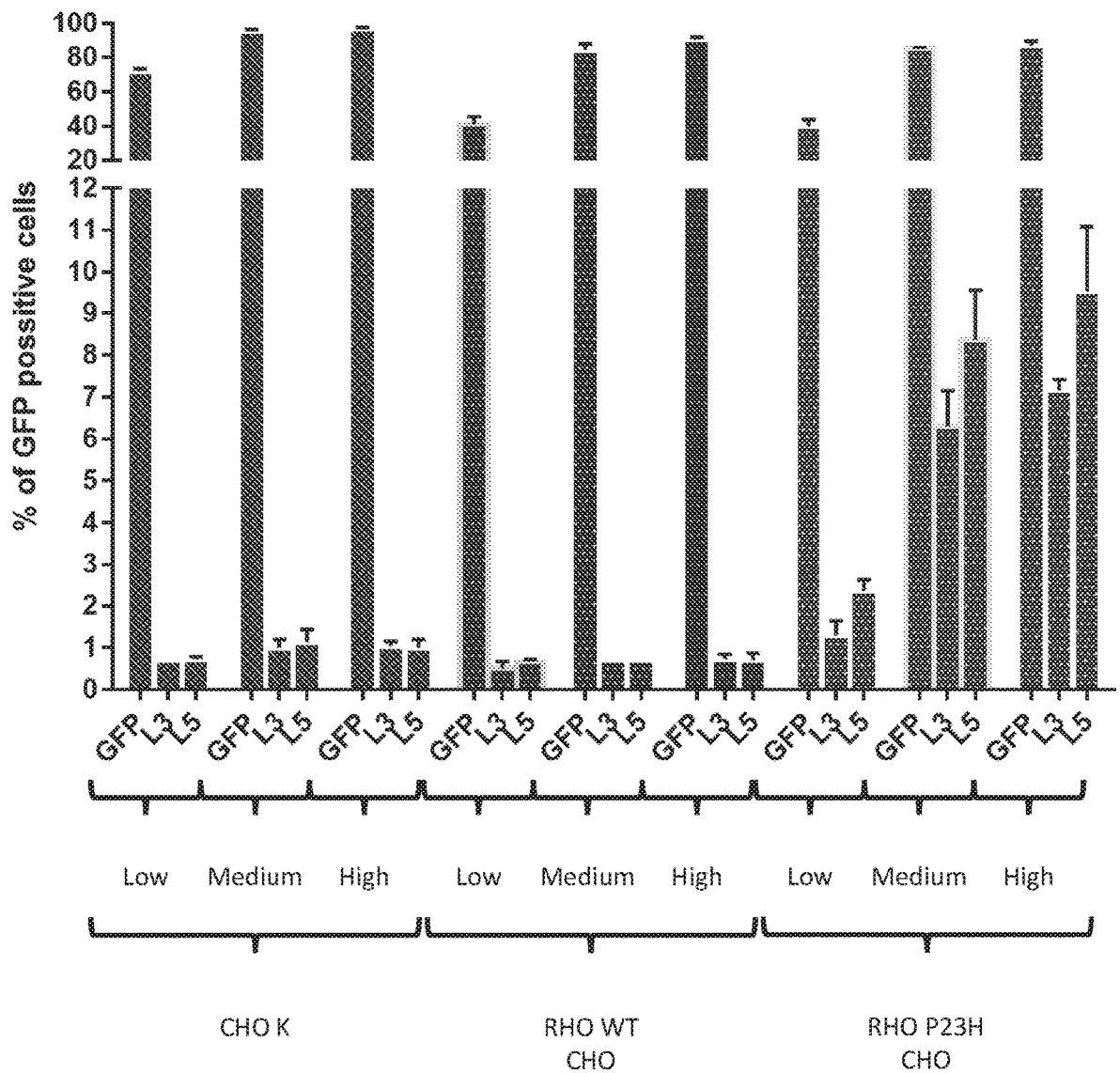
FIG. 12. CHO GFFP reporter assay demonstrating specificity of RHO 1-2 meganucleases for RHO 1-2 recognition sequence. CHO-K cells (controls), WT RHO cells (comprising wild-type RHO sequence of SEQ ID NO:5), or P23H RHO cells (comprising P23H RHO sequence of SEQ ID NO:1) were transduced with low, medium, or high titers of recombinant AAV vectors encoding a GFP protein, the RHO2-L3-59 meganuclease (SEQ ID NO:6), or the RHO2-L5-14 meganuclease (SEQ ID NO:7). The percent of GFP-positive cells was determined in each cell line following transduction as a measure of recognition sequence cleavage.

WT RHO cells, P23H RHO cells, or wild-type CHO K cells (negative control) were infected with recombinant scAAV described above. Reporter cells were infected at three MOIs: $1\times10^8$, $1\times10^9$ or $2\times10^9$ ("low," "medium," and "high," respectively). At 48 hours post-infection, cells were evaluated by flow cytometry to determine the percentage of GFP-positive cells compared to wild-type control CHO cells. As shown in FIG. 12, control wild-type CHO cells infected with either the RHO2-L3-59 or RHO2-L5-14 scAAV provided background GFP expression, less than 1%. Cells harboring the wild-type RHO 3-4 target ("WT RHO cells") did not display GFP expression significantly higher than the control cells, indicating that the RHO 1-2 meganucleases are not capable of cleaving the RHO 3-4 recognition sequence. In P23H RHO cells, both the RHO2-L3-59 and RHO2-L5-14 meganucleases resulted in significant GFP expression in a dose-dependent manner, with levels approaching 10% GFP+ in the highest dose.

Western blot analysis was used to confirm both GFP and meganuclease expression in the P23H RHO cells. Whole cell lysates were prepared only from P23H RHO and WT RHO cells infected with the three different doses of scAAV. Lysates for duplicates were harvested to provide a measure of reproducibility. Equivalent amounts of lysates (determined by protein concentration) were resolved by SDS-PAGE, transferred to a membrane and probed using antibodies against either GFP, the I-CreI meganuclease, or for loading control, β-actin. RHO 1-2 meganucleases are detectable with the polyclonal antibody against I-CreI.

Figure 13:
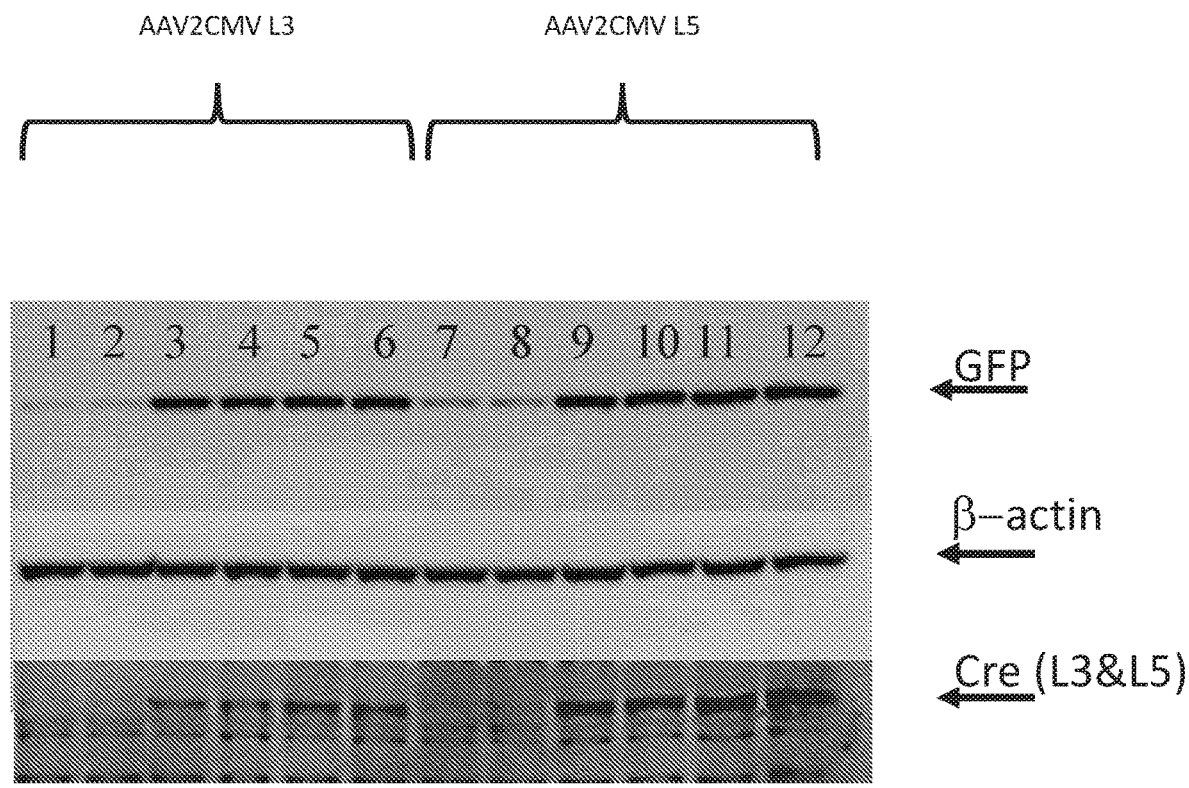
FIG. 13. Western blot analysis of meganuclease expression in CHO RHO 1-2 cells following transduction of recombinant AAV vectors. P23H RHO cells, comprising the RHO 1-2 recognition sequence, were transduced with 1e8, 1e9, or 2e9 viral genomes per cell of recombinant AAV vectors encoding the RHO2-L3-59 meganuclease (SEQ ID NO:6) or the RHO2-L5-14 meganuclease (SEQ ID NO:7). Cell lysates were analyzed for expression of GFP as a measure of RHO 1-2 recognition sequence cleavage (top panel), meganuclease expression (bottom panel), and β-actin as a loading control. Lanes 1-6 were transduced to express the RHO2-L3-59 meganuclease. Lanes 7-12 were transduced to express the RHO2-L5-14 meganuclease.

As shown in FIG. 13, western blot analysis clearly demonstrates detection of GFP in a dose-dependent manner, confirming the flow cytometry data shown in FIG. 12 and described above. Western blot analysis also shows expression of the RHO 1-2 meganucleases, also in a dose-dependent manner. The blot does suggest that RHO2-L5-14 expressed to higher levels than RHO2-L3-59. β-actin levels were consistent, indicating proper gel loading.

3. Conclusions

Together, these data demonstrate recombinant scAAV carrying expression cassettes for RHO 1-2 meganucleases of the invention are able to infect CHO reporter lines, resulting in expression of the RHO 1-2 meganucleases which are then able to specifically cleave the P23H RHO 1-2 recognition sequence (SEQ ID NO:1) and not the WT RHO 3-4 recognition Example 5

In Vivo Cleavage of P23H Allele in Mouse Model of RP

1. Production of Recombinant AAV Vectors and Sub-Retinal Delivery to Mouse Eye

The purpose of this study was to determine whether RHO 1-2 meganucleases of the invention could target and cleave the RHO 1-2 recognition sequence in vivo within photoreceptor cells of a mouse retina.

Figure 14:
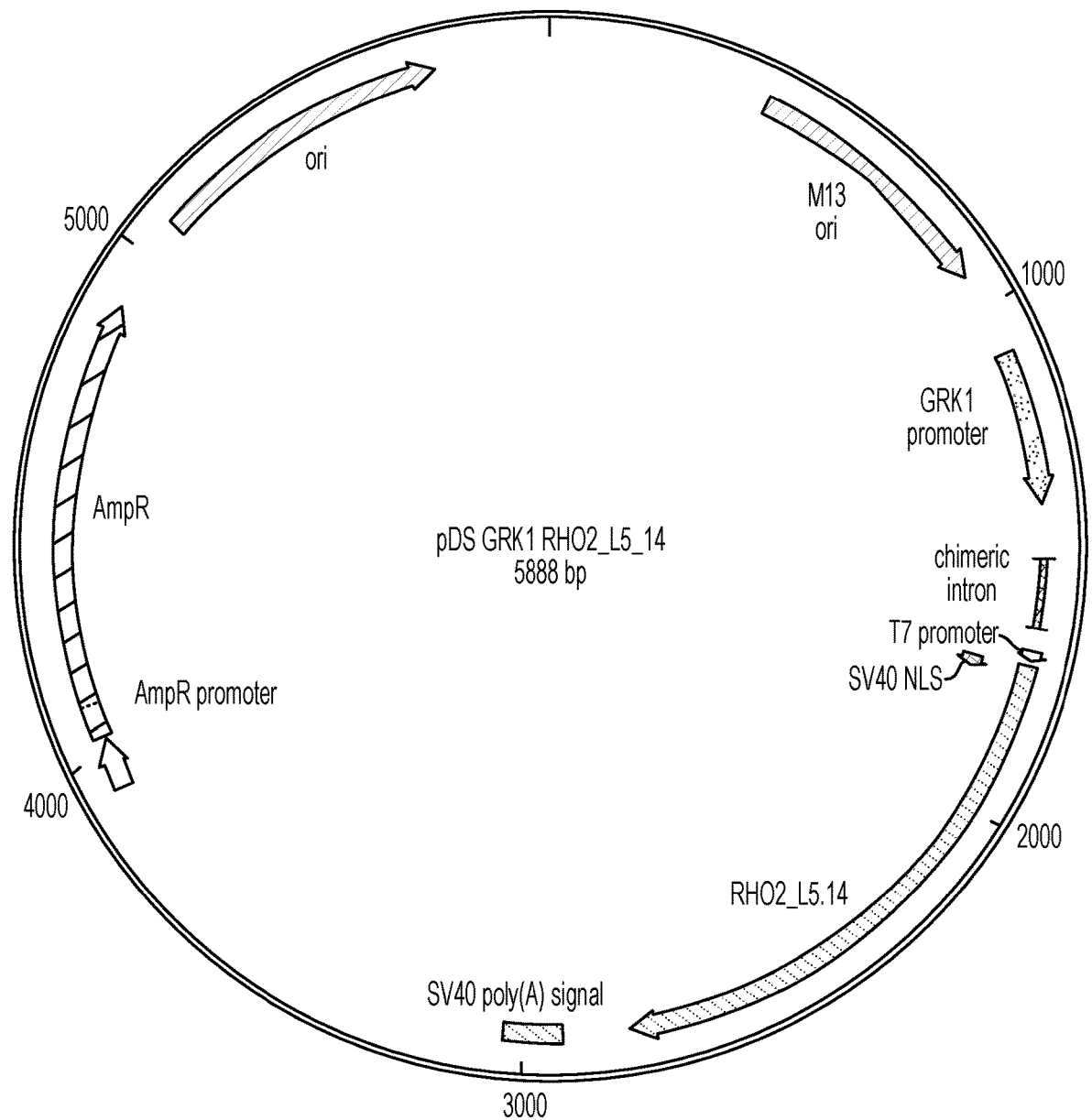
FIG. 14. Vector map of the pDS GRK1 RHO2_L5_14 plasmid (SEQ ID NO:281).

Recombinant scAAV were prepared using the triple-transfection method as described above and were tested in a murine model of retinitis pigmentosa. In this model, transgenic mice carry a single copy of the human P23H mutant RHO gene in addition to the endogenous murine RHO alleles. While these mice do not exhibit a retinitis pigmentosa phenotype, they are useful for molecular analysis of in vivo cleavage of the RHO 1-2 recognition sequence. Since RHO2-L5-14 performed better in the GFP reporter CHO lines, only scAAV encoding RHO2-L5-14 was used to infect mice (though the present experiments could be performed using the RHO2-L3-59 meganuclease, including the production of an scAAV using the donor plasmid set forth in SEQ ID NO:280). The pDS GRK1 RHO2_L5_14 donor plasmid (SEQ ID NO: 281) used in the scAAV triple transfection protocol is illustrated in FIG. 14. As shown, the RHO2-L5-14 meganuclease was under the control of a rod cell-specific GRK1 promoter. As a control, a recombinant scAAV encoding a GFP expression cassette was also prepared. The capsid from AAV serotype 5 was used to generate these recombinant scAAV vectors.

One of the P23H transgenic mice was used to test whether sub-retinal injection of an AAV encoding a RHO2-L5-14 expression cassette could result in cleavage at the RHO 1-2 recognition sequence. Briefly, at postnatal day 30, a mouse was placed under general anesthesia by intraperitoneal injection of Ketamine 100 mg/kg and Xylazine 10 mg/kg. Pupils were dilated with Tropicamide (0.5%) and 1% Proparacaine. Under an ophthalmic surgery microscope, with a 30-gauge needle a small incision was made through the cornea adjacent to the limbus. A 33-gauge blunt needle fitted to a Hamilton syringe was inserted through the incision. All injections were made sub-retinally within the nasal quadrant of the retina. The mouse received 1 μL of scAAV encoding RHO2-L5-14 in one eye and 1 μL of scAAV encoding GFP in the other eye (both viral preparations were at a concentration of $7 \times 10^{12}$ particles/mL). Visualization during injection was aided by the addition of fluorescein to the vector suspensions. Fundus and OCT examination were performed to confirm the successful sub-retinal delivery.

The mouse was euthanized with isoflurane and eyes were enucleated at 30 days post-injection. The retinas were carefully dissected free from the other ocular tissues under surgical microscope. DNA was isolated from dissected retinas by using DNA isolation kit (Qiagen). Briefly, retinas were digested with lysis buffer containing protease K at 55° C. for 2 hrs. After lysis, crude extract was passed through the column and bound DNA washed several times. The DNA was eluted and concentration was estimated by NanoDrop (Thermo).

To determine the presence and relative frequency of mutations at the RHO 1-2 recognition sequence, the RHO 1-2 locus was PCR-amplified and subjected to deep sequencing analysis. Briefly, PCR primers were designed to amplify a ~200 bp region spanning the RHO 1-2 recognition sequence and gel-purified PCR bands were subjected to deep sequencing analysis using an Illumina MiSeq instrument.

2. Results

Deep sequencing of the PCR bands provided over $5 \times 10^5$ sequences per sample. Retinas injected with scAAV encoding GFP showed about $4 \times 10^3$ sequences with indels (insertions or deletions) at the RHO 1-2 recognition sequence, establishing the background at 0.54%. In DNA isolated from a mouse retina that had been injected with AAV encoding the RHO2-L5-14 meganuclease, indels were detected at 3.92%, approximately 7-fold higher than background (Table 3). In other experiments (data not shown), control mice showed a lower frequency of indels, typically around 0.01%.

TABLE 3

|  | Sequences with indels | Sequences with no indels | % Indel |
| --- | --- | --- | --- |
| AAV-GFP | 4155 | 766145 | 0.54 |
| AAV-RHO 1-2L5.14 | 22330 | 547763 | 3.92 |

3. Conclusions

The deep sequencing data demonstrates that sub-retinal injection with an AAV encoding the RHO2-L5-14 meganuclease resulted in mutation of the P23H RHO 1-2 recognition sequence in a murine model of retinitis pigmentosa following cleavage and non-homologous end joining.

Example 6

In Vivo Expression of RHO 1-2 Meganucleases in Retinal Cells

1. Western blot analysis of retinal cells

To confirm that the RHO2-L5-14 meganuclease could be expressed in the retinal cells of wild-type mice following AAV delivery, five wild-type mice were administered scAAV encoding RHO2-L5-14 by sub-retinal injection as described above. Both the OS (left) and OD (right) eyes were infected. 30 days following injection, retinas were dissected, whole cell lysates were prepared and western blot analysis was performed, using the anti-I-CreI antibody as described above.

Western blot analysis showed that in most retinas, RHO2L-5-14 expression is readily detected (FIG. 15, lanes 3, 5, 7 and 10). In other retinas, expression was considerably less, but still detectable (FIG. 15, lanes 1, 4, and 6). The remaining retinas had almost undetectable levels of expression (FIG. 15, lanes 2, 8 and 9). Sub-retinal injection relies on precise delivery to a very small area behind the eye. Although this procedure is fairly common in adult patients, it is not a common lab practice in mouse models. Therefore, the difference in expression was attributed to the difficulty of murine sub-retinal injections.

2. Conclusions

Western blot analysis demonstrated that scAAV encoding RHO2L-5-14 delivered sub-retinally to mice resulted in expression of the RHO 1-2 meganuclease. Taken together with indel data from a murine model for the human P23H RHO gene, these data suggest that AAV delivery of a RHO 1-2 meganuclease is effective in causing deletions in the P23H RHO allele.

The invention claimed is:

1. An engineered meganuclease that recognizes and cleaves a P23H recognition sequence consisting of SEQ ID NO: 1, wherein said engineered meganuclease comprises a first subunit and a second subunit, and wherein said first subunit binds to a first recognition half-site of said P23H recognition sequence and comprises a first hypervariable (HVR1) region, and wherein said second subunit binds to a second recognition half-site of said P23H recognition sequence and comprises a second hypervariable (HVR2) region, and wherein said engineered meganuclease comprises an amino acid sequence having at least 97% sequence identity to SEQ ID NO:7.

2. The engineered meganuclease of claim 1, wherein said first subunit comprises an amino acid sequence having at least 97% sequence identity to residues 198-344 of SEQ ID NO: 7, and wherein said second subunit comprises an amino acid sequence having at least 97% sequence identity to residues 7-153 of SEQ ID NO: 7.

3. The engineered meganuclease of claim 1, wherein said first subunit comprises residues 198-344 of SEQ ID NO: 7.

4. The engineered meganuclease of claim 1, wherein said second subunit comprises residues 7-153 of SEQ ID NO: 7.

5. The engineered meganuclease of claim 1, wherein said engineered meganuclease comprises the amino acid sequence of SEQ ID NO: 7.

6. The engineered meganuclease of claim 1, wherein said engineered meganuclease preferentially recognizes and cleaves a P23H recognition sequence consisting of SEQ ID NO: 1 relative to a recognition sequence consisting of SEQ ID NO: 5.

7. An isolated polynucleotide comprising a nucleic acid sequence encoding said engineered meganuclease of claim 1.

8. A recombinant DNA construct comprising said isolated polynucleotide of claim 7.

9. The recombinant DNA construct of claim 8, wherein said recombinant DNA construct encodes a recombinant adeno-associated virus (AAV) vector.

10. A recombinant viral vector comprising said isolated polynucleotide of claim 7.

* * * * *